US011833215B2

(12) United States Patent
Abrams et al.

(10) Patent No.: US 11,833,215 B2
(45) Date of Patent: *Dec. 5, 2023

(54) CKIT ANTIBODY DRUG CONJUGATES

(71) Applicant: Novartis AG, Basel (CH)

(72) Inventors: Tinya Abrams, Acton, MA (US);
Steven Bruce Cohen, San Diego, CA (US); Dylan Daniel, San Francisco, CA (US); Catrin Finner, Planegg (DE);
Bernhard Hubert Geierstanger, Solana Beach, CA (US); Thomas Huber, Allschwil (CH); William Mallet, Redwood City, CA (US);
Matthew John Meyer, Framingham, MA (US); Weijia Ou, San Diego, CA (US); Siew Ho Schleyer, El Cerrito, CA (US); Kathrin Ulrike Tissot-Daguette, Neuried (DE)

(73) Assignee: Novartis AG, Basel (CH)

(*) Notice: Subject to any disclaimer, the term of this patent is extended or adjusted under 35 U.S.C. 154(b) by 46 days.

This patent is subject to a terminal disclaimer.

(21) Appl. No.: 16/893,359

(22) Filed: Jun. 4, 2020

(65) Prior Publication Data
US 2020/0405875 A1    Dec. 31, 2020

Related U.S. Application Data

(62) Division of application No. 15/329,818, filed as application No. PCT/IB2015/055678 on Jul. 27, 2015, now Pat. No. 10,786,578.

(60) Provisional application No. 62/033,571, filed on Aug. 5, 2014.

(51) Int. Cl.
| *C07K 16/00* | (2006.01) |
| *A61K 39/00* | (2006.01) |
| *A61K 47/68* | (2017.01) |
| *C07K 16/28* | (2006.01) |
| *A61K 51/10* | (2006.01) |
| *A61K 49/00* | (2006.01) |
| *A61P 35/02* | (2006.01) |
| *A61K 39/395* | (2006.01) |

(52) U.S. Cl.
CPC .... *A61K 47/6803* (2017.08); *A61K 39/39558* (2013.01); *A61K 47/6849* (2017.08); *A61K 49/00* (2013.01); *A61K 51/103* (2013.01); *A61K 51/1093* (2013.01); *A61P 35/02* (2018.01); *C07K 16/2803* (2013.01); *A61K 2039/505* (2013.01); *A61K 2039/545* (2013.01); *C07K 2317/21* (2013.01); *C07K 2317/24* (2013.01); *C07K 2317/33* (2013.01); *C07K 2317/34* (2013.01); *C07K 2317/55* (2013.01); *C07K 2317/565* (2013.01); *C07K 2317/77* (2013.01); *C07K 2317/92* (2013.01)

(58) Field of Classification Search
CPC ............ A61K 47/6803; A61K 47/6849; A61K 2039/505; A61P 35/02; C07K 16/2803; C07K 2317/33; C07K 2317/34; C07K 2317/55; C07K 2317/565
See application file for complete search history.

(56) References Cited

U.S. PATENT DOCUMENTS

| 5,677,425 | A | 10/1997 | Bodmer | |
| 6,638,499 | B2 | 10/2003 | Martinez | |
| 7,504,405 | B2 | 3/2009 | Wang | |
| 7,939,539 | B2 | 5/2011 | Wang | |
| 2008/0171040 | A1 | 7/2008 | Ebens et al. | |
| 2014/0271688 | A1* | 9/2014 | Abrams | A61K 47/6921 424/181.1 |
| 2014/0322247 | A1 | 10/2014 | Barsanti et al. | |
| 2017/0021033 | A1 | 1/2017 | Geierstanger et al. | |

FOREIGN PATENT DOCUMENTS

| WO | WO 2001/005950 | 1/2001 |
| WO | WO 2006/002236 | 1/2006 |
| WO | WO 2006/049835 | 5/2006 |
| WO | WO 2007/021794 | 2/2007 |
| WO | WO 2008/063912 | 5/2008 |
| WO | WO 2008/115300 | 9/2008 |
| WO | WO 2008/151183 | 12/2008 |
| WO | WO 2009/077448 | 6/2009 |
| WO | WO 2010/015608 | 2/2010 |
| WO | WO 2011/128381 | 10/2011 |
| WO | WO 2011/128388 | 10/2011 |
| WO | WO 2012/047583 | 4/2012 |
| WO | WO 2012/058137 | 5/2012 |
| WO | WO 2012/113847 | 8/2012 |
| WO | WO2014151030 | * 3/2013 |
| WO | WO 2013/059885 | 5/2013 |
| WO | WO 2014/037899 | 3/2014 |
| WO | WO 2014/064187 | 5/2014 |
| WO | WO 2014/150937 | 9/2014 |

(Continued)

OTHER PUBLICATIONS

Rabia et al, Biochem Eng J. Sep. 15, 2018; 137: 365-374 (Year: 2018).*

(Continued)

*Primary Examiner* — Lei Yao

(74) *Attorney, Agent, or Firm* — Jana E. Harris

(57) ABSTRACT

The present invention relates to anti-cKIT antibodies, antibody fragments, antibody drug conjugates, and their uses for the treatment of cancer.

17 Claims, 15 Drawing Sheets

Specification includes a Sequence Listing.

(56) References Cited

FOREIGN PATENT DOCUMENTS

| WO | WO 2014/151030 | 9/2014 |
|---|---|---|
| WO | WO 2015/138615 | 10/2015 |

OTHER PUBLICATIONS

Allen, "Ligand-Targeted Therapeutics in Anticancer Therapy" Nat. Rev. Cancer 2:750-763, 2002.

Besmer et al., "A new acute transforming feline retrovirus and relationship of its oncogene v-kit with the protein kinase gene family" Nature 320:415-421, 1986.

Broudy et al., "Isolation and Characterization of a Monoclonal Antibody that Recognizes the Human c-kit Receptor" Blood 79(2):338, 1992.

DeNrdo et al., "Comparison of 1,4,7,10-tetraazacyclododecane-N,N',N",N"'-tetraacetic acid (DOTA)-peptide-ChL6, a Novel Immunoconjugate with Catabolizable Linker, to 2-iminothiolane-2-[p-(bromoacetamido)benzyl]-DOTA-ChL6 in Breast Cancer Xenografts" Clinical Cancer Research 4(10):2483-2490, 1998.

Edris et al., "Anti-KIT Monoclonal Antibody Inhibits Imatinib-Resistant Gastrointestinal Stromal Tumor Growth" Proc. Natl. Acad. Sci. USA 110(9):3501-3506, 2013.

Espositio et al., "The Stem Cell Factor-c-kit System and Mast Cells in Human Pancreatic Cancer" Laboratory Investigation 82(11):1481-1491, 2002.

Gadd et al., "A Murine Monoclonal Antibody Specific for a Cell-Surface Antigen Expressed by a Sub-Group of Human Myeloid Leukaemias" Leukemia Research 9(11):1329-1336, 1985.

Hamblett et al., "Effects of Drug Loading on the Antitumor Activity of a Monoclonal Antibody Drug Conjugate" Clin Cancer Res. 10(20):7063-7070, 2004.

Hirota et al., "Gain-of-Function Mutations of c-kit in Human Gastrointestinal Stromal Tumors" Science 279:577-580, 1998.

Kindblom et al., "Gastrointestinal Pacemaker Cell Tumor (GIPACT) Gastrointestinal Stromal Tumors Show Phenotypic Characteristics of the Interstitial Cells of Cajal" Am J. Path. 152(5):1259-1269, 1998.

King, "Monoclonal Antibody Conjugates of Doxorubicin Prepared with Branched Linkers: A Novel Method for Increasing the Potency of Doxorubicin Immunoconjugates" Bioconjugate Chemistry 10(2):279-288, Mar.-Apr. 1999.

Lash "Antibody-Drug Conjugates: the Next Generation of Moving Parts", Start-Up, pp. 1-6, Dec. 2011.

Lehar et al., "Synergistic Drug Combinations Tend to Improve Therapuetically Relevant Selectivity" Nature Biotechnology 27(7):659-666, 2009.

Pastan and Kreitman, "Immunotoxins in Cancer Therapy" Curr. Opin. Investig. Drugs 3:1089-1091, 2002.

Payne, "Progress in Immunoconjugate Cancer Therapeutics" Cancer Cell 3:207-212, 2003.

Peterson et al., "Enzymatic Cleavage of Peptide-Linked Radiolabels from Immunoconjugates" Bioconjugate Chemistry 10(4):553-557, 1999.

Rapley et al., "The NIMA-Family Kinase Nek6 Phosphorylates the Kinesin Eg5 at a Novel Site Necessary for Mitotic Spindle Formation" J. Cell Sci. 121:3912-3921, 2008.

Rath and Kozielski, "Kinesins and Cancer" Nature Rev. Cancer 12:527-539, 2012.

Saito et al., "Drug Delivery Strategy Utilizing Conjugation via Reversible Disulfide Linkages: Role and Site of Cellular Reducing Activities" Advanced Drug Delivery Reviews 55:199-215, 2003.

Senter and Springer, "Selective Activation of Anticancer Prodrugs by Monoclonal Antibody-Enzyme Conjugates" Advanced Drug Delivery Reviews 53:247-264, 2001.

Singh et al., "Antibody-Cytotoxic Agent Conjugates: Preparation and Characterization" Therapeutic Antibodies: Methods and Protocols 525:445-467, 2009.

Trail et al., "Monoclonal Antibody Drug Immunoconjugates for Targeted Treatment of Cancer" Cancer Immunol. Immunother. 52:328-337, 2003.

Trouet et al., "A Covalent Linkage Between Daunorubicin and Proteins that is Stable in Serum and Reversible by Lysosomal Hydrolases, as Required for a Lysosomotropic Drug-Carrier Conjugate: In vitro and in vivo Studies" Proc. Natl. Acad. Sci. USA 79:626-629, 1982.

Umemoto et al., "Preparation and In vitro Cytotoxicity of a Methotrexate-anti-MM46 Monoclonal Antibody Conjugate via an Oligopeptide Spacer" Int. J. Cancer 43:677-684, 1989.

Yuzawa et al., "Structural Basis for Activation of the Receptor Tyrosine Kinase KIT by Stem Cell Factor" Cell 130:323-334, Jul. 27, 2007.

Zimmerman et al., "A Triglycine Linker Improves Tumor Uptake and Biodistributions of 67-Cu-Labeled Anti-Neuroblastoma MAb chCE7 F(ab')2 Fragments" Nuclear Medicine Biology 26(8):943-950, 1999.

Zimmerman et al., "Multi-Target Therapeutics: When the Whole is Greater than the Sum of the Parts" Drug Discovery Today 12:34-42, 2007.

\* cited by examiner

Representation of the 3.1-Å crystal structure of the Kit D1-D2/NEG085 Fab complex showing the Fab heavy chains (dark grey), Fab light chains (white), and Kit D1-D2 (light grey) domains. Epitopes and paratopes are colored black.

NEG085 and 20376 mediate rapid internalization of c-Kit on cells

NEG085 and 20376 do not mediate in vitro ADCC cKIT antibodies do not lead to apoptosis of human primary mast cells NEG085 and 20376 do not mediate mast cell degranulation on ex vivo primary human mast cells Figure 8A Dose dependent efficacy in NCI-H526 small cell lung cancer xenograft model in mouse
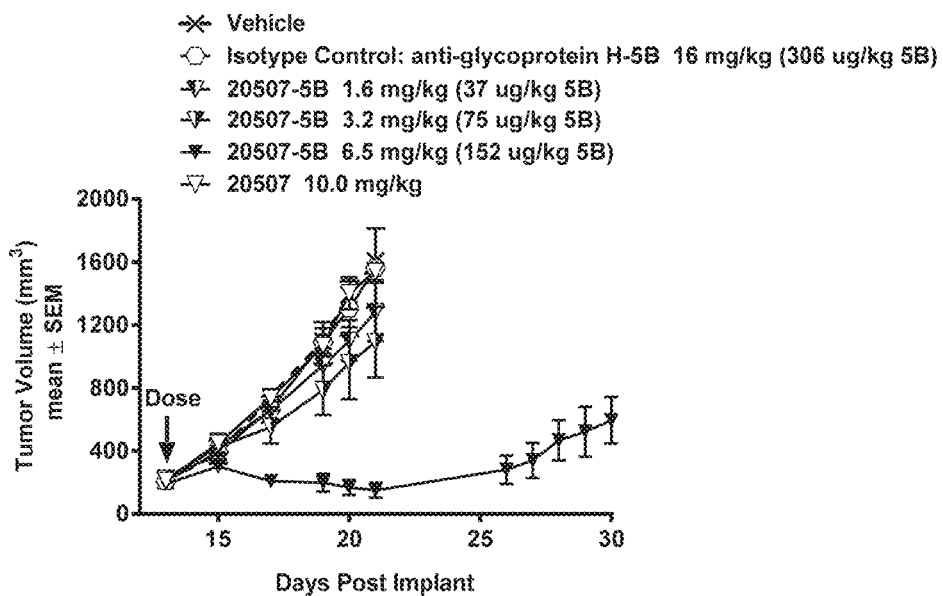
Figure 8B Change in body weight over course of treatment
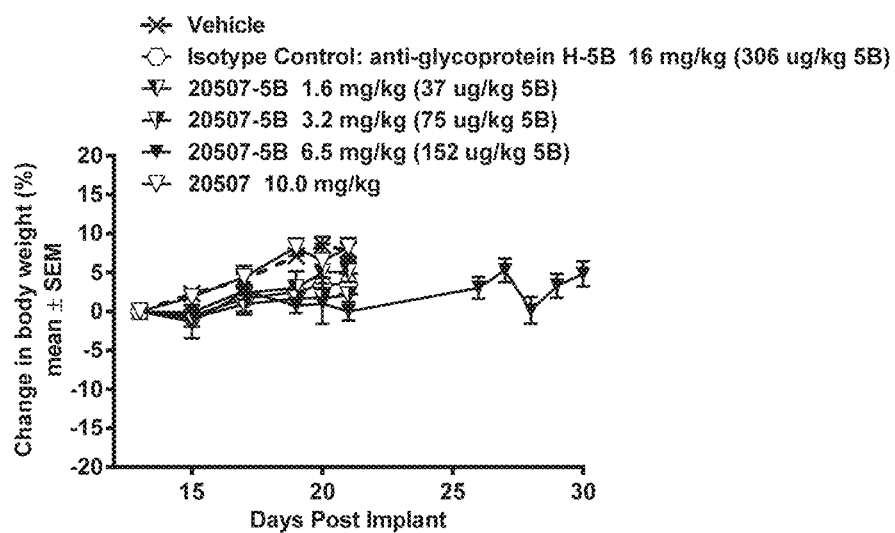

Efficacy in mice with c-KIT positive NCI-H526 small cell lung cancer and SKOV3ip c-KIT negative ovarian xenograft models in the same mouse to demonstrate specificity Figure 11A Efficacy and body weight change of 20507 ADC with different conjugated toxins at 5 mg/kg in NCI-H526 (SCLC) xenograft mouse model

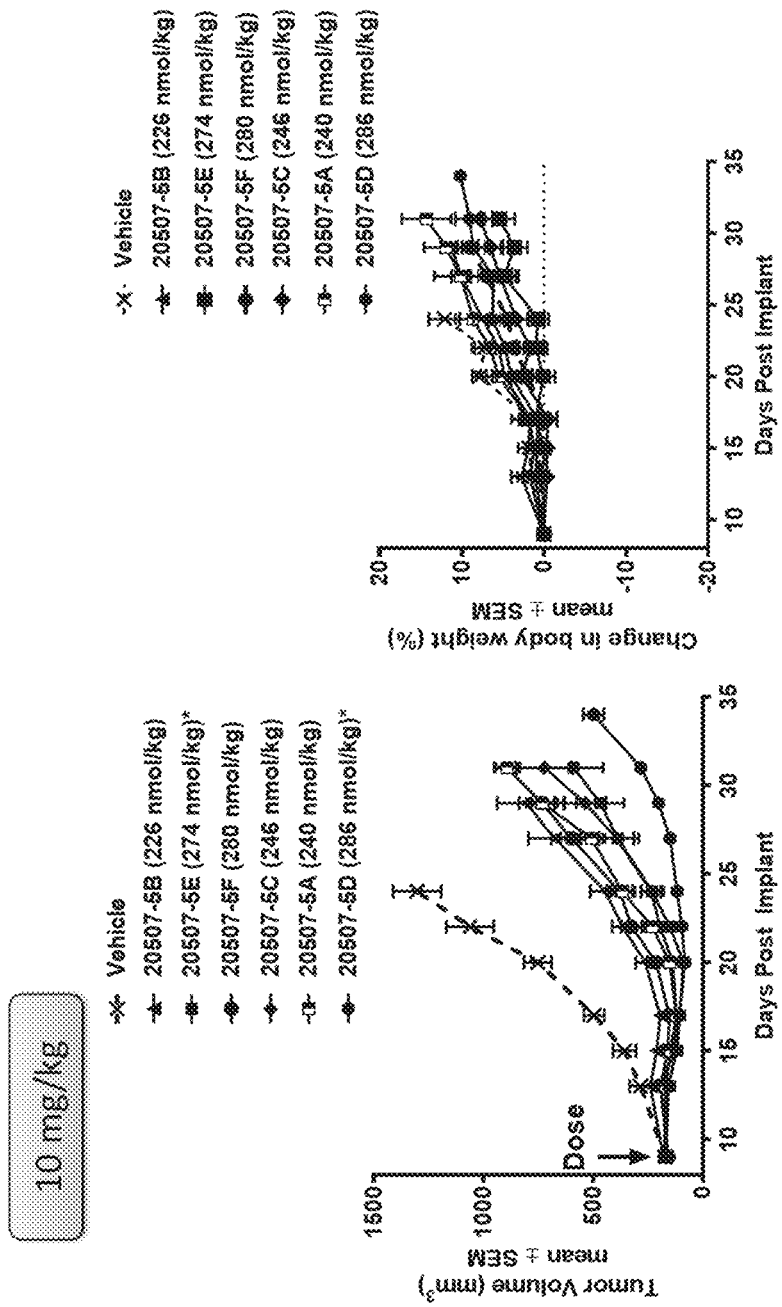
Figure 11B Efficacy and body weight change of 20507 ADC with different conjugated toxins at 10 mg/kg in NCI-H526 (SCLC) xenograft mouse model Efficacy of 20507 and TBS ADC with different site directed conjugations in NCI-H526 (SCLC) xenograft mouse model n = 6/group
No significant body weight loss in any group
No statistical significance between c-Kit ADC groups

CKIT ANTIBODY DRUG CONJUGATES

FIELD OF THE INVENTION

The present disclosure is directed to anti-cKIT antibodies, antibody fragments, antibody drug conjugates, and their uses for the treatment of cancer.

SEQUENCE LISTING

This application contains a Sequence Listing which has been submitted in ASCII format via EFS-WEB and is hereby incorporated by reference in its entirety. Sais ASCII copy, created on Aug. 19, 2020, is named PAT056353WOPCT_SL_ST25.txt and is 176,365 bytes in size.

BACKGROUND OF THE INVENTION cKIT is a single transmembrane, receptor tyrosine kinase that binds the ligand Stem Cell Factor (SCF). SCF induces homodimerization of cKIT which activates its tyrosine kinase activity and signals through both the PI3-AKT and MAPK pathways (Kindblom et al., Am J. Path. 1998 152 (5):1259). cKIT was initially discovered as an oncogene as a truncated form expressed by a feline retrovirus (Besmer et al., Nature 1986 320:415-421). Cloning of the corresponding human gene demonstrated that cKIT is a member of the type III class of receptor tyrosine kinases, which count among the family members; FLT3, CSF-1 receptor and PDGF receptor.

Mice that are mutant for cKIT have shown that cKIT is required for the development of hematopoietic cells, germ cells, mast cells and melanocytes. In the human, cKIT loss of function may lead to deafness and de-pigmentation of the skin and hair. A number of gain of function mutations for cKIT have been described in various cancers. Such cancers include gastro-intestinal-stromal tumors (GIST), acute myeloid leukemia (AML), small cell lung cancer (SCLC), mast cell leukemia (MCL) and pancreatic cancer (Hirota et al., Science 1998 (279):577; Esposito et al., Lab. Invets. 2002 82(11):1481).

Because of these preliminary indications that cKIT was an oncogene, an antibody was generated that identified cKIT as a marker of AML (Gadd et al., Leuk. Res. 1985 (9):1329). This murine monoclonal, known as YB5.B8, was generated by using leukemic blast cells from a human patient and bound cKIT, which was abundantly expressed on the surface of the AML cells, but did not detect cKIT on normal blood or bone marrow cells (Gadd et al., supra). A second cKIT antibody (SR-1) was generated that blocked the binding of SCF to cKIT and thus blocked cKIT signaling (Broudy et al., Blood 1992 79(2):338). The biological effect of the SR-1 antibody was to inhibit BFU-E and CFU-GM growth, and based on this evidence, suggested using it for further studies on hematopoiesis or tumor cell growth (Broudy et al., supra).

In further cancer studies, investigators found that treatment with imatinib, a small molecule inhibitor of cKIT, would significantly reduce proliferation of GIST cell lines. However, Imatinib treated cells become resistant over time due to secondary mutations in cKIT (Edris et al., Proc. Nat. Acad. Sci. USA, Early On-line Edition 2013). However, if the GIST cells were treated with the SR-1 antibody as a second therapeutic, there was significant decrease in cell proliferation, and a decrease in cKIT expression on the cell surface (Edris et al., supra). Thus, a naked SR-1 antibody was efficacious in addressing the problem of Imatinib resistance in human GIST lines, suggesting that an Imatinib/anti-cKIT antibody combination may be useful.

Antibody drug conjugates ("ADCs") have been used for the local delivery of cytotoxic agents in the treatment of cancer (see e.g., Lambert, Curr. Opinion In Pharmacology 5:543-549, 2005). ADCs allow targeted delivery of the drug moiety where maximum efficacy with minimal toxicity may be achieved. As more ADCs show promising clinical results, there is an increased need to develop new therapeutics for cancer therapy. In spite of the extensive work on ADCs, though, only a few classes of cell proliferation inhibitors or cytotoxins have been used extensively as ADC payloads. Even though the first ADC approved for use in humans in the U.S. was launched in 2000 (Mylotarg®, which was later withdrawn from the market), a decade later only a few chemical classes of drug compounds (maytansinoids, auristatins, calicheamycins and duocarmycins) had reached clinical trials as payloads for ADCs (Antibody-Drug Conjugates: the Next Generation of Moving Parts, A. Lash, Start-Up, December 2011, 1-6). This suggests how difficult it is to identify a suitable class of drug compounds that make effective ADC payloads. Given the widely acknowledged value of ADCs as therapeutics, particularly for treating cancer, there thus remains a need for novel cell proliferation inhibitors suited for use as payloads in ADCs.

SUMMARY OF THE INVENTION

The present disclosure is directed to an antibody drug conjugate of the formula

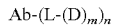

or a pharmaceutically acceptable salt thereof; wherein
 Ab is an antibody or antigen binding fragment thereof that specifically binds to an epitope of human cKIT;
 L is a linker;
 D is a drug moiety;
 m is an integer from 1 to 8; and
 n is an integer from 1 to 10.
The antibody drug conjugate, wherein said n is 2 or 4.

The antibody drug conjugate according to any of the preceding embodiments, wherein said antibody or antigen binding fragment thereof specifically binds the extracellular domain of cKIT (SEQ ID NO:178).

The antibody drug conjugate according to any of the preceding embodiments, wherein said antibody or antigen binding fragment specifically binds to an epitope of human cKIT at domains 1-3 (SEQ ID NO:173).

The antibody drug conjugate according to any of the preceding embodiments, wherein said antibody or antigen binding fragment thereof specifically binds human cKIT at SEQ ID NO: 179 and SEQ ID NO: 180.

The antibody drug conjugate according to any of the preceding embodiments, wherein said antibody or antigen binding fragment thereof comprises:
 (i) a heavy chain variable region that comprises (a) a HCDR1 (CDR-Complementarity Determining Region) of SEQ ID NO: 76, (b) a HCDR2 of SEQ ID NO: 77, (c) a HCDR3 of SEQ ID NO: 78; and a light chain variable region that comprises: (d) a LCDR1 of SEQ ID NO: 85, (e) a LCDR2 of SEQ ID NO: 86, and (f) a LCDR3 of SEQ ID NO: 87;
 (ii) a heavy chain variable region that comprises (a) a HCDR1 of SEQ ID NO: 22, (b) a HCDR2 of SEQ ID NO: 23, (c) a HCDR3 of SEQ ID NO: 24; and a light chain variable region that comprises: (d) a LCDR1 of SEQ ID NO: 31, (e) a LCDR2 of SEQ ID NO: 32, and (f) a LCDR3 of SEQ ID NO: 33;
(iii) a heavy chain variable region that comprises (a) a HCDR1 of SEQ ID NO: 130, (b) a HCDR2 of SEQ ID NO: 131, (c) a HCDR3 of SEQ ID NO: 132; and a light chain variable region that comprises: (d) a LCDR1 of SEQ ID NO: 139, (e) a LCDR2 of SEQ ID NO: 140, and (f) a LCDR3 of SEQ ID NO: 141;
(iv) a heavy chain variable region that comprises: (a) a HCDR1 of SEQ ID NO: 58, (b) a HCDR2 of SEQ ID NO: 59, (c) a HCDR3 of SEQ ID NO: 60; and a light chain variable region that comprises: (d) a LCDR1 of SEQ ID NO: 67, (e) a LCDR2 of SEQ ID NO: 68, and (f) a LCDR3 of SEQ ID NO: 69;
(v) a heavy chain variable region that comprises: (a) a HCDR1 of SEQ ID NO: 40, (b) a HCDR2 of SEQ ID NO: 41, (c) a HCDR3 of SEQ ID NO: 42; and a light chain variable region that comprises: (d) a LCDR1 of SEQ ID NO: 49, (e) a LCDR2 of SEQ ID NO: 50, and (f) a LCDR3 of SEQ ID NO: 51;
(vi) a heavy chain variable region that comprises: (a) a HCDR1 of SEQ ID NO: 94, (b) a HCDR2 of SEQ ID NO: 95, (c) a HCDR3 of SEQ ID NO: 96; and a light chain variable region that comprises: (d) a LCDR1 of SEQ ID NO: 103, (d) a LCDR2 of SEQ ID NO: 104, and (f) a LCDR3 of SEQ ID NO: 105;
(vii) a heavy chain variable region that comprises: (a) a HCDR1 of SEQ ID NO: 112, (b) a HCDR2 of SEQ ID NO: 113, (c) a HCDR3 of SEQ ID NO: 114; and a light chain variable region that comprises: (d) a LCDR1 of SEQ ID NO: 121, (e) a LCDR2 of SEQ ID NO: 122, and (f) a LCDR3 of SEQ ID NO: 123;
(viii) a heavy chain variable region that comprises: (a) a HCDR1 of SEQ ID NO: 3, (b) a HCDR2 of SEQ ID NO: 4, (c) a HCDR3 of SEQ ID NO: 5; and a light chain variable region that comprises: (d) a LCDR1 of SEQ ID NO: 12, (e) a LCDR2 of SEQ ID NO: 13, and (f) a LCDR3 of SEQ ID NO: 14; or
(ix) a heavy chain variable region that comprises: (a) a HCDR1 of SEQ ID NO: 148, (b) a HCDR2 of SEQ ID NO: 149, (c) a HCDR3 of SEQ ID NO: 150; and a light chain variable region that comprises: (d) a LCDR1 of SEQ ID NO: 157, (e) a LCDR2 of SEQ ID NO: 158, and (f) a LCDR3 of SEQ ID NO: 159.

The antibody drug conjugate according to any of the preceding embodiments, in which at least one amino acid within a CDR is substituted by a corresponding residue of a corresponding CDR of another anti-cKIT antibody in Table 3.

The antibody drug conjugate according to any of the preceding embodiments, in which one or two amino acids within a CDR have been modified, deleted or substituted.

The antibody drug conjugate of any of claims 1-3, wherein said antibody or antigen binding fragment thereof comprises:
(i) a heavy chain variable region (VH) that comprises (a) SEQ ID NO: 82, and a light chain variable region (VL) that comprises: (b) SEQ ID NO: 91;
(ii) a heavy chain variable region (VH) that comprises (a) SEQ ID NO: 28, and a light chain variable region (VL) that comprises: (b) SEQ ID NO: 37;
(iii) a heavy chain variable region (VH) that comprises (a) SEQ ID NO: 136, and a light chain variable region (VL) that comprises: (b) SEQ ID NO: 145;
(iv) a heavy chain variable region (VH) that comprises (a) SEQ ID NO: 64, and a light chain variable region (VL) that comprises: (b) SEQ ID NO: 73;
(v) a heavy chain variable region (VH) that comprises (a) SEQ ID NO: 46, and a light chain variable region (VL) that comprises: (b) SEQ ID NO: 55;
(vi) a heavy chain variable region (VH) that comprises (a) SEQ ID NO: 100, and a light chain variable region (VL) that comprises: (b) SEQ ID NO: 109;
(vii) a heavy chain variable region (VH) that comprises (a) SEQ ID NO: 118, and a light chain variable region (VL) that comprises: (b) SEQ ID NO: 127;
(viii) a heavy chain variable region (VH) that comprises (a) SEQ ID NO: 11, and a light chain variable region (VL) that comprises: (b) SEQ ID NO: 20; or
(ix) a heavy chain variable region (VH) that comprises (a) SEQ ID NO: 154, and a light chain variable region (VL) that comprises: (b) SEQ ID NO: 163.

The antibody drug conjugate according to any of the preceding embodiments, that retains at least 90, 91, 92, 93, 94, 95, 96, 97, 98 or 99% identity over either the variable light chain or variable heavy chain region.

The antibody drug conjugate according to any of the preceding embodiments, wherein the antibody is a monoclonal antibody, a chimeric antibody, a humanized antibody, a human engineered antibody, a human antibody, a single chain antibody(scFv) or an antibody fragment.

The antibody drug conjugate according to any of the preceding embodiments, wherein said linker (L) is selected from the group consisting of a cleavable linker, a non-cleavable linker, a hydrophilic linker, a procharged linker and a dicarboxylic acid based linker.

The antibody drug conjugate according to any of the preceding embodiments, wherein the linker is derived from a cross-linking reagent selected from the group consisting of N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)2-sulfo-butanoate (sulfo-SPDB), N-succinimidyl iodoacetate (SIA), N-succinimidyl(4-iodoacetyl)aminobenzoate (SIAB), maleimide PEG NHS, N-succinimidyl 4-(maleimidomethyl) cyclohexanecarboxylate (SMCC), N-sulfosuccinimidyl 4-(maleimidomethyl) cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1).

The antibody drug conjugate according to any of the preceding embodiments, wherein said linker (L) comprises a group of the formula —C(O)NR$^{21}$— or —NR$^{21}$—C(O)— wherein R$^{21}$ is of the formula —(CH$_2$)$_{1-4}$—R$^{22}$, where R$^{22}$ is a polar group selected from —OH, —NH$_2$, N(R$^{23}$)$_2$, COOR$^{23}$, CON(R$^{23}$)$_2$, —(OCH$_2$CH$_2$O)$_k$—OCH$_2$CH$_2$OR$^{23}$, and —SO$_2$R$^{23}$, where k is 0 to 4 and each R$^{23}$ is independently H or C$_{1-4}$ alkyl.

The antibody drug conjugate according to any of the preceding embodiments, wherein said drug moiety (D) is selected from a group consisting of: an Eg5 inhibitor, a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a RNA polymerase inhibitor, a topoisomerase inhibitor and a DHFR inhibitor.

The antibody drug conjugate according to any of the preceding embodiments, wherein the drug moiety (D) and linker (L) is selected from Table 1.

The antibody drug conjugate according to any of the preceding embodiments, wherein the antibody contains at least one non-native cysteine introduced into a constant region, and the linker (L) is attached to the non-native cysteine.

The antibody drug conjugate according to any of the preceding embodiments, wherein the at least one non-native cysteine introduced into the constant region is selected from the group consisting of SEQ ID NO: 185, SEQ ID NO:186, SEQ ID NO:187 and SEQ ID NO:188.

The antibody drug conjugate according to any of the preceding embodiments, in combination with another therapeutic agent.

The antibody drug conjugate according to any of the preceding embodiments, in combination with a therapeutic agent listed in Table 14.

An antibody drug conjugate of the formula:

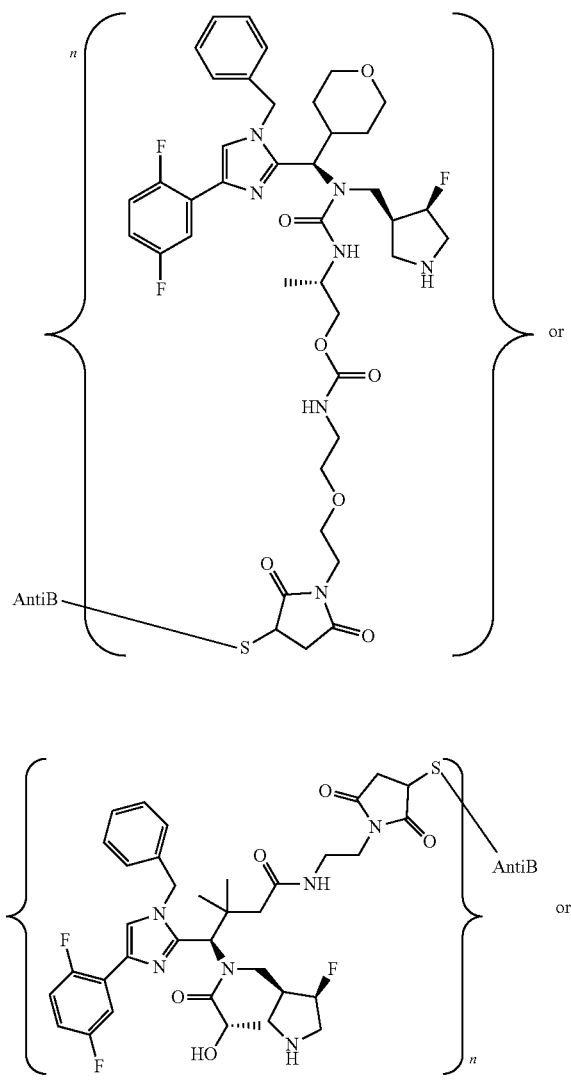

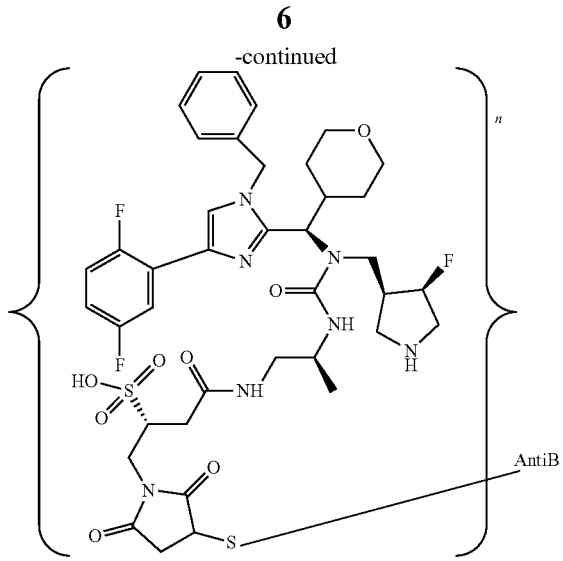

or a pharmaceutically acceptable salt thereof; wherein; antibody (AntiB) is an antibody or antigen binding fragment thereof that specifically binds to human cKIT, and n is an integer from 1 to 10.

The antibody drug conjugate according to any of the preceding embodiments, wherein said antibody or antigen binding fragment specifically binds to an epitope of human cKIT at domains 1-3 (SEQ ID NO:173).

The antibody drug conjugate according to any of the preceding embodiments, wherein said antibody or antigen binding fragment thereof specifically binds human cKIT at SEQ ID NO: 179 and SEQ ID NO: 180.

The antibody drug conjugate according to any of the preceding embodiments, wherein said antibody (antiB) is an antibody or antigen binding fragment thereof comprises:

(i) a heavy chain variable region that comprises (a) a HCDR1 (CDR-Complementarity Determining Region) of SEQ ID NO: 76, (b) a HCDR2 of SEQ ID NO: 77, (c) a HCDR3 of SEQ ID NO: 78; and a light chain variable region that comprises: (d) a LCDR1 of SEQ ID NO: 85, (e) a LCDR2 of SEQ ID NO: 86, and (f) a LCDR3 of SEQ ID NO: 87;

(ii) a heavy chain variable region that comprises (a) a HCDR1 of SEQ ID NO: 22, (b) a HCDR2 of SEQ ID NO: 23, (c) a HCDR3 of SEQ ID NO: 24; and a light chain variable region that comprises: (d) a LCDR1 of SEQ ID NO: 31, (e) a LCDR2 of SEQ ID NO: 32, and (f) a LCDR3 of SEQ ID NO: 33;

(iii) a heavy chain variable region that comprises (a) a HCDR1 of SEQ ID NO: 130, (b) a HCDR2 of SEQ ID NO: 131, (c) a HCDR3 of SEQ ID NO: 132; and a light chain variable region that comprises: (d) a LCDR1 of SEQ ID NO: 139, (e) a LCDR2 of SEQ ID NO: 140, and (f) a LCDR3 of SEQ ID NO: 141;

(iv) a heavy chain variable region that comprises: (a) a HCDR1 of SEQ ID NO: 58, (b) a HCDR2 of SEQ ID NO: 59, (c) a HCDR3 of SEQ ID NO: 60; and a light chain variable region that comprises: (d) a LCDR1 of SEQ ID NO: 67, (e) a LCDR2 of SEQ ID NO: 68, and (f) a LCDR3 of SEQ ID NO: 69;

(v) a heavy chain variable region that comprises: (a) a HCDR1 of SEQ ID NO: 40, (b) a HCDR2 of SEQ ID NO: 41, (c) a HCDR3 of SEQ ID NO: 42; and a light chain variable region that comprises: (d) a LCDR1 of SEQ ID NO: 49, (e) a LCDR2 of SEQ ID NO: 50, and (f) a LCDR3 of SEQ ID NO: 51;
(vi) a heavy chain variable region that comprises: (a) a HCDR1 of SEQ ID NO: 94, (b) a HCDR2 of SEQ ID NO: 95, (c) a HCDR3 of SEQ ID NO: 96; and a light chain variable region that comprises: (d) a LCDR1 of SEQ ID NO: 103, (d) a LCDR2 of SEQ ID NO: 104, and (f) a LCDR3 of SEQ ID NO: 105;
(vii) a heavy chain variable region that comprises: (a) a HCDR1 of SEQ ID NO: 112, (b) a HCDR2 of SEQ ID NO: 113, (c) a HCDR3 of SEQ ID NO: 114; and a light chain variable region that comprises: (d) a LCDR1 of SEQ ID NO: 121, (e) a LCDR2 of SEQ ID NO: 122, and (f) a LCDR3 of SEQ ID NO: 123;
(viii) a heavy chain variable region that comprises: (a) a HCDR1 of SEQ ID NO: 3, (b) a HCDR2 of SEQ ID NO: 4, (c) a HCDR3 of SEQ ID NO: 5; and a light chain variable region that comprises: (d) a LCDR1 of SEQ ID NO: 12, (e) a LCDR2 of SEQ ID NO: 13, and (f) a LCDR3 of SEQ ID NO: 14; or
(ix) a heavy chain variable region that comprises: (a) a HCDR1 of SEQ ID NO: 148, (b) a HCDR2 of SEQ ID NO: 149, (c) a HCDR3 of SEQ ID NO: 150; and a light chain variable region that comprises: (d) a LCDR1 of SEQ ID NO: 157, (e) a LCDR2 of SEQ ID NO: 158, and (f) a LCDR3 of SEQ ID NO: 159.

The antibody drug conjugate according to any of the preceding embodiments, in which at least one amino acid within a CDR is substituted by a corresponding residue of a corresponding CDR of another anti-cKIT antibody of Table 3.

The antibody drug conjugate according to any of the preceding embodiments, in which one or two amino acids within a CDR have been modified, deleted or substituted.

The antibody drug conjugate according to any of the preceding embodiments, wherein said antibody or antigen binding fragment thereof comprises:
(i) a heavy chain variable region (VH) that comprises (a) SEQ ID NO: 82, and a light chain variable region (VL) that comprises: (b) SEQ ID NO: 91;
(ii) a heavy chain variable region (VH) that comprises (a) SEQ ID NO: 28, and a light chain variable region (VL) that comprises: (b) SEQ ID NO: 37;
(iii) a heavy chain variable region (VH) that comprises (a) SEQ ID NO: 136, and a light chain variable region (VL) that comprises: (b) SEQ ID NO: 145;
(iv) a heavy chain variable region (VH) that comprises (a) SEQ ID NO: 64, and a light chain variable region (VL) that comprises: (b) SEQ ID NO: 73;
(v) a heavy chain variable region (VH) that comprises (a) SEQ ID NO: 46, and a light chain variable region (VL) that comprises: (b) SEQ ID NO: 55;
(vi) a heavy chain variable region (VH) that comprises (a) SEQ ID NO: 100, and a light chain variable region (VL) that comprises: (b) SEQ ID NO: 109;
(vii) a heavy chain variable region (VH) that comprises (a) SEQ ID NO: 118, and a light chain variable region (VL) that comprises: (b) SEQ ID NO: 127;
(viii) a heavy chain variable region (VH) that comprises (a) SEQ ID NO: 11, and a light chain variable region (VL) that comprises: (b) SEQ ID NO: 20; or
(ix) a heavy chain variable region (VH) that comprises (a) SEQ ID NO: 154, and a light chain variable region (VL) that comprises: (b) SEQ ID NO: 163.

The antibody drug conjugate according to any of the preceding embodiments, that retains at least 90, 91, 92, 93, 94, 95, 96, 97, 98 or 99% identity over either the variable light chain or variable heavy chain region.

The antibody drug conjugate according to any of the preceding embodiments, wherein the antibody is a monoclonal antibody, a chimeric antibody, a humanized antibody, a human engineered antibody, a human antibody, a single chain antibody(scFv) or an antibody fragment.

The antibody drug conjugate according to any of the preceding embodiments, wherein said n is an integer from 2 to 8.

The antibody drug conjugate according to any of the preceding embodiments, wherein said n is an integer from 3 to 4.

The antibody drug conjugate according to any of the preceding embodiments, in combination with another therapeutic agent.

The antibody drug conjugate according to any of the preceding embodiments, in combination with a therapeutic agent listed in Table 14.

The antibody drug conjugate according to any of the preceding embodiments, wherein the antibody contains at least one non-native cysteine introduced into a constant region, and the linker (L) is attached to the non-native cysteine.

The antibody drug conjugate according to any of the preceding embodiments, wherein the at least one non-native cysteine introduced into the constant region is selected from the group consisting of SEQ ID NO: 185, SEQ ID NO:186, SEQ ID NO:187 and SEQ ID NO:188.

A pharmaceutical composition comprising the antibody drug conjugate according to any of the preceding embodiments, and a pharmaceutically acceptable carrier.

The pharmaceutical composition according to any of the preceding embodiments, wherein said composition is prepared as a lyophilisate.

A method of treating an cKIT positive cancer in a patient in need thereof, comprising administering to said patient the antibody drug conjugate, or the pharmaceutical composition.

The method according to any of the preceding embodiments, wherein said cancer is selected from the group consisting of gastrointestinal stromal tumors (GIST), small cell lung cancer (SCLC), acute myeloid leukemia (AML), melanoma, mast cell leukemia (MCL), mastocytosis, neurofibromatosis, breast cancer, non-small cell lung cancer (NSCLC), and pancreatic cancer.

The method wherein the antibody drug conjugate or the pharmaceutical composition according to any of the preceding embodiments, is administered in combination with another therapeutic agent.

The method according to any of the preceding embodiments, wherein the antibody drug conjugate or the pharmaceutical composition is administered in combination with a therapeutic listed in Table 14.

The antibody drug conjugate any of the preceding embodiments for use as a medicament.

The antibody drug conjugate, or the pharmaceutical composition according to any of the preceding embodiments, for use in the treatment of a cKIT positive cancer.

The antibody drug conjugate according to any of the preceding embodiments, administered in combination with another therapeutic agent.

The antibody drug conjugate according to any of the preceding embodiments, administered in combination with a therapeutic agent listed in Table 14.

A nucleic acid that encodes the antibody or antigen binding fragment any of the preceding embodiments.

A vector comprising the nucleic acid any of the preceding embodiments.

A host cell comprising the vector any of the preceding embodiments.

A process for producing an antibody or antigen binding fragment comprising cultivating the host cell and recovering the antibody from the culture.

The antibody or antigen binding fragment produced according to any of the preceding embodiments and conjugated to a drug moiety (D) and linker (L) of Table 1, comprising an average drug to antibody ratio (DAR), measured with a UV spectrophotometer, about 3.5.

An antibody or antigen binding fragment thereof that comprises:
(i) a heavy chain variable region that comprises (a) a HCDR1 (CDR-Complementarity Determining Region) of SEQ ID NO: 76, (b) a HCDR2 of SEQ ID NO: 77, (c) a HCDR3 of SEQ ID NO: 78; and a light chain variable region that comprises: (d) a LCDR1 of SEQ ID NO: 85, (e) a LCDR2 of SEQ ID NO: 86, and (f) a LCDR3 of SEQ ID NO: 87;
(ii) a heavy chain variable region that comprises (a) a HCDR1 of SEQ ID NO: 22, (b) a HCDR2 of SEQ ID NO: 23, (c) a HCDR3 of SEQ ID NO: 24; and a light chain variable region that comprises: (d) a LCDR1 of SEQ ID NO: 31, (e) a LCDR2 of SEQ ID NO: 32, and (f) a LCDR3 of SEQ ID NO: 33;
(iii) a heavy chain variable region that comprises (a) a HCDR1 of SEQ ID NO: 130, (b) a HCDR2 of SEQ ID NO: 131, (c) a HCDR3 of SEQ ID NO: 132; and a light chain variable region that comprises: (d) a LCDR1 of SEQ ID NO: 139, (e) a LCDR2 of SEQ ID NO: 140, and (f) a LCDR3 of SEQ ID NO: 141;
(iv) a heavy chain variable region that comprises: (a) a HCDR1 of SEQ ID NO: 58, (b) a HCDR2 of SEQ ID NO: 59, (c) a HCDR3 of SEQ ID NO: 60; and a light chain variable region that comprises: (d) a LCDR1 of SEQ ID NO: 67, (e) a LCDR2 of SEQ ID NO: 68, and (f) a LCDR3 of SEQ ID NO: 69;
(v) a heavy chain variable region that comprises: (a) a HCDR1 of SEQ ID NO: 40, (b) a HCDR2 of SEQ ID NO: 41, (c) a HCDR3 of SEQ ID NO: 42; and a light chain variable region that comprises: (d) a LCDR1 of SEQ ID NO: 49, (e) a LCDR2 of SEQ ID NO: 50, and (f) a LCDR3 of SEQ ID NO: 51;
(vi) a heavy chain variable region that comprises: (a) a HCDR1 of SEQ ID NO: 94, (b) a HCDR2 of SEQ ID NO: 95, (c) a HCDR3 of SEQ ID NO: 96; and a light chain variable region that comprises: (d) a LCDR1 of SEQ ID NO: 103, (d) a LCDR2 of SEQ ID NO: 104, and (f) a LCDR3 of SEQ ID NO: 105;
(vii) a heavy chain variable region that comprises: (a) a HCDR1 of SEQ ID NO: 112, (b) a HCDR2 of SEQ ID NO: 113, (c) a HCDR3 of SEQ ID NO: 114; and a light chain variable region that comprises: (d) a LCDR1 of SEQ ID NO: 121, (e) a LCDR2 of SEQ ID NO: 122, and (f) a LCDR3 of SEQ ID NO: 123;
(viii) a heavy chain variable region that comprises: (a) a HCDR1 of SEQ ID NO: 3, (b) a HCDR2 of SEQ ID NO: 4, (c) a HCDR3 of SEQ ID NO: 5; and a light chain variable region that comprises: (d) a LCDR1 of SEQ ID NO: 12, (e) a LCDR2 of SEQ ID NO: 13, and (f) a LCDR3 of SEQ ID NO: 14; or
(ix) a heavy chain variable region that comprises: (a) a HCDR1 of SEQ ID NO: 148, (b) a HCDR2 of SEQ ID NO: 149, (c) a HCDR3 of SEQ ID NO: 150; and a light chain variable region that comprises: (d) a LCDR1 of SEQ ID NO: 157, (e) a LCDR2 of SEQ ID NO: 158, and (f) a LCDR3 of SEQ ID NO: 159.

A diagnostic reagent comprising the antibody or antigen binding fragment thereof which is labeled.

The diagnostic reagent any of the preceding embodiments, wherein the label is selected from the group consisting of a radiolabel, a fluorophore, a chromophore, an imaging agent, and a metal ion.

Definitions

Unless stated otherwise, the following terms and phrases as used herein are intended to have the following meanings:

The term "alkyl" refers to a monovalent saturated hydrocarbon chain having the specified number of carbon atoms. For example, $C_{1-6}$ alkyl refers to an alkyl group having from 1 to 6 carbon atoms. Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl.

The term "antibody" as used herein refers to a polypeptide of the immunoglobulin family that is capable of binding a corresponding antigen non-covalently, reversibly, and in a specific manner For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the present disclosure). The antibodies can be of any isotype/class (e.g., IgG, IgE, IgM, IgD, IgA and IgY), or subclass (e.g., IgG1, IgG2, IgG3, IgG4, IgA1 and IgA2).

"Complementarity-determining domains" or "complementary-determining regions" ("CDRs") interchangeably refer to the hypervariable regions of VL and VH. The CDRs are the target protein-binding site of the antibody chains that harbors specificity for such target protein. There are three CDRs (CDR1-3, numbered sequentially from the N-terminus) in each human VL or VH, constituting about 15-20% of the variable domains. CDRs can be referred to by their region and order. For example, "VHCDR1" or "HCDR1" both refer to the first CDR of the heavy chain variable region. The CDRs are structurally complementary to the epitope of the target protein and are thus directly responsible for the binding specificity. The remaining stretches of the VL or VH, the so-called framework regions, exhibit less variation in amino acid sequence (Kuby, Immunology, 4th ed., Chapter 4. W.H. Freeman & Co., New York, 2000).

The positions of the CDRs and framework regions can be determined using various well known definitions in the art, e.g., Kabat, Chothia, and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262: 732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996).

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminal domains of the heavy and light chain, respectively.

The term "antigen binding fragment", as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH—CH1-VH—CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000).

The human antibodies of the present disclosure can include amino acid residues not encoded by human sequences (e.g., mutations introduced by random or site-specific mutagenesis in vitro or by somatic mutation in vivo, or a conservative substitution to promote stability or manufacturing).

The term "recognize" as used herein refers to an antibody or antigen binding fragment thereof that finds and interacts (e.g., binds) with its epitope, whether that epitope is linear or conformational. The term "epitope" refers to a site on an antigen to which an antibody or antigen binding fragment of the disclosure specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art, for example, x-ray crystallography and 2-dimensional nuclear magnetic resonance (see, e.g., Epitope Mapping Protocols in Methods in Molecular Biology, Vol. 66, G. E. Morris, Ed. (1996)). A "paratope" is the part of the antibody which recognizes the epitope of the antigen.

The phrase "specifically binds" or "selectively binds," when used in the context of describing the interaction between an antigen (e.g., a protein) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one aspect, under designated immunoassay conditions, the antibody or binding agent with a particular binding specificity binds to a particular antigen at least ten (10) times the background and does not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some aspects, antibodies or antibody fragments are selected that cross-react with certain desired molecules.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91%, 92%, 93%, 94%, 95%, 96%, 97%, 98%, 99%, or 100% sequence identity with the reference variable region nucleic acid or amino acid sequence.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least 10 to 100 times over the background.

The term "equilibrium dissociation constant (KD, M)" refers to the dissociation rate constant (kd, time-1) divided by the association rate constant (ka, time-1, M-1). Equilibrium dissociation constants can be measured using any known method in the art. The antibodies of the present disclosure generally will have an equilibrium dissociation constant of less than about $10^{-7}$ or $10^{-8}$ M, for example, less than about $10^{-9}$ M or $10^{-10}$ M, in some aspects, less than about $10^{-11}$ M, $10^{-12}$ M or $10^{-13}$ M.

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

As used herein, the phrase "consisting essentially of" refers to the genera or species of active pharmaceutical agents included in a method or composition, as well as any excipients inactive for the intended purpose of the methods or compositions. In some aspects, the phrase "consisting essentially of" expressly excludes the inclusion of one or more additional active agents other than an antibody drug conjugate of the present disclosure. In some aspects, the phrase "consisting essentially of" expressly excludes the inclusion of one or more additional active agents other than an antibody drug conjugate of the present disclosure and a second co-administered agent.

The term "amino acid" refers to naturally occurring, synthetic, and unnatural amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some aspects, the term "conservative sequence modifications" are used to refer to amino acid modifications that do not significantly affect or alter the binding characteristics of the antibody containing the amino acid sequence.

The term "optimized" as used herein refers to a nucleotide sequence that has been altered to encode an amino acid sequence using codons that are preferred in the production cell or organism, generally a eukaryotic cell, for example, a yeast cell, a *Pichia* cell, a fungal cell, a *Trichoderma* cell, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

The terms "percent identical" or "percent identity," in the context of two or more nucleic acids or polypeptide sequences, refers to the extent to which two or more sequences or subsequences that are the same. Two sequences are "identical" if they have the same sequence of amino acids or nucleotides over the region being compared. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c (1970), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4:11-17, (1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444-453, (1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260: 2605-2608; and Rossolini et al., (1994) Mol. Cell. Probes 8:91-98).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "immunoconjugate" or "antibody drug conjugate" as used herein refers to the linkage of an antibody or an antigen binding fragment thereof with another agent, such as a chemotherapeutic agent, a toxin, an immunotherapeutic agent, an imaging probe, and the like. The linkage can be covalent bonds, or non-covalent interactions such as through electrostatic forces. Various linkers, known in the art, can be employed in order to form the immunoconjugate. Additionally, the immunoconjugate can be provided in the form of a fusion protein that may be expressed from a polynucleotide encoding the immunoconjugate. As used herein, "fusion protein" refers to proteins created through the joining of two or more genes or gene fragments which originally coded for separate proteins (including peptides and polypeptides). Translation of the fusion gene results in a single protein with functional properties derived from each of the original proteins.

The term "subject" includes human and non-human animals Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "toxin," "cytotoxin" or "cytotoxic agent" as used herein, refers to any agent that is detrimental to the growth and proliferation of cells and may act to reduce, inhibit, or destroy a cell or malignancy.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein refers to a chemical moiety that is conjugated to an antibody or antigen binding fragment, and can include any therapeutic or diagnostic agent, for example, an anti-cancer, anti-inflammatory, anti-infective (e.g., anti-fungal, antibacterial, antiparasitic, anti-viral), or an anesthetic agent. In certain aspects, a drug moiety is selected from an Eg5 inhibitor, a V-ATPase inhibitor, a HSP90 inhibitor, an IAP inhibitor, an mTor inhibitor, a microtubule stabilizer, a microtubule destabilizer, an auristatin, a dolastatin, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder, an RNA polymerase inhibitor, a topoisomerase inhibitor and a DHFR inhibitor. Methods for attaching each of these to a linker compatible with the antibodies and method of the present disclosure are known in the art. See, e.g., Singh et al., (2009) Therapeutic Antibodies: Methods and Protocols, vol. 525, 445-457. In addition, a payload can be a biophysical probe, a fluorophore, a spin label, an infrared probe, an affinity probe, a chelator, a spectroscopic probe, a radioactive probe, a lipid molecule, a polyethylene glycol, a polymer, a spin label, DNA, RNA, a protein, a peptide, a surface, an antibody, an antibody fragment, a nanoparticle, a quantum dot, a liposome, a PLGA particle, a saccharide or a polysaccharide.

"Eg5," "kinesin-like protein (KIF11)," "kinesin-like spindle protein (KSP)," and "TRIPS" refer to a 1056 amino acid protein, Genbank Accession number U37426. Eg5 is a motor protein involved cross linking of microtubules during mitosis, and is required for cell division (Rapley et al., J. Cell Sci. 2008, 121:3912-3921).

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. A possible way of showing anti-tumor activity is to show a decline in growth rate of tumor cells, tumor size stasis or tumor size reduction. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

The term "cKIT" refers to a tyrosine kinase receptor that is a member of the receptor tyrosine kinase III family. The nucleic acid and amino acid sequences of cKIT are known, and have been published in GenBank Accession Nos. X06182.1. See also SEQ ID NO:1 for the human cKIT cDNA sequence and SEQ ID NO:2 for the human cKIT protein sequence. Structurally, cKIT receptor is a type I transmembrane protein and contains a signal peptide, 5 Ig-like C2 domains in the extracellular domain and has a protein kinase domain in its intracellular domain and has over its full length at least about 90%, 91%, 92%, 93%, 94%, 95%, 96%, 97%, 98%, 99%, or 100% sequence identity with the amino acid sequence of SEQ ID NO:2. Structurally, a cKIT nucleic acid sequence has over its full length at least about 90%, 91%, 92%, 93%, 94%, 95%, 96%, 97%, 98%, 99%, or 100% sequence identity with the nucleic acid sequence of SEQ ID NO 1.

The terms "cKIT expressing cancer" or "cKIT positive cancer" refers to a cancer that express cKIT and/or a mutant form of cKIT on the surface of cancer cells.

As used herein, the terms "treat," "treating," or "treatment" of any disease or disorder refer in one aspect, to ameliorating the disease or disorder (i.e., slowing or arresting or reducing the development of the disease or at least one of the clinical symptoms thereof). In another aspect, "treat," "treating," or "treatment" refers to alleviating or ameliorating at least one physical parameter including those which may not be discernible by the patient. In yet another aspect, "treat," "treating," or "treatment" refers to modulating the disease or disorder, either physically, (e.g., stabilization of a discernible symptom), physiologically, (e.g., stabilization of a physical parameter), or both. In yet another aspect, "treat," "treating," or "treatment" refers to preventing or delaying the onset or development or progression of the disease or disorder.

The term "therapeutically acceptable amount" or "therapeutically effective dose" interchangeably refers to an amount sufficient to effect the desired result (i.e., a reduction in tumor size, inhibition of tumor growth, prevention of metastasis, inhibition or prevention of viral, bacterial, fungal or parasitic infection). In some aspects, a therapeutically acceptable amount does not induce or cause undesirable side effects. A therapeutically acceptable amount can be determined by first administering a low dose, and then incrementally increasing that dose until the desired effect is achieved. A "prophylactically effective dosage," and a "therapeutically effective dosage," of the molecules of the present disclosure can prevent the onset of, or result in a decrease in severity of, respectively, disease symptoms, including symptoms associated with cancer.

The term "co-administer" refers to the simultaneous presence of two active agents in the blood of an individual. Active agents that are co-administered can be concurrently or sequentially delivered.

The term 'thiol-maleimide' as used herein refers to a group formed by reaction of a thiol with maleimide, having this general formula:

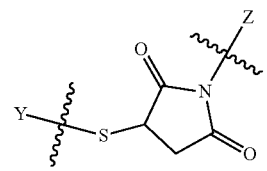

where Y and Z are groups to be connected via the thiol-maleimide linkage and can comprise linker components, antibodies or payloads.

'Cleavable' as used herein refers to a linking group or linker component that connects two moieties by covalent connections, but breaks down to sever the covalent connection between the moieties under physiologically relevant conditions, typically a cleavable linking group is severed in vivo more rapidly in an intracellular environment than when outside a cell, causing release of the payload to preferentially occur inside a targeted cell. Cleavage may be enzymatic or non-enzymatic, but generally releases a payload from an antibody without degrading the antibody. Cleavage may leave some portion of a linking group or linker component attached to the payload, or it may release the payload without any residue of the linking group.

'Non-cleavable' as used herein refers to a linking group or linker component that is not especially susceptible to breaking down under physiological conditions, e.g., it is at least as stable as the antibody or antigen binding fragment portion of the immunoconjugate. Such linking groups are sometimes referred to as 'stable', meaning they are sufficiently resistant to degradation to keep the payload connected to antibody or antigen binding fragment until the antibody or antigen binding fragment is itself at least partially degraded, i.e., the degradation of the antibody or antigen binding fragment precedes cleavage of the linking group in vivo. Degradation of the antibody portion of an ADC having a stable or non-cleavable linking group may leave some or all of the linking group, e.g., one or more amino acid groups from an antibody, attached to the payload or drug moiety that is delivered in vivo.

BRIEF DESCRIPTION OF THE DRAWINGS

FIG. 8A/B demonstrates that anti-cKIT antibodies conjugated to Eg5 inhibitor payload have dose dependent efficacy in a small cell lung cancer mouse model.

FIG. 11B graphically depicts the efficacy and body weight change of an anti-cKIT antibody conjugated to different Eg5 inhibitor payloads at a dose of 10 mg/kg in a small cell lung cancer xenograft mouse model.

DETAILED DESCRIPTION

Figure 1:
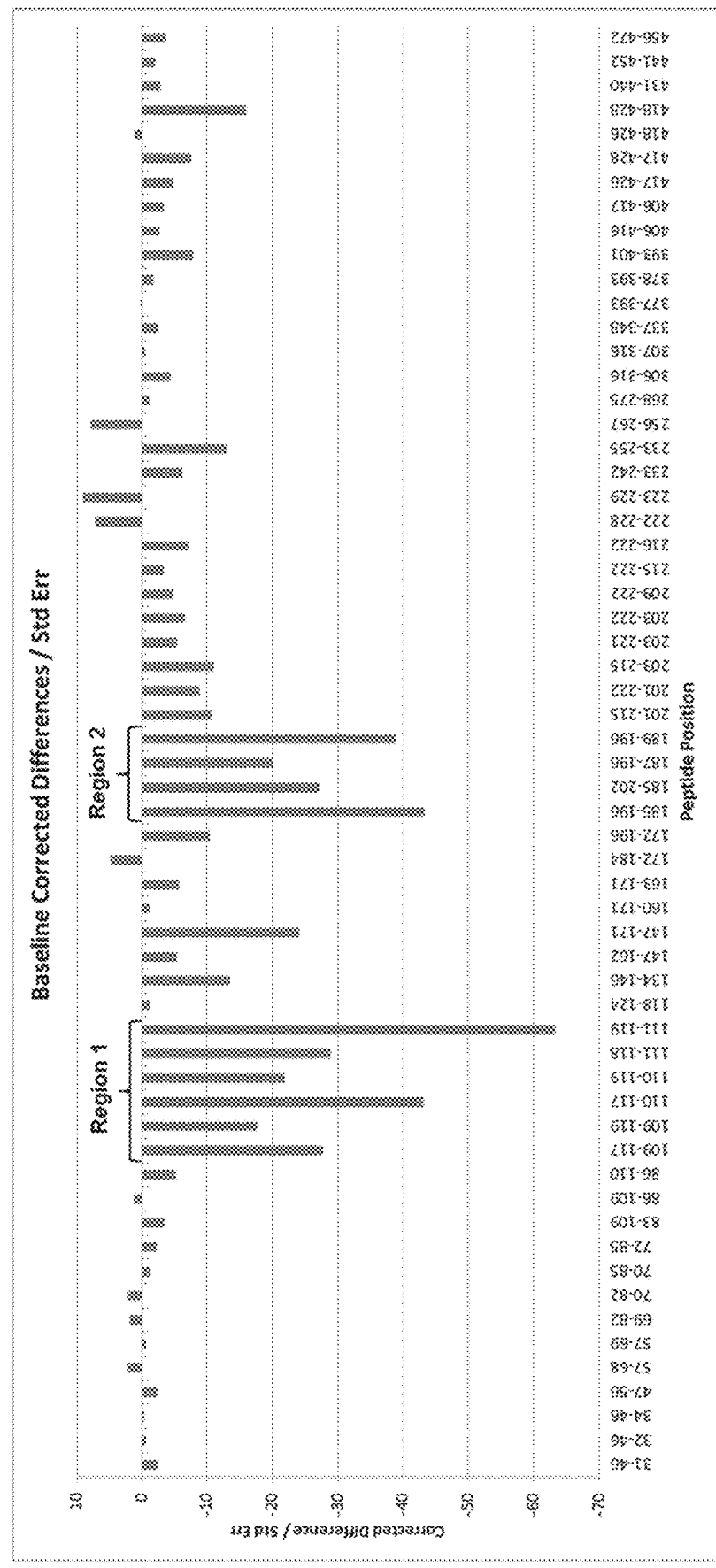
FIG. 1 is HDx-MS raw data plotted as the corrected difference over the standard error in measurement. A more negative value indicates more protection from deuterium exchange upon binding of the anti-cKIT antibody 9P3 to cKIT antigen. The two most significant regions of protection are denoted as Region 1 and Region 2.

The present disclosure provides for antibodies, antibody fragments (e.g., antigen binding fragments), and antibody drug conjugates that bind to cKIT. In particular, the present disclosure is directed to antibodies and antibody fragments (e.g., antigen binding fragments) that bind to cKIT, and internalize upon such binding. The antibodies and antibody fragments (e.g., antigen binding fragments) of the present disclosure can be used for producing antibody drug conjugates. Furthermore, the present disclosure provides antibody drug conjugates that have desirable pharmacokinetic characteristics and other desirable attributes, and thus can be used for treating cancer expressing cKIT, without limitation, for example: gastrointestinal stromal tumors (GIST), small cell lung cancer (SCLC), acute myeloid leukemia (AML), melanoma, mast cell leukemia (MCL), mastocytosis, neurofibromatosis, breast cancer, non-small cell lung cancer (NSCLC) and pancreatic cancer. The present disclosure further provides pharmaceutical compositions comprising the antibody drug conjugates, and methods of making and using such pharmaceutical compositions for the treatment of cancer.

Antibody Drug Conjugates

The present disclosure provides antibody drug conjugates, where an antibody, antigen binding fragment or its functional equivalent that specifically binds to cKIT is linked to a drug moiety. In one aspect, the antibodies, antigen binding fragments or their functional equivalents are linked, via covalent attachment by a linker, to a drug moiety that is an anti-cancer agent. The antibody drug conjugates can selectively deliver an effective dose of an anti-cancer agent (e.g., a cytotoxic agent) to tumor tissues expressing cKIT, whereby greater selectivity (and lower efficacious dose) may be achieved.

In one aspect, the disclosure provides for an immunoconjugate of Formula (I):

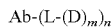

Wherein Ab represents an cKIT binding antibody or antibody fragment (e.g., antigen binding fragment) described herein;

L is a linker;
D is a drug moiety;
m is an integer from 1-8; and
n is an integer from 1-10. In one aspect, n is an integer from 1 to 10, 2 to 8, or 2 to 5. In a specific aspect, n is 3 to 4. In some aspects, m is 1. In some aspects, m is 2, 3 or 4.

While the drug to antibody ratio has an exact integer value for a specific conjugate molecule (e.g., n multiplied by m in Formula (I)), it is understood that the value will often be an average value when used to describe a sample containing many molecules, due to some degree of inhomogeneity, typically associated with the conjugation step. The average loading for a sample of an immunoconjugate is referred to herein as the drug to antibody ratio, or "DAR." In some aspects, the DAR is between about 1 and about 5, and typically is about 3, 3.5, 4, 4.5, or 5. In some aspects, at least 50% of a sample by weight is compound having the average DAR plus or minus 2, and preferably at least 50% of the sample is a conjugate that contains the average DAR plus or minus 1. Other aspects include immunoconjugates wherein the DAR is about 3.5. In some aspects, a DAR of 'about n' means the measured value for DAR is within 20% of n.

The present disclosure provides immunoconjugates comprising the antibodies, antibody fragments (e.g., antigen binding fragments) and their functional equivalents as disclosed herein, linked or conjugated to a drug moiety. In one aspect, the drug moiety D is an Eg5 inhibitor, including those having the structure of 5B, 5E, 5F, 5C, 5A or 5D in Table 1, where the wavy line indicates the covalent attachment of the sulfur atom of the Eg5 inhibitor/linker combination to a linker of an antibody (antiB).

The drug moiety D can be linked to the antibody through a linker L. L is any chemical moiety that is capable of linking the antibody Ab to the drug moiety D. The linker, L attaches the antibody Ab to the drug D through covalents bond(s). The linker reagent is a bifunctional or multifunctional moiety which can be used to link a drug moiety D and an antibody Ab to form antibody drug conjugates. Antibody drug conjugates can be prepared using a linker having a reactive functionality for binding to the drug moiety D and to the antibody. A cysteine, thiol or an amine, e.g. N-terminus or amino acid side chain such as lysine of the antibody Ab can form a bond with a functional group of a linker reagent.

In one aspect, L is a cleavable linker. In another aspect, L is a non-cleavable linker. In some aspects, L is an acid-labile linker, photo-labile linker, peptidase cleavable linker, esterase cleavable linker, a disulfide bond reducible linker, a hydrophilic linker, a procharged linker, or a dicarboxylic acid based linker.

In one aspect, the average molar ratio of Eg5 inhibitor to the antibody in the conjugate (i.e., average w value, also known as Drug Antibody Ratio (DAR)) is about 1 to about 10, about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, or 8.1), about 2.5 to about 7, about 3 to about 5, about 2.5 to about 4.5 (e.g., about 2.5, about 2.6, about 2.7, about 2.8, about 2.9, about 3.0, about 3.1, about 3.3, about 3.4, about 3.5, about 3.6, about 3.7, about 3.8, about 3.9, about 4.0, about 4.1, about 4.2, about 4.3, about 4.4, about 4.5), about 3.0 to about 4.0, about 3.2 to about 4.2, or about 4.5 to 5.5 (e.g., about 4.5, about 4.6, about 4.7, about 4.8, about 4.9, about 5.0, about 5.1, about 5.2, about 5.3, about 5.4, or about 5.5).

In one aspect provided by the disclosure, the conjugate has substantially high purity and has one or more of the following features: (a) greater than about 90% (e.g., greater than or equal to about 91%, 92%, 93%, 94%, 95%, 96%, 97%, 98%, 99%, or 100%), preferably greater than about 95%, of conjugate species are monomeric, (b) unconjugated linker level in the conjugate preparation is less than about 10% (e.g., less than or equal to about 9%, 8%, 7%, 6%, 5%, 4%, 3%, 2%, 1%, or 0%) (relative to total linker), (c) less than 10% of conjugate species are crosslinked (e.g., less than or equal to about 9%, 8%, 7%, 6%, 5%, 4%, 3%, 2%, 1%, or 0%), (d) free drug (e.g., Eg5 inhibitor) level in the conjugate preparation is less than about 2% (e.g., less than or equal to about 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (mol/mol relative to total cytotoxic agent).

1. Drug Moiety

The present disclosure provides immunoconjugates that specifically bind to cKIT. The immunoconjugates of the present disclosure comprise anti-cKIT antibodies, antibody fragments (e.g., antigen binding fragments) or functional equivalents that are conjugated to a drug moiety, e.g., an anti-cancer agent, an anti-hematological disorder agent, an autoimmune treatment agent, an anti-inflammatory agent, an antifungal agent, an antibacterial agent, an anti-parasitic agent, an anti-viral agent, or an anesthetic agent. The antibodies, antibody fragments (e.g., antigen binding fragments) or functional equivalents can be conjugated to several identical or different drug moieties using any methods known in the art.

In certain aspects, the drug moiety of the immunoconjugates of the present disclosure is selected from a group consisting of an Eg5 inhibitor, a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, an amatoxin, an amanitin, a MetAP (methionine aminopeptidase), an inhibitor of nuclear export of proteins CRM1, a DPPIV inhibitor, proteasome inhibitors, an inhibitor of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, an RNA polymerase inhibitor, a topoisomerase inhibitor and a DHFR inhibitor.

Eg5, also known as kinesin spindle protein or KSP, is a kinesin motor protein, involved in cross-linking of microtubules during mitosis, and is thus required for cell division. Inhibitors of Eg5 are known to be useful to treat cell proliferation disorders like cancer (Rath and Kozielski, Nature Rev. Cancer, vol. 12, 527-39 (2012); see also WO06/002236, WO2007/021794, WO2008/063912, WO2009/077448, WO2011/128381, WO2011/128388, and WO2006/049835). While a number of different chemical families of Eg5 inhibitors are known, they have not heretofore been used in ADCs. The present invention includes use of Eg5 inhibitors as drug payloads for ADCs, and novel Eg5 inhibitors that are useful as ADC payloads and as small-molecule pharmaceuticals. The invention further includes methods and intermediates useful for incorporating certain Eg5 inhibitors into ADCs, and methods to use the novel compounds and conjugates to treat cell proliferation disorders.

Examples of Eg5 inhibitors include: ispinesib, SB-743921, AZD4877, ARQ621, ARRY-520, LY2523355, MK-0731, EMD534085, and GSK-923295, and Eg5 inhibitors described in WO06/002236, WO2007/021794, WO2008/063912, WO2009/077448, WO2011/128381, WO2011/128388, and WO2006/049835. Other Eg5 inhibitors known in the art that could be adapted for use as ADC payloads include, for example, compounds disclosed in U.S. Pat. Nos. 7,504,405, 7,939,539, and in FIG. 3 of Rath and Kozielski, Nature Reviews: Cancer, vol. 12, 527-39 (August 2012).

In one aspect, the drug moiety of the immunoconjugates of the present disclosure is an Eg5 inhibitor, such as but not limited to, the Eg5 inhibitor/linker combinations disclosed in Table 1. These payloads are also disclosed in PCT/US2014/024795.

Immunoconjugates include immunoconjugates comprising any of the payload/linkers in Table 1 conjugated with an antibody (AntiB), where the conjugate has the structure shown in Table 1, wherein AntiB-S-represents an antibody bonded to the maleimide ring via a sulfur atom (S in the structure) of a cysteine residue of the anti-cKIT antibody.

TABLE 1
Payload/Linker Combinations and Conjugates.
| No. | Payload + Linker |
|---|---|
| 5A | 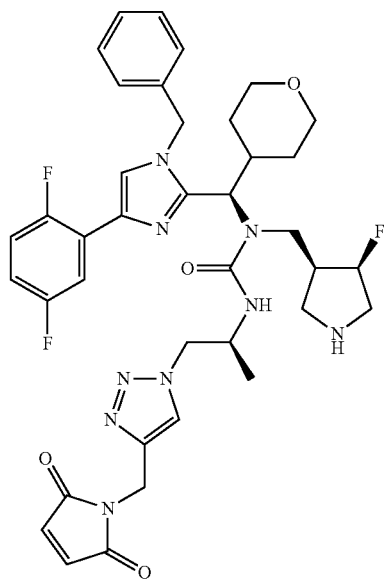 [SMILES: C[C@@H](Cn1cc(CN2C(=O)C=CC2=O)nn1)NC(=O)N(C[C@@H]1CNC[C@@H]1F)[C@@H](c1nc(-c2cc(F)ccc2F)cn1Cc1ccccc1)C1CCOCC1] |
| 5B | 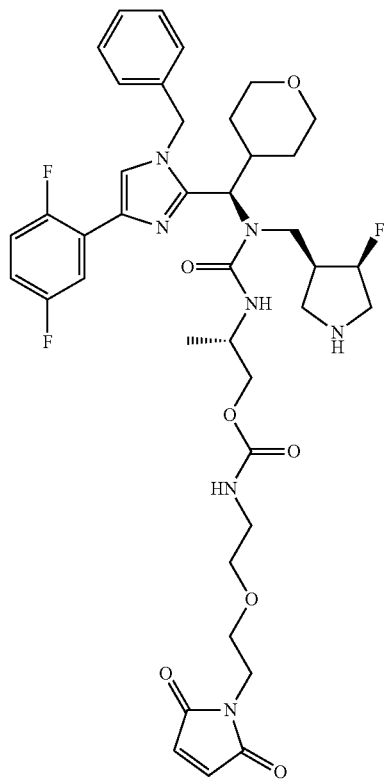 [SMILES: C[C@@H](COC(=O)NCCOCCN1C(=O)C=CC1=O)NC(=O)N(C[C@@H]1CNC[C@@H]1F)[C@@H](c1nc(-c2cc(F)ccc2F)cn1Cc1ccccc1)C1CCOCC1] |

US 11,833,215 B2
27                                                              28
TABLE 1-continued
Payload/Linker Combinations and Conjugates.
5C
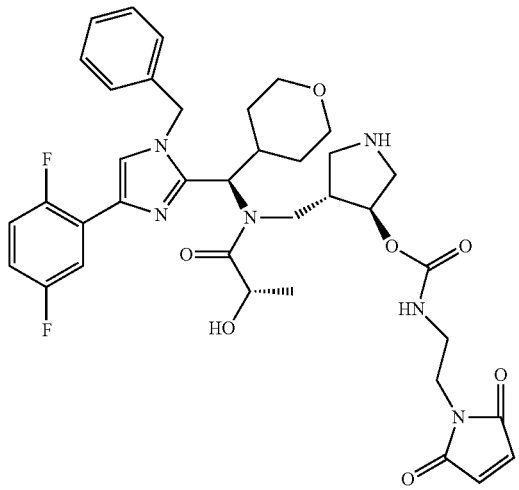 [SMILES: C[C@H](O)C(=O)N(C[C@@H]1CNC[C@H]1OC(=O)NCCN1C(=O)C=CC1=O)[C@@H](c1nc(-c2cc(F)ccc2F)cn1Cc1ccccc1)C1CCOCC1]
5D
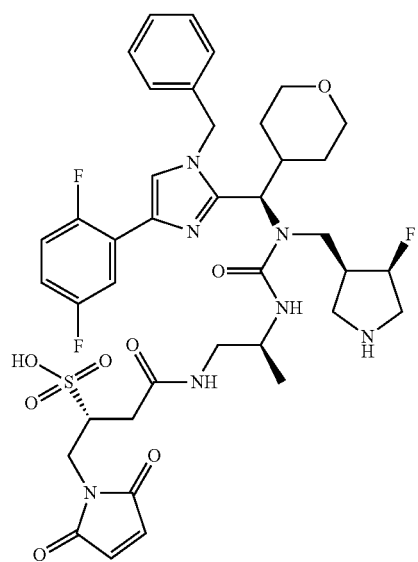 [SMILES: C[C@@H](CNC(=O)C[C@H](CN1C(=O)C=CC1=O)S(=O)(=O)O)NC(=O)N(C[C@@H]1CNC[C@@H]1F)[C@@H](c1nc(-c2cc(F)ccc2F)cn1Cc1ccccc1)C1CCOCC1]
5E
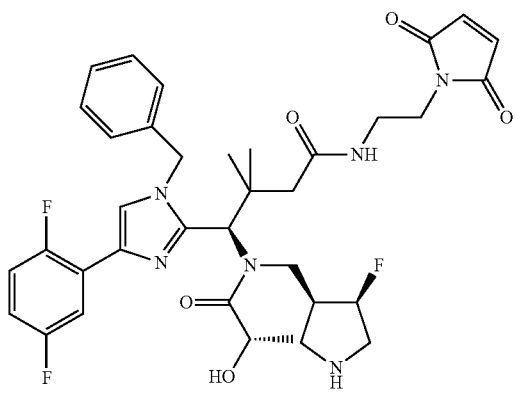 [SMILES: C[C@H](O)C(=O)N(C[C@@H]1CNC[C@@H]1F)[C@@H](c1nc(-c2cc(F)ccc2F)cn1Cc1ccccc1)C(C)(C)CC(=O)NCCN1C(=O)C=CC1=O]

TABLE 1-continued
Payload/Linker Combinations and Conjugates.
5F
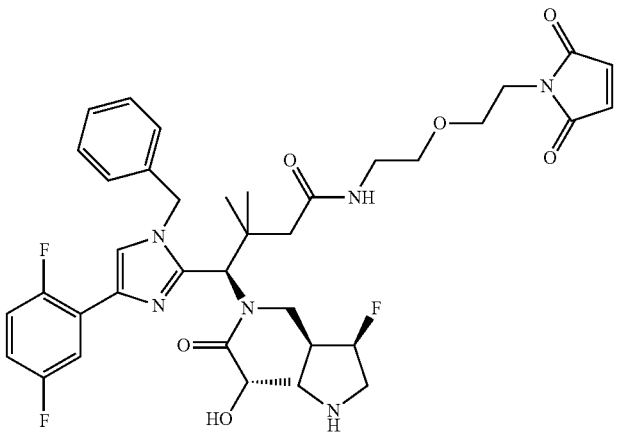 [SMILES: C[C@H](O)C(=O)N(C[C@@H]1CNC[C@@H]1F)[C@@H](c1nc(-c2cc(F)ccc2F)cn1Cc1ccccc1)C(C)(C)CC(=O)NCCOCCN1C(=O)C=CC1=O]
| No. | Antibody (AntiB) Drug Conjugate |
|---|---|
| 5A | 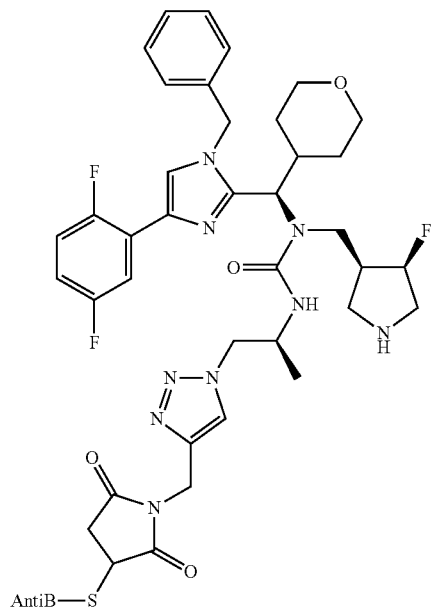 |

TABLE 1-continued
Payload/Linker Combinations and Conjugates.
5B
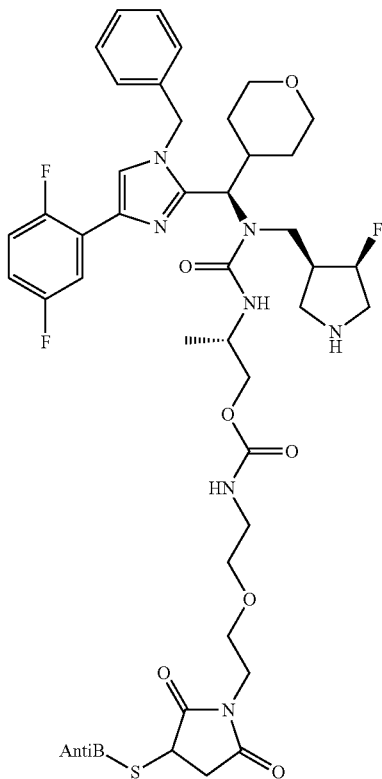
5C
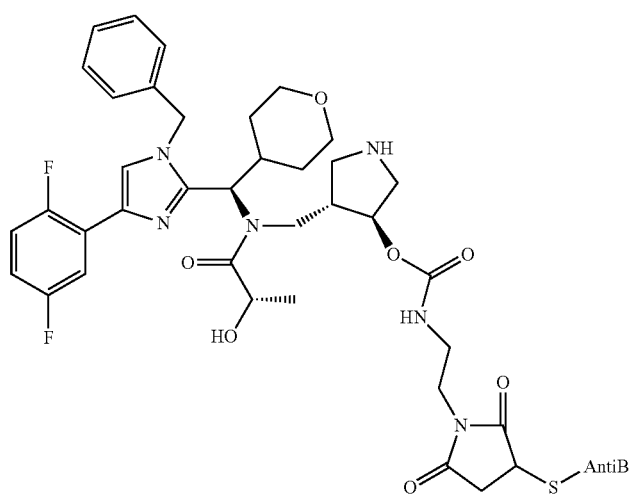

TABLE 1-continued

Payload/Linker Combinations and Conjugates.

5D
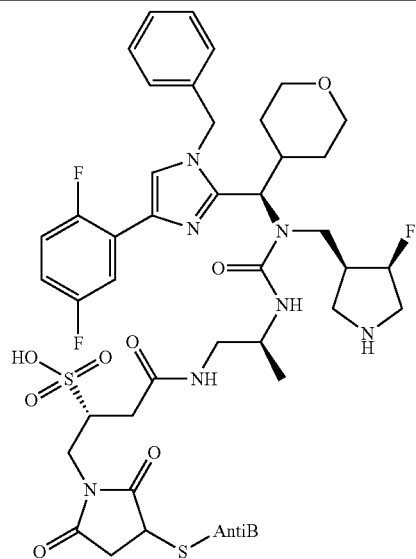

5E
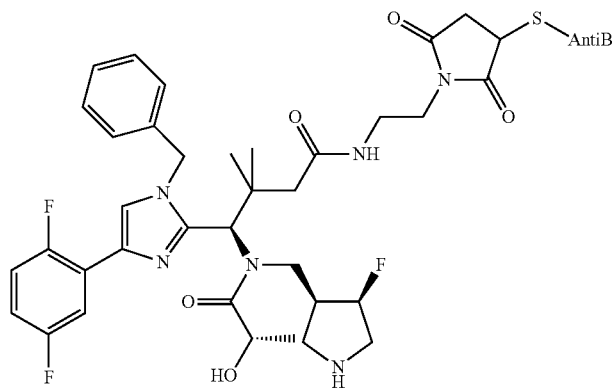

5F
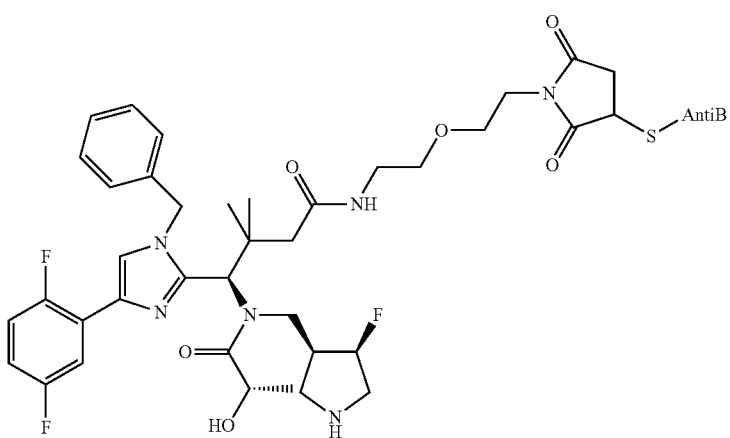

Eg5 inhibitors for use as ADC payloads can be attached to the linker or directly to the antibody at various positions on the inhibitor. Any available valence on the Eg5 inhibitors can be attached to a linker, but for convenient preparation of the conjugate attachment to the linker typically occurs at a heteroatom (N, O or S). In some embodiments, the Eg5 inhibitor comprises a free —NH— or free —OH or free —SH, which is used to attach the compound to a linker. Note that the free —NH— can be an amino group (—NH₂), cyclic amine (e.g., —NH— in a cyclic group such as pyrrolidone, piperidine, or morpholine), or a secondary acyclic amine; in each case, the —NH— group is preferably not part of an amide or conjugated to a carbonyl or to an aryl or heteroaryl ring, which would reduce its reactivity.

Further, the antibodies, antibody fragments (e.g., antigen binding fragments) or functional equivalents of the present disclosure may be conjugated to a drug moiety that modifies a given biological response. Drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin, a protein such as tumor necrosis factor, α-interferon, β-interferon, nerve growth factor, platelet derived growth factor, tissue plasminogen activator, a cytokine, an apoptotic agent, an anti-angiogenic agent, or, a biological response modifier such as, for example, a lymphokine.

In one aspect, the antibodies, antibody fragments (e.g., antigen binding fragments) or functional equivalents of the present disclosure are conjugated to a drug moiety, such as a cytotoxin, a drug (e.g., an immunosuppressant) or a radiotoxin. Examples of cytotoxin include but are not limited to, taxanes (see, e.g., International (PCT) Patent Application Nos. WO 01/38318 and PCT/US03/02675), DNA-alkylating agents (e.g., CC-1065 analogs), anthracyclines, amantins, tubulysin analogs, duocarmycin analogs, auristatin E, auristatin F, and cytotoxic agents comprising a reactive polyethylene glycol moiety (see, e.g., Sasse et al., J. Antibiot. (Tokyo), 53, 879-85 (2000), Suzawa et al., Bioorg. Med. Chem., 8, 2175-84 (2000), Ichimura et al., J. Antibiot. (Tokyo), 44, 1045-53 (1991), Francisco et al., Blood 2003 15; 102(4):1458-65), U.S. Pat. Nos. 5,475,092, 6,340,701, 6,372,738, and 6,436,931, U.S. Patent Application Publication No. 2001/0036923 A1, Pending U.S. patent application Ser. Nos. 10/024,290 and 10/116,053, and International (PCT) Patent Application No. WO 01/49698), taxon, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, anti-metabolites (e.g., methotrexate, 6-mercaptopurine, 6-thioguanine, cytarabine, 5-fluorouracil decarbazine), ablating agents (e.g., mechlorethamine, thiotepa chlorambucil, meiphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). (See e.g., Seattle Genetics US20090304721).

Other examples of cytotoxins that can be conjugated to the antibodies, antibody fragments (antigen binding fragments) or functional equivalents of the present disclosure include duocarmycins, calicheamicins, and auristatins, and derivatives thereof.

Various types of cytotoxins, linkers and methods for conjugating therapeutic agents to antibodies are known in the art, see, e.g., Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Curr. Opin. Investig. Drugs 3:1089-1091; Senter and Springer, (2001) Adv. Drug Deliv. Rev. 53:247-264.

The antibodies, antibody fragments (e.g., antigen binding fragments) or functional equivalents of the present disclosure can also be conjugated to a radioactive isotope to generate cytotoxic radiopharmaceuticals, referred to as radioimmunoconjugates. Examples of radioactive isotopes that can be conjugated to antibodies for use diagnostically or therapeutically include, but are not limited to, iodine-131, indium-111, yttrium-90, and lutetium-177. Methods for preparing radioimmunoconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies disclosed herein. In certain aspects, the macrocyclic chelator is 1,4,7,10-tetraazacyclododecane-N,N',N'', N'''-tetraacetic acid (DOTA) which can be attached to the antibody via a linker molecule. Such linker molecules are commonly known in the art and described in Denardo et al., (1998) Clin Cancer Res. 4(10):2483-90; Peterson et al., (1999) Bioconjug. Chem. 10(4):553-7; and Zimmerman et al., (1999) Nucl. Med. Biol. 26(8):943-50.

The antibodies, antibody fragments (e.g., antigen binding fragments) or functional equivalents of the present disclosure can also conjugated to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the present disclosure provides fusion proteins comprising an antibody fragment (e.g., antigen binding fragment) described herein (e.g., a Fab fragment, Fd fragment, Fv fragment, F(ab)2 fragment, a VH domain, a VH CDR, a VL domain or a VL CDR) and a heterologous protein, polypeptide, or peptide.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the present disclosure or fragments thereof (e.g., antibodies or fragments thereof with higher affinities and lower dissociation rates). See, generally, U.S. Pat. Nos. 5,605,793, 5,811,238, 5,830,721, 5,834,252, and 5,837,458; Patten et al., (1997) Curr. Opinion Biotechnol. 8:724-33; Harayama, (1998) Trends Biotechnol. 16(2): 76-82; Hansson et al., (1999) J. Mol. Biol. 287:265-76; and Lorenzo and Blasco, (1998) Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding an antibody or fragment thereof that specifically binds to an antigen may be recombined with one or more components, motifs, sections, parts, domains, fragments, etc. of one or more heterologous molecules.

Moreover, the antibodies, antibody fragments (e.g., antigen binding fragments) or functional equivalents of the present disclosure can be conjugated to marker sequences, such as a peptide, to facilitate purification. In preferred aspects, the marker amino acid sequence is a hexa-histidine peptide, such as the tag provided in a pQE vector (QIAGEN, Inc., Chatsworth, CA, 91311), among others, many of which are commercially available. As described in Gentz et al., (1989) Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "FLAG" tag (A. Einhauer et al., J.

Biochem. Biophys. Methods 49: 455-465, 2001). As described in the present disclosure, antibodies or antigen binding fragments can also be conjugated to tumor-penetrating peptides in order to enhance their efficacy.

In other aspects, the antibodies, antibody fragments (e.g., antigen binding fragments) or functional equivalents of the present disclosure are conjugated to a diagnostic or detectable agent. Such immunoconjugates can be useful for monitoring or prognosing the onset, development, progression and/or severity of a disease or disorder as part of a clinical testing procedure, such as determining the efficacy of a particular therapy. Such diagnosis and detection can be accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, umbelliferone, fluorescein, fluorescein isothiocyanate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In) technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Z, $^{85}$Sr, $^{32}$P, $^{153}$Gd, $^{169}$Yb, $^{51}$Cr, $^{54}$Mn, $^{75}$Se, $^{64}$Cu, $^{113}$Sn, and $^{117}$Sn; and positron emitting metals using various positron emission tomographies, and non-radioactive paramagnetic metal ions.

The antibodies, antibody fragments (e.g., antigen binding fragments) or functional equivalents of the present disclosure may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

2. Linker

As used herein, a "linker" is any chemical moiety that is capable of linking an antibody, antibody fragment (e.g., antigen binding fragments) or functional equivalent to another moiety, such as a drug moiety. Linkers can be susceptible to cleavage (cleavable linker), such as, acid-induced cleavage, photo-induced cleavage, peptidase-induced cleavage, esterase-induced cleavage, and disulfide bond cleavage, at conditions under which the compound or the antibody remains active. Alternatively, linkers can be substantially resistant to cleavage (e.g., stable linker or noncleavable linker). In some aspects, the linker is a procharged linker, a hydrophilic linker, or a dicarboxylic acid based linker.

A linking group may be divalent, meaning it can link only one drug group (D) to Ab, or it can be trivalent (able to link two drug groups (D) to Ab), or it can be polyvalent. Trivalent, tetravalent, and polyvalent linking group can be used to increase the loading of drug on an antibody, increasing the drug to antibody ratio (DAR) without requiring additional sites on the antibody for attaching linking groups. Such linking groups are known in the art, see e.g., Bioconjugate Chem., 1999 March-April; 10(2):279-88; U.S. Pat. No. 6,638,499; Clin Cancer Res Oct. 15, 2004 10; 7063; WO2012/113847A1.

Suitable linkers for use in ADCs are well known in the art, and can be used in the conjugates described herein (Lash et al., Start-Up 1-6, 2011). The linker can be attached to the antibody at any suitable available position on the antibody. Typically, the linker is attached to an available amino nitrogen atom (i.e., a primary or secondary amine, rather than an amide) or a hydroxylic oxygen atom, or to an available sulfhydryl, such as on a cysteine.

Non-cleavable linkers are any chemical moiety capable of linking a drug, such as an Eg5 inhibitor to an antibody in a stable, covalent manner and does not fall off under the categories listed above for cleaveable linkers. Thus, non-cleavable linkers are substantially resistant to acid-induced cleavage, photo-induced cleavage, peptidase-induced cleavage, esterase-induced cleavage and disulfide bond cleavage. Furthermore, non-cleavable refers to the ability of the chemical bond in the linker or adjoining to the linker to withstand cleavage induced by an acid, photolabile-cleaving agent, a peptidase, an esterase, or a chemical or physiological compound that cleaves a disulfide bond, at conditions under which the drug, such as an Eg5 inhibitor or the antibody does not lose its activity.

Acid-labile linkers are linkers cleavable at acidic pH. For example, certain intracellular compartments, such as endosomes and lysosomes, have an acidic pH (pH 4-5), and provide conditions suitable to cleave acid-labile linkers.

Photo-labile linkers are linkers that are useful at the body surface and in many body cavities that are accessible to light. Furthermore, infrared light can penetrate tissue.

Some linkers can be cleaved by peptidases, i.e. peptidase cleavable linkers. Only certain peptides are readily cleaved inside or outside cells, see e.g., Trout et al., 79 Proc. Natl. Acad. Sci. USA, 626-629 (1982) and Umemoto et al. 43 Int. J. Cancer, 677-684 (1989). Furthermore, peptides are composed of α-amino acids and peptidic bonds, which chemically are amide bonds between the carboxylate of one amino acid and the amino group of a second amino acid. Other amide bonds, such as the bond between a carboxylate and the ε-amino group of lysine, are understood not to be peptidic bonds and are considered non-cleavable.

Some linkers can be cleaved by esterases, i.e. esterase cleavable linkers. Again, only certain esters can be cleaved by esterases present inside or outside of cells. Esters are formed by the condensation of a carboxylic acid and an alcohol. Simple esters are esters produced with simple alcohols, such as aliphatic alcohols, and small cyclic and small aromatic alcohols.

Cleavable linking groups such as those containing a hydrazone, a disulfide, the dipeptide Val-Cit, and ones containing a glucuronidase-cleavable p-aminobenzyloxycarbonyl moiety, are well known in the art, and can be used, see, e.g., Ducry, et al., Bioconjugate Chem., vol. 21, 5-13 (2010). For these immunoconjugates, the linking group is substantially stable in vivo until the immunoconjugate binds to or enters a cell, at which point either intracellular enzymes or intracellular chemical conditions (pH, reduction capacity) cleave the linking group to free the Eg5 inhibitor.

There are improved linking groups that connect an antibody with a payload such as a cytotoxin, including the Eg5 inhibitors described herein. These immunoconjugates comprise a linking group that comprises a group of the formula —C(O)NR$^{21}$— or —NR$^{21}$—C(O)—, which may be an amide or a carbamate, wherein R$^{21}$ is of the formula —(CH$_2$)$_{1-4}$—R$^{22}$, R$^{22}$ is a polar group selected from —OH, —NH$_2$, N(R$^{23}$)$_2$, COOR$^{23}$, CON(R$^{23}$)$_2$, —(OCH$_2$CH$_2$O)$_k$—OCH$_2$CH$_2$OR$^{23}$, and —SO$_2$R$^{23}$, where k is 0 to 4 and each R$^{23}$ is independently H or C$_{1-4}$ alkyl. These linking groups are improved as they reduce aggregation of the immunoconjugate.

Other linkers include for example, in addition to a bond, alkylene groups —(CH$_2$)n- (where n is typically 1-10 or 1-6), ethylene glycol units (—CH$_2$CH$_2$O—)n (where n is typically 1-10 or 1-6), —O—, —S—, carbonyl (—C(=O)—), amides —C(=O)—NH— or —NH—C(=O)—, esters —C(=O)—O— or —O—C(=O)—, rings having two available points of attachment such as divalent phenyl, C$_{5-6}$ heteroaryl, C$_{3-8}$ cycloalkyl or C$_{4-8}$ heterocyclyl groups, amino acids —NH—CHR*—C=O— or —C(=O)—CHR*—NH—, or groups derived from amino acids that attach to N (e.g., to a maleimide nitrogen) having the formula [N]—CHR*—C(=O)—, where R* is the side chain of a known amino acid (frequently one of the canonical amino acids, but also including e.g. norvaline, norleucine, homoserine, homocysteine, phenylglycine, citrulline, and other named alpha-amino acids), polypeptides of known amino acids (e.g., dipeptides, tripeptides, tetrapeptides, etc.), thiol-maleimide linkages (from addition of —SH to maleimide), —S—CR$_2$— and other thiol ethers such as —S—CR$_2$—C(=O)— or —C(=O)—CR$_2$—S—, where R is independently at each occurrence H or C$_{1-4}$ alkyl, —CH$_2$—C(=O)—, and disulfides (—S—S—), as well as combinations of any of these with other linker components described below, e.g., a bond, a non-enzymatically cleavable linker, a non-cleavable linker, an enzymatically cleavable linker, a photo-stable linker, a photo-cleavable linker or a self-immolative spacer.

1-(2-((2-Hydroxyethyl)amino)ethyl)-1H-pyrrole-2,5-dione (Linker)

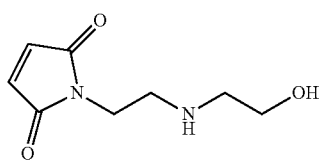 [SMILES: O=C1C=CC(=O)N1CCNCCO]

Tert-Butyl 3-((2-(2,5-dioxo-2,5-dihydro-1H-pyrrol-1-yl)ethyl)amino)propanoate (Linker)

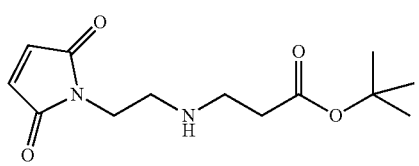 [SMILES: CC(C)(C)OC(=O)CCNCCN1C(=O)C=CC1=O]

tert-Butyl 3-((2-(2,5-dioxo-2,5-dihydro-1H-pyrrol-1-yl)ethyl)amino)propanoate (Linker)

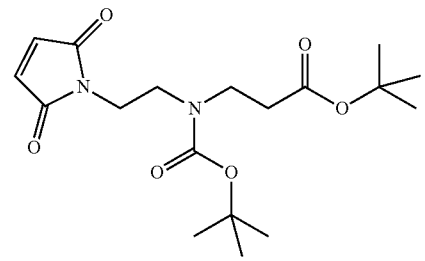 [SMILES: CC(C)(C)OC(=O)CCN(CCN1C(=O)C=CC1=O)C(=O)OC(C)(C)C]

3-((2,5-dioxo-2,5-dihydro-1H-pyrrol-1-yl)methyl)azetidin-1-ium 2,2,2-trifluoroacetate (Linker)

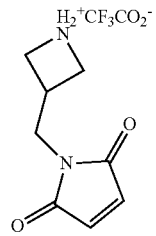

3-((2-(2,5-dioxo-2,5-dihydro-1H-pyrrol-1-yl)ethyl)amino)-3-oxopropan-1-aminium 2,2,2-trifluoroacetate (Linker)

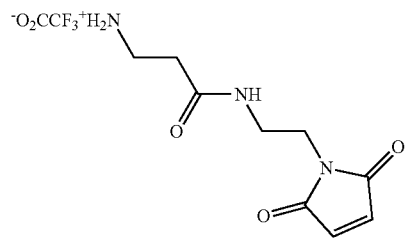

2-(2,5-dioxo-2,5-dihydro-1H-pyrrol-1-yl)ethyl (4-nitrophenyl) carbonate (Linker)

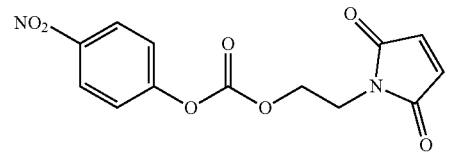 [SMILES: O=C(OCCN1C(=O)C=CC1=O)Oc1ccc([N+](=O)[O-])cc1]

1-(2-(2-hydroxyethoxy)ethyl)-1H-pyrrole-2,5-dione
(Linker)

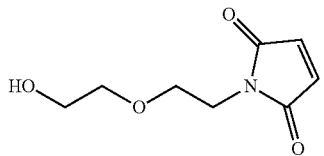 [SMILES: O=C1C=CC(=O)N1CCOCCO]

2-(2-(2,5-dioxo-2,5-dihydro-1H-pyrrol-1-yl)ethoxy)
ethyl (4-nitrophenyl) carbonate (Linker)

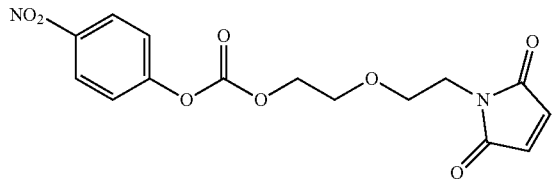 [SMILES: O=C(OCCOCCN1C(=O)C=CC1=O)Oc1ccc([N+](=O)[O-])cc1]

3. Conjugation and Preparation of ADCs
Cleavable Linkers: MC-ValCit-PABC ADCs:

To a solution of the payload (0.05 mmol, 1 eq) in DMSO (0.1 M) were added iPr₂EtN (6 eq) and 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (0.09 mmol, 1.6 eq). The reaction mixture was stirred at room temperature. Upon completion of the reaction by LC/MS (uplc, Method A, see Example 22), the crude was filtered to remove solids and directly purified by reverse phase column chromatography (using PrepLC Method C or D (see Example 22)) to yield the desire MC-ValCit-PABC-payload as the TFA salt.

Stable Linkers:
a) Carbamate Attachment

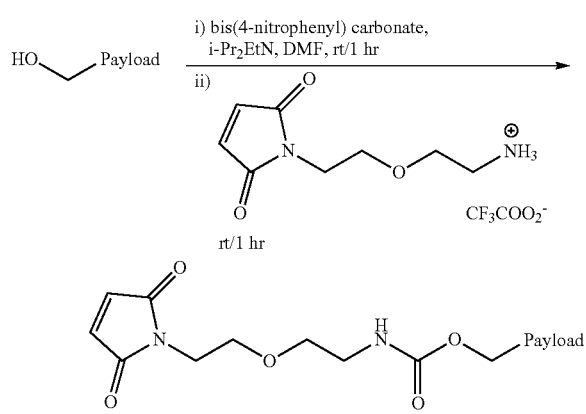

To a solution of the Boc-payload (0.09 mmol, 1 eq) in DMF (0.1 M) was added iPr₂EtN (0.9 mmol, 10 eq) followed by bis(4-nitrophenyl) carbonate (0.14 mmol, 1.6 eq) and stirred at room temperature for 1 h. Upon completion of the reaction by LC/MS (uplc, Method A, see Example 22), was added the linker (3 eq), and the reaction mixture stirred at room temperature. Upon completion of the reaction by LC/MS (uplc, Method A, see Example 22), solvent was evaporated under reduce pressure and the desire product (Boc-L-P) was obtained after purification by normal phase column chromatography (PrepLC Method B, see Example 22).

b) Amide Attachment

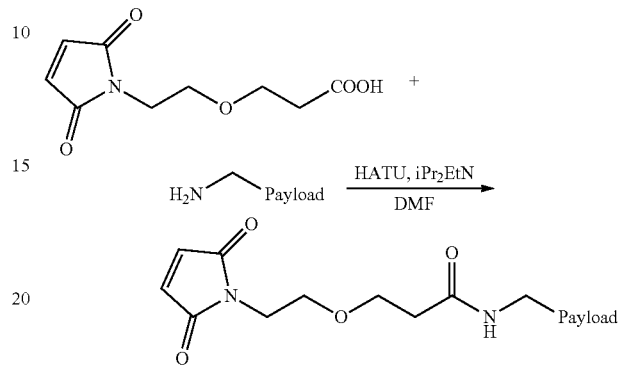

To a solution of the carboxilic acid linker (0.23 mmol, 1.8 eq), HATU (0.27 mmol, 2.1 eq) in DMF (0.3 M), was added iPr2EtN (1.4 mmol, 11 eq), followed by addition of the Boc-payload (0.13 mmol, 1 eq). The reaction mixture was stirred at room temperature. Upon completion of the reaction by LC/MS (uplc, Method A, see Example 22), the reaction mixture was diluted in EtOAc, and partitioned between EtOAc and H₂O. The organic layer was separated and washed with H₂O (twice), dried over Na₂SO₄, filtered and solvent evaporated under reduce pressure. The desired product was obtained after purification by normal phase column chromatography (PrepLC Method B, see Example 22).

c) Click Chemistry

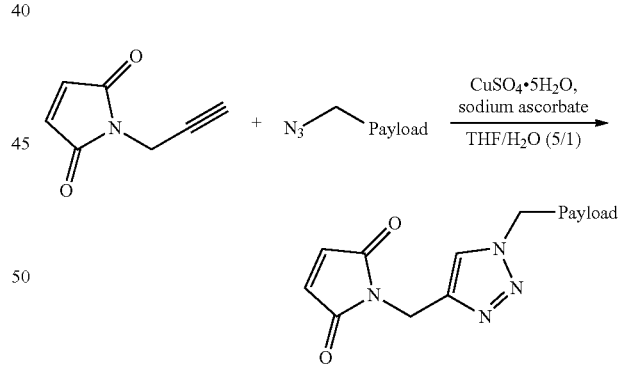

To a solution of azide-Boc-payload (0.05 mmol, 1 eq) and 1-(prop-2-yn-1-yl)-1H-pyrrole-2,5-dione (0.078 mmol, 1.5 eq) in THF (0.1M), a solution of CuSO₄·5H₂O and sodium ascorbate in H₂O (1M) was added. The reaction mixture was stirred at room temperature. Upon completion of the reaction by LC/MS (uplc, Method A, see Example 22), the reaction mixture was diluted in EtOAc and partitioned between EtOAc and H₂O. The organic layer was separated, washed with H₂O, dried over Na₂SO₄, filtered, and solvent evaporated under reduce pressure. The desired product was isolated by normal phase column chromatography (PrepLC Method B, see Example 22).

d) Sulfo GMBS Coupling

General Protocol for Linker Attachment

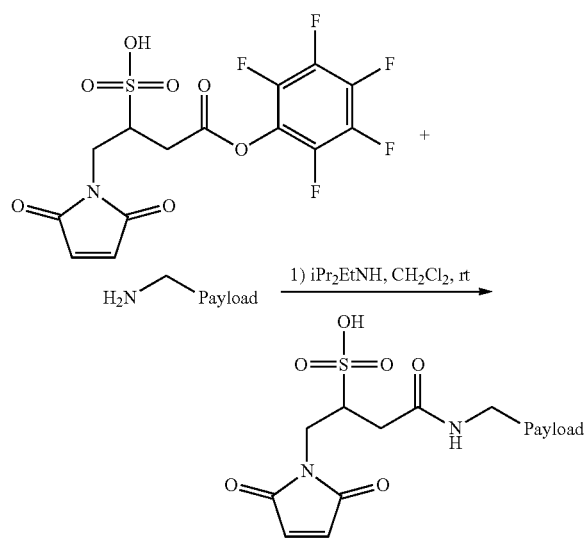

Over a solution of the Boc-payload (0.05 mmol, 1 eq) in CH$_2$Cl$_2$ (0.1 M) were added iPr$_2$EtNH (0.30 mmol, 6 eq) and 1-(2,5-dioxo-2,5-dihydro-1H-pyrrol-1-yl)-4-oxo-4-(perfluorophenoxy)butane-2-sulfonic acid (0.15 mmol, 3 eq). The reaction was stirred at room temperature. Upon completion of the reaction by LC/MS (uplc, Method A, see Example 22), the solvent was evaporated under reduce pressure. The desired product was isolated as a mixture of diastereoisomers by normal phase column chromatography (PrepLC Method B, see Example 22).

To a solution of the Boc-payload (1 equiv.) in dry DMF (0.1 M) was added iPr$_2$EtN (10 equiv.) followed by bis(4-nitrophenyl) carbonate (2.2 equiv.) and the reaction was stirred at room temperature for 30 minutes. Upon completion by LC/MS (uplc), the linker (4 eq) was added and the reaction stirred at room temperature for 1 h. The reaction was quenched with water and extracted with ethyl acetate. The organic extracts were combined, dried over Na$_2$SO$_4$, filtered and concentrated to dryness. Purification of the crude product by chromatography on silica eluting with 0-100% ethylacetate in heptane afforded the title compound.

Cysteine Metabolites:

General Protocol for the Synthesis of Cysteine-Metabolites:

To a solution of Boc-Linker-Payload (0.1 mmol, 1 eq)) in Acetonitrile (1 mL) were added L-cysteine (1 mmol, 10 eq) and water (0.1 mL). The reaction mixture was stirred for 1 h at room temperature. Upon completion of the reaction by LC/MS (uplc, Method A, see Example 22), the crude (Boc-Cys-Metabolite) was used as is in the next step.

To the solution of the previous step, TFA (150 mmol) was added and the reaction mixture stirred at room temperature. Upon completion of the reaction by LC/MS (uplc, Method A, see Example 22), the crude was purified by reverse phase column chromatography (PrepLC Method C or D, see Example 22), gradient MeCN (+0.1% TFA) in H₂O (+0.1% TFA). The product was isolated as the TFA salt.

General Protocol 2 for Catabolite Synthesis

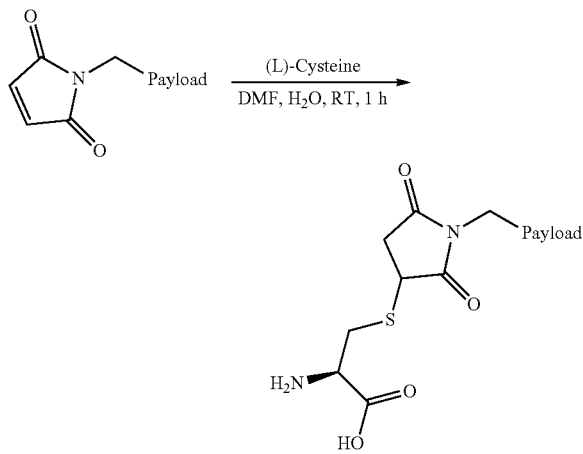

To a solution of (L)-Cysteine (10 equiv.) in water (0.1 M) was added the Boc-protected linker-payload (1.0 equiv.) in DMF (0.1 M) and the reaction was stirred at room temperature for 1 h. The reaction was with ethyl acetate. The organic extracts were combined, dried over Na₂SO₄, filtered and concentrated to dryness. The residue was dissolved in DCM (0.1 M) and trifluoroacetic acid (50 equiv.) was added. The reaction was stirred at room temperature for 2 h before it was concentrated to dryness. Purification of the crude product by chromatography on silica eluting with 0-100% methanol in DCM afforded the title compound.

Methods of attaching such payloads to a linking group for constructing conjugates are known in the art. Commonly, a free primary or secondary amine or a hydroxyl group is conjugated by an acylation reaction, using a linker component that comprises an activated ester, such as an N-hydroxysuccinimide ester or sulfonate-substituted N-hydroxysuccinimide ester to form an ester or amide linkage. Alternatively, a primary amine can be conjugated by formation of a Schiff base with a carbonyl (typically —CH (=O) or —C(=O)Me) of a linker component. Where the Eg5 inhibitor comprises a thiol group, the conjugate can be formed with a linker component comprising a maleimide or an alpha-halo acetamide (—NH—C(=O)—CH₂LG where LG is Br, Cl or I), or it can be conjugated to a thiol-containing linker component or antigen binding moiety by forming a disulfide linkage.

Immunoconjugates include immunoconjugates comprising any of the payload/linker combinations in Table 1 conjugated with an antibody (AntiB), where the conjugate has the structure shown in the Table, wherein AntiB-S— represents an antibody bonded to the maleimide ring via a sulfur atom (S in the structure) of a cysteine residue of the cKIT antibody.

The cysteine residue connecting the antibody to the maleimide compound may be naturally present in the native antibody, or it may have been introduced into the antibody by protein engineering methods known in the art. Antibodies engineered to contain a cysteine residue introduced by protein engineering are sometimes preferred. In particular, antibodies engineered to introduce cysteine in place of at least one of the following sites are particularly suited for use in the immunoconjugates of the invention: heavy chain sites K360, E152, and S375; and Light chain residue K107. In particular, the combinations HC-K360C with LC-K107C, and HC-E152C with HC-S375C are well suited (EU Numbering).

TABLE 2

SEQ ID NO: 183 (constant region of the wild type heavy chain of cKIT antibodies)
SASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSR
WQQGNVFSCSVMHEALHNHYTQKSLSLSPGK SEQ ID NO: 184 (constant region of wild type light chain of cKIT antibodies)
KRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVT
KSFNRGEC SEQ ID NO: 185 (constant region of the mutant heavy chain of cKIT antibodies with mutation HC-S375C, the mutated Cys residue is bolded/underlined)
SASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLT
CLVKGFYPCDIAVEWESNGQPENNYKTTPPVLDSDGSFFLYSKLTVDKSR
WQQGNVFSCSVMHEALHNHYTQKSLSLSPGK SEQ ID NO: 186 (constant region of the mutant light chain of cKIT antibodies with mutation LC-K107C, the mutated Cys residue is bolded/underlined)
CRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVT
KSFNRGEC SEQ ID NO: 187 (constant region of the mutant heavy chain of cKIT antibodies with the double mutation HC-E152C-S375C, the mutated Cys residues are bolded/underlined)
SASTKGPSVFPLAPSSKSTSGGTAALGCLVKDYFPCPVTVSWNSGALTSG
VHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLT
CLVKGFYPCDIAVEWESNGQPENNYKTTPPVLDSDGSFFLYSKLTVDKSR
WQQGNVFSCSVMHEALHNHYTQKSLSLSPGK SEQ ID NO: 188 (constant region of mutant heavy chain cKIT antibodies with mutation at HC-K360C, the mutated Cys residue is bolded/underlined)
SASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSREEMTCNQVSLT
CLVKGFYPSDIAVEWESNGQPENNYKTTPPVLDSDGSFFLYSKLTVDKSR
WQQGNVFSCSVMHEALHNHYTQKSLSLSPGK It is understood that the antibody may contain more than one payload: in typical embodiments, the conjugate contains 2-6, preferably 3-5 payload compounds (Eg5 inhibitors) on an antibody that consists of two heavy chain and two light chain peptides.

Synthesis of ADCs

General Methods for Conjugation of Linker-Payload (L-P) with Antigen Binding Moiety Payloads were conjugated to antigen binding moieties (e.g., IgG1 kappa or lambda of an antibody) at partially reduced hinge and inter-chains disulfides in a 2-step process. The antibody at a concentration of 5-10 mg/ml in PBS containing 2 mM EDTA, was first partially reduced for 1 to 1.5 hour at 37° C. with 50 mM mercaptoethylamine (added as a solid). After desalting and addition of 1% w/v PS-20 detergent, the partially reduced antibody (1-2 mg/ml) was reacted overnight at 4° C. with an amount of 0.5-1 mg of the Linker-Payload compound, dissolved at 10 mg/ml in DMSO or other suitable solvents, per 10 mg antibody. The antibody-drug conjugate is purified by Protein A chromatography. After base-line washing with PBS, the conjugate is eluted with 50 mM citrate, pH 2.7, 140 mM NaCl, neutralized and sterile filtered. The ADCs described in Table 1 were prepared according to this procedure. This procedure yields an average drug loading of 4-6 molecules of payload per antibody.

A different process was used for antibodies where new cysteine residues were introduced by protein engineering as conjugation sites. In order to reduce all native disulfide bonds and the disulfide bound between the cysteine or GSH adducts of the engineered cysteine residue, freshly prepared DTT was added to previously purified Cys mutants of the antibody, to a final concentration of 20 mM. After incubation with DTT at 37° C. for 1 hour, the mixtures were dialyzed at 4° C. against PBS for three days with daily buffer exchange to remove DTT and re-oxidize the native disulfide bonds. An alternative method is to remove the reducing reagents through a desalting column, Sephadex G-25. Once the protein is fully reduced, 1 mM oxidized ascorbate (dehydro-ascorbic acid) is added to the desalted samples and the re-oxidation incubations are carried out for 20 hours. Reoxidation restores intra-chain disulfides, while dialysis allows cysteines and glutathiones connected to the newly-introduced cysteine(s) to dialyze away. Both of these methods produce similar results, but attempts to follow the re-oxidation protocols previously described in the literature using $CuSO_4$ resulted in protein precipitation. All examples herein use the dialysis protocol described above.

For example, reoxidized antibodies were conjugated with 5B (Table 1) by incubating 5 mg/ml antibody with 0.35 mM of the maleimide compound for 1 hour in 50 mM sodium phosphate buffer (pH 7.2). The completeness of the reaction was monitored by RP-HPLC and a DAR of 3-4 was typically obtained. The DAR for a sample made by this process was 3.2. Cysteine engineered antibodies gave slightly higher DAR under the same condition, with DAR=3.9-4.0 for the cKIT-5B conjugates. DAR measurements were further verified by MS.

4. Characterization and Selection of Desirable Antibodies and Antibody Drug Conjugates The immunoconjugates prepared as described above were characterized by LC/MS. Conjugation typically provides a mixture of conjugates that differ in the number of copies of the Linker-Payload moiety bound to the antibody. Mass spectral analysis demonstrates that Linker-Payload groups are attached to light chains and/or heavy chains in each of the conjugates in Table 1. The conjugates were characterized in terms of average drug loading for a sample (DAR, drug to antibody ratio) and aggregation (expressed in %).

The DAR value is extrapolated from LC-MS data for reduced and deglycosylated samples. LC/MS allows quantitation of the average number of molecules of payload (drug) attached to an antibody in an ADC. HPLC separates the antibody into light and heavy chains, and separates the heavy chain (HC) and light chain (LC) according to the number of Linker-Payload groups per chain Mass spectral data enables identification of the component species in the mixture, e.g., LC, LC+1, LC+2, HC, HC+1, HC+2, etc. From the average loading on the LC and HC chains, the average drug to antibody ratio (DAR) can be calculated for an ADC. The DAR for a given conjugate sample represents the average number of drug (payload) molecules attached to a tetrameric antibody containing two light chains and two heavy chains.

Some conjugates were found to form aggregates, and conjugates described herein were also characterized by the extent of aggregation. Aggregation was measured by analytical size exclusion chromatography (Superdex® 200 5/150 GL run in PBS). It was observed that the extent of aggregation depends on the Linker-Payload and the DAR. Conjugates having a lower percent aggregation may be more useful for some purposes, thus immunoconjugates that exhibit less than 50% aggregation, and preferably less than 20% aggregation, may be preferred. Thus, the extent of aggregation for a given payload can be manipulated by selection of linking group and DAR.

The antibodies, antibody fragments (e.g., antigen binding fragments) or antibody drug conjugates of the present disclosure can be characterized and selected for their physical/chemical properties and/or biological activities by various assays known in the art.

For example, an antibody of the present disclosure can be tested for its antigen binding activity by known methods such as ELISA, FACS, Biacore or Western blot.

Transgenic animals and cell lines are particularly useful in screening antibody drug conjugates (ADCs) that have potential as prophylactic or therapeutic treatments of cancer overexpression of tumor-associated antigens and cell surface receptors. Screening for a useful ADC may involve administering a candidate ADC over a range of doses to the transgenic animal, and assaying at various time points for the effect(s) of the ADC on the disease or disorder being evaluated. Alternatively, or additionally, the drug can be administered prior to or simultaneously with exposure to an inducer of the disease, if applicable. The candidate ADC may be screened serially and individually, or in parallel under medium or high-throughput screening format.

One aspect is a screening method comprising (a) transplanting cells from a stable cancer cell line or human patient tumor expressing cKIT (e.g., a GIST cell line or tumor fragment, a melanoma cell line or tumor fragment, AML primary cells) into a non-human animal, (b) administering an ADC drug candidate to the non-human animal and (c) determining the ability of the candidate to inhibit the growth of tumors from the transplanted cell line. The present disclosure also encompasses a method of screening ADC candidates for the treatment of a disease or disorder characterized by the overexpression of cKIT comprising (a) contacting cells from a stable cancer cell line expressing cKIT with a drug candidate, and (b) evaluating the ability of the ADC candidate to inhibit the growth of the stable cell line.

Another aspect is a screening method comprising (a) contacting cells from a stable cancer cell line expressing cKIT with an ADC drug candidate and (b) evaluating the ability of the ADC candidate to block ligand activation of cKIT. In another aspect the ability of the ADC candidate to block ligand-stimulated tyrosine phosphorylation is evaluated.

A further aspect is a screening method comprising (a) contacting cells from a stable cancer cell line expressing cKIT with an ADC drug candidate and (b) evaluating the ability of the ADC candidate to induce cell death. In one aspect the ability of the ADC candidate to induce apoptosis is evaluated.

Candidate ADC can be screened by being administered to the transgenic animal over a range of doses, and evaluating the animal's physiological response to the compounds over time. In some cases, it can be appropriate to administer the compound in conjunction with co-factors that would enhance the efficacy of the compound. If cell lines derived from the subject transgenic animals are used to screen for ADCs useful in treating various disorders associated with overexpression of cKIT, the test ADCs are added to the cell culture medium at an appropriate time, and the cellular response to the ADCs is evaluated over time using the appropriate biochemical and/or histological assays.

Thus, the present disclosure provides assays for identifying ADC which specifically target and bind to cKIT, and cKIT overexpression on tumor cells.

cKIT Antibodies

The present disclosure provides for antibodies or antibody fragments (e.g., antigen binding fragments) that specifically bind to human cKIT. Antibodies or antibody fragments (e.g., antigen binding fragments) of the present disclosure include, but are not limited to, the human monoclonal antibodies or fragments thereof, isolated as described, in the Examples below.

The present disclosure in certain aspects provides antibodies or antibody fragments (e.g., antigen binding fragments) that specifically bind cKIT, said antibodies or antibody fragments (e.g., antigen binding fragments) comprise a VH domain having an amino acid sequence of SEQ ID NO: 9, 28, 46, 64, 82, 100, 118, 136 or 154 (Table 3). The present disclosure also provides antibodies or antibody fragments (e.g., antigen binding fragments) that specifically bind to cKIT, said antibodies or antibody fragments (e.g., antigen binding fragments) comprise a VH CDR having an amino acid sequence of any one of the VH CDRs listed in Table 3. In particular aspects, the present disclosure provides antibodies or antibody fragments (e.g., antigen binding fragments) that specifically bind to cKIT, said antibodies comprising (or alternatively, consist of) one, two, three, four, five or more VH CDRs having an amino acid sequence of any of the VH CDRs listed in Table 3, infra.

The present disclosure provides antibodies or antibody fragments (e.g., antigen binding fragments) that specifically bind to cKIT, said antibodies or antibody fragments (e.g., antigen binding fragments) comprise a VL domain having an amino acid sequence of SEQ ID NO: 18, 37, 55, 73, 91, 109, 127, 145 or 163 (Table 3). The present disclosure also provides antibodies or antibody fragments (e.g., antigen binding fragments) that specifically bind to cKIT, said antibodies or antibody fragments (e.g., antigen binding fragments) comprise a VL CDR having an amino acid sequence of any one of the VL CDRs listed in Table 3, infra. In particular, the disclosure provides antibodies or antibody fragments (e.g., antigen binding fragments) that specifically bind to cKIT, said antibodies or antibody fragments (e.g., antigen binding fragments) comprise (or alternatively, consist of) one, two, three or more VL CDRs having an amino acid sequence of any of the VL CDRs listed in Table 3.

Other antibodies or antibody fragments (e.g., antigen binding fragments) of the present disclosure include amino acids that have been mutated, yet have at least 60, 70, 80, 90 or 95 percent identity in the CDR regions with the CDR regions depicted in the sequences described in Table 3. In some aspects, it includes mutant amino acid sequences wherein no more than 1, 2, 3, 4 or 5 amino acids have been mutated in the CDR regions when compared with the CDR regions depicted in the sequence described in Table 3.

The present disclosure also provides nucleic acid sequences that encode VH, VL, the full length heavy chain, and the full length light chain of the antibodies that specifically bind to cKIT. Such nucleic acid sequences can be optimized for expression in mammalian cells.

TABLE 3

Examples of anti- cKIT Antibodies

9P3

| | | | |
|---|---|---|---|
| SEQ ID NO 3: | (Kabat) | HCDR1 | DYYMA |
| SEQ ID NO 4: | (Kabat) | HCDR2 | NINYDGSSTYYLDSLKS |
| SEQ ID NO 5: | (Kabat) | HCDR3 | GDYYGTTYWYFDV |
| SEQ ID NO 6: | (Chothia) | HCDR1 | GFTFSDY |
| SEQ ID NO 7: | (Chothia) | HCDR2 | NYDGSS |
| SEQ ID NO 8: | (Chothia) | HCDR3 | GDYYGTTYWYFDV |
| SEQ ID NO 9: | | VH | EVRLVESEGGLVQPRSSMKLSCTASGFTFSDYYMAWVRQVPE KGLEWVANINYDGSSTYYLDSLKSRFIISRDNAKNILYLQMSSL KSEDTATYYCARGDYYGTTYWYFDVVVGTGTTVTVSS |
| SEQ ID NO 10 | | Constant heavy chain | VAAPSVFIFPPSDEQLKSGTASVVCLLNNFYPREAKVQWKVDN ALQSGNSQESVTEQDSKDSTYSLSSTLTLSKADYEKHKVYACE VTHQGLSSPVTKSFNRGEC |
| SEQ ID NO 11: | | Heavy Chain (humanized) | EVQLVESGGGLVQPGGSLRLSCAASGFTFSDYYMAWVRQAPG KGLEWVANINYDGSSTYYLDSVKGRFTISRDNAKNSLYLQMN SLRAEDTAVYYCARGDYYGTTYWYFDVWGQGTTVTVSSAST KGPSVFPLAPSSKSTSGGTAALGCLVKDYFPEPVTVSWNSGAL TSGVHTFPAVLQSSGLYSLSSVVTVPSSSLGTQTYICNVNHKPS NTKVDKRVEPKSCDKTHTCPPCPAPELLGGPSVFLFPPKPKDTL MISRTPEVTCVVVDVSHEDPEVKFNWYVDGVEVHNAKTKPRE EQYNSTYRVVSVLTVLHQDWLNGKEYKCKVSNKALPAPIEKTI SKAKGQPREPQVYTLPPSREEMTKNQVSLTCLVKGFYPSDIAV EWESNGQPENNYKTTPPVLDSDGSFFLYSKLTVDKSRWQQGN VFSCSVMHEALHNHYTQKSLSLSPGK |

TABLE 3-continued

Examples of anti- cKIT Antibodies

| | | | |
|---|---|---|---|
| SEQ ID NO 12: | (Kabat) | LCDR1 | RASQDISNYLN |
| SEQ ID NO 13: | (Kabat) | LCDR2 | YTSRLQS |
| SEQ ID NO 14: | (Kabat) | LCDR3 | QQGKKLWS |
| SEQ ID NO 15: (Chothia) | | LCDR1 | SQDISNY |
| SEQ ID NO 16: (Chothia) | | LCDR2 | YTS |
| SEQ ID NO 17: (Chothia) | | LCDR3 | GKKLW |
| SEQ ID NO 18: | | VL | DIQMTQTTSSLSASLGDRVTISCRASQDISNYLNWYQQKPDGT VKLLIYYTSRLQSGVPSRFSGSGSGTDYSLTISNLEQEDIATYFC QQGKKLWSFGGGTKLEIKR |
| SEQ ID NO: 19 | | Constant light chain | ASTKGPSVFPLAPSSKSTSGGTAALGCLVKDYFPEPVTVSWNS GALTSGVHTFPAVLQSSGLYSLSSVVTVPSSSLGTQTYICNVNH KPSNTKVDKRVEPKSCDKTHTCPPCPAPELLGGPSVFLFPPKPK DTLMISRTPEVTCVVVDVSHEDPEVKFNWYVDGVEVHNAKTK PREEQYNSTYRVVSVLTVLHQDWLNGKEYKCKVSNKALPAPI EKTISKAKGQPREPQVYTLPPSREEMTKNQVSLTCLVKGFYPSD IAVEWESNGQPENNYKTTPPVLDSDGSFFLYSKLTVDKSRWQQ GNVFSCSVMHEALHNHYTQKSLSLSPGK |
| SEQ ID NO 20: | | Light Chain (humanized VK1) | DIQMTQSPSSLSASVGDRVTITCRASQSISSYLNWYQQKPGKAP KLLIYYTSRLQSGVPSRFSGSGSGTDYTLTISSLQPEDFATYYCQ QGKKLWSFGGGTKVEIKRTVAAPSVFIFPPSDEQLKSGTASVVC LLNNFYPREAKVQWKVDNALQSGNSQESVTEQDSKDSTYSLS STLTLSKADYEKHKVYACEVTHQGLSSPVTKSFNRGEC |
| SEQ ID NO 21: | | DNA Light Chain (humanized VK3 NEG009) | EIVMTQSPATLSLSPGERATLSCRASQDISNYLNWYQQKPGQA PRLLIYYTSRLQSGIPARFSGSGSGTDYTLTISSLEPEDFAVYYC QQGKKLWSFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC |

NEG024

| | | | |
|---|---|---|---|
| SEQ ID NO 22: | (Kabat) | HCDR1 | DYYMA |
| SEQ ID NO 23: | (Kabat) | HCDR2 | NINQIAGSTYYLDSVRG |
| SEQ ID NO 24: | (Kabat) | HCDR3 | GDYYGTTYWYFDV |
| SEQ ID NO 25: (Chothia) | | HCDR1 | GFTFSDY |
| SEQ ID NO 26: (Chothia) | | HCDR2 | NQIAGS |
| SEQ ID NO 27: (Chothia) | | HCDR3 | GDYYGTTYWYFDV |
| SEQ ID NO 28: | | VH | EVQLVESGGGLVQPGGSLRLSCAASGFTFSDYYMAWVRQAPG KGLEWVANINQIAGSTYYLDSVRGRFTISRDNAKNSLYLQMNS LRAEDTAVYYCARGDYYGTTYWYFDVWGQGTTVTVSS |
| SEQ ID NO 29: | | Heavy Chain | EVQLVESGGGLVQPGGSLRLSCAASGFTFSDYYMAWVRQAPG KGLEWVANINQIAGSTYYLDSVRGRFTISRDNAKNSLYLQMNS LRAEDTAVYYCARGDYYGTTYWYFDVWGQGTTVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNT KVDKRVEPKSCDKTHTCPPCPAPELLGGPSVFLFPPKPKDTLMI SRTPEVTCVVVDVSHEDPEVKFNWYVDGVEVHNAKTKPREEQ YNSTYRVVSVLTVLHQDWLNGKEYKCKVSNKALPAPIEKTISK AKGQPREPQVYTLPPSREEMTKNQVSLTCLVKGFYPSDIAVEW ESNGQPENNYKTTPPVLDSDGSFFLYSKLTVDKSRWQQGNVFS CSVMHEALHNHYTQKSLSLSPGK |
| SEQ ID NO 30: | | DNA Heavy Chain | GAAGTGCAATTGGTGGAAAGCGGCGGAGGCCTGGTGCAGCC TGGCGGCTCTCTGAGACTGAGCTGTGCCGCCAGCGGCTTCA CCTTCAGCGACTACTACATGGCCTGGGTCCGACAGGCCCCT GGCAAGGGCCTGGAATGGGTGGCCAATATCAACCAAATCGC CGGCAGCACCTACTACCTGGACAGCGTGAGAGGCCGGTTCA CCATCAGCCGGGACAACGCCAAGAACAGCCTGTACCTGCAG ATGAACAGCCTGCGGGCCGAGGACACCGCCGTGTACTACTG CGCCAGAGGCGATTACTACGGCACCACCTACTGGTACTTCG ACGTGTGGGGCCAGGGCACCACCGTGACCGTCAGCTCAGCT AGCACCAAGGGCCCCAGCGTGTTCCCCCTGGCCCCCAGCAG CAAGAGCACCAGCGGCGGCACAGCCGCCCTGGGCTGCCTGG TGAAGGACTACTTCCCCGAGCCCGTGACCGTGTCCTGGAAC AGCGGAGCCCTGACCTCCGGCGTGCACACCTTCCCCGCCGT GCTGCAGAGCAGCGGCCTGTACAGCCTGTCCAGCGTGGTGA CAGTGCCCAGCAGCAGCCTGGGCACCCAGACCTACATCTGC AACGTGAACCACAAGCCCAGCAACACCAAGGTGGACAAGA GAGTGGAGCCCAAGAGCTGCGACAAGACCCACACCTGCCCC CCCTGCCCAGCCCCAGAGCTGCTGGGCGGACCCTCCGTGTTC CTGTTCCCCCCCAAGCCCAAGGACACCCTGATGATCAGCAG GACCCCCGAGGTGACCTGCGTGGTGGTGGACGTGAGCCACG AGGACCCAGAGGTGAAGTTCAACTGGTACGTGGACGGCGTG GAGGTGCACAACGCCAAGACCAAGCCCAGAGAGGAGCAGT |

TABLE 3-continued

Examples of anti- cKIT Antibodies

| | | | |
|---|---|---|---|
| | | | ACAACAGCACCTACAGGGTGGTGTCCGTGCTGACCGTGCTG<br>CACCAGGACTGGCTGAACGGCAAGGAATACAAGTGCAAGG<br>TCTCCAACAAGGCCCTGCCAGCCCCCATCGAAAAGACCATC<br>AGCAAGGCCAAGGGCCAGCCACGGGAGCCCCAGGTGTACA<br>CCCTGCCCCCCTCCCGGGAGGAGATGACCAAGAACCAGGTG<br>TCCCTGACCTGTCTGGTGAAGGGCTTCTACCCCAGCGACATC<br>GCCGTGGAGTGGGAGAGCAACGGCCAGCCCGAGAACAACT<br>ACAAGACCACCCCCCCAGTGCTGGACAGCGACGGCAGCTTC<br>TTCCTGTACAGCAAGCTGACCGTGGACAAGTCCAGGTGGCA<br>GCAGGGCAACGTGTTCAGCTGCAGCGTGATGCACGAGGCCC<br>TGCACAACCACTACACCCAGAAGAGCCTGAGCCTGTCCCCC<br>GGCAAG |
| SEQ ID NO 31: (Kabat) | LCDR1 | | RASQDISNYLN |
| SEQ ID NO 32: (Kabat) | LCDR2 | | YTSRLQS |
| SEQ ID NO 33: (Kabat) | LCDR3 | | QQGKKLWS |
| SEQ ID NO 34:<br>(Chothia) | LCDR1 | | SQDISNY |
| SEQ ID NO 35:<br>(Chothia) | LCDR2 | | YTS |
| SEQ ID NO 36:<br>(Chothia) | LCDR3 | | GKKLW |
| SEQ ID NO 37: | VL | | EIVMTQSPATLSLSPGERATLSCRASQDISNYLNWYQQKPGQA<br>PRLLIYYTSRLQSGIPARFSGSGSGTDYTLTISSLEPEDFAVYYC<br>QQGKKLWSFGGGTKVEIK |
| SEQ ID NO 38: | Light<br>Chain | | EIVMTQSPATLSLSPGERATLSCRASQDISNYLNWYQQKPGQA<br>PRLLIYYTSRLQSGIPARFSGSGSGTDYTLTISSLEPEDFAVYYC<br>QQGKKLWSFGGGTKVEIKRTVAAPSVFIFPPSDEQLKSGTASV<br>VCLLNNFYPREAKVQWKVDNALQSGNSQESVTEQDSKDSTYS<br>LSSTLTLSKADYEKHKVYACEVTHQGLSSPVTKSFNRGEC |
| SEQ ID NO 39: | DNA Light<br>Chain | | GAGATCGTGATGACCCAGAGCCCCGCCACCCTGAGCCTGAG<br>CCCTGGCGAAAGAGCCACCCTGTCCTGCAGAGCCAGCCAGG<br>ACATCAGCAACTACCTGAACTGGTATCAGCAGAAGCCCGGC<br>CAGGCCCCCAGACTGCTGATCTACTACACCAGCCGGCTGCA<br>GAGCGGCATCCCCGCCAGATTTTCTGGCAGCGGCAGCGGCA<br>CCGACTACACCCTGACCATCAGCAGCCTGGAACCCGAGGAC<br>TTCGCCGTGTACTACTGCCAGCAGGGCAAGAAGCTGTGGTC<br>CTTCGGCGGAGGCACCAAGGTGGAAATCAAGCGTACGGTGG<br>CCGCTCCCAGCGTGTTCATCTTCCCCCCCAGCGACGAGCAGC<br>TGAAGAGCGGCACCGCCAGCGTGGTGTGCCTGCTGAACAAC<br>TTCTACCCCCGGGAGGCCAAGGTGCAGTGGAAGGTGGACAA<br>CGCCCTGCAGAGCGGCAACAGCCAGGAGAGCGTCACCGAG<br>CAGGACAGCAAGGACTCCACCTACAGCCTGAGCAGCACCCT<br>GACCCTGAGCAAGGCCGACTACGAGAAGCATAAGGTGTACG<br>CCTGCGAGGTGACCCACCAGGGCCTGTCCAGCCCCGTGACC<br>AAGAGCTTCAACAGGGGCGAGTGC |

NEG026

| | | | |
|---|---|---|---|
| SEQ ID NO 40: (Kabat) | HCDR1 | | DYYMA |
| SEQ ID NO 41: (Kabat) | HCDR2 | | NINQNTGSTYYVDSVQG |
| SEQ ID NO 42: (Kabat) | HCDR3 | | GDYYGTTYWYFDV |
| SEQ ID NO 43:<br>(Chothia) | HCDR1 | | GFTFSDY |
| SEQ ID NO 44:<br>(Chothia) | HCDR2 | | NQNTGS |
| SEQ ID NO 45:<br>(Chothia) | HCDR3 | | GDYYGTTYWYFDV |
| SEQ ID NO 46: | VH | | EVQLVESGGGLVQPGGSLRLSCAASGFTFSDYYMAWVRQAPG<br>KGLEWVANINQNTGSTYYVDSVQGRFTISRDNAKNSLYLQMN<br>SLRAEDTAVYYCARGDYYGTTYWYFDVVVGQGTTVTVSS |
| SEQ ID NO 47: | Heavy<br>Chain | | EVQLVESGGGLVQPGGSLRLSCAASGFTFSDYYMAWVRQAPG<br>KGLEWVANINQNTGSTYYVDSVQGRFTISRDNAKNSLYLQMN<br>SLRAEDTAVYYCARGDYYGTTYWYFDVWGQGTTVTVSSAST<br>KGPSVFPLAPSSKSTSGGTAALGCLVKDYFPEPVTVSWNSGAL<br>TSGVHTFPAVLQSSGLYSLSSVVTVPSSSLGTQTYICNVNHKPS<br>NTKVDKRVEPKSCDKTHTCPPCPAPELLGGPSVFLFPPKPKDTL<br>MISRTPEVTCVVVDVSHEDPEVKFNWYVDGVEVHNAKTKPRE<br>EQYNSTYRVVSVLTVLHQDWLNGKEYKCKVSNKALPAPIEKTI<br>SKAKGQPREPQVYTLPPSREEMTKNQVSLTCLVKGFYPSDIAV<br>EWESNGQPENNYKTTPPVLDSDGSFFLYSKLTVDKSRWQQGN<br>VFSCSVMHEALHNHYTQKSLSLSPGK |
| SEQ ID NO 48: | DNA<br>Heavy<br>Chain | | GAAGTGCAATTGGTGGAAAGCGGCGGAGGCCTGGTGCAGCC<br>TGGCGGCTCTCTGAGACTGAGCTGCGCCGCCAGCGGCTTCA<br>CCTTCAGCGACTACTACATGGCCTGGGTCCGACAGGCCCCT<br>GGCAAGGGCCTGGAATGGGTGGCCAATATCAACCAAAACAC<br>CGGCAGCACCTACTACGTGGACAGCGTGCAAGGCCGGTTCA<br>CCATCAGCCGGGACAACGCCAAGAACAGCCTGTACCTGCAG<br>ATGAACAGCCTGCGGGCCGAGGACACCGCCGTGTACTACTG |

TABLE 3-continued

Examples of anti- cKIT Antibodies

|  |  |  |  |
|---|---|---|---|
|  |  |  | CGCCAGAGGCGATTACTACGGCACCACCTACTGGTACTTCG |
|  |  |  | ACGTGTGGGGCCAGGGCACCACCGTGACCGTCAGCTCAGCT |
|  |  |  | AGCACCAAGGGCCCCAGCGTGTTCCCCCTGGCCCCCAGCAG |
|  |  |  | CAAGAGCACCAGCGGCGGCACAGCCGCCCTGGGCTGCCTGG |
|  |  |  | TGAAGGACTACTTCCCCGAGCCCGTGACCGTGTCCTGGAAC |
|  |  |  | AGCGGAGCCCTGACCTCCGGCGTGCACACCTTCCCCGCCGT |
|  |  |  | GCTGCAGAGCAGCGGCCTGTACAGCCTGTCCAGCGTGGTGA |
|  |  |  | CAGTGCCCAGCAGCAGCCTGGGCACCCAGACCTACATCTGC |
|  |  |  | AACGTGAACCACAAGCCCAGCAACACCAAGGTGGACAAGA |
|  |  |  | GAGTGGAGCCCAAGAGCTGCGACAAGACCCACACCTGCCCC |
|  |  |  | CCCTGCCCAGCCCCAGAGCTGCTGGGCGGACCCTCCGTGTTC |
|  |  |  | CTGTTCCCCCCCAAGCCCAAGGACACCCTGATGATCAGCAG |
|  |  |  | GACCCCCGAGGTGACCTGCGTGGTGGTGGACGTGAGCCACG |
|  |  |  | AGGACCCAGAGGTGAAGTTCAACTGGTACGTGGACGGCGTG |
|  |  |  | GAGGTGCACAACGCCAAGACCAAGCCCAGAGAGGAGCAGT |
|  |  |  | ACAACAGCACCTACAGGGTGGTGTCCGTGCTGACCGTGCTG |
|  |  |  | CACCAGGACTGGCTGAACGGCAAGGAATACAAGTGCAAGG |
|  |  |  | TCTCCAACAAGGCCCTGCCAGCCCCCATCGAAAAGACCATC |
|  |  |  | AGCAAGGCCAAGGGCCAGCCACGGGAGCCCCAGGTGTACA |
|  |  |  | CCCTGCCCCCCTCCCGGGAGGAGATGACCAAGAACCAGGTG |
|  |  |  | TCCCTGACCTGTCTGGTGAAGGGCTTCTACCCCAGCGACATC |
|  |  |  | GCCGTGGAGTGGGAGAGCAACGGCCAGCCCGAGAACAACT |
|  |  |  | ACAAGACCACCCCCCCAGTGCTGGACAGCGACGGCAGCTTC |
|  |  |  | TTCCTGTACAGCAAGCTGACCGTGGACAAGTCCAGGTGGCA |
|  |  |  | GCAGGGCAACGTGTTCAGCTGCAGCGTGATGCACGAGGCCC |
|  |  |  | TGCACAACCACTACACCCAGAAGAGCCTGAGCCTGTCCCCC |
|  |  |  | GGCAAG |
| SEQ ID NO 49: (Kabat) | LCDR1 | RASQDISNYLN |
| SEQ ID NO 50: (Kabat) | LCDR2 | YTSRLQS |
| SEQ ID NO 51: (Kabat) | LCDR3 | QQGKKLWS |
| SEQ ID NO 52: (Chothia) | LCDR1 | SQDISNY |
| SEQ ID NO 53: (Chothia) | LCDR2 | YTS |
| SEQ ID NO 54: (Chothia) | LCDR3 | GKKLW |
| SEQ ID NO 55: | VL | EIVMTQSPATLSLSPGERATLSCRASQDISNYLNWYQQKPGQA PRLLIYYTSRLQSGIPARFSGSGSGTDYTLTISSLEPEDFAVYYC QQGKKLWSFGGGTKVEIK |
| SEQ ID NO 56: | Light Chain | EIVMTQSPATLSLSPGERATLSCRASQDISNYLNWYQQKPGQA PRLLIYYTSRLQSGIPARFSGSGSGTDYTLTISSLEPEDFAVYYC QQGKKLWSFGGGTKVEIKRTVAAPSVFIFPPSDEQLKSGTASV VCLLNNFYPREAKVQWKVDNALQSGNSQE SVTEQDSKDSTYSLSSTLTLSKADYEKHKVYACEVTHQGLSSP VTKSFNRGEC |
| SEQ ID NO 57: | DNA Light Chain | GAGATCGTGATGACCCAGAGCCCCGCCACCCTGAGCCTGAG CCCTGGCGAAAGAGCCACCCTGTCCTGCAGAGCCAGCCAGG ACATCAGCAACTACCTGAACTGGTATCAGCAGAAGCCCGGC CAGGCCCCCAGACTGCTGATCTACTACACCAGCCGGCTGCA GAGCGGCATCCCCGCCAGATTTTCTGGCAGCGGCAGCGGCA CCGACTACACCCTGACCATCAGCAGCCTGGAACCCGAGGAC TTCGCCGTGTACTACTGCCAGCAGGGCAAGAAGCTGTGGTC CTTCGGCGGAGGCACCAAGGTGGAAATCAAGCGTACGGTGG CCGCTCCCAGCGTGTTCATCTTCCCCCCCAGCGACGAGCAGC TGAAGAGCGGCACCGCCAGCGTGGTGTGCCTGCTGAACAAC TTCTACCCCCGGGAGGCCAAGGTGCAGTGGAAGGTGGACAA CGCCCTGCAGAGCGGCAACAGCCAGGAGAGCGTCACCGAG CAGGACAGCAAGGACTCCACCTACAGCCTGAGCAGCACCCT GACCCTGAGCAAGGCCGACTACGAGAAGCATAAGGTGTACG CCTGCGAGGTGACCCACCAGGGCCTGTCCAGCCCCGTGACC AAGAGCTTCAACAGGGGCGAGTGC |

NEG027

| SEQ ID NO 58: (Kabat) | HCDR1 | DYYMA |
| SEQ ID NO 59: (Kabat) | HCDR2 | SINQNTGSTYYLDSVRG |
| SEQ ID NO 60: (Kabat) | HCDR3 | GDYYGTTYWYFDV |
| SEQ ID NO 61: (Chothia) | HCDR1 | GFTFSDY |
| SEQ ID NO 62: (Chothia) | HCDR2 | NQNTGS |
| SEQ ID NO 63: (Chothia) | HCDR3 | GDYYGTTYWYFDV |
| SEQ ID NO 64: | VH | EVQLVESGGGLVQPGGSLRLSCAASGFTFSDYYMAWVRQAPG KGLEWVASINQNTGSTYYLDSVRGRFTISRDNAKNSLYLQMNS LRAEDTAVYYCARGDYYGTTYWYFDVWGQGTTVTVSS |
| SEQ ID NO 65: | Heavy Chain | EVQLVESGGGLVQPGGSLRLSCAASGFTFSDYYMAWVRQAPG KGLEWVASINQNTGSTYYLDSVRGRFTISRDNAKNSLYLQMNS |

TABLE 3-continued

Examples of anti- cKIT Antibodies

| | | |
|---|---|---|
| | | LRAEDTAVYYCARGDYYGTTYWYFDVWGQGTTVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNT KVDKRVEPKSCDKTHTCPPCPAPELLGGPSVFLFPPKPKDTLMI SRTPEVTCVVVDVSHEDPEVKFNWYVDGVEVHNAKTKPREEQ YNSTYRVVSVLTVLHQDWLNGKEYKCKVSNKALPAPIEKTISK AKGQPREPQVYTLPPSREEMTKNQVSLTCLVKGFYPSDIAVEW ESNGQPENNYKTTPPVLDSDGSFFLYSKLTVDKSRWQQGNVFS CSVMHEALHNHYTQKSLSLSPGK |
| SEQ ID NO 66: | DNA Heavy Chain | GAAGTGCAATTGGTGGAAAGCGGCGGAGGCCTGGTGCAGCC TGGCGGCTCTCTGAGACTGAGCTGTGCCGCCAGCGGCTTCA CCTTCAGCGACTACTACATGGCCTGGGTCCGACAGGCCCCT GGCAAGGGCCTGGAATGGGTGGCCAGTATCAACCAAAACAC CGGCAGCACCTACTACCTGGACAGCGTGCGAGGCCGGTTCA CCATCAGCCGGGACAACGCCAAGAACAGCCTGTACCTGCAG ATGAACAGCCTGCGGGCCGAGGACACCGCCGTGTACTACTG CGCCAGAGGCGATTACTACGGCACCACCTACTGGTACTTCG ACGTGTGGGGCCAGGGCACCACCGTGACCGTCAGCTCAGCT AGCACCAAGGGCCCCAGCGTGTTCCCCCTGGCCCCCAGCAG CAAGAGCACCAGCGGCGGCACAGCCGCCCTGGGCTGCCTGG TGAAGGACTACTTCCCCGAGCCCGTGACCGTGTCCTGGAAC AGCGGAGCCCTGACCTCCGGCGTGCACACCTTCCCCGCCGT GCTGCAGAGCAGCGGCCTGTACAGCCTGTCCAGCGTGGTGA CAGTGCCCAGCAGCAGCCTGGGCACCCAGACCTACATCTGC AACGTGAACCACAAGCCCAGCAACACCAAGGTGGACAAGA GAGTGGAGCCCAAGAGCTGCGACAAGACCCACACCTGCCCC CCCTGCCCAGCCCCAGAGCTGCTGGGCGGACCCTCCGTGTTC CTGTTCCCCCCCAAGCCCAAGGACACCCTGATGATCAGCAG GACCCCCGAGGTGACCTGCGTGGTGGTGGACGTGAGCCACG AGGACCCAGAGGTGAAGTTCAACTGGTACGTGGACGGCGTG GAGGTGCACAACGCCAAGACCAAGCCCAGAGAGGAGCAGT ACAACAGCACCTACAGGGTGGTGTCCGTGCTGACCGTGCTG CACCAGGACTGGCTGAACGGCAAGGAATACAAGTGCAAGG TCTCCAACAAGGCCCTGCCAGCCCCCATCGAAAAGACCATC AGCAAGGCCAAGGGCCAGCCACGGGAGCCCCAGGTGTACA CCCTGCCCCCCTCCCGGGAGGAGATGACCAAGAACCAGGTG TCCCTGACCTGTCTGGTGAAGGGCTTCTACCCCAGCGACATC GCCGTGGAGTGGGAGAGCAACGGCCAGCCCGAGAACAACT ACAAGACCACCCCCCCAGTGCTGGACAGCGACGGCAGCTTC TTCCTGTACAGCAAGCTGACCGTGGACAAGTCCAGGTGGCA GCAGGGCAACGTGTTCAGCTGCAGCGTGATGCACGAGGCCC TGCACAACCACTACACCCAGAAGAGCCTGAGCCTGTCCCCC GGCAAG |
| SEQ ID NO 67: (Kabat) | LCDR1 | RASQDISNYLN |
| SEQ ID NO 68: (Kabat) | LCDR2 | YTSRLQS |
| SEQ ID NO 69: (Kabat) | LCDR3 | QQGKKLWS |
| SEQ ID NO 70: (Chothia) | LCDR1 | SQDISNY |
| SEQ ID NO 71: (Chothia) | LCDR2 | YTS |
| SEQ ID NO 72: (Chothia) | LCDR3 | GKKLW |
| SEQ ID NO 73: | VL | EIVMTQSPATLSLSPGERATLSCRASQDISNYLNWYQQKPGQA PRLLIYYTSRLQSGIPARFSGSGSGTDYTLTISSLEPEDFAVYYC QQGKKLWSFGGGTKVEIK |
| SEQ ID NO 74: | Light Chain | EIVMTQSPATLSLSPGERATLSCRASQDISNYLNWYQQKPGQA PRLLIYYTSRLQSGIPARFSGSGSGTDYTLTISSLEP EDFAVYYCQQGKKLWSFGGGTKVEIKRTVAAPSVFIFPPSDEQ LKSGTASVVCLLNNFYPREAKVQWKVDNALQSGNSQESVTEQ DSKDSTYSLSSTLTLSKADYEKHKVYACEVTHQGLSSPVTKSF NRGEC |
| SEQ ID NO 75: | DNA Light Chain | GAGATCGTGATGACCCAGAGCCCCGCCACCCTGAGCCTGAG CCCTGGCGAAAGAGCCACCCTGTCCTGCAGAGCCAGCCAGG ACATCAGCAACTACCTGAACTGGTATCAGCAGAAGCCCGGC CAGGCCCCCAGACTGCTGATCTACTACACCAGCCGGCTGCA GAGCGGCATCCCCGCCAGATTTTCTGGCAGCGGCAGCGGCA CCGACTACACCCTGACCATCAGCAGCCTGGAACCCGAGGAC TTCGCCGTGTACTACTGCCAGCAGGGCAAGAAGCTGTGGTC CTTCGGCGGAGGCACCAAGGTGGAAATCAAGCGTACGGTGG CCGCTCCCAGCGTGTTCATCTTCCCCCCCAGCGACGAGCAGC TGAAGAGCGGCACCGCCAGCGTGGTGTGCCTGCTGAACAAC TTCTACCCCCGGGAGGCCAAGGTGCAGTGGAAGGTGGACAA CGCCCTGCAGAGCGGCAACAGCCAGGAGAGCGTCACCGAG CAGGACAGCAAGGACTCCACCTACAGCCTGAGCAGCACCCT GACCCTGAGCAAGGCCGACTACGAGAAGCATAAGGTGTACG CCTGCGAGGTGACCCACCAGGGCCTGTCCAGCCCCGTGACC AAGAGCTTCAACAGGGGCGAGTGC |

TABLE 3-continued

Examples of anti- cKIT Antibodies

NEG085

| SEQ ID NO 76: (Kabat) | HCDR1 | GYYMA |
|---|---|---|
| SEQ ID NO 77: (Kabat) | HCDR2 | NINYPGSSTYYLDSVKG |
| SEQ ID NO 78: (Kabat) | HCDR3 | GDYYGTTYWYFDV |
| SEQ ID NO 79: (Chothia) | HCDR1 | GFAFSGY |
| SEQ ID NO 80: (Chothia) | HCDR2 | NYPGSS |
| SEQ ID NO 81: (Chothia) | HCDR3 | GDYYGTTYWYFDV |
| SEQ ID NO 82: | VH | EVQLVESGGGLVQPGGSLRLSCAASGFAFSGYYMAWVRQAPG KGLEWVANINYPGSSTYYLDSVKGRFTISRDNAKNSLYLQMNS LRAEDTAVYYCARGDYYGTTYWYFDVVVGQGTTVTVSS |
| SEQ ID NO 83: | Heavy Chain | EVQLVESGGGLVQPGGSLRLSCAASGFAFSGYYMAWVRQAPG KGLEWVANINYPGSSTYYLDSVKGRFTISRDNAKNSLYLQMNS LRAEDTAVYYCARGDYYGTTYWYFDVWGQGTTVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNT KVDKRVEPKSCDKTHTCPPCPAPELLGGPSVFLFPPKPKDTLMI SRTPEVTCVVVDVSHEDPEVKFNWYVDGVEVHNAKTKPREEQ YNSTYRVVSVLTVLHQDWLNGKEYKCKVSNKALPAPIEKTISK AKGQPREPQVYTLPPSREEMTKNQVSLTCLVKGFYPSDIAVEW ESNGQPENNYKTTPPVLDSDGSFFLYSKLTVDKSRWQQGNVFS CSVMHEALHNHYTQKSLSLSPGK |
| SEQ ID NO 84: | DNA Heavy Chain | GAAGTGCAATTGGTGGAAAGCGGCGGAGGCCTGGTGCAGCC TGGCGGCTCTCTGAGACTGAGCTGTGCCGCCAGCGGCTTCG CCTTCAGCGGCTACTACATGGCCTGGGTCCGACAGGCCCCT GGCAAGGGCCTGGAATGGGTGGCCAACATCAACTACCCCGG CAGCAGCACCTACTACCTGGACAGCGTGAAGGGCCGGTTCA CCATCAGCCGGGACAACGCCAAGAACAGCCTGTACCTGCAG ATGAACAGCCTGCGGGCCGAGGACACCGCCGTGTACTACTG CGCCAGAGGCGATTACTACGGCACCACCTACTGGTACTTCG ACGTGTGGGGCCAGGGCACCACCGTGACCGTCAGCTCAGCT AGCACCAAGGGCCCCAGCGTGTTCCCCCTGGCCCCCAGCAG CAAGAGCACCAGCGGCGGCACAGCCGCCCTGGGCTGCCTGG TGAAGGACTACTTCCCCGAGCCCGTGACCGTGTCCTGGAAC AGCGGAGCCCTGACCTCCGGCGTGCACACCTTCCCCGCCGT GCTGCAGAGCAGCGGCCTGTACAGCCTGTCCAGCGTGGTGA CAGTGCCCAGCAGCAGCCTGGGCACCCAGACCTACATCTGC AACGTGAACCACAAGCCCAGCAACACCAAGGTGGACAAGA GAGTGGAGCCCAAGAGCTGCGACAAGACCCACACCTGCCCC CCCTGCCCAGCCCCAGAGCTGCTGGGCGGACCCTCCGTGTTC CTGTTCCCCCCCAAGCCCAAGGACACCCTGATGATCAGCAG GACCCCCGAGGTGACCTGCGTGGTGGTGGACGTGAGCCACG AGGACCCAGAGGTGAAGTTCAACTGGTACGTGGACGGCGTG GAGGTGCACAACGCCAAGACCAAGCCCAGAGAGGAGCAGT ACAACAGCACCTACAGGGTGGTGTCCGTGCTGACCGTGCTG CACCAGGACTGGCTGAACGGCAAGGAATACAAGTGCAAGG TCTCCAACAAGGCCCTGCCAGCCCCCATCGAAAAGACCATC AGCAAGGCCAAGGGCCAGCCACGGGAGCCCCAGGTGTACA CCCTGCCCCCCTCCCGGGAGGAGATGACCAAGAACCAGGTG TCCCTGACCTGTCTGGTGAAGGGCTTCTACCCCAGCGACATC GCCGTGGAGTGGGAGAGCAACGGCCAGCCCGAGAACAACT ACAAGACCACCCCCCCAGTGCTGGACAGCGACGGCAGCTTC TTCCTGTACAGCAAGCTGACCGTGGACAAGTCCAGGTGGCA GCAGGGCAACGTGTTCAGCTGCAGCGTGATGCACGAGGCCC TGCACAACCACTACACCCAGAAGAGCCTGAGCCTGTCCCCC GGCAAG |
| SEQ ID NO 85: (Kabat) | LCDR1 | RASQSISSYLN |
| SEQ ID NO 86: (Kabat) | LCDR2 | YTSRLQS |
| SEQ ID NO 87: (Kabat) | LCDR3 | QQGRRLWS |
| SEQ ID NO 88: (Chothia) | LCDR1 | SQSISSY |
| SEQ ID NO 89: (Chothia) | LCDR2 | YTS |
| SEQ ID NO 90: (Chothia) | LCDR3 | GRRLW |
| SEQ ID NO 91: | VL | DIQMTQSPSSLSASVGDRVTITCRASQSISSYLNWYQQKPGKAP KLLIYYTSRLQSGVPSRFSGSGSGTDFTLTISSLQPEDFATYYCQ QGRRLWSFGGGTKVEIK |
| SEQ ID NO 92: | Light Chain | DIQMTQSPSSLSASVGDRVTITCRASQSISSYLNWYQQKPGKAP KLLIYYTSRLQSGVPSRFSGSGSGTDFTLTISSLQPEDFATYYCQ QGRRLWSFGGGTKVEIKRTVAAPSVFIFPPSDEQLKSGTASVVC LLNNFYPREAKVQWKVDNALQSGNSQESVTEQDSKDSTYSLS STLTLSKADYEKHKVYACEVTHQGLSSPVTKSFNRGEC |
| SEQ ID NO 93: | DNA Light Chain | GATATCCAGATGACCCAGAGCCCCAGCAGCCTGAGCGCCAG CGTGGGCGACAGAGTGACCATCACCTGTCGGGCCAGCCAGA |

TABLE 3-continued

Examples of anti- cKIT Antibodies

```
GCATCAGCAGCTACCTGAACTGGTATCAGCAGAAGCCCGGC
AAGGCCCCCAAGCTGCTGATCTACTACACCAGCCGGCTGCA
GAGCGGCGTGCCCAGCAGATTTTCTGGCAGCGGCAGCGGCA
CCGACTTCACCCTGACCATCAGCAGCCTGCAGCCCGAGGAC
TTCGCCACCTACTACTGCCAGCAGGGCCGCCGCCTGTGGTCC
TTCGGCGGAGGCACCAAGGTGGAAATCAAGCGTACGGTGGC
CGCTCCCAGCGTGTTCATCTTCCCCCCCAGCGACGAGCAGCT
GAAGAGCGGCACCGCCAGCGTGGTGTGCCTGCTGAACAACT
TCTACCCCGGGAGGCCAAGGTGCAGTGGAAGGTGGACAAC
GCCCTGCAGAGCGGCAACAGCCAGGAGAGCGTCACCGAGC
AGGACAGCAAGGACTCCACCTACAGCCTGAGCAGCACCCTG
ACCCTGAGCAAGGCCGACTACGAGAAGCATAAGGTGTACGC
CTGCGAGGTGACCCACCAGGGCCTGTCCAGCCCCGTGACCA
AGAGCTTCAACAGGGGCGAGTGC
```

NEG086

| | | |
|---|---|---|
| SEQ ID NO 94: (Kabat) | HCDR1 | DYYMA |
| SEQ ID NO 95: (Kabat) | HCDR2 | NINQIAGSTYYVDSVQG |
| SEQ ID NO 96: (Kabat) | HCDR3 | GDYYGTTYWYFDV |
| SEQ ID NO 97: (Chothia) | HCDR1 | GFTFSDY |
| SEQ ID NO 98: (Chothia) | HCDR2 | NQIAGS |
| SEQ ID NO 99: (Chothia) | HCDR3 | GDYYGTTYWYFDV |
| SEQ ID NO 100: | VH | EVQLVESGGGLVQPGGSLRLSCAASGFTFSDYYMAWVRQAPG KGLEWVANINQIAGSTYYVDSVQGRFTISRDNAKNSLYLQMNS LRAEDTAVYYCARGDYYGTTYWYFDVWGQGTTVTVSS |
| SEQ ID NO 101: | Heavy Chain | EVQLVESGGGLVQPGGSLRLSCAASGFTFSDYYMAWVRQAPG KGLEWVANINQIAGSTYYVDSVQGRFTISRDNAKNSLYLQMNS LRAEDTAVYYCARGDYYGTTYWYFDVWGQGTTVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNT KVDKRVEPKSCDKTHTCPPCPAPELLGGPSVFLFPPKPKDTLMI SRTPEVTCVVVDVSHEDPEVKFNWYVDGVEVHNAKTKPREEQ YNSTYRVVSVLTVLHQDWLNGKEYKCKVSNKALPAPIEKTISK AKGQPREPQVYTLPPSREEMTKNQVSLTCLVKGFYPSDIAVEW ESNGQPENNYKTTPPVLDSDGSFFLYSKLTVDKSRWQQGNVFS CSVMHEALHNHYTQKSLSLSPGK |
| SEQ ID NO 102: | DNA Heavy Chain | GAAGTGCAATTGGTGGAAAGCGGCGGAGGCCTGGTGCAGCC TGGCGGCTCTCTGAGACTGAGCTGTGCCGCCAGCGGCTTCA CCTTCAGCGACTACTACATGGCCTGGGTCCGACAGGCCCCT GGCAAGGGCCTGGAATGGGTGGCCAATATCAACCAAATCGC CGGCAGCACCTACTACGTGGACAGCGTGCAAGGCCGGTTCA CCATCAGCCGGGACAACGCCAAGAACAGCCTGTACCTGCAG ATGAACAGCCTGCGGGCCGAGGACACCGCCGTGTACTACTG CGCCAGAGGCGATTACTACGGCACCACCTACTGGTACTTCG ACGTGTGGGGCCAGGGCACCACCGTGACCGTCAGCTCAGCT AGCACCAAGGGCCCCAGCGTGTTCCCCCTGGCCCCCAGCAG CAAGAGCACCAGCGGCGGCACAGCCGCCCTGGGCTGCCTGG TGAAGGACTACTTCCCCGAGCCCGTGACCGTGTCCTGGAAC AGCGGAGCCCTGACCTCCGGCGTGCACACCTTCCCCGCCGT GCTGCAGAGCAGCGGCCTGTACAGCCTGTCCAGCGTGGTGA CAGTGCCCAGCAGCAGCCTGGGCACCCAGACCTACATCTGC AACGTGAACCACAAGCCCAGCAACACCAAGGTGGACAAGA GAGTGGAGCCCAAGAGCTGCGACAAGACCCACACCTGCCCC CCCTGCCCAGCCCCAGAGCTGCTGGGCGGACCCTCCGTGTTC CTGTTCCCCCCCAAGCCCAAGGACACCCTGATGATCAGCAG GACCCCCGAGGTGACCTGCGTGGTGGTGGACGTGAGCCACG AGGACCCAGAGGTGAAGTTCAACTGGTACGTGGACGGCGTG GAGGTGCACAACGCCAAGACCAAGCCCAGAGAGGAGCAGT ACAACAGCACCTACAGGGTGGTGTCCGTGCTGACCGTGCTG CACCAGGACTGGCTGAACGGCAAGGAATACAAGTGCAAGG TCTCCAACAAGGCCCTGCCAGCCCCCATCGAAAAGACCATC AGCAAGGCCAAGGGCCAGCCACGGGAGCCCCAGGTGTACA CCCTGCCCCCCTCCCGGGAGGAGATGACCAAGAACCAGGTG TCCCTGACCTGTCTGGTGAAGGGCTTCTACCCCAGCGACATC GCCGTGGAGTGGGAGAGCAACGGCCAGCCCGAGAACAACT ACAAGACCACCCCCCCAGTGCTGGACAGCGACGGCAGCTTC TTCCTGTACAGCAAGCTGACCGTGGACAAGTCCAGGTGGCA GCAGGGCAACGTGTTCAGCTGCAGCGTGATGCACGAGGCCC TGCACAACCACTACACCCAGAAGAGCCTGAGCCTGTCCCCC GGCAAG |

TABLE 3-continued

Examples of anti-cKIT Antibodies

| SEQ ID NO 103: (Kabat) | LCDR1 | RASQSISSYLN |
|---|---|---|
| SEQ ID NO 104: (Kabat) | LCDR2 | YTSRLQS |
| SEQ ID NO 105: (Kabat) | LCDR3 | QQGRRLWS |
| SEQ ID NO 106: (Chothia) | LCDR1 | SQSISSY |
| SEQ ID NO 107: (Chothia) | LCDR2 | YTS |
| SEQ ID NO 108: (Chothia) | LCDR3 | GRRLW |
| SEQ ID NO 109: | VL | DIQMTQSPSSLSASVGDRVTITCRASQSISSYLNWYQQKPGKAP KLLIYYTSRLQSGVPSRFSGSGSGTDFTLTISSLQPEDFATYYCQ QGRRLWSFGGGTKVEIK |
| SEQ ID NO 110: | Light Chain | DIQMTQSPSSLSASVGDRVTITCRASQSISSYLNWYQQKPGKAP KLLIYYTSRLQSGVPSRFSGSGSGTDFTLTISSLQPEDFATYYCQ QGRRLWSFGGGTKVEIKRTVAAPSVFIFPPSDEQLKSGTASVVC LLNNFYPREAKVQWKVDNALQSGNSQESVTEQDSKDSTYSLS STLTLSKADYEKHKVYACEVTHQGLSSPVTKSFNRGEC |
| SEQ ID NO 111: | DNA Light Chain | GATATCCAGATGACCCAGAGCCCCAGCAGCCTGAGCGCCAG CGTGGGCGACAGAGTGACCATCACCTGTCGGGCCAGCCAGA GCATCAGCAGCTACCTGAACTGGTATCAGCAGAAGCCCGGC AAGGCCCCCAAGCTGCTGATCTACTACACCAGCCGGCTGCA GAGCGGCGTGCCCAGCAGATTTTCTGGCAGCGGCAGCGGCA CCGACTTCACCCTGACCATCAGCAGCCTGCAGCCCGAGGAC TTCGCCACCTACTACTGCCAGCAGGGCCGCCGCCTGTGGTCC TTCGGCGGAGGCACCAAGGTGGAAATCAAGCGTACGGTGGC CGCTCCCAGCGTGTTCATCTTCCCCCCCAGCGACGAGCAGCT GAAGAGCGGCACCGCCAGCGTGGTGTGCCTGCTGAACAACT TCTACCCCCGGGAGGCCAAGGTGCAGTGGAAGGTGGACAAC GCCCTGCAGAGCGGCAACAGCCAGGAGAGCGTCACCGAGC AGGACAGCAAGGACTCCACCTACAGCCTGAGCAGCACCCTG ACCCTGAGCAAGGCCGACTACGAGAAGCATAAGGTGTACGC CTGCGAGGTGACCCACCAGGGCCTGTCCAGCCCCGTGACCA AGAGCTTCAACAGGGGCGAGTGC |

NEG087

| SEQ ID NO 112: (Kabat) | HCDR1 | DYYMA |
|---|---|---|
| SEQ ID NO 113: (Kabat) | HCDR2 | SINQNTGSTYYLDSVRG |
| SEQ ID NO 114: (Kabat) | HCDR3 | GDYYGTTYVVYFDV |
| SEQ ID NO 115: (Chothia) | HCDR1 | GFTFSDY |
| SEQ ID NO 116: (Chothia) | HCDR2 | NQNTGS |
| SEQ ID NO 117: (Chothia) | HCDR3 | GDYYGTTYWYFDV |
| SEQ ID NO 118: | VH | EVQLVESGGGLVQPGGSLRLSCAASGFTFSDYYMAWVRQAPG KGLEWVASINQNTGSTYYLDSVRGRFTISRDNAKNSLYLQMNS LRAEDTAVYYCARGDYYGTTYWYFDVWGQGTTVTVSS |
| SEQ ID NO 119: | Heavy Chain | EVQLVESGGGLVQPGGSLRLSCAASGFTFSDYYMAWVRQAPG KGLEWVASINQNTGSTYYLDSVRGRFTISRDNAKNSLYLQMNS LRAEDTAVYYCARGDYYGTTYWYFDVWGQGTTVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNT KVDKRVEPKSCDKTHTCPPCPAPELLGGPSVFLFPPKPKDTLMI SRTPEVTCVVVDVSHEDPEVKFNWYVDGVEVHNAKTKPREEQ YNSTYRVVSVLTVLHQDWLNGKEYKCKVSNKALPAPIEKTISK AKGQPREPQVYTLPPSREEMTKNQVSLTCLVKGFYPSDIAVEW ESNGQPENNYKTTPPVLDSDGSFFLYSKLTVDKSRWQQGNVFS CSVMHEALHNHYTQKSLSLSPGK |
| SEQ ID NO 120: | DNA Heavy Chain | GAAGTGCAATTGGTGGAAAGCGGCGGAGGCCTGGTGCAGCC TGGCGGCTCTCTGAGACTGAGCTGTGCCGCCAGCGGCTTCA CCTTCAGCGACTACTACATGGCCTGGGTCCGACAGGCCCCT GGCAAGGGCCTGGAATGGGTGGCCAGTATCAACCAAAACAC CGGCAGCACCTACTACCTGGACAGCGTGCGAGGCCGGTTCA CCATCAGCCGGGACAACGCCAAGAACAGCCTGTACCTGCAG ATGAACAGCCTGCGGGCCGAGGACACCGCCGTGTACTACTG CGCCAGAGGCGATTACTACGGCACCACCTACTGGTACTTCG ACGTGTGGGGCCAGGGCACCACCGTGACCGTCAGCTCAGCT AGCACCAAGGGCCCCAGCGTGTTCCCCCTGGCCCCCAGCAG CAAGAGCACCAGCGGCGGCACAGCCGCCCTGGGCTGCCTGG TGAAGGACTACTTCCCCGAGCCCGTGACCGTGTCCTGGAAC AGCGGAGCCCTGACCTCCGGCGTGCACACCTTCCCCGCCGT GCTCCAGAGCAGCGGCCTGTACAGCCTGAGCAGCGTGGTGA CAGTGCCCAGCAGCAGCCTGGGCACCCAGACCTACATCTGC AACGTGAACCACAAGCCCAGCAACACCAAGGTGGACAAGA GAGTGGAGCCCAAGAGCTGCGACAAGACCCACACCTGCCCC CCCTGCCCAGCCCCAGAGCTGCTGGGCGGACCCTCCGTGTTC CTGTTCCCCCCCAAGCCCAAGGACACCCTGATGATCAGCAG |

TABLE 3-continued

Examples of anti- cKIT Antibodies

| | | | |
|---|---|---|---|
| | | | GACCCCCGAGGTGACCTGCGTGGTGGTGGACGTGAGCCACG
AGGACCCAGAGGTGAAGTTCAACTGGTACGTGGACGGCGTG
GAGGTGCACAACGCCAAGACCAAGCCCAGAGAGGAGCAGT
ACAACAGCACCTACAGGGTGGTGTCCGTGCTGACCGTGCTG
CACCAGGACTGGCTGAACGGCAAGGAATACAAGTGCAAGG
TCTCCAACAAGGCCCTGCCAGCCCCCATCGAAAAGACCATC
AGCAAGGCCAAGGGCCAGCCACGGGAGCCCCAGGTGTACA
CCCTGCCCCCCTCCCGGGAGGAGATGACCAAGAACCAGGTG
TCCCTGACCTGTCTGGTGAAGGGCTTCTACCCCAGCGACATC
GCCGTGGAGTGGGAGAGCAATGGCCAGCCCGAGAACAACT
ACAAGACCACCCCCCCAGTGCTGGACAGCGACGGCAGCTTC
TTCCTGTACAGCAAGCTGACCGTGGACAAGTCCAGGTGGCA
GCAGGGCAACGTGTTCAGCTGCAGCGTGATGCACGAGGCCC
TGCACAACCACTACACCCAGAAGAGCCTGAGCCTGTCCCCC
GGCAAG |
| SEQ ID NO 121: | (Kabat) | LCDR1 | RASQSISSYLN |
| SEQ ID NO 122: | (Kabat) | LCDR2 | YTSRLQS |
| SEQ ID NO 123: | (Kabat) | LCDR3 | QQGRRLWS |
| SEQ ID NO 124: (Chothia) | | LCDR1 | SQSISSY |
| SEQ ID NO 125: (Chothia) | | LCDR2 | YTS |
| SEQ ID NO 126: (Chothia) | | LCDR3 | GRRLW |
| SEQ ID NO 127: | | VL | DIQMTQSPSSLSASVGDRVTITCRASQSISSYLNWYQQKPGKAP
KLLIYYTSRLQSGVPSRFSGSGSGTDFTLTISSLQPEDFATYYCQ
QGRRLWSFGGGTKVEIK |
| SEQ ID NO 128: | | Light Chain | DIQMTQSPSSLSASVGDRVTITCRASQSISSYLNWYQQKPGKAP
KLLIYYTSRLQSGVPSRFSGSGSGTDFTLTISSLQPEDFATYYCQ
QGRRLWSFGGGTKVEIKRTVAAPSVFIFPPSDEQLKSGTASVVC
LLNNFYPREAKVQWKVDNALQSGNSQESVTEQDSKDSTYSLS
STLTLSKADYEKHKVYACEVTHQGLSSPVTKSFNRGEC |
| SEQ ID NO 129: | | DNA Light Chain | GATATCCAGATGACCCAGAGCCCCAGCAGCCTGAGCGCCAG
CGTGGGCGACAGAGTGACCATCACCTGTCGGGCCAGCCAGA
GCATCAGCAGCTACCTGAACTGGTATCAGCAGAAGCCCGGC
AAGGCCCCCAAGCTGCTGATCTACTACACCAGCCGGCTGCA
GAGCGGCGTGCCCAGCAGATTTTCTGGCAGCGGCAGCGGCA
CCGACTTCACCCTGACCATCAGCAGCCTGCAGCCCGAGGAC
TTCGCCACCTACTACTGCCAGCAGGGCCGCCGCCTGTGGTCC
TTCGGCGGAGGCACCAAGGTGGAAATCAAGCGTACGGTGGC
CGCTCCCAGCGTGTTCATCTTCCCCCCCAGCGACGAGCAGCT
GAAGAGCGGCACCGCCAGCGTGGTGTGCCTGCTGAACAACT
TCTACCCCCGGGAGGCCAAGGTGCAGTGGAAGGTGGACAAC
GCCCTGCAGAGCGGCAACAGCCAGGAGAGCGTCACCGAGC
AGGACAGCAAGGACTCCACCTACAGCCTGAGCAGCACCCTG
ACCCTGAGCAAGGCCGACTACGAGAAGCATAAGGTGTACGC
CTGCGAGGTGACCCACCAGGGCCTGTCCAGCCCCGTGACCA
AGAGCTTCAACAGGGGCGAGTGC |

20376

| | | | |
|---|---|---|---|
| SEQ ID NO 130: | (Kabat) | HCDR1 | SYAIS |
| SEQ ID NO 131: | (Kabat) | HCDR2 | GIIPMSGRTTYAQKFQG |
| SEQ ID NO 132: | (Kabat) | HCDR3 | DYGPEAPDYGQSTSYFWYYAFDP |
| SEQ ID NO 133: (Chothia) | | HCDR1 | GGTFSSY |
| SEQ ID NO 134: (Chothia) | | HCDR2 | IPMSGR |
| SEQ ID NO 135: (Chothia) | | HCDR3 | DYGPEAPDYGQSTSYFWYYAFDP |
| SEQ ID NO 136: | | VH | QVQLVQSGAEVKKPGSSVKVSCKASGGTFSSYAISWVRQAPG
QGLEWMGGIIPMSGRTTYAQKFQGRVTITADESTSTAYMELSS
LRSEDTAVYYCARDYGPEAPDYGQSTSYFWYYAFDPWGQGTL
VTVSS |
| SEQ ID NO 137: | | Heavy Chain | QVQLVQSGAEVKKPGSSVKVSCKASGGTFSSYAISWVRQAPG
QGLEWMGGIIPMSGRTTYAQKFQGRVTITADESTSTAYMELSS
LRSEDTAVYYCARDYGPEAPDYGQSTSYFWYYAFDPWGQGTL
VTVSSASTKGPSVFPLAPSSKSTSGGTAALGCLVKDYFPEPVTV
SWNSGALTSGVHTFPAVLQSSGLYSLSSVVTVPSSSLGTQTYIC
NVNHKPSNTKVDKRVEPKSCDKTHTCPPCPAPELLGGPSVFLFP
PKPKDTLMISRTPEVTCVVVDVSHEDPEVKFNWYVDGVEVHN
AKTKPREEQYNSTYRVVSVLTVLHQDWLNGKEYKCKVSNKA
LPAPIEKTISKAKGQPREPQVYTLPPSREEMTKNQVSLTCLVKG
FYPSDIAVEWESNGQPENNYKTTPPVLDSDGSFFLYSKLTVDKS
RWQQGNVFSCSVMHEALHNHYTQKSLSLSPGK |
| SEQ ID NO 138: | | DNA Heavy Chain | CAGGTGCAGCTGGTGCAGTCAGGCGCCGAAGTGAAGAAACC
CGGCTCTAGCGTGAAAGTCAGCTGTAAAGCTAGTGGGGGCA
CCTTCTCTAGCTACGCTATTAGCTGGGTCAGACAGGCCCCAG |

TABLE 3-continued

Examples of anti- cKIT Antibodies

|  |  |  |
|---|---|---|
|  |  | GTCAAGGCTTGGAGTGGATGGGCGGAATTATCCCTATGAGC<br>GGTAGAACTACCTACGCTCAGAAATTTCAGGGTAGAGTGAC<br>TATCACCGCCGACGAGTCTACTAGCACCGCCTATATGGAAC<br>TGAGTTCTCTGAGGTCAGAGGACACCGCCGTCTACTACTGC<br>GCTAGAGACTACGGCCCCGAGGCCCCCGACTACGGTCAATC<br>AACTAGCTACTTCTGGTACTACGCCTTCGACCCTTGGGGTCA<br>AGGCACCCTGGTCACCGTGTCTTCAGCTAGCACTAAGGGCC<br>CAAGTGTGTTTCCCCTGGCCCCCAGCAGCAAGTCTACTTCCG<br>GCGGAACTGCTGCCCTGGGTTGCCTGGTGAAGGACTACTTC<br>CCCGAGCCCGTGACAGTGTCCTGGAACTCTGGGGCTCTGAC<br>TTCCGGCGTGCACACCTTCCCCGCCGTGCTGCAGAGCAGCG<br>GCCTGTACAGCCTGAGCAGCGTGGTGACAGTGCCCTCCAGC<br>TCTCTGGGAACCCAGACCTATATCTGCAACGTGAACCACAA<br>GCCCAGCAACACCAAGGTGGACAAGAGAGTGGAGCCCAAG<br>AGCTGCGACAAGACCCACACCTGCCCCCCCTGCCCAGCTCC<br>AGAACTGCTGGGAGGGCCTTCCGTGTTCCTGTTCCCCCCCAA<br>GCCCAAGGACACCCTGATGATCAGCAGGACCCCCGAGGTGA<br>CCTGCGTGGTGGTGGACGTGTCCCACGAGGACCCAGAGGTG<br>AAGTTCAACTGGTACGTGGACGGCGTGGAGGTGCACAACGC<br>CAAGACCAAGCCCAGAGAGGAGCAGTACAACAGCACCTAC<br>AGGGTGGTGTCCGTGCTGACCGTGCTGCACCAGGACTGGCT<br>GAACGGCAAAGAATACAAGTGCAAAGTCTCCAACAAGGCC<br>CTGCCAGCCCCAATCGAAAAGACAATCAGCAAGGCCAAGG<br>GCCAGCCACGGGAGCCCCAGGTGTACACCCTGCCCCCCAGC<br>CGGGAGGAGATGACCAAGAACCAGGTGTCCCTGACCTGTCT<br>GGTGAAGGGCTTCTACCCCAGCGATATCGCCGTGGAGTGGG<br>AGAGCAACGGCCAGCCCGAGAACAACTACAAGACCACCCC<br>CCCAGTGCTGGACAGCGACGGCAGCTTCTTCCTGTACAGCA<br>AGCTGACCGTGGACAAGTCCAGGTGGCAGCAGGGCAACGTG<br>TTCAGCTGCAGCGTGATGCACGAGGCCCTGCACAACCACTA<br>CACCCAGAAGTCCCTGAGCCTGAGCCCCGGCAAG |
| SEQ ID NO 139: (Kabat) | LCDR1 | SGDNIPSYFVH |
| SEQ ID NO 140: (Kabat) | LCDR2 | DDNDRPS |
| SEQ ID NO 141: (Kabat) | LCDR3 | SSWDQDTVV |
| SEQ ID NO 142: (Chothia) | LCDR1 | DNIPSYF |
| SEQ ID NO 143: (Chothia) | LCDR2 | DDN |
| SEQ ID NO 144: (Chothia) | LCDR3 | WDQDTV |
| SEQ ID NO 145: | VL | DIELTQPPSVSVSPGQTASITCSGDNIPSYFVHWYQQKPGQAPV<br>LVIYDDNDRPSGIPERFSGSNSGNTATLTISGTQAEDEADYYCSS<br>WDQDTVVFGGGTKLTVL |
| SEQ ID NO 146: | Light Chain | DIELTQPPSVSVSPGQTASITCSGDNIPSYFVHWYQQKPGQAPV<br>LVIYDDNDRPSGIPERFSGSNSGNTATLTISGTQAEDEADYYCSS<br>WDQDTVVFGGGTKLTVLGQPKAAPSVTLFPPSSEELQANKATL<br>VCLISDFYPGAVTVAWKADSSPVKAGVETTTPSKQSNNKYAAS<br>SYLSLTPEQWKSHRSYSCQVTHEGSTVEKTVAPTECS |
| SEQ ID NO 147: | DNA Light Chain | GATATCGAGCTGACTCAGCCCCCTAGCGTCAGCGTCAGCCC<br>TGGTCAAACCGCCTCTATCACCTGTAGCGGCGATAATATCCC<br>TAGCTACTTCGTGCACTGGTATCAGCAGAAGCCCGGTCAAG<br>CCCCCGTGCTGGTGATCTACGACGATAACGATAGACCTAGC<br>GGAATCCCCGAGCGGTTTAGCGGCTCTAATAGCGGTAACAC<br>CGCTACCCTGACTATTAGCGGCACTCAGGCCGAGGACGAGG<br>CCGACTACTACTGCTCTAGCTGGGATCAGGACACCGTGGTG<br>TTCGGCGGAGGCACTAAGCTGACCGTGCTGGGTCAACCTAA<br>GGCTGCCCCCAGCGTGACCCTGTTCCCCCCCAGCAGCGAGG<br>AGCTGCAGGCCAACAAGGCCACCCTGGTGTGCCTGATCAGC<br>GACTTCTACCCAGGCGCCGTGACCGTGGCCTGGAAGGCCGA<br>CAGCAGCCCCGTGAAGGCCGGCGTGGAGACCACCACCCCCA<br>GCAAGCAGAGCAACAACAAGTACGCCGCCAGCAGCTACCTG<br>AGCCTGACCCCCGAGCAGTGGAAGAGCCACAGGTCCTACAG<br>CTGCCAGGTGACCCACGAGGGCAGCACCGTGGAAAAGACC<br>GTGGCCCCAACCGAGTCAGC |
|  | 20507 |  |
| SEQ ID NO 148: (Kabat) | HCDR1 | SYAIS |
| SEQ ID NO 149: (Kabat) | HCDR2 | TIGPFEGQPRYAQKFQG |
| SEQ ID NO 150: (Kabat) | HCDR3 | GGYISDFDV |
| SEQ ID NO 151: (Chothia) | HCDR1 | GGTFSSY |
| SEQ ID NO 152: (Chothia) | HCDR2 | GPFEGQ |
| SEQ ID NO 153: (Chothia) | HCDR3 | GYISDFDV |

TABLE 3-continued

Examples of anti- cKIT Antibodies

| | | |
|---|---|---|
| SEQ ID NO 154: | VH | QVQLVQSGAEVKKPGSSVKVSCKASGGTFSSYAISWVRQAPG<br>QGLEWMGTIGPFEGQPRYAQKFQGRVTITADESTSTAYMELSS<br>LRSEDTAVYYCARGGYISDFDVWGQGTLVTVSS |
| SEQ ID NO 155: | Heavy<br>Chain | QVQLVQSGAEVKKPGSSVKVSCKASGGTFSSYAISWVRQAPG<br>QGLEWMGTIGPFEGQPRYAQKFQGRVTITADESTSTAYMELSS<br>LRSEDTAVYYCARGGYISDFDVWGQGTLVTVSSASTKGPSVFP<br>LAPSSKSTSGGTAALGCLVKDYFPEPVTVSWNSGALTSGVHTF<br>PAVLQSSGLYSLSSVVTVPSSSLGTQTYICNVNHKPSNTKVDKR<br>VEPKSCDKTHTCPPCPAPELLGGPSVFLFPPKPKDTLMISRTPEV<br>TCVVVDVSHEDPEVKFNWYVDGVEVHNAKTKPREEQYNSTY<br>RVVSVLTVLHQDWLNGKEYKCKVSNKALPAPIEKTISKAKGQP<br>REPQVYTLPPSREEMTKNQVSLTCLVKGFYPSDIAVEWESNGQ<br>PENNYKTTPPVLDSDGSFFLYSKLTVDKSRWQQGNVFSCSVM<br>HEALHNHYTQKSLSLSPGK |
| SEQ ID NO 156: | DNA<br>Heavy<br>Chain | CAGGTGCAATTGGTGCAGAGCGGTGCCGAAGTGAAAAAACC<br>GGGCAGCAGCGTGAAAGTTAGCTGCAAAGCATCCGGAGGG<br>ACGTTTAGCAGCTATGCGATTAGCTGGGTGCGCCAGGCCCC<br>GGGCCAGGGCCTCGAGTGGATGGGCACTATCGGTCCGTTCG<br>AAGGCCAGCCGCGTTACGCCCAGAAATTTCAGGGCCGGGTG<br>ACCATTACCGCCGATGAAAGCACCAGCACCGCCTATATGGA<br>ACTGAGCAGCCTGCGCAGCGAAGATACGGCCGTGTATTATT<br>GCGCGCGTGGTGGTTACATCTCTGACTTCGATGTTTGGGGCC<br>AAGGCACCCTGGTGACTGTTAGCTCAGCCTCCACCAAGGGT<br>CCATCGGTCTTCCCCCTGGCACCCTCCTCAAGAGCACCTCT<br>GGGGGCACAGCGGCCCTGGGCTGCCTGGTCAAGGACTACTT<br>CCCCGAACCGGTGACGGTGTCGTGGAACTCAGGCGCCCTGA<br>CCAGCGGCGTGCACACCTTCCCGGCTGTCCTACAGTCCTCAG<br>GACTCTACTCCCTCAGCAGCGTGGTGACCGTGCCCTCCAGCA<br>GCTTGGGCACCCAGACCTACATCTGCAACGTGAATCACAAG<br>CCCAGCAACACCAAGGTGGACAAGAGAGTTGAGCCCAAATC<br>TTGTGACAAAACTCACACATGCCCACCGTGCCCAGCACCTG<br>AACTCCTGGGGGGACCGTCAGTCTTCCTCTTCCCCCCAAAAC<br>CCAAGGACACCCTCATGATCTCCCGGACCCCTGAGGTCACA<br>TGCGTGGTGGTGGACGTGAGCCACGAAGACCCTGAGGTCAA<br>GTTCAACTGGTACGTGGACGGCGTGGAGGTGCATAATGCCA<br>AGACAAAGCCGCGGGAGGAGCAGTACAACAGCACGTACCG<br>GGTGGTCAGCGTCCTCACCGTCCTGCACCAGGACTGGCTGA<br>ATGGCAAGGAGTACAAGTGCAAGGTCTCCAACAAAGCCCTC<br>CCAGCCCCCATCGAGAAAACCATCTCCAAAGCCAAAGGGCA<br>GCCCCGAGAACCACAGGTGTACACCCTGCCCCCATCCCGGG<br>AGGAGATGACCAAGAACCAGGTCAGCCTGACCTGCCTGGTC<br>AAAGGCTTCTATCCCAGCGACATCGCCGTGGAGTGGGAGAG<br>CAATGGGCAGCCGGAGAACAACTACAAGACCACGCCTCCCG<br>TGCTGGACTCCGACGGCTCCTTCTTCCTCTACAGCAAGCTCA<br>CCGTGGACAAGAGCAGGTGGCAGCAGGGGAACGTCTTCTCA<br>TGCTCCGTGATGCATGAGGCTCTGCACAACCACTACACGCA<br>GAAGAGCCTCTCCCTGTCTCCGGGTAAA |
| SEQ ID NO 157: (Kabat) | LCDR1 | RASQSISNYLA |
| SEQ ID NO 158: (Kabat) | LCDR2 | DASSLQS |
| SEQ ID NO 159: (Kabat) | LCDR3 | QQYYESIT |
| SEQ ID NO 160:<br>(Chothia) | LCDR1 | RASQSISNYLA |
| SEQ ID NO 161:<br>(Chothia) | LCDR2 | DASSLQS |
| SEQ ID NO 162:<br>(Chothia) | LCDR3 | QQYYESIT |
| SEQ ID NO 163: | VL | DIQMTQSPSSLSASVGDRVTITCRASQSISNYLAWYQQKPGKAP<br>KLLIYDASSLQSGVPSRFSGSGSGTDFTLTISSLQPEDFATYYCQ<br>QYYESITFGQGTKVEIKR |
| SEQ ID NO 164: | Light<br>Chain | DIQMTQSPSSLSASVGDRVTITCRASQSISNYLAWYQQKPGKAP<br>KLLIYDASSLQSGVPSRFSGSGSGTDFTLTISSLQPEDFATYYCQ<br>QYYESITFGQGTKVEIKRTVAAPSVFIFPPSDEQLKSGTASVVC<br>LLNNFYPREAKVQWKVDNALQSGNSQESVTEQDSKDSTYSLS<br>STLTLSKADYEKHKVYACEVTHQGLSSPVTKSFNRGEC |
| SEQ ID NO 165: | DNA Light<br>Chain | GATATCCAGATGACCCAGAGCCCGAGCAGCCTGAGCGCCAG<br>CGTGGGCGATCGCGTGACCATTACCTGCAGAGCCAGCCAGT<br>CTATTTCTAACTACCTGGCTTGGTACCAGCAGAAACCGGGC<br>AAAGCGCCGAAACTATTAATCTACGACGCTTCTTCTCTGCAA<br>AGCGGCGTGCCGAGCCGCTTTAGCGGCAGCGGATCCGGCAC<br>CGATTTCACCCTGACCATTAGCTCTCTGCAACCGGAAGACTT<br>TGCGACCTATTATTGCCAGCAGTACTACTACGAATCTATCAC<br>CTTTGGCCAGGGCACGAAAGTTGAAATTAAACGTACGGTGG<br>CCGCTCCCAGCGTGTTCATCTTCCCCCCAGCGACGAGCAGC<br>TGAAGAGCGGCACCGCCAGCGTGGTGTGCCTGCTGAACAAC |

TABLE 3-continued

Examples of anti- cKIT Antibodies

```
TTCTACCCCCGGGAGGCCAAGGTGCAGTGGAAGGTGGACAA
CGCCCTGCAGAGCGGCAACAGCCAGGAAAGCGTCACCGAG
CAGGACAGCAAGGACTCCACCTACAGCCTGAGCAGCACCCT
GACCCTGAGCAAGGCCGACTACGAGAAGCACAAGGTGTAC
GCCTGCGAGGTGACCCACCAGGGCCTGTCCAGCCCCGTGAC
CAAGAGCTTCAACCGGGGCGAGTGT
```

Other antibodies of the present disclosure include those where the amino acids or nucleic acids encoding the amino acids have been mutated, yet have at least 60, 70, 80, 90 or 95 percent identity to the sequences described in Table 3. In some aspects, it includes mutant amino acid sequences wherein no more than 1, 2, 3, 4 or 5 amino acids have been mutated in the variable regions when compared with the variable regions depicted in the sequence described in Table 3, while retaining substantially the same therapeutic activity.

Since each of these antibodies can bind to cKIT, the VH, VL, full length light chain, and full length heavy chain sequences (amino acid sequences and the nucleotide sequences encoding the amino acid sequences) can be "mixed and matched" to create other cKIT-binding antibodies. Such "mixed and matched" cKIT-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise, a full length light chain sequence from a particular full length heavy chain/full length light chain pairing should be replaced with a structurally similar full length light chain sequence. Accordingly, in one aspect, the disclosure provides for an isolated monoclonal antibody or antigen binding region thereof having: a heavy chain variable region comprising an amino acid sequence selected from the group consisting of SEQ ID NOs: 9, 28, 46, 64, 82, 100, 118, 136 or 154 (Table 3); and a light chain variable region comprising an amino acid sequence selected from the group consisting of SEQ ID NOs: 18, 37, 55, 73, 91, 109, 127, 145 or 163 (Table 3); wherein the antibody specifically binds to cKIT.

In another aspect, the disclosure provides (i) an isolated monoclonal antibody having: a full length heavy chain comprising an amino acid sequence that has been optimized for expression in the cell of a mammalian selected from the group consisting of SEQ ID NOs: 11, 29, 47, 65, 83, 101, 119, 137 or 155; and a full length light chain comprising an amino acid sequence that has been optimized for expression in the cell of a mammalian selected from the group consisting of SEQ ID NOs: 20, 21, 38, 56, 74, 92, 110, 128, 146 or 164; or (ii) a functional protein comprising an antigen binding portion thereof.

In another aspect, the present disclosure provides cKIT-binding antibodies that comprise the heavy chain and light chain CDR1s, CDR2s and CDR3s as described in Table 3, or combinations thereof. The amino acid sequences of the VH CDR1s of the antibodies are shown in SEQ ID NOs: 3, 22, 40, 58, 76, 94, 112, 130 and 148. The amino acid sequences of the VH CDR2s of the antibodies and are shown in SEQ ID NOs: 4, 23, 41, 59, 77, 95, 113, 131 and 149. The amino acid sequences of the VH CDR3s of the antibodies are shown in SEQ ID NOs: 5, 24, 42, 60, 78, 96, 114, 132 and 150. The amino acid sequences of the VL CDR1s of the antibodies are shown in SEQ ID NOs: 12, 31, 49, 67, 85, 103, 121, 139 and 157. The amino acid sequences of the VL CDR2s of the antibodies are shown in SEQ ID NOs 13, 32, 50, 68, 86, 104, 122, 140 and 158. The amino acid sequences of the VL CDR3s of the antibodies are shown in SEQ ID NOs:14, 33, 51, 69, 87, 105, 123, 141 and 159.

Given that each of these antibodies can bind to cKIT and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and match, although each antibody must contain a VH CDR1, 2 and 3 and a VL CDR1, 2 and 3 to create other C5-binding binding molecules. Such "mixed and matched" cKIT-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present disclosure.

Accordingly, the present disclosure provides an isolated monoclonal antibody or antigen binding region thereof comprising a heavy chain CDR1 comprising an amino acid sequence selected from the group consisting of SEQ ID NOs: 3, 22, 40, 58, 76, 94, 112 and 130; a heavy chain CDR2 comprising an amino acid sequence selected from the group consisting of SEQ ID NOs: 4, 23, 41, 59, 77, 95, 113 and 131; a heavy chain CDR3 comprising an amino acid sequence selected from the group consisting of SEQ ID NOs: 5, 24, 42, 60, 78, 96, 114 and 132; a light chain CDR1 comprising an amino acid sequence selected from the group consisting of SEQ ID NOs: 12, 31, 49, 67, 85, 103, 121 and 139; a light chain CDR2 comprising an amino acid sequence selected from the group consisting of SEQ ID NOs: 13, 32, 50, 68, 86, 104, 122 and 140; and a light chain CDR3 comprising an amino acid sequence selected from the group consisting of SEQ ID NOs: 14, 33, 51, 69, 87, 105, 123 and 141; wherein the antibody specifically binds cKIT.

In a specific aspect, an antibody or antibody fragment (e.g., antigen binding fragments) that specifically binds to cKIT comprising a heavy chain CDR1 of SEQ ID NO:3, a heavy chain CDR2 of SEQ ID NO: 4; a heavy chain CDR3 of SEQ ID NO:5; a light chain CDR1 of SEQ ID NO:12; a light chain CDR2 of SEQ ID NO: 13; and a light chain CDR3 of SEQ ID NO: 14.

In a specific aspect, an antibody or antibody fragment (e.g., antigen binding fragments) that specifically binds to cKIT comprising a heavy chain CDR1 of SEQ ID NO:22, a heavy chain CDR2 of SEQ ID NO: 23; a heavy chain CDR3 of SEQ ID NO:24; a light chain CDR1 of SEQ ID NO:31; a light chain CDR2 of SEQ ID NO: 32; and a light chain CDR3 of SEQ ID NO: 33.

In a specific aspect, an antibody or antibody fragment (e.g., antigen binding fragments) that specifically binds to cKIT comprising a heavy chain CDR1 of SEQ ID NO:40, a heavy chain CDR2 of SEQ ID NO: 41; a heavy chain CDR3 of SEQ ID NO:42; a light chain CDR1 of SEQ ID NO:49; a light chain CDR2 of SEQ ID NO: 50; and a light chain CDR3 of SEQ ID NO: 51.

In a specific aspect, an antibody or antibody fragment (e.g., antigen binding fragments) that specifically binds to cKIT comprising a heavy chain CDR1 of SEQ ID NO:58, a heavy chain CDR2 of SEQ ID NO: 59; a heavy chain CDR3 of SEQ ID NO:60; a light chain CDR1 of SEQ ID NO:67; a light chain CDR2 of SEQ ID NO: 68; and a light chain CDR3 of SEQ ID NO: 69.

In a specific aspect, an antibody or antibody fragment (e.g., antigen binding fragments) that specifically binds to cKIT comprising a heavy chain CDR1 of SEQ ID NO:76, a heavy chain CDR2 of SEQ ID NO: 77; a heavy chain CDR3 of SEQ ID NO:78; a light chain CDR1 of SEQ ID NO:85; a light chain CDR2 of SEQ ID NO: 86; and a light chain CDR3 of SEQ ID NO: 87.

In a specific aspect, an antibody or antibody fragment (e.g., antigen binding fragments) that specifically binds to cKIT comprising a heavy chain CDR1 of SEQ ID NO:94, a heavy chain CDR2 of SEQ ID NO: 95; a heavy chain CDR3 of SEQ ID NO:96; a light chain CDR1 of SEQ ID NO:103; a light chain CDR2 of SEQ ID NO: 104; and a light chain CDR3 of SEQ ID NO: 105.

In a specific aspect, an antibody or antibody fragment (e.g., antigen binding fragments) that specifically binds to cKIT comprising a heavy chain CDR1 of SEQ ID NO:112, a heavy chain CDR2 of SEQ ID NO: 113; a heavy chain CDR3 of SEQ ID NO:114; a light chain CDR1 of SEQ ID NO:121; a light chain CDR2 of SEQ ID NO: 122; and a light chain CDR3 of SEQ ID NO: 123.

In a specific aspect, an antibody or antibody fragment (e.g., antigen binding fragments) that specifically binds to cKIT comprising a heavy chain CDR1 of SEQ ID NO:130, a heavy chain CDR2 of SEQ ID NO: 131; a heavy chain CDR3 of SEQ ID NO:132; a light chain CDR1 of SEQ ID NO:139; a light chain CDR2 of SEQ ID NO: 140; and a light chain CDR3 of SEQ ID NO: 141.

In a specific aspect, an antibody or antibody fragment (e.g., antigen binding fragments) that specifically binds to cKIT comprising a heavy chain CDR1 of SEQ ID NO:148, a heavy chain CDR2 of SEQ ID NO: 149; a heavy chain CDR3 of SEQ ID NO:150; a light chain CDR1 of SEQ ID NO:157; a light chain CDR2 of SEQ ID NO: 158; and a light chain CDR3 of SEQ ID NO: 159.

In certain aspects, an antibody that specifically binds to cKIT is an antibody or antibody fragment (e.g., antigen binding fragment) that is described in Table 3.

1. Identification of Epitopes and Antibodies that Bind to the Same Epitope

The present disclosure provides antibodies and antibody fragments (e.g., antigen binding fragments) that bind to an epitope of within the extracellular domain of the cKIT receptor. In certain aspects the antibodies and antibody fragments can bind to epitopes with domains 1-3 of the cKIT extracellular domain.

The present disclosure also provides antibodies and antibody fragments (e.g., antigen binding fragments) that bind to the same epitope as do the anti-cKIT antibodies described in Table 3. Additional antibodies and antibody fragments (e.g., antigen binding fragments) can therefore be identified based on their ability to cross-compete (e.g., to competitively inhibit the binding of, in a statistically significant manner) with other antibodies in cKIT binding assays. The ability of a test antibody to inhibit the binding of antibodies and antibody fragments (e.g., antigen binding fragments) of the present disclosure to a cKIT protein (e.g., human cKIT) demonstrates that the test antibody can compete with that antibody or antibody fragment (e.g., antigen binding fragments) for binding to cKIT; such an antibody may, according to non-limiting theory, bind to the same or a related (e.g., a structurally similar or spatially proximal) epitope on the cKIT protein as the antibody or antibody fragment (e.g., antigen binding fragments) with which it competes. In a certain aspect, the antibody that binds to the same epitope on cKIT as the antibodies or antibody fragments (e.g., antigen binding fragments) of the present disclosure is a human or humanized monoclonal antibody. Such human or humanized monoclonal antibodies can be prepared and isolated as described herein.

2. Further Alteration of the Framework of Fc Region

The present disclosure provides site-specific labeled immunoconjugates. These immunoconjugates can comprise modified antibodies or antigen binding fragments thereof that further comprise modifications to framework residues within VH and/or VL, e.g. to improve the properties of the antibody. Typically such framework modifications are made to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis. Such "back-mutated" antibodies are also intended to be encompassed.

Another type of framework modification involves mutating one or more residues within the framework region, or even within one or more CDR regions, to remove T-cell epitopes to thereby reduce the potential immunogenicity of the antibody. This approach is also referred to as "deimmunization" and is described in further detail in U.S. Patent Publication No. 2003/0153043 by Carr et al.

In addition or alternative to modifications made within the framework or CDR regions, antibodies can be engineered to include modifications within the Fc region, typically to alter one or more functional properties of the antibody, such as serum half-life, complement fixation, Fc receptor binding, and/or antigen-dependent cellular cytotoxicity. Furthermore, an antibody can be chemically modified (e.g., one or more chemical moieties can be attached to the antibody) or be modified to alter its glycosylation, again to alter one or more functional properties of the antibody. Each of these aspects is described in further detail below.

In one aspect, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another aspect, the Fc hinge region of an antibody is mutated to decrease the biological half-life of the antibody. More specifically, one or more amino acid mutations are introduced into the $CH_2$—$CH_3$ domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al.

In yet other aspects, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another aspect, one or more amino acids selected from amino acid residues can be replaced with a different amino acid residue such that the antibody has altered C1q binding and/or reduced or abolished complement dependent cytotoxicity (CDC). This approach is described in, e.g., U.S. Pat. No. 6,194,551 by Idusogie et al.

In another aspect, one or more amino acid residues are altered to thereby alter the ability of the antibody to fix complement. This approach is described in, e.g., the PCT Publication WO 94/29351 by Bodmer et al. In a specific aspect, one or more amino acids of an antibody or antigen binding fragment thereof of the present disclosure are replaced by one or more allotypic amino acid residues, for the IgG1 subclass and the kappa isotype. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In yet another aspect, the Fc region is modified to increase the ability of the antibody to mediate antibody dependent cellular cytotoxicity (ADCC) and/or to increase the affinity of the antibody for an Fcγ receptor by modifying one or more amino acids. This approach is described in, e.g., the PCT Publication WO 00/42072 by Presta. Moreover, the binding sites on human IgG1 for FcγRl, FcγRII, FcγRIII and FcRn have been mapped and variants with improved binding have been described (see Shields et al., J. Biol. Chem. 276:6591-6604, 2001).

In still another aspect, the glycosylation of an antibody is modified. For example, an aglycosylated antibody can be made (i.e., the antibody lacks glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in, e.g., U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields et al., (2002) J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

In another aspect, the antibody is modified to increase its biological half-life. Various approaches are possible. For example, one or more of the following mutations can be introduced: T252L, T254S, and T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In order to minimize the ADCC activity of an antibody, specific mutations in the Fc region result in "Fc silent" antibodies that have minimal interaction with effector cells. In general, the "IgG Fc region" is used to define the C-terminal region of an immunoglobulin heavy chain, including native sequence Fc region and variant Fc regions. The human IgG heavy chain Fc region is generally defined as comprising the amino acid residue from position C226 or from P230 to the carboxyl-terminus of the IgG antibody. The numbering of residues in the Fc region is that of the EU index of Kabat. The C-terminal lysine (residue K447) of the Fc region may be removed, for example, during production or purification of the antibody.

Silenced effector functions can be obtained by mutation in the Fc region of the antibodies and have been described in the art: LALA and N297A (Strohl, W., Curr. Opin. Biotechnol. 2009, vol. 20(6):685-691); and D265A (Baudino et al., J. Immunol. 2008, 181:6664-69) see also Heusser et al., WO2012065950. Examples of silent Fc IgG1 antibodies are the LALA mutant comprising L234A and L235A mutation in the IgG1 Fc amino acid sequence. Another example of a silent IgG1 antibody is the DAPA (D265A, P329A) mutation (U.S. Pat. No. 6,737,056). Another silent IgG1 antibody comprises the N297A mutation, which results in aglycosylated/non-glycosylated antibodies.

Fc silent antibodies result in no or low ADCC activity, meaning that an Fc silent antibody exhibits an ADCC activity that is below 50% specific cell lysis, No ADCC activity means that the Fc silent antibody exhibits an ADCC activity (specific cell lysis) that is below 1%.

3. Production of the cKIT Antibodies

Anti-cKIT antibodies and antibody fragments (e.g., antigen binding fragments) thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The disclosure further provides polynucleotides encoding the antibodies described herein, e.g., polynucleotides encoding heavy or light chain variable regions or segments comprising the complementarity determining regions as described herein. In some aspects, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 30, 48, 66, 84, 102, 120 and 137. In some aspects, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs:39, 57, 75, 93, 111, 129 and 147.

In some aspects, the polynucleotide encoding the heavy chain has at least 85%, 89%, 90%, 91%, 92%, 93%, 94%, 95%, 96%, 97%, 98%, 99%, or 100% nucleic acid sequence identity with a polynucleotide of SEQ ID NO: 30, 48, 66, 84, 102, 120. In some aspects, the polynucleotide encoding the light chain has at least 85%, 89%, 90%, 91%, 92%, 93%, 94%, 95%, 96%, 97%, 98%, 99%, or 100% nucleic acid sequence identity with a polynucleotide of SEQ ID NO: 39, 57, 75, 93, 111, 129 and 147.

The polynucleotides of the present disclosure can encode only the variable region sequence of an anti-cKIT antibody. They can also encode both a variable region and a constant region of the antibody. Some of the polynucleotide sequences encode a polypeptide that comprises variable regions of both the heavy chain and the light chain of one of an exemplified anti-cKIT antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence (e.g., sequences as described in the Examples below) encoding an anti-cKIT antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, NY, 1992; PCR Protocols: A Guide to Methods and Applications, Innis et al. (Ed.), Academic Press, San Diego, CA, 1990; Mattila et al., Nucleic Acids Res. 19:967, 1991; and Eckert et al., PCR Methods and Applications 1:17, 1991.

Also provided in the present disclosure are expression vectors and host cells for producing the anti-cKIT antibodies described above. Various expression vectors can be employed to express the polynucleotides encoding the anti-cKIT antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the anti-cKIT polynucleotides and polypeptides in mammalian (e.g., human) cells include pThioHis A, B & C, pcDNA3.1/His, pEBVHis A, B & C (Invitrogen, San Diego, CA), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-cKIT antibody chain or fragment. In some aspects, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an anti-cKIT antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-cKIT antibody sequences. More often, the inserted anti-cKIT antibody sequences are linked to a signal sequences before inclusion in the vector. Vectors to be used to receive sequences encoding anti-cKIT antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-cKIT antibody chains can be either prokaryotic or eukaryotic. *E. coli* is one prokaryotic host useful for cloning and expressing the polynucleotides of the present disclosure. Other microbial hosts suitable for use include bacilli, such as

*Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-cKIT polypeptides. Insect cells in combination with baculovirus vectors can also be used.

In other aspects, mammalian host cells are used to express and produce the anti-cKIT polypeptides of the present disclosure. For example, they can be either a hybridoma cell line expressing endogenous immunoglobulin genes (e.g., the myeloma hybridoma clones as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed, including the CHO cell lines, various COS cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-cKIT antibody chains or binding fragments can be prepared using expression vectors which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Therapeutic and Diagnostic Uses

The antibodies, antibody fragments (e.g., antigen binding fragments), and antibody drug conjugates of the present disclosure are useful in a variety of applications including, but not limited to, treatment of cancer, such as solid cancers. In certain aspects, the antibodies, antibody fragments (e.g., antigen binding fragments), and antibody drug conjugates are useful for inhibiting tumor growth, inducing differentiation, reducing tumor volume, and/or reducing the tumorigenicity of a tumor. The methods of use can be in vitro, ex vivo, or in vivo methods.

In one aspect, the antibodies, antibody fragments (e.g., antigen binding fragments), and antibody drug conjugates are useful for detecting the presence of cKIT in a biological sample. The term "detecting" as used herein encompasses quantitative or qualitative detection. In certain aspects, a biological sample comprises a cell or tissue. In certain aspects, such tissues include normal and/or cancerous tissues that express cKIT at higher levels relative to other tissues.

In one aspect, the present disclosure provides a method of detecting the presence of cKIT in a biological sample. In certain aspects, the method comprises contacting the biological sample with an anti-c KIT antibody under conditions permissive for binding of the antibody to the antigen, and detecting whether a complex is formed between the antibody and the antigen.

Also included is a method of diagnosing a disorder associated with increased expression of cKIT. In certain aspects, the method comprises contacting a test cell with an anti-cKIT antibody; determining the level of expression (either quantitatively or qualitatively) of cKIT on the test cell by detecting binding of the anti-cKIT antibody to the cKIT antigen; and comparing the level of expression of cKIT in the test cell with the level of expression of cKIT in a control cell (e.g., a normal cell of the same tissue origin as the test cell or a cell that expresses cKIT at levels comparable to such a normal cell), wherein a higher level of expression of cKIT on the test cell as compared to the control cell indicates the presence of a disorder associated with increased expression of cKIT. In certain aspects, the test cell is obtained from an individual suspected of having a disorder associated with increased expression of cKIT. In certain aspects, the disorder is a cell proliferative disorder, such as a cancer or a tumor.

In certain aspects, a method of diagnosis or detection, such as those described above, comprises detecting binding of an anti-cKIT antibody to cKIT expressed on the surface of a cell or in a membrane preparation obtained from a cell expressing cKIT on its surface. An exemplary assay for detecting binding of an anti-cKIT antibody to cKIT expressed on the surface of a cell is a "FACS" assay.

Certain other methods can be used to detect binding of anti-cKIT antibodies to cKIT. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain aspects, anti-cKIT antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain aspects, anti-cKIT antibodies are immobilized on an insoluble matrix. Immobilization entails separating the anti-cKIT antibody from any cKIT proteins that remains free in solution. This conventionally is accomplished by either insolubilizing the anti-cKIT antibody before the assay procedure, as by adsorption to a water-insoluble matrix or surface (Bennich et al, U.S. Pat. No. 3,720,760), or by covalent coupling (for example, using glutaraldehyde cross-linking), or by insolubilizing the anti-cKIT antibody after formation of a complex between the anti-cKIT antibody and cKIT protein, e.g., by immunoprecipitation.

Any of the above aspects of diagnosis or detection can be carried out using an immunoconjugate of the present disclosure in place of or in addition to an anti-cKIT antibody.

In one aspect, the disclosure provides for a method of treating, preventing or ameliorating a disease comprising administering the antibodies, antibody fragments (e.g., antigen binding fragments), and antibody drug conjugates to a patient, thereby treating the disease. In certain aspects, the disease treated with the antibodies, antibody fragments (e.g., antigen binding fragments), and antibody drug conjugates is a cancer. Examples of diseases which can be treated and/or prevented include, but are not limited to, gastrointestinal stromal tumors (GIST), small cell lung cancer (SCLC), acute myeloid leukemia (AML), melanoma, mast cell leukemia (MCL), mastocytosis, neurofibromatosis, breast cancer, non-small cell lung cancer (NSCLC), and pancreatic cancer. In certain aspects, the cancer is characterized by cKIT expressing cells to which the antibodies, antibody fragments (e.g., antigen binding fragments), and antibody drug conjugates can specifically bind.

The present disclosure provides for methods of treating cancer comprising administering a therapeutically effective amount of the antibodies, antibody fragments (e.g., antigen binding fragments), or antibody drug conjugates. In certain aspects, the cancer is a solid cancer. In certain aspects, the subject is a human.

In certain aspects, the method of inhibiting tumor growth comprises administering to a subject a therapeutically effective amount of the antibodies, antibody fragments (e.g., antigen binding fragments), or antibody drug conjugates. In certain aspects, the subject is a human. In certain aspects, the subject has a tumor or has had a tumor removed.

In certain aspects, the tumor expresses the cKIT to which the anti-cKIT antibody binds. In certain aspects, the tumor overexpresses the human cKIT.

For the treatment of the disease, the appropriate dosage of the antibodies, antibody fragments (e.g., antigen binding fragments), or antibody drug conjugates depend on various factors, such as the type of disease to be treated, the severity and course of the disease, the responsiveness of the disease, previous therapy, patient's clinical history, and so on. The antibody or agent can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody, antibody fragment (e.g., antigen binding fragment), or antibody drug conjugates. In certain aspects, dosage is from 0.01 mg to 10 mg (e.g., 0.01 mg, 0.05 mg, 0.1 mg, 0.5 mg, 1 mg, 2 mg, 3 mg, 4 mg, 5 mg, 7 mg, 8 mg, 9 mg, or 10 mg) per kg of body weight, and can be given once or more daily, weekly, monthly or yearly. In certain aspects, the antibody, antibody fragment (e.g., antigen binding fragment), or antibody drug conjugate of the present disclosure is given once every two weeks or once every three weeks. The treating physician can estimate repetition rates for dosing based on measured residence times and concentrations of the drug in bodily fluids or tissues.

Combination Therapy

In certain instances, an antibody, antibody fragment (e.g., antigen binding fragment), or antibody drug conjugate of the present disclosure is combined with other therapeutic agents, such as other anti-cancer agents, anti-allergic agents, anti-nausea agents (or anti-emetics), pain relievers, cytoprotective agents, and combinations thereof.

General chemotherapeutic agents considered for use in combination therapies include anastrozole (Arimidex®), bicalutamide (Casodex®), bleomycin sulfate (Blenoxane®), busulfan (Myleran®), busulfan injection (Busulfex), capecitabine (Xeloda), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid), fludarabine phosphate (Fludara®), 5-fluorouracil (Adrucil Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan)(Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

In one aspect, an antibody, antibody fragment (e.g., antigen binding fragment), or antibody drug conjugate of the present disclosure is combined in a pharmaceutical combination formulation, or dosing regimen as combination therapy, with a second compound having anti-cancer properties. The second compound of the pharmaceutical combination formulation or dosing regimen can have complementary activities to the antibody or immunoconjugate of the combination such that they do not adversely affect each other. For example, an antibody, antibody fragment (e.g., antigen binding fragment), or antibody drug conjugate of the present disclosure can be administered in combination with, but not limited to, a chemotherapeutic agent, a tyrosine kinase inhibitor, for example, Imatinib, and other cKIT pathway inhibitors.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In one aspect, the present disclosure provides a method of treating cancer by administering to a subject in need thereof an antibody drug conjugate in combination with one or more tyrosine kinase inhibitors, including but not limited to, EGFR inhibitors, Her2 inhibitors, Her3 inhibitors, IGFR inhibitors, and Met inhibitors.

For example, tyrosine kinase inhibitors include but are not limited to, Erlotinib hydrochloride (Tarceva®); Linifanib (N-[4-(3-amino-1H-indazol-4-yl)phenyl]-N'-(2-fluoro-5-methylphenyl)urea, also known as ABT 869, available from Genentech); Sunitinib malate (Sutent®); Bosutinib (4-[(2, 4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996); Dasatinib (Sprycel®); Pazopanib (Votrient®); Sorafenib (Nexavar®); Zactima (ZD6474); nilotinib (Tasigna®); Regorafenib (Stivarga®) and Imatinib or Imatinib mesylate (Gilvec® and Gleevec®).

Epidermal growth factor receptor (EGFR) inhibitors include but are not limited to, Erlotinib hydrochloride (Tarceva®), Gefitnib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo [2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS 187724-61-4).

EGFR antibodies include but are not limited to, Cetuximab (Erbitux®); Panitumumab (Vectibix®); Matuzumab (EMD-72000); Nimotuzumab (hR3); Zalutumumab; TheraClM h-R3; MDX0447 (CAS 339151-96-1); and ch806 (mAb-806, CAS 946414-09-1).

Human Epidermal Growth Factor Receptor 2 (HER2 receptor) (also known as Neu, ErbB-2, CD340, or p185) inhibitors include but are not limited to, Trastuzumab (Herceptin®); Pertuzumab (Omnitarg®); Neratinib (HKI-272, (2E)-N-[4-[[3-chloro-4-[(pyridin-2-yl)methoxy]phenyl] amino]-3-cyano-7-ethoxyquinolin-6-yl]-4-(dimethylamino) but-2-enamide, and described PCT Publication No. WO 05/028443); Lapatinib or Lapatinib ditosylate (Tykerb®); (3R,4R)-4-amino-1-((4-((3-methoxyphenyl)amino)pyrrolo [2,1-f][1,2,4]triazin-5-yl)methyl)piperidin-3-ol (BMS690514); (2E)-N-[4-[(3-Chloro-4-fluorophenyl) amino]-7-[[(3S)-tetrahydro-3-furanyl]oxy]-6-quinazolinyl]-4-(dimethylamino)-2-butenamide (BIBW-2992, CAS 850140-72-6); N-[4-[[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS 599626, CAS 714971-09-2); Canertinib dihydrochloride (PD183805 or CI-1033); and N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8).

HER3 inhibitors include but are not limited to, LJM716, MM-121, AMG-888, RG7116, REGN-1400, AV-203, MP-RM-1, MM-111, and MEHD-7945A.

MET inhibitors include but are not limited to, Cabozantinib (XL184, CAS 849217-68-1); Foretinib (GSK1363089, formerly XL880, CAS 849217-64-7); Tivantinib (ARQ197, CAS 1000873-98-2); 1-(2-Hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (AMG 458); Cryzotinib (Xalkori®, PF-02341066); (3Z)-5-(2,3-Dihydro-1H-indol-1-ylsulfonyl)-3-({3,5-dimethyl-4-[(4-methylpiperazin-1-yl)carbonyl]-1H-pyrrol-2-yl}methylene)-1,3-dihydro-2H-indol-2-one (SU11271); (3Z)—N-(3-Chlorophenyl)-3-({3,5-dimethyl-4-[(4-methylpiperazin-1-yl)carbonyl]-1H-pyrrol-2-yl}methylene)-N-methyl-2-oxoindoline-5-sulfonamide (SU11274); (3Z)—N-(3-Chlorophenyl)-3-{[3,5-dimethyl-4-(3-morpholin-4-ylpropyl)-1H-pyrrol-2-yl]methylene}-N-methyl-2-oxoindoline-5-sulfonamide (SU11606); 6-[Difluoro[6-(1-methyl-1H-pyrazol-4-yl)-1,2,4-triazolo[4,3-b]pyridazin-3-yl]methyl]-quinoline (JNJ38877605, CAS 943540-75-8); 2-[4-[1-(Quinolin-6-ylmethyl)-1H-[1,2,3]triazolo[4,5-b] pyrazin-6-yl]-1H-pyrazol-1-yl]ethanol (PF04217903, CAS 956905-27-4); N-((2R)-1,4-Dioxan-2-ylmethyl)-N-methyl-N'-[3-(1-methyl-1H-pyrazol-4-yl)-5-oxo-5H-benzo[4,5]cyclohepta[1,2-b]pyridin-7-yl]sulfamide (MK2461, CAS 917879-39-1); 6-[[6-(1-Methyl-1H-pyrazol-4-yl)-1,2,4-triazolo[4,3-b]pyridazin-3-yl]thio]-quinoline (SGX523, CAS 1022150-57-7); and (3Z)-5-[[(2,6-Dichlorophenyl)methyl] sulfonyl]-3-[[3,5-dimethyl-4-[[(2R)-2-(1-pyrrolidinylmethyl)-1-pyrrolidinyl]carbonyl]-1H-pyrrol-2-yl]methylene]-1,3-dihydro-2H-indol-2-one (PHA665752, CAS 477575-56-7).

IGF1R inhibitors include but are not limited to, BMS-754807, XL-228, OSI-906, GSK0904529A, A-928605, AXL1717, KW-2450, MK0646, AMG479, IMCA12, MEDI-573, and BI836845. See e.g., Yee, JNCI, 104; 975 (2012) for review.

In another aspect, the present disclosure provides a method of treating cancer by administering to a subject in need thereof an antibody drug conjugate in combination with one or more FGF downstream signaling pathway inhibitors, including but not limited to, MEK inhibitors, Braf inhibitors, PI3K/Akt inhibitors, SHP2 inhibitors, and also mTor inhibitors.

For example, mitogen-activated protein kinase (MEK) inhibitors include but are not limited to, XL-518 (also known as GDC-0973, Cas No. 1029872-29-4, available from ACC Corp.); 2-[(2-Chloro-4-iodophenyl)amino]-N-(cyclopropylmethoxy)-3,4-difluoro-benzamide (also known as CI-1040 or PD184352 and described in PCT Publication No. W2000035436); N-[(2R)-2,3-Dihydroxypropoxy]-3,4-difluoro-2-[(2-fluoro-4-iodophenyl)amino]-benzamide (also known as PD0325901 and described in PCT Publication No. WO2002006213); 2,3-Bis[amino[(2-aminophenyl)thio] methylene]-butanedinitrile (also known as U0126 and described in U.S. Pat. No. 2,779,780); N-[3,4-Difluoro-2-[(2-fluoro-4-iodophenyl)amino]-6-methoxyphenyl]-1-[(2R)-2,3-dihydroxypropyl]-cyclopropanesulfonamide (also known as RDEA119 or BAY869766 and described in PCT Publication No. W2007014011); (3S,4R,5Z,8S,9S,11E)-14-(Ethylamino)-8,9,16-trihydroxy-3,4-dimethyl-3,4,9, 19-tetrahydro-1H-2-benzoxacyclotetradecine-1,7(8H)-dione] (also known as E6201 and described in PCT Publication No. WO2003076424); 2'-Amino-3'-methoxyflavone (also known as PD98059 available from Biaffin GmbH & Co., KG, Germany); Vemurafenib (PLX-4032, CAS 918504-65-1); (R)-3-(2,3-Dihydroxypropyl)-6-fluoro-5-(2-fluoro-4-iodophenylamino)-8-methylpyrido[2,3-d]pyrimidine-4,7(3H,8H)-dione (TAK-733, CAS 1035555-63-5); Pimasertib (AS-703026, CAS 1204531-26-9); and Trametinib dimethyl sulfoxide (GSK-1120212, CAS 1204531-25-80).

Phosphoinositide 3-kinase (P3K) inhibitors include but are not limited to, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS,9aR)-5-(Acetyloxy)-1-[(di-2-propenylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran-2,7,10(1H)-trione (PX866, CAS 502632-66-8); and 8-Phenyl-2-(morpholin-4-yl)-chromen-4-one (LY294002, CAS 154447-36-6).

mTor inhibitors include but are not limited to, Temsirolimus (Torisel®); Ridaforolimus (formally known as deferolimus, (1R,2R,4S)-4-[(2R)-2 [(1R,9S,12S,15R,16E,18R,19R,21R, 23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3S)-3-methylmorpholin-4-yl] pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d] pyrimidin-7(8H)-one (PF04691502, CAS 1013101-36-4); and N$^2$-[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-, inner salt (SF1126, CAS 936487-67-1).

In yet another aspect, the present disclosure provides a method of treating cancer by administering to a subject in need thereof an antibody drug conjugate in combination with one or more pro-apoptotics, including but not limited to, IAP inhibitors, Bcl2 inhibitors, MCl1 inhibitors, Trail agents, Chk inhibitors.

For examples, IAP inhibitors include but are not limited to, NVP-LCL161, GDC-0917, AEG-35156, AT406, and TL32711. Other examples of IAP inhibitors include but are not limited to those disclosed in WO04/005284, WO 04/007529, WO05/097791, WO 05/069894, WO 05/069888, WO 05/094818, US2006/0014700, US2006/0025347, WO 06/069063, WO 06/010118, WO 06/017295, and WO08/134679, all of which are incorporated herein by reference.

BCL-2 inhibitors include but are not limited to, 4-[4-[[2-(4-Chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl] phenyl]sulfonyl]benzamide (also known as ABT-263 and described in PCT Publication No. WO 09/155386); Tetrocarcin A; Antimycin; Gossypol ((−)BL-193); Obatoclax; Ethyl-2-amino-6-cyclopentyl-4-(1-cyano-2-ethoxy-2-oxoethyl)-4Hchromone-3-carboxylate (HA14-1); Oblimersen (G3139, Genasense®); Bak BH3 peptide; (−)-Gossypol acetic acid (AT-101); 4-[4-[(4'-Chloro[1,1'-biphenyl]-2-yl) methyl]-1-piperazinyl]-N-[[4-[[(1R)-3-(dimethylamino)-1-[(phenylthio)methyl]propyl]amino]-3-nitrophenyl] sulfonyl]-benzamide (ABT-737, CAS 852808-04-9); and Navitoclax (ABT-263, CAS 923564-51-6).

Proapoptotic receptor agonists (PARAs) including DR4 (TRAILR1) and DR5 (TRAILR2), including but are not limited to, Dulanermin (AMG-951, RhApo2L/TRAIL); Mapatumumab (HRS-ETR1, CAS 658052-09-6); Lexatumumab (HGS-ETR2, CAS 845816-02-6); Apomab (Apomab®); Conatumumab (AMG655, CAS 896731-82-1); and Tigatuzumab (CS1008, CAS 946415-34-5, available from Daiichi Sankyo).

Checkpoint Kinase (CHK) inhibitors include but are not limited to, 7-Hydroxystaurosporine (UCN-01); 6-Bromo-3-(1-methyl-1H-pyrazol-4-yl)-5-(3R)-3-piperidinyl-pyrazolo [1,5-a]pyrimidin-7-amine (SCH900776, CAS 891494-63-6); 5-(3-Fluorophenyl)-3-ureidothiophene-2-carboxylic acid N—[(S)-piperidin-3-yl]amide (AZD7762, CAS 860352-01-8); 4-[((3S)-1-Azabicyclo[2.2.2]oct-3-yl)amino]-3-(1H-benzimidazol-2-yl)-6-chloroquinolin-2(1H)-one (CHIR 124, CAS 405168-58-3); 7-Aminodactinomycin (7-AAD), Isogranulatimide, debromohymenialdisine; N-[5-Bromo-4-methyl-2-[(2S)-2-morpholinylmethoxy]-phenyl]-N'-(5-methyl-2-pyrazinyl)urea (LY2603618, CAS 911222-45-2); Sulforaphane (CAS 4478-93-7, 4-Methylsulfinylbutyl isothiocyanate); 9,10,11,12-Tetrahydro-9,12-epoxy-1H-diindolo[1,2,3-fg:3',2',1'-kl]pyrrolo[3,4-i][1,6]benzodiazocine-1,3(2H)-dione (SB-218078, CAS 135897-06-2); and TAT-S216A (Sha et al., Mol. Cancer. Ther 2007; 6(1):147-153), and CBP501.

In one aspect, the present disclosure provides a method of treating cancer by administering to a subject in need thereof an antibody drug conjugate in combination with one or more FGFR inhibitors. For example, FGFR inhibitors include but are not limited to, Brivanib alaninate (BMS-582664, (S)-((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); Vargatef (BIBF1120, CAS 928326-83-4); Dovitinib dilactic acid (TKI258, CAS 852433-84-2); 3-(2, 6-Dichloro-3,5-dimethoxy-phenyl)-1-{6-[4-(4-ethyl-piperazin-1-yl)-phenylamino]-pyrimidin-4-yl}-1-methyl-urea (BGJ398, CAS 872511-34-7); Danusertib (PHA-739358); and (PD173074, CAS 219580-11-7). In a specific aspect, the present disclosure provides a method of treating cancer by administering to a subject in need thereof an antibody drug conjugate in combination with an FGFR2 inhibitor, such as 3-(2,6-dichloro-3,5-dimethoxyphenyl)-1-(6((4-(4-ethylpiperazin-1-yl)phenyl)amino)pyrimidin-4-yl)-1-methylurea (also known as BGJ-398); or 4-amino-5-fluoro-3-(5-(4-methylpiperazin1-yl)-1H-benzo[d]imidazole-2-yl)quinolin-2(1H)-one (also known as dovitinib or TKI-258). AZD4547 (Gavine et al., 2012, Cancer Research 72, 2045-56, N-[5-[2-(3,5-Dimethoxyphenyl)ethyl]-2H-pyrazol-3-yl]-4-(3R, 5S)-diemthylpiperazin-1-yl)benzamide), Ponatinib (AP24534; Gozgit et al., 2012, Mol Cancer Ther., 11; 690-99; 3-[2-(imidazo[1,2-b]pyridazin-3-yl)ethynyl]-4-methyl-N-{4-[(4-methylpiperazin-1-yl)methyl]-3-(trifluoromethyl)phenyl}benzamide, CAS 943319-70-8)

Pharmaceutical Compositions

To prepare pharmaceutical or sterile compositions including immunoconjugates, the immunoconjugates of the present disclosure are mixed with a pharmaceutically acceptable carrier or excipient. The compositions can additionally contain one or more other therapeutic agents that are suitable for treating or preventing cancer gastrointestinal stromal tumors (GIST), small cell lung cancer (SCLC), acute myeloid leukemia (AML), melanoma, mast cell leukemia (MCL), mastocytosis, neurofibromatosis, breast cancer, non-small cell lung cancer (NSCLC) and pancreatic cancer.

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman et al., Goodman and Gilman's The Pharmacological Basis of Therapeutics, McGraw-Hill, New York, N.Y., 2001; Gennaro, Remington: The Science and Practice of Pharmacy, Lippincott, Williams, and Wilkins, New York, N.Y., 2000; Avis, et al. (eds.), Pharmaceutical Dosage Forms: Parenteral Medications, Marcel Dekker, NY, 1993; Lieberman, et al. (eds.), Pharmaceutical Dosage Forms: Tablets, Marcel Dekker, NY, 1990; Lieberman, et al. (eds.) Pharmaceutical Dosage Forms: Disperse Systems, Marcel Dekker, NY, 1990; Weiner and Kotkoskie, Excipient Toxicity and Safety, Marcel Dekker, Inc., New York, N.Y., 2000).

In a specific aspect, the clinical service form (CSF) of the antibody drug conjugates of the present disclosure is a lyophilisate in vial containing the ADC, sodium succinate, and polysorbate 20. The lyophilisate can be reconstituted with water for injection; the solution comprises the ADC, sodium succinate, sucrose, and polysorbate 20 at a pH of about 5.0. For subsequent intravenous administration, the obtained solution will usually be further diluted into a carrier solution.

Selecting an administration regimen for a therapeutic depends on several factors, including the serum or tissue turnover rate of the entity, the level of symptoms, the immunogenicity of the entity, and the accessibility of the target cells in the biological matrix. In certain aspects, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak, Antibody Therapy, Bios Scientific Pub. Ltd, Oxfordshire, UK, 1996; Kresina (ed.), Monoclonal Antibodies, Cytokines and Arthritis, Marcel Dekker, New York, N.Y., 1991; Bach (ed.), Monoclonal Antibodies and Peptide Therapy in Autoimmune Diseases, Marcel Dekker, New York, N.Y., 1993; Baert et al., New Engl. J. Med. 348:601-608, 2003; Milgrom et al., New Engl. J. Med. 341:1966-1973, 1999; Slamon et al., New Engl. J. Med. 344:783-792, 2001; Beniaminovitz et al., New Engl. J. Med. 342:613-619, 2000; Ghosh et al., New Engl. J. Med. 348:24-32, 2003; Lipsky et al., New Engl. J. Med. 343:1594-1602, 2000).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions antibody drug conjugates can be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising antibodies or fragments thereof can be provided by continuous infusion, or by doses at intervals of, e.g., one day, one week, or 1-7 times per week. Doses can be provided intravenously, subcutaneously, topically, orally, nasally, rectally, intramuscular, intracerebral, or by inhalation. A specific dose protocol is one involving the maximal dose or dose frequency that avoids significant undesirable side effects.

For the immunoconjugates of the present disclosure, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. The dosage of the antibodies or fragments thereof can be calculated using the patient's weight in kilograms (kg) multiplied by the dose to be administered in mg/kg.

Doses of the immunoconjugates the can be repeated and the administrations may be separated by at least 1 day, 2 days, 3 days, 5 days, 10 days, 15 days, 30 days, 45 days, 2 months, 75 days, 3 months, or at least 6 months. In a specific aspect, doses of the immunoconjugates of the present disclosure are repeated every 3 weeks.

An effective amount for a particular patient may vary depending on factors such as the condition being treated, the overall health of the patient, the method, route and dose of administration and the severity of side effects (see, e.g., Maynard et al., A Handbook of SOPs for Good Clinical Practice, Interpharm Press, Boca Raton, Fla., 1996; Dent, Good Laboratory and Good Clinical Practice, Urch Publ., London, UK, 2001).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al., Biopolymers 22:547-556, 1983; Langer et al., J. Biomed. Mater. Res. 15:167-277, 1981; Langer, Chem. Tech. 12:98-105, 1982; Epstein et al., Proc. Natl. Acad. Sci. USA 82:3688-3692, 1985; Hwang et al., Proc. Natl. Acad. Sci. USA 77:4030-4034, 1980; U.S. Pat. Nos. 6,350,466 and 6,316,024). Where necessary, the composition may also include a solubilizing agent or a local anesthetic such as lidocaine to ease pain at the site of the injection, or both. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present disclosure can also be administered via one or more routes of administration using one or more of a variety of methods known in the art. As will be appreciated by the skilled artisan, the route and/or mode of administration will vary depending upon the desired results. Selected routes of administration for the immunoconjugates include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the present disclosure can be administered via a non-parenteral route, such as a topical, epidermal or mucosal route of administration, for example, intranasally, orally, vaginally, rectally, sublingually or topically. In one aspect, the immunoconjugates of the present disclosure are administered by infusion. In another aspect, the immunoconjugates are administered subcutaneously.

If the immunoconjugates of the present disclosure are administered in a controlled release or sustained release system, a pump may be used to achieve controlled or sustained release (see Langer, supra; Sefton, CRC Crit. Ref Biomed. Eng. 14:20, 1987; Buchwald et al., Surgery 88:507, 1980; Saudek et al., N. Engl. J. Med. 321:574, 1989). Polymeric materials can be used to achieve controlled or sustained release of the therapies of the immunoconjugates (see e.g., Medical Applications of Controlled Release, Langer and Wise (eds.), CRC Pres., Boca Raton, Fla., 1974; Controlled Drug Bioavailability, Drug Product Design and Performance, Smolen and Ball (eds.), Wiley, New York, 1984; Ranger and Peppas, J. Macromol. Sci. Rev. Macromol. Chem. 23:61, 1983; see also Levy et al., Science 228:190, 1985; During et al., Ann. Neurol. 25:351, 1989; Howard et al., J. Neurosurg. 7 1:105, 1989; U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one aspect, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138, 1984).

Controlled release systems are discussed in the review by Langer, Science 249:1527-1533, 1990). Any technique known to one of skill in the art can be used to produce sustained release formulations comprising one or more immunoconjugates of the present disclosure. See, e.g., U.S. Pat. No. 4,526,938, PCT publication WO 91/05548, PCT publication WO 96/20698, Ning et al., Radiotherapy & Oncology 39:179-189, 1996; Song et al., PDA Journal of Pharmaceutical Science & Technology 50:372-397, 1995; Cleek et al., Pro. Int'l. Symp. Control. Rel. Bioact. Mater. 24:853-854, 1997; and Lam et al., Proc. Int'l. Symp. Control Rel. Bioact. Mater. 24:759-760, 1997, each of which is incorporated herein by reference in their entirety.

If the immunoconjugates of the disclosure are administered topically, they can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as Freon) or in a squeeze bottle. Moisturizers or humectants can also be added to pharmaceutical compositions and dosage forms if desired. Examples of such additional ingredients are well-known in the art.

If the compositions comprising the immunoconjugates are administered intranasally, it can be formulated in an aerosol form, spray, mist or in the form of drops. In particular, prophylactic or therapeutic agents for use according to the present disclosure can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the immunoconjugates may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the immunoconjugates of the present disclosure. The two or more therapies may be administered within the same patient visit.

In certain aspects, immunoconjugates can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (Bloeman et al., (1995) FEBS Lett. 357:140; Owais et al., (1995) Antimicrob. Agents Chemother. 39:180); surfactant protein A receptor (Briscoe et al., (1995) Am. J. Physiol. 1233:134); p 120 (Schreier et al, (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The present disclosure provides protocols for the administration of pharmaceutical composition comprising immunoconjugates alone or in combination with other therapies to a subject in need thereof. The combination therapies (e.g., prophylactic or therapeutic agents) can be administered concomitantly or sequentially to a subject. The therapy (e.g., prophylactic or therapeutic agents) of the combination therapies can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the disclosure can be administered to a subject concurrently.

The term "concurrently" is not limited to the administration of therapies (e.g., prophylactic or therapeutic agents) at exactly the same time, but rather it is meant that a pharmaceutical composition comprising antibodies or fragments thereof are administered to a subject in a sequence and within a time interval such that the immunoconjugates can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various aspects, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other aspects, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

EXAMPLES

Example 1: Generation of cKIT Abs by Hybridoma Technology

Antigen and Other Proteins

A transient expression cell line secreting human cKIT protein was generated by transfection of 293 Freestyle™ cells (Invitrogen, Carlsbad, Ca). Briefly, the cells cultivated in Freestyle™ medium (Invitrogen) were transfected using 293Fectin™ transfection reagent and a recombinant plasmid containing the ECD of the human cKIT cDNA and either a His6 tag at the C-terminus of the sequence, or a murine Fc (pFUSE, Invivogen, San Diego, CA). 48-72 hours later the media is centrifuged to remove the cells, sterile filtered, and the cleared lysate used for protein purification.

For the His6 tagged cKIT: The resulting concentrate was applied to a NiNTA His-Bind Superflow® column at 0.5 mL/min. After baseline washing with PBS, bound material was eluted with PBS with a stepwise gradient of Imidazole (10-500 mM). The resulting eluate was dialyzed against PBS, pH 7.3, sterile filtered and aliquotted. For Fc-cKit fusion, Protein G Sepharose® FastFlow columns were used (instead of NiNTA) as outlined above, and eluted with a pH 3 Glycine buffer, which was neutralized with Tris, pH 8.

Hybridoma Generation
Immunization of Mice and Production of Hybridomas

Purified cKIT was diluted 1:1 with Freunds Complete Adjuvant prior to immunization of Bcl-2 transgenic mice (C57BL/6-Tgn (bcl-2) 22 Wehi strain). Mice were immunized using a procedure that calls for Repetitive Immunization at Multiple Sites (RIMMS) (McIntyre G D., Hybridoma, 1997). Briefly, mice were injected with 1-3 μg of antigen at 8 specific sites proximal to peripheral lymph nodes (PLN). This procedure was repeated 8 times over a 12-day period. On Day 12, a test bleed was collected and the serum antibody titer was analyzed by ELISA. Pooled PLN were removed from high titer mice on Day 15. To harvest lymphocytes, PLN were washed twice with plain DMEM and then dissociated by passage through a 0.22 micron screen (Falcon #352350, BD Bioscience, San Jose, CA). The resulting lymphocytes were washed 2 additional times prior to fusion. F0 myeloma cells were mixed with lymphocytes at a ratio of 2.5 lymphocytes to 1 F0 cell. The cell mixture was centrifuged and 1 mL of PEG 1500 was subsequently added dropwise to the cell pellet for 1 min. After 30 seconds, 1 mL of DMEM was slowly added, and 1 min later, 19 mL of DMEM was added for 5 min. Fused cells were pelleted, suspended at a density of $2\times10^5$ cells/mL in HAT media (DMEM+20% FBS, Pen/Strep/Glu, 1×NEAA, 1×HAT, 0.5× HFCS), and placed at 37° C. for one hr. The cells were then plated in 384-well plates at 60 μL/well.

Screening of Hybridomas Secreting Antibodies to cKIT

Ten days after fusion, hybridoma plates were screened for the presence of cKIT specific antibodies. For the ELISA screen, Maxisorp® 384-well plates (Nunc #464718) were coated with 50 μL of cKIT (diluted to 15 ng/well in PBS) and incubated overnight at 4° C. The remaining protein was aspirated and wells were blocked with 1% BSA in PBS. After 30 min incubation at room temperature, the wells were washed four times with PBS+0.05% Tween (PBST). 15 μL of hybridoma supernatant was transferred to the ELISA plates. 15 μL of mouse serum, taken at the time of PLN removal, was diluted 1:1000 in PBS and added as a positive control. 50 μL of secondary antibody (goat anti mouse IgG-HRP (Jackson Immuno Research #115-035-071, West Grove, PA), diluted 1:5000 in PBS) was added to all wells on the ELISA plates. After incubation at room temperature for 1 h, the plates were washed eight times with PBST. 25 μL of TMB (KPL #50-76-05) was added and after 30 min incubation at room temperature; the plates were read at an absorbance of 605 nm. Cells from positive wells were expanded into 24-well plates in HT media (DMEM+20% FBS, Pen/Strep/Glu, 1×NEAA, 1×HT, 0.5×HFCS).

Antibody Purification

Supernatant containing cKIT antibodies were purified using protein G (Upstate #16-266 (Billerica, MA)). Prior to loading the supernatant, the resin was equilibrated with 10 column volumes of PBS. Following binding of the sample, the column was washed with 10 column volumes of PBS, and the antibody was then eluted with 5 column volumes of 0.1 M Glycine, pH 2.0. Column fractions were immediately neutralized with 1/10th volume of Tris HCl, pH 9.0. The OD280 of the fractions was measured, and positive fractions were pooled and dialyzed overnight against PBS, pH 7.2.

Example 2: Humanization and Affinity Maturation of Anti-cKIT Antibodies

Design of Humanization

VH and VL sequences of hybridoma derived anti-cKIT antibody 9P3 are SEQ ID NO:9 and SEQ ID NO:18, respectively Amino acid sequences of human IgG1 constant domains used to generate full IgG1 are SEQ ID NO:10 for the heavy chain and SEQ ID NO:19 for the light chain Humanization of the heavy chain was accomplished by grafting the 3 CDR regions (GFTFSDYYMA (SEQ ID NO: 166,)) (NINYDGSSTYYLDS (SEQ ID NO:167)) and (GDYYGTTYWYFDV (SEQ ID NO:168) from anti-cKIT antibody 9P3, onto human germline acceptor framework VH3_3-07 (vBASE database). Humanization of the light chain was accomplished by either grafting the 3 CDR regions (RASQDISNYLN (SEQ ID NO:169)), (YTSRLQS (SEQ ID NO:170)) and (QQGKKLWS (SEQ ID NO:171)) from anti-cKIT antibody 9P3, onto human germline acceptor framework VK3-L25 (vBASE database) or grafting 2 CDR regions (SEQ ID NO:170 and SEQ ID NO:171) onto human germline acceptor framework VK1-012 (vBASE database). In addition to the CDR regions, one framework residue of the variable light chain domain, i.e. VL #71 and in the case of VK3-L25 VL #79 (residue numbering based on SEQ ID NO:21) was retained from the 9P3 sequence. Further, the human J elements JH4 and JK4 were used for the heavy and light chain, respectively. The resulting amino acid sequences of the humanized antibody heavy chain is SEQ ID NO: 11 and for the two light chains SEQ ID NO: 20 (VK1-012) and SEQ ID NO: 21 (VK3-L6).

We hypothesized that the amino acid motif aspartate followed by glycine (DG) may be susceptible to post-translational modification (iso-aspartate formation) and that lysines within the CDRs may decrease the fraction of active antibody after antibody-drug conjugation. A combination of random mutagenesis (i.e. error-prone PCR) and directed mutagenesis was applied to optimize the humanized antibodies.

Generation of Humanized Sequences

DNA sequences coding for humanized VL and VH domains were ordered at GeneArt (Life Technologies Inc. Regensburg, Germany) including codon optimization for Homo sapiens. Sequences coding for VL and VH domains were subcloned by cut and paste from the GeneArt derived vectors into expression vectors suitable for secretion in mammalian cells. The heavy and light chains were cloned into individual expression vectors to allow co-transfection. Elements of the expression vector include a promoter (Cytomegalovirus (CMV) enhancer-promoter), a signal sequence to facilitate secretion, a polyadenylation signal and transcription terminator (Bovine Growth Hormone (BGH) gene), an element allowing episomal replication and replication in prokaryotes (e.g. SV40 origin and ColE1 or others known in the art) and elements to allow selection (ampicillin resistance gene and zeocin marker).

Expression and Purification of Humanized Antibodies

Human Embryonic Kidney cells constitutively expressing the SV40 large T antigen (HEK293-T, ATCC11268) are one of the preferred host cell lines for transient expression of humanized and/or optimized IgG proteins. Transfection is performed using PEI (Polyethylenimine, MW 25.000 linear, Polysciences, USA Cat. No. 23966) as transfection reagent. The PEI stock solution is prepared by carefully dissolving 1 g of PEI in 900 ml cell culture grade water at room temperature (RT). To facilitate dissolution of PEI, the solution is acidified by addition of HCl to pH 3-5, followed by neutralization with NaOH to a final pH of 7.05. Finally, the volume is adjusted to 1 L and the solution is filtered through a 0.22 µm filter, aliquotted and frozen at −80° C. until further use. Once thawed, an aliquot can be re-frozen up to 3 times at −20° C. but should not be stored long term at −20° C. HEK 293T cells are cultivated using a Novartis proprietary serum-free culture medium for transfection and propagation of the cells, and ExCell® VPRO serum-free culture medium (SAFC Biosciences, USA, Cat. No. 24561C) as production/feed medium. Cells prepared for transient transfections are cultivated in suspension culture. For small scale (<5 L) transfections, cells are grown in Corning shake flasks (Corning, Tewksbury, MA) on an orbital shaker (100-120 rpm) in a humidified incubator at 5% CO2 (seed flasks). Cells in the seed cultures should be maintained in the exponential growth phase (cell densities between $5 \times 10^5$ and $3 \times 10^6$/mL) and display a viability of >90% for transfection. Cell densities outside of this range will result in either a lag phase after dilution or reduced transfection efficiency. For small scale (<5 L) transfection an aliquot of cells is taken out of the seed cultures and adjusted to $1.4 \times 10^6$ cells/mL in 36% of the final volume with Novartis serum-free culture medium. The DNA solution (Solution 1: 0.5 mg of heavy chain and 0.5 mg of light chain expression plasmid for a 1 L transfection) is prepared by diluting the DNA to 1 mg/L (final volume) in 7% of the final culture volume followed by gentle mixing. To prevent bacterial contamination, this solution is filtered using a 0.22 µm filter (e.g. Millipore Stericup). Then 3 mg/L (final volume) of PEI solution is also diluted in 7% of final culture volume and mixed gently (Solution 2). Both solutions are incubated for 5-10 min at room temperature (RT). Thereafter solution 2 is added to solution 1 with gentle mixing and incubated for another 5-15 minutes at room temperature. The transfection mix is then added to the cells and the cultivation of cells is continued for 4 to 6 hours. Finally, the remaining 50% of total production volume are achieved by addition of ExCell® VPRO serum-free culture medium. The cell cultivation is continued for eleven days post transfection. The culture is harvested by centrifugation at 4500 rpm for 20 minutes at 4° C. (Heraeus®, Multifuge 3 S-R, Thermo Scientific, Rockford, IL). The cell supernatant recovered is sterile filtered through a stericup filter (0.22 µm) and stored at 4° C. until further processing.

Purification was performed on an "ÄKTA 100 explorer Air" chromatography system at 4° C. in a cooling cabinet, using a freshly sanitized (0.25 M NaOH) HiTrap ProtA MabSelect®SuRe, 5 ml column. The column was equilibrated with 5 column volumes (CV) of PBS (Gibco, Life Technologies, Carlsbad, CA), and then the sterile filtered supernatant (2 L) was loaded at 4.0 ml/min. The column was washed with 8 CV of PBS to elute the unbound sample and again washed with 5 CV of PBS. Antibody was eluted with 5 CV of 50 mM citrate, 70 mM NaCl pH 3.2. The eluate was collected in 3 ml fractions; fractions were pooled and adjusted at pH 7 with 1 M Tris HCl pH10. The pools were pooled and sterile filtered (Millipore Steriflip, 0.22 um), the OD 280 nm was measured in a Spectrophotometer ND-1000 (NanoDrop), and the protein concentration was calculated based on the sequence data. The eluate was tested for aggregation (SEC-MALS) and purity (SDS-PAGE, LAL and MS). For the second purification step, if needed, pools from the first purification were loaded into a freshly sanitised (0.5 M NaOH) SPX (Hi Load 16/60 Superdex 200 grade 120 mL (GE-Healthcare). The column was equilibrated with PBS and the run was done with PBS buffer at 1 ml/min, the eluate was collected in 1.2 ml fractions and analyzed as described for the first purification step.

Example 3: Screening for Anti-cKIT Antibodies

HuCAL PLATINUM® Pannings

For selection of antibodies recognizing human cKIT multiple panning strategies were employed. Therapeutic antibodies against human cKIT proteins were generated by selection of clones having high affinity binding affinities, using as the source of antibody variant proteins a commercially available phage display library, the Morphosys HuCAL PLATINUM® library (Morphosys, Munich DE). The phagemid library is based on the HuCAL® concept (Knappik et al., (2000) J Mol Biol 296: 57-86) and employs the CysDisplay® technology for displaying the Fab on the phage surface (Lohning, WO 01/05950). For isolation of anti-cKIT antibodies, standard panning strategies were performed using solid phase, solution, whole cell and differential whole cell panning approaches.

Solid Phase Panning Against cKIT

An 96-well Maxisorp® plate was coated with human or mouse cKIT Fc fusion protein overnight at 4° C. For each panning, about $4 \times 10^{13}$ HuCAL PLATINUM® phage-antibodies were added to each antigen coated and incubated for 2 h at room temperature (RT) on a microtiter plate shaker. Afterwards, unspecific bound phages were washed off by several washing steps and specifically bound phages, were eluted using 25 mM DTT in 10 mM Tris/HCl pH 8.

The eluate was transferred into 14 ml of *E. coli* bacteria and incubated for phage infection. The infected bacteria were resuspended in 2×YT medium, plated on LB/Cam agar plates and incubated overnight. Colonies were scraped off the plates and were used for phage rescue, polyclonal amplification of selected clones, and phage production. With purified phage the next panning round was started.

The second and third round of solid phase panning was performed according to the protocol of the first round except for decreased amounts of antigen and more stringent washing conditions.

Capture Panning Against cKIT

For capture panning, the antigen cKIT/murine Fc fusion proteins were immobilized on a 96-well Maxisorp® plate via an goat anti-mouse Fc capture antibody. During phage blocking, human and mouse γ globulin were added to the blocking buffer to avoid selection of antibodies against the capture antibody and mouse Fc part of the antigen. The antigen coating and phage blocking procedures in the capture panning was performed as described in the Solid Phase Panning protocol (see above).

Solution Panning Protocol with Streptavidin-Coupled Magnetic Beads

Solution pannings were performed in two different modes ("classical" and "alternative"). For each panning, about $4 \times 10^{13}$ HuCAL PLATINUM® phage-antibodies were blocked with an equal volume of 2× Chemiblocker/0.1% Tween20. For removal of Streptavidin- or bead-binding phage, pre-adsorption of blocked phage particles was performed twice using 1 mg blocked Streptavidin beads each.

a) "Classical" mode: Biotinylated 16P23 mAb was incubated with human cKIT ECD-His protein and was added to the blocked phage particles. The 16P23 antibody is an internally generated hybridoma and was used in various screening protocols as a capture antibody to expose different domains on the ECD of cKIT. The 16P23 antibody was also used for antibody binning purposes. After incubation the phage-antigen complexes were captured using Streptavidin beads and phage particles bound to the Streptavidin beads were collected with a magnetic separator.

b) "Alternative" mode: Biotinylated 16P23 mAb was added to streptavidin beads and the antibody-bead mix was incubated on a rotator at room temperature for 30 min. Beads were washed and resuspended in PBS containing human cKIT ECD-His protein. Subsequently, the phages were added and the antibody-bead-antigen-phage complex was rotated for an additional 1 hour at room temperature on a rotator. After this last incubation step the beads were captured with a magnetic separator and the supernatants were discarded.

Using both display methods unspecific bound phage were washed off by several washing steps using PBS/0.05% Tween20 and PBS. Specifically bound phages were eluted from Streptavidin beads by using 25 mM DTT in 10 mM Tris/HCl pH 8. Subsequent phage infection and phage production was performed according to the Solid Phase Panning protocol.

The second and third round of the solution panning was performed according to the protocol of the first round except for decreased amounts of antigen and more stringent washing conditions.

Whole Cell Panning Against cKIT

Target cells expressing antigen human, mouse or rat cKIT were used as antigens and were contacted with HuCAL PLATINUM® phage-antibodies for pannings The phage-cell complexes were washed three times in PBS/5% FCS. Elution of specifically bound phage from target cells was performed with 0.1M glycine-HCl/0.5M NaCl, pH 2.2. Subsequent phage infection and phage production was performed according to the Solid Phase Panning protocol. The second and third round of the whole cell panning was performed according to the protocol of the first round.

Differential Whole Cell Panning Against cKIT

In the differential whole cell panning, the selection was done alternating on cells and purified protein. The selection rounds on purified antigen were performed as described in the Solid Phase Panning protocol For the selection rounds on cells please refer to the procedure in the Whole Cell Panning Against cKIT section.

Maturation Pannings

In order to obtain specific antibodies with increased affinities, maturation pannings were performed (Prassler et al., Future Med. Immuno. 2009 1(4):571-583). For this purpose, sequenced clones already tested for cKIT specific binding were used for LCDR3 or HCDR2 cassette exchange. Afterwards two rounds of solid phase pannings were performed with human and/or mouse cKIT Fc fusion protein as described in the Solid Phase Panning protocol.

a) For LCDR3 RapMAT®: Fab-encoding fragments of phage derived pMORPH30® vector DNA (Morphosys, Munich DE) were enzymatically digested and inserts were replaced with TRIM™ LCDR3 maturation cassettes (Virnekaes et al., NAR 1994 22(25):5600-5607). Subsequently, 1.25 µg pMORPH30® display vector was ligated with the insert fragment carrying the diversified LCDR3 s.

b) For HCDR2 RapMAT®: After the 2nd round of panning, Fab-encoding fragments of phage derived pMORPH30® vector DNA were enzymatically digested and inserts were replaced with TRIM™ HCDR2 maturation cassettes (Virnekas et al., supra). Subsequently, 1.25 µg pMORPH30® display vector was ligated with the insert fragment carrying the diversified HCDR2s.

The generated libraries were amplified and subjected to two rounds of panning with either increased stringency and reduced antigen concentration or alternation of human and mouse cKIT antigen to identify affinity improved clones.

Preparation of Fab Containing Bacterial Lysates for ELISA Screening

For initial screening and characterization an overnight culture of individual Fab-expressing *E. coli* clones were lysed using lysozyme, 4 mM EDTA and 10 U/µl Benzonase. Fab containing *E. coli* lysates were used for ELISA, FACS and SET screening.

Screening of Fab-Containing Raw Bacterial Lysates

ELISA Screening

Using ELISA screening, single Fab clones are identified from panning output for binding to the target antigen. Fabs are tested using Fab containing crude *E. coli* lysates.

Fab Expression Check ELISA

For verification of Fab expression in the prepared *E. coli* lysates, Maxisorp® 384 well plates (Nunc, Sigma-Aldrich, St. Louis MO) were coated with Fd fragment specific sheep anti-human IgG diluted 1:1000 in PBS. After blocking with 5% skim milk powder in PBS containing 0.05% Tween20, Fab-containing *E. coli* lysates were added. Subsequently the bound HuCAL®-Fab fragments were detected by incubation with F(ab)2 specific goat anti-human IgG conjugated to alkaline phosphatase (diluted 1:5000) followed by addition of AttoPhos® fluorescence substrate (Roche, #11681982001, Mannheim, DE). Fluorescence emission at 535 nm was recorded with excitation at 430 nm.

ELISA Screening on Directly Coated Antigen

Maxisorp® 384 well plates were coated with mFc tagged human cKIT ECD protein at a concentration of 10 µg/ml in PBS. After blocking of plates with 5% skim milk powder in PBS, Fab-containing *E. coli* lysates were added. Binding of Fabs was detected by $F(ab)_2$ specific goat anti-human IgG conjugated to alkaline phosphatase (diluted 1:5000) using Attophos® fluorescence substrate (Roche, #11681982001, Mannheim, DE). Fluorescence emission at 535 nm was recorded with excitation at 430 nm.

Epitope Binning with Fab BEL Lysates

To identify potential ligand binding competitors prior to affinity maturation, a competition ELISA screening with Fab *E. coli* lysates and 16P23 antibody, a known ligand binding competitor, was performed. For this purpose, Maxisorp® 384 well plates were coated with mFc tagged human cKIT ECD protein and blocked as described above (ELISA Screening on Directly Coated Antigen).

16P23 mAb was added at a final concentration of 5 µg/ml followed by incubation with Fab-containing *E. coli* lysates. Finally, binding of Fabs was detected with an anti-FLAG alkaline phosphatase-conjugated antibody (Sigma A-9469, diluted to 1:10000) using Attophos® fluorescence substrate (Roche, #11681982001). Fluorescence emission at 535 nm was recorded with excitation at 430 nm.

FACS Screening

In FACS screening, single Fab clones binding to cell surface expressed antigen are identified from the panning output. Fabs are tested using Fab containing crude *E. coli* lysates.

FACS Screening was performed either in 96- or 384-well plate format:

a) In 96-well plate format using a BD FACS array device, 100 µl of cell-suspension were transferred into a fresh 96-well plate (resulting in 1×10$^5$ cells/well). Target cell suspension containing plate was centrifuged and supernatant was discarded. Remaining cell pellet was resuspended and 50 µl of Fab containing BEL extracts was added to the corresponding wells. Plate was incubated on ice for 1 hour. Following incubation, cells were spun down and washed three times with 200 µl FACS buffer (PBS, 3% FCS). After each washing step, cells were centrifuged and carefully resuspended. Secondary detection antibody (PE conjugated goat anti human IgG; Dianova, Hamburg, DE) was added and samples were incubate on ice and subsequently washed according to Fab incubation. Finally, cell pellets were resuspended in 150 µl FACS buffer per well and samples were analyzed in BD FACS array.

b) In 384-well plate format using a BD Calibur® HTS device (BD Biosciences, San Jose, CA), 20 µl of cell-suspension were transferred into a fresh 384 round well plate (resulting in 4×10$^4$ cells/well). Target cell suspension containing plate was centrifuged and supernatant was discarded. Remaining cell pellet was resuspended and 20 µl of Fab containing extracts was added to the corresponding wells. Plate was incubated for 1 hour shaking at 4° C. Following incubation, cells were spun down and washed three times with 40 µl FACS buffer (PBS, 3% FCS). After each washing step, cells were centrifuged and carefully resuspended. 40 µl of PE conjugated goat anti human detection antibody was added and samples were incubated on ice and subsequently washed according to Fab incubation. Finally, cell pellets were resuspended in 35 µl FACS buffer per well and samples were measured with BD FACS Calibur®/HTS device.

Affinity Determination

For $K_D$ determinations, monomer fractions of antibody protein were used (at least 90% monomer content, analyzed by analytical SEC; Superdex® 75 PC3.2/30 (GE Healthcare, Pittsburgh, PA) for Fab, or Tosoh TSKgel G3000 SW$_{XL}$ (7.8 mm/30.0 cm) (Tosoh Bioscience GmbH, Stuttgart, DE) for IgG, respectively).

Solution Equilibrium Titration (SET) Method for KD Determination Using Sector Imager 6000 (MSD)

Affinity determination in solution was basically performed as described in the literature (Friquet et al., J. Immuno. Meth. 1985; 77:305-319). In order to improve the sensitivity and accuracy of the SET method, it was transferred from classical ELISA to ECL based technology (Haenel et al., Anal. Biochem. 2005 339(1):182-4). 1 mg/ml goat-anti-human (Fab)2 fragment specific antibodies (Dianova) were labeled with MSD Sulfo-TAG' NHS-Ester (Meso Scale Discovery, Gaithersburg, MD, USA) according to the manufacturer's instructions. MSD plates were coated with antigen and the equilibrated samples were transferred to those plates. After washing, 30 µl per well of the MSD-Sulfo-tag labeled detection antibody (anti-human (Fab)2) was added to the MSD plate and incubated on a shaker. After washing the MSD plate and adding 30 µl/well MSD Read Buffer T with surfactant, electrochemiluminescence signals were detected using a Sector® Imager 6000 (Meso Scale Discovery, Gaithersburg, MD, USA).

The data was evaluated with XLfit (IDBS) software applying customized fitting models. For KD determination of Fab molecules the following fit model was used (according to (Haenel et al., Anal. Biochem 2005; 339(1):182-184), modified according to (Abraham et al., J. Mol. Recogn 1996; 9:456-461)):

$$y = B_{max} - \left( \frac{B_{max}}{2[Fab]_t} \left( [Fab]_t + x + K_D - \sqrt{([Fab]_t + x + K_D)^2 - 4x[Fab]_t} \right) \right)$$

[Fab]$_t$: applied total Fab concentration
x: applied total soluble antigen concentration (binding sites)
$B_{max}$: maximal signal of Fab without antigen
$K_D$: affinity For $K_D$ determination of IgG molecules the following fit model for IgG was used (modified according to (Pichler et al., 1997)):

$$y = \frac{2B_{max}}{[IgG]} \left( [IgG] - \frac{\left( \frac{x + [IgG] + K_D}{2} - \sqrt{\frac{(x + [IgG] + K_D)^2}{4} - x[IgG]} \right)^2}{2[IgG]} \right)$$

[IgG]: applied total IgG concentration
x: applied total soluble antigen concentration (binding sites)
$B_{max}$: maximal signal of IgG without antigen
$K_D$: affinity Experimental Settings:

$K_D$ determination of HuCAL® anti cKIT IgGs was basically performed as follows: human cKIT-Fc was coated at 0.1 µg/ml in PBS overnight at 4° C. on standard MSD plates/assay buffer for 1 hour at room temperature on streptavidin MSD plates. Subsequently MSD plates were blocked with PBS with 3% BSA for 1 hour at room temperature. Streptavidin plates were blocked overnight at 4° C. with PBS with 5% BSA before antigen coating. For titration of antigen human cKIT-His was applied.

Subsequently, the concentration of unbound Fab was quantified via ECL detection using the Sector Imager 6000 (Meso Scale Discovery, Gaithersburg, MD, USA). Results were processed using XLfit (IDBS) software, applying the corresponding fit model to estimate affinities and thus identify clones most improved by the maturation.

In Vitro Biochemical Assays (Cross-Reactivity and Domain-Binding Analysis)

Purified IgGs were tested in ELISA for binding to human, cyno and mouse cKIT full-length ECD proteins as well as human cKIT ECD domain constructs D1-3 and D4-5. For this purpose plates were coated with antigen at a concentration of 5 µg/ml in PBS over night at 4° C. Binding of IgGs was detected by anti-human or anti-mouse F(ab)2 conjugated to alkaline phosphatase (diluted 1:5000 in 1% MPBS) using Attophos® as substrate. Fluorescence emission was measured at an excitation of 430 nm and an emission of 535 nm.

Epitope Binning of Purified IgGs

Purified IgG candidates were tested for competition with internally generated tool antibodies, previously shown to define individual bins on the extracellular domain of cKIT. For this purpose, IgGs were coated at constant amounts on Maxisorp® plates and tested for competition with increasing amounts of competitor IgG in solution. As positive control, the coated IgG was analyzed for competition with itself in solution. All tested IgGs were preincubated in 50× excess with glycobiotinylated human cKIT-Fc fusion for 1 hour at room temperature in solution. Antigen/antibody complexes were then added to the coated antibodies and detection of bound complexes occurred via the biotinylated antigen. In general, signals at high IgG concentration could only be obtained when the coated IgG was able to bind to accessible epitopes on the antigen different to the tested IgG in solution (i.e. a non competitive antibody). In contrast, for competitive antibodies, antibodies with partially overlapping epitopes or antibodies that block the epitope by steric hindrance, binding signals at high IgG concentration were significantly decreased in contrast to controls.

Respective wells of Maxisorp® plates were coated with 20 µl/well of IgG dilution at a concentration of 1.2 µg/ml in PBS, incubated overnight at 4° C. and then washed 3× with PBST. Plates were blocked with 90 µl 3% BSA/PBS well for 1 hour at room temperature and washed 3× with PBST.

EC50 Determination on Cells Via FACS

Purified IgGs were tested at a single concentration or titrated in FACS to determine EC50 values for binding to cell surface expressed human, mouse or rat cKIT. For this purpose, Mo7e, P815 or RBL-2H3 cells were harvested with Accutase® (Life Technologies, Carlsbad, CA) and diluted to $1\times10^6$/ml in FACS buffer. All subsequent steps were done on ice to prevent internalization of the receptor. The cell suspension was filled with 100 µl/well into a 96 well U bottom plate. After centrifugation at 210 g for 5 min at 4° C., buffer was discarded. 100 µl of the specific mAbs diluted in FACS buffer was then added per well at a concentration of 15 µg/ml or in titration experiments at a serial dilution of antibody concentrations (1:3 dilution steps, starting concentration of 15 µg/ml). After 1 h incubation on ice, cells were washed three times with 150 µl FACS buffer. Secondary PE conjugated goat anti human detection antibody (diluted 1:200 in FACS buffer) was added to the cells with 100 µl/well and incubated on ice for 1 h. Cells were washed three times with 150 µl FACS buffer. Finally, cell pellets were resuspended in 200 µl FACS buffer per well and samples were analyzed in BD FACS array.

In Vitro Bio-Assays

SCF-Dependent Proliferation Assay

Proliferation assays were performed on the Mo7e cell line (human acute megakaryoblastic leukemia, DSMZ no.: ACC 104) cultured in RPMI1640 with stable glutamine (PAN #P04-18500), 10% FCS and 10 ng/ml SCF (R&D CAT #255-SC; Lot #CM2810061, R&D Corp, Berkeley CA).

In the SCF-dependent proliferation assay purified IgGs or IgG containing cell culture supernatants were tested. In both experimental settings cells were harvested and resuspended in 50 µl starve medium (culture medium without SCF) at a concentration of $0.5\times10^6$ cells/ml and incubated at 37° C. for 18 h. Cells were then resuspended at a concentration of $1\times10^6$ cells/ml in starving medium with 60 ng/ml SCF (2× concentrated, final concentration after addition of antibody is 30 ng/ml). 50 µl of cells ($5\times10^4$ cells/well) and 50 µl of 2× concentrated purified antibodies or undiluted cell culture supernatants were added per well of a white 96-well flat with clear bottom plates. For negative and positive controls, cells without SCF and without antibody or cells with SCF and without antibody were included. Plates were incubated for 48 h at 37° C. and finally cell numbers were determined using CellTiter-Glo® (Promega #G7571, Promega, Madison, WI) according to the manufacturer's instructions.

Fab-ZAP ADC Piggyback Assay

To test the ability of antibodies to internalize after receptor binding, an ADC assay was performed mixing Fab-ZAP reagent (goat anti-hu-mAb-saporin-coupled; ATS Biotechnology, Cat #IT-51-250, ATS Bio, San Diego, CA) either with purified IgGs or with IgG containing cell culture supernatants. Cytotoxic potential was tested on the cancer cell line CMK-11-5 (acute megakaryoblastic leukemia cells (Hamamoto et al., Int. J. Hematol. 1993 58(1-2):105-112) (JCRB #IFO50430)) cultured in RPMI1640+10% FCS) as these cells show high expression of cKIT.

Cells in culture were counted and diluted in medium to a concentration of $1\times10^5$ cells/ml. 50 µl cell suspension (5000 cells/well) were transferred to 96-well plates (Flat Clear Bottom White Plate TC-Treated, Corning Cat #3903, Corning, Tewksbury, MA). In a separate plate (96 Well V bottom, Nunc, Cat #249946, Nunc Sigma-Aldrich, St. Louis, MO) IgGs were diluted in medium. IgG containing cell culture supernatants were diluted 1:125 and purified IgGs to a concentration of 0.4 nM resulting in a total volume of 60 µl/well. An equal volume of FabZAP solution at a concentration of 5 nM was added and the plate was incubated for 60 min at 37° C. 50 µl of antibody/Fab-ZAP conjugates were transferred to CMK-11-5 cells (total volume 100 µl). For controls, wells with cells only (=100% viability control) and cells only incubated with Fab-ZAP (to check for unspecific killing of the secondary reagent) were prepared. Final concentration of Fab-ZAP was 1.25 nM. Plates were incubated for 72 h at 37° C. and 5% $CO_2$. Cell numbers were determined using CellTiter-Glo® (Promega #G7571) according to the manufacturer's instructions. Viability was normalized to the cells only control.

Summary

In screening for cKIT antibodies, 2 different strategies were performed:

Strategy 1:

Candidates with human/cyno x-reactivity (217 HCDR3 families) were selected on high affinity and after IgG conversion clones were screened for functionality in CMK-11-5 FabZAP ADC assay and Mole proliferation assay. Based on functional activity and diversity candidates were selected for exploratory scale expression. An example of an antibody to come from this type of strategy is antibody 20507.

Strategy 2:

Candidates with human/cyno/mouse x-reactivity (5 HCDR3 families) were affinity matured and after IgG conversion candidates were selected for expression.

In summary, 82 purified IgG candidates from strategy 1 and 2 were subjected to in-depth characterization. From this pool of 82, 26 IgG candidates were selected for upscaled production, toxin conjugation and subsequent testing as antibody drug conjugates in in vitro and in vivo experiments. An example of an antibody to come from this type of strategy is antibody 20376.

Upon in-depth characterization, the 26 antibodies (14 candidates from strategy 1 and 12 candidates from strategy 2) belonging to 16 different HCDR3 families were selected for upscaled production and testing as antibody-drug conjugate. Candidates were selected according to following criteria: 1) Potent killing of wildtype and mutant cKIT expressing cells in Fab-DM1 piggyback assay with EC50 in the sub- to low-nanomolar range, 2) the KD values of 24/26 IgGs for cyno cKIT are within 3-fold range to that determined for the human cKIT. In addition, 12/26 IgGs cross-react with mouse and rat cKIT expressed on cells.

Selected candidates from this screening could be assigned to different epitope bins:

1) 19/26 IgGs belong to Bin 1 or Bin 6 (binding to cKIT D1-3, ligand binding domains)
2) 6/26 IgGs belong to Bin 8 (binding to cKIT D4-5, dimerization domains)
3) 1/26 IgGs belong to Bin 2, which had high affinity to human cKIT but had only weak affinity to cyno cKIT.

Example 4: Constructs for Human, Cyno, Mouse and Rat cKIT ECD Proteins

Human, mouse and rat cKIT extracellular domains were gene synthesized based on amino acid sequences from the GenBank or Uniprot databases (see Table 4 below). Cynomolgus cKIT and 1 ECD cDNA template were gene synthesized based on amino acid sequences information generated using mRNA from various cyno tissues (e.g. Zyagen Laboratories; Table 5 below). All synthesized DNA fragments were cloned into appropriate expression vectors e.g. hEF1-HTLV based vector (pFUSE-mIgG2A-Fc2) with C-terminal tags to allow for purification.

TABLE 4

Constructs

| Name | Description | Accession Number | SEQ ID NO: |
|---|---|---|---|
| Human cKIT D1-5 | Human cKIT tr. variant 2, residues 26-520-TAG QPSVSPGEPSPPSIHPGKSDLIVRVGDEIRLLCTDPGFVK WTFEILDETNENKQNEWITEKAEATNTGKYTCTNKHG LSNSIYVFVRDPAKLFLVDRSLYGKEDNDTLVRCPLTD PEVTNYSLKGCQGKPLPKDLRFIPDPKAGIMIKSVKRA YHRLCLHCSVDQEGKSVLSEKFILKVRPAFKAVPVVS VSKASYLLREGEEFTVTCTIKDVSSSVYSTWKRENSQT KLQEKYNSWHHGDFNYERQATLTISSARVNDSGVFM CYANNTFGSANVTTTLEVVDKGFINIFPMINTTVFVND GENVDLIVEYEAFPKPEHQQWIYMNRTFTDKWEDYPK SENESNIRYVSELHLTRLKGTEGGTYTFLVSNSDVNAA IAFNVYVNTKPEILTYDRLVNGMLQCVAAGFPEPTID WYFCPGTEQRCSASVLPVDVQTLNSSGPPFGKLVVQS SIDSSAFKHNGTVECKAYNDVGKTSAYFNFAFKEQIHP HTLFTPRSHHHHHH | NM_001093772 | (SEQ ID NO: 172) |
| Human cKIT D1-3 | Human cKIT tr. Variant 1, residues 26-311-TAG QPSVSPGEPSPPSIHPGKSDLIVRVGDEIRLLCTDPGFVK WTFEILDETNENKQNEWITEKAEATNTGKYTCTNKHG LSNSIYVFVRDPAKLFLVDRSLYGKEDNDTLVRCPLT DPEVTNYSLKGCQGKPLPKDLRFIPDPKAGIMIKSVKR AYHRLCLHCSVDQEGKSVLSEKFILKVRPAFKAVPVV SVSKASYLLREGEEFTVTCTIKDVSSSVYSTWKRENSQ TKLQEKYNSWHHGDFNYERQATLTISSARVNDSGVF MCYANNTFGSANVTTTLEVVDKGRSHHHHHH | NM_000222 | (SEQ ID NO: 173) |
| Human cKIT D4-5 | Human cKIT tr. variant 1, residues 311-524-TAG GFINIFPMINTTVFVNDGENVDLIVEYEAFPKPEHQQWI YMNRTFTDKWEDYPKSENESNIRYVSELHLTRLKGTE GGTYTFLVSNSDVNAAIAFNVYVNTKPEILTYDRLVN GMLQCVAAGFPEPTIDWYFCPGTEQRCSASVLPVDVQ TLNSSGPPFGKLVVQSSIDSSAFKHNGTVECKAYNDVG KTSAYFNFAFKGNNKEQIHPHTLFTPRSHHHHHH | NM_000222 | (SEQ ID NO: 174) |
| Mouse cKIT D1-5 | Mouse cKIT tr. variant 1, residues 26-527-TAG SQPSASPGEPSPPSIHPAQSELIVEAGDTLSLTCIDPDFV RWTFPKTYFNEMVENKKNEWIQEKAEATRTGTYTCSN SNGLTSSIYVFVRDPAKLFLVGLPLFGKEDSDALVRCP LTDPQVSNYSLIECDGKSLPTDLTFVPNPKAGITIKNVK RAYHRLCVRCAAQRDGTWLHSDKFTLKVRAAIKAIPV VSVPETSHLLKKGDTFTVVCTIKDVSTSVNSMWLKMN PQPQHIAQVKHNSWHRGDFNYERQETLTISSARVDDS GVFMCYANNTFGSANVTTTLKVVEKGFINISPVKNTT VFVTDGENVDLVVEYEAYPKPEHQQWIYMNRTSANK GKDYVKSDNKSNIRYVNQLRLTRLKGTEGGTYTFLVS NSDASASVTFNVYVNTKPEILTYDRLINGMLQCVAEG FPEPTIDWYFCTGAEQRCTTPVSPVDVQVQNVSVSPFG KLVVQSSIDSSVFRHNGTVECKASNDVGKSSAFFNFAF KEQIQAHTLFTPLEVLFQGPRSPRGPTIKPCPPCKPAP NLLGGPSVFIFPPKIKDVLMISLSPIVTCVVVDVSEDDP DVQISWFVNNVEVHTAQTQTHREDYNSTLRVVSALPI QHQDWMSGKEFKCKVNNKDLPAPIERTISKPKGSVRA PQVYVLPPPEEEMTKKQVTLTCMVTDFMPEDIYVEWT NNGKTELNYKNTEPVLDSDGSYFMYSKLRVEKKNWV ERNSYSCSVVHEGLHNHHTTKSFSRTPGK | NM_001122733 | (SEQ ID NO: 175) |
| Rat cKIT D1-5 | Rat cKIT, residues 25-526-TAG SQPSASPGEPSPPSIQPAQSELIVEAGDTIRLTCTDPAFV KWTFEILDVRIENKQSEWIREKAEATHTGKYTCVSGSG LRSSIYVFVRDPAVLFLVGLPLFGKEDNDALVRCPLTD PQVSNYSLIECDGKSLPTDLKFVPNPKAGITIKNVKRA YHRLCIRCAAQREGKWMRSDKFTLKVRAAIKAIPVVS VPETSHLLKEGDTFTVICTIKDVSTSVDSMWIKLNPQP QSKAQVKRNSWHQGDFNYERQETLTISSARVNDSGVF MCYANNTFGSANVTTTLKVVEKGFINIFPVKNTTVFVT DGENVDLVVEFEAYPKPEHQQWIYMNRTPTNRGEDY VKSDNQSNIRYVNELRLTRLKGTEGGTYTFLVSNSDVS ASVTFDVYVNTKPEILTYDRLMNGRLQCVAAGFPEPTI DWYFCTGAEQRCTVPVPPVDVQIQNASVSPFGKLVVQ | NM_022264 | (SEQ ID NO: 176) |

TABLE 4-continued

Constructs

| Name | Description | Accession Number | SEQ ID NO: |
|------|-------------|------------------|------------|
| | SSIDSSVFRHNGTVECKASNAVGKSSAFFNFAFKGNSK EQIQPHTLFTPRSLEVLFQGPGSPPPLKECPPCAAPDLLG GPSVFIFPPKIKDVLMISLSPMVTCVVVDVSEDDPDVQI SWFVNNVEVHTAQTQTHREDYNSTLRVVSALPIQHQD WMSGKEFKCKVNNRALPSPIEKTISKPRGPVRAPQVY VLPPPAEEMTKKEFSLTCMITGFLPAEIAVDWTSNGRT EQNYKNTATVLDSDGSYFMYSKLRVQKSTWERGSLF ACSVVHEGLHNHLTTKTISRSLGK | | |

TABLE 5

Sequences of cynomolgus cKIT protein

| Construct | Amino acid sequence in one letter code, signal peptide underlined Cynomolgus monkey cKIT, residues 25-520-TAG | SEQ ID NO |
|-----------|----------------------------------------------------------------------------------------|-----------|
| Cynomolgus monkey cKIT D1-5 | MYRMQLLSCIALSLALVTNSQPSVSPGEPSPPSIHPAKSELIVRVGNEIRLLCID PGFVKWTFEILDETNENKQNEWITEKAEATNTGKYTCTNKHGLSSSIYVFVR DPAKLFLVDRSLYGKEDNDTLVRCPLTDPEVTSYSLKGCQGKPLPKDLRFVP DPKAGITIKSVKRAYHRLCLHCSADQEGKSVLSDKFILKVRPAFKAVPVVSV SKASYLLREGEEFTVTCTIKDVSSSVYSTWKRENSQTKLQEKYNSWHHGDF NYERQATLTISSARVNDSGVFMCYANNTFGSANVTTTLEVVDKGFINIFPMIN TTVFVNDGENVDLIVEYEAFPKPEHQQWIYMNRTFTDKWEDYPKSENESNIR YVSELHLTRLKGTEGGTYTFLVSNSDVNASIAFNVYVNTKPEILTYDRLVNG MLQCVAAGFPEPTIDWYFCPGTEQRCSASVLPVDVQTLNASGPPFGKLVVQS SIDSSAFKHNGTVECKAYNDVGKTSAYFNFAFKGNNKEQIHPHTLFTPRSHH HHHH | (SEQ ID NO: 177) |

Expression of Recombinant cKIT Proteins

The desired cKIT recombinant proteins were expressed in HEK293 derived cell lines (293FS) previously adapted to suspension culture and grown in serum-free medium FreeStyle-293 (Gibco, catalogue #12338018). Both small scale and large scale protein production were via transient transfection and was performed in multiple shaker flasks (Nalgene), up to 1 L each, with 293Fectin® (Life Technologies, catalogue #12347019) as a plasmid carrier. Total DNA and 293Fectin was used at a ratio of 1:1.5 (w:v). DNA to culture ratio was 1 mg/L. The cell culture supernatants were harvested 3-4 days post transfection, centrifuged and sterile filtered prior to purification.

Example 5: Purification of Human, Cyno, Mouse and Rat cKIT ECD Protein, and of cKIT Subdomains 1-3, and 4-5

Tagged Protein Purification

Recombinant Fc-tagged cKIT extracellular domain proteins (e.g., human cKIT ECD-Fc, human cKIT (ECD subdomains 1-3, 4-5)-Fc, cyno cKIT-mFc, rat cKIT-mFc, mouse cKIT-mFc) were purified from the cell culture supernatant. The clarified supernatant was passed over a Protein A Sepharose® column which had been equilibrated with PBS. After washing to baseline, the bound material was eluted with Pierce Immunopure® low pH Elution Buffer, or 100 mM glycine (pH 2.7) and immediately neutralized with $\frac{1}{8}^{th}$ the elution volume of 1 M Tris pH 9.0. The pooled protein was concentrated if necessary using Amicon® Ultra 15 mL centrifugal concentrators with 10 kD or 30 kD nominal molecular weight cut-offs. The pools were then purified by SEC using a Superdex® 200 26/60 column to remove aggregates. The purified protein was then characterized by SDS-PAGE and SEC-MALLS (Multi-angle laser light scattering). Concentration was determined by absorbance at 280 nm, using the theoretical absorption coefficients calculated from the sequence by Vector NTI.

Example 6: Binding of cKIT Abs to cKIT ECD Subdomains

To help define the binding sites of the cKIT Abs, the human cKIT ECD was divided into subdomains 1-3 (ligand binding domain) and subdomains 4-5 (dimerization domain) To determine which subdomains were bound, a sandwich ELISA assay was employed. 1 μg/ml of ECD diluted in 1× Phosphate buffered saline corresponding to cKIT subdomains 1-3, subdomains 4-5 or full-length cKIT ECD were coated on 96 well Immulon® 4-HBX plates (Thermo Scientific Cat #3855, Rockford, IL) and incubated overnight at 4° C. Plates were washed three times with wash buffer (1× Phosphate buffered saline (PBS) with 0.01% Tween-20 (Bio-Rad 101-0781)). Plates were blocked with 280 μl/well 3% Bovine Serum Albumin diluted in 1×PBS for 2 hrs at room temperature. Plates were washed three times with wash buffer. Antibodies were prepared at 2 μg/ml in wash buffer with 5-fold dilutions for 8 points and added to ELISA plates at 100 μl/well in triplicate. Plates were incubated on an orbital shaker shaking at 200 rpm for 1 hr at room temperature. Assay plates were washed three times with wash buffer. Secondary antibody F(ab')2 Fragment Goat anti-human IgG (H+L) (Jackson Immunoresearch Cat #109-036-088, West Grove, PA) was prepared 1:10,000 in wash buffer and added to ELISA plates at 100 μl/well. Plates were incubated with secondary antibody for 1 hr at room temperature shaking at 200 rpm on an orbital shaker. Assay plates were washed three times with wash buffer. To develop the ELISA signal, 100 μl/well of Sure Blue® TMB substrate (KPL Cat #52-00-03, Gaithersburg, MD) was added to plates and allowed to incubate for 10 mins at room temperature. To stop the reaction 50 µl of 1N Hydrochloric Acid was added to each well. Absorbance was measured at 450 nM using a Molecular Devices SpectraMax® M5 plate reader. To determine the binding response of each antibody the optical density measurements were averaged, standard deviation values generated and graphed using Excel. The binding domains of each individual anti-cKIT antibody is found in Table 7 below.

Example 7: Affinity Measurements of cKIT Abs

Affinity of the antibodies to cKIT species orthologues and also to cKIT was determined using SPR technology using a Biacore® 2000 instrument (GE Healthcare, Pittsburgh, PA) and with CM5 sensor chips.

Briefly, HBS-P (0.01 M HEPES, pH 7.4, 0.15 M NaCl, 0.005% Surfactant P20) supplemented with 2% Odyssey® blocking buffer (Li-Cor Biosciences, Lincoln, NE) was used as the running buffer for all the experiments. The immobilization level and analyte interactions were measured by response unit (RU). Pilot experiments were performed to test and confirm the feasibility of the immobilization of the anti-human Fc antibody (Catalog number BR100839, GE Healthcare, Pittsburgh, PA) and the capture of the test antibodies.

For kinetic measurements, the experiments were performed in which the antibodies were captured to the sensor chip surface via the immobilized anti-human Fc antibody and the ability of the cKIT proteins to bind in free solution was determined. Briefly, 25 µg/ml of anti-human Fc antibody at pH 5 was immobilized on a CM5 sensor chip through amine coupling at flow rate of 5 µl/minute on all two flow cells to reach 10,500 RUs. 0.1-1 µg/ml of test antibodies were then injected at 10 µl/min for 1 minute. Captured levels of the antibodies were generally kept below 200 RUs. Subsequently, 3.125 –50 nM of cKIT receptor extracellular domains (ECD) were diluted in a 2-fold series and injected at a flow rate of 40 µl/min for 3 min over both reference and test flow cells. Table of tested ECDs is listed below (Table 6). Dissociation of the binding was followed for 10 min. After each injection cycle, the chip surface was regenerated with 3 M MgCl$_2$ at 10 µl/min for 30 seconds. All experiments were performed at 25° C. and the response data were globally fitted with a simple 1:1 interaction model (using Scrubber 2 ® software version 2.0b (BioLogic Software) to obtain estimates of on rate ($k_a$), off-rate ($k_d$) and affinity ($K_D$).

TABLE 6

ECD isotype and source

| ECD Isotype | Tag | Source |
|---|---|---|
| Human | C-terminal 6x His | Novartis construct |
| Cyno | C-terminal 6x His | Novartis construct |
| Mouse | C-terminal 6x His | Sino Biological Inc (Catalog number: 50530-M08H) |
| Rat | C-terminal mFc | Novartis construct |

Table 7 lists the domain binding and affinity. As shown in the Table, the antibodies 9p3, NEG024, NEG027, NEG085, NEG086, NEG087, 20376 and 20507 all react with human cKIT at the nanomolar level, and have similar affinities for those tested against cynomolgus monkey ECD. However, only 20376 cross reacted with mouse. None of the antibodies tested cross-reacted with rat cKIT.

TABLE 7 antibody affinity and cross reactivity

| Ab | Domain binding | Affinity human cKIT (nM) | Affinity cyno cKIT (nM) | Affinity mouse cKIT (nM) | Affinity to rat cKIT (nM) |
|---|---|---|---|---|---|
| 9P3 | d1-3 | 20 | not determined | Not reactive | Not reactive |
| NEG024 | d1-3 | 1.31 | 1.15 | Not reactive | Not reactive |
| NEG026 | d1-3 | not determined | not determined | Not reactive | Not reactive |
| NEG027 | d1-3 | 1.34 | not determined | Not reactive | Not reactive |
| NEG085 | d1-3 | 8.4 | 6.14 | Not reactive | Not reactive |
| NEG086 | d1-3 | 1.44 | 1.34 | Not reactive | Not reactive |
| NEG087 | d1-3 | 1.13 | 1.39 | Not reactive | Not reactive |
| 20376 | d1-3 | 9.1 | 4.8 | 2.5 | Not reactive |
| 20507 | d1-3 | 1.8 | 0.56 | Not reactive | Not reactive |

Example 8: Epitope Mapping of cKIT to 9P3 Antibody by Deuterium Exchange Mass Spectrometry (HDx-MS)

Deuterium exchange mass spectrometry (HDx-MS) measures the deuterium uptake on the amide backbone of a protein. These measurements are sensitive to the amide's solvent accessibility and to changes in the hydrogen bonding network of the backbone amides. HDx-MS is often used to compare proteins in two different states, such as apo and ligand-bound, and coupled with rapid digestion with pepsin. In such experiments one can locate regions, typically of 10 to 15 amino acids, that show differential deuterium uptake between two different states. Regions that are protected are either directly involved in ligand binding or allosterically affected by binding of the antibody to the ligand.

In these experiments, the deuterium uptake of cKIT extra-cellular domain (SEQ ID NO:178, see below) was measured in the absence and presence of the anti-cKIT antibody, 9P3. Regions in cKIT that show a decrease in deuterium uptake upon binding of the antibody are likely to be involved in the epitope; however, due to the nature of the measurement it is also possible to detect changes remote from the direct binding site (allosteric effects). Usually, the regions that have the greatest amount of protection are involved in direct binding although this may not always be the case. In order to delineate direct binding events from allosteric effects orthogonal measurements (e. g. X-ray crystallography, alanine mutagenesis) are necessary.

TABLE 8 cKIT extra-cellular domain construct

SEQ ID NO: 178
LENGTH: 503 amino acids
TYPE: Protein
ORGANISM: Human
QPSVSPGEPSPPSIHPGKSDLIVRVGDEIRLLCTDPGFVKWTFEILDETN

ENKQNEWITEKAEATNTGKYTCTNKHGLSNSIYVFVRDPAKLFLVDRSLY

GKEDNDTLVRCPLTDPEVTNYSLKGCQGKPLPKDLRFIPDPKAGIMIKSV

KRAYHRLCLHCSVDQEGKSVLSEKFILKVRPAFKAVPVVSVSKASYLLRE

GEEFTVTCTIKDVSSSVYSTWKRENSQTKLQEKYNSWHHGDFNYERQATL

TABLE 8-continued cKIT extra-cellular domain construct

TISSARVNDSGVFMCYANNTFGSANVTTTLEVVDKGFINIFPMINTTVFV

NDGENVDLIVEYEAFPKPEHQQWIYMNRTFTDKWEDYPKSENESNIRYVS

ELHLTRLKGTEGGTYTFLVSNSDVNAAIAFNVYVNTKPEILTYDRLVNGM

LQCVAAGFPEPTIDWYFCPGTEQRCSASVLPVDVQTLNSSGPPFGKLVVQ

SSIDSSAFKHNGTVECKAYNDVGKTSAYFNFAFKEQIHPHTLFTPRSHHH

HHH

The cKIT epitope mapping experiments are performed on a Waters Synapt® G2 HDx-MS platform, which includes LEAP® robot system, nanoACQUITY® UPLC System, and Synapt® G2 mass spectrometer. In this method, triplicate control experiments are carried out as follows. 300 pmol (1.4 mg/ml) of cKIT antigen is diluted into 110 µl of 95% deuterated PBS buffer (pH 7.4) and incubates at room temperature on a bench rotator for 25 minutes (% D=85.5%). Deuterium exchange is quenched by 1:1 dilution with cold quench buffer (6M Urea and 1M TCEP pH=2.5) on ice for 5 min. After quenching the tube is transferred onto a LEAP system (Thermo box is set at 2° C.) and the quenched sample is injected by the LEAP system onto the UPLC system for analysis. The UPLC system incorporates an immobilized pepsin column 2.1 mm×30 mm (Life Technologies 2-3131-00) that is maintained at 12° C. An 8-minute 2 to 35% acetonitrile gradient and Waters UPLC CSH C18 1.0×100 mm column is used for separation. Next, triplicate experiments are carried out using the antibody. 300 pmol of 9P3 antibody is immobilized on Protein G agarose beads (Thermo Scientific Cat #22851) using standard techniques. Briefly, the antibody is centrifuged to remove a storage buffer. Then 200 µl of PBS buffer (pH 7.4) and 300 pmol of cKIT are added to the immobilized Ab and incubate for 30 min at room temperature. After incubation, the complex is centrifuged and washed with 200 µl PBS buffer and centrifuged again. For deuterium exchange, 200 of deuterated PBS is added to the antigen-antibody complex for incubation at room temperature for 25 minutes (% D=85.5%). Deuterium buffer is then removed, and immediately, 125 µl ice cold quench buffer is added. After quenching for 5 minutes, the column is centrifuged and the flow-through is transferred into a prechilled HPLC vial. The sample is analyzed using the same on-line pepsin digestion/LC-MS setup as the control experiment.

Figure 2:
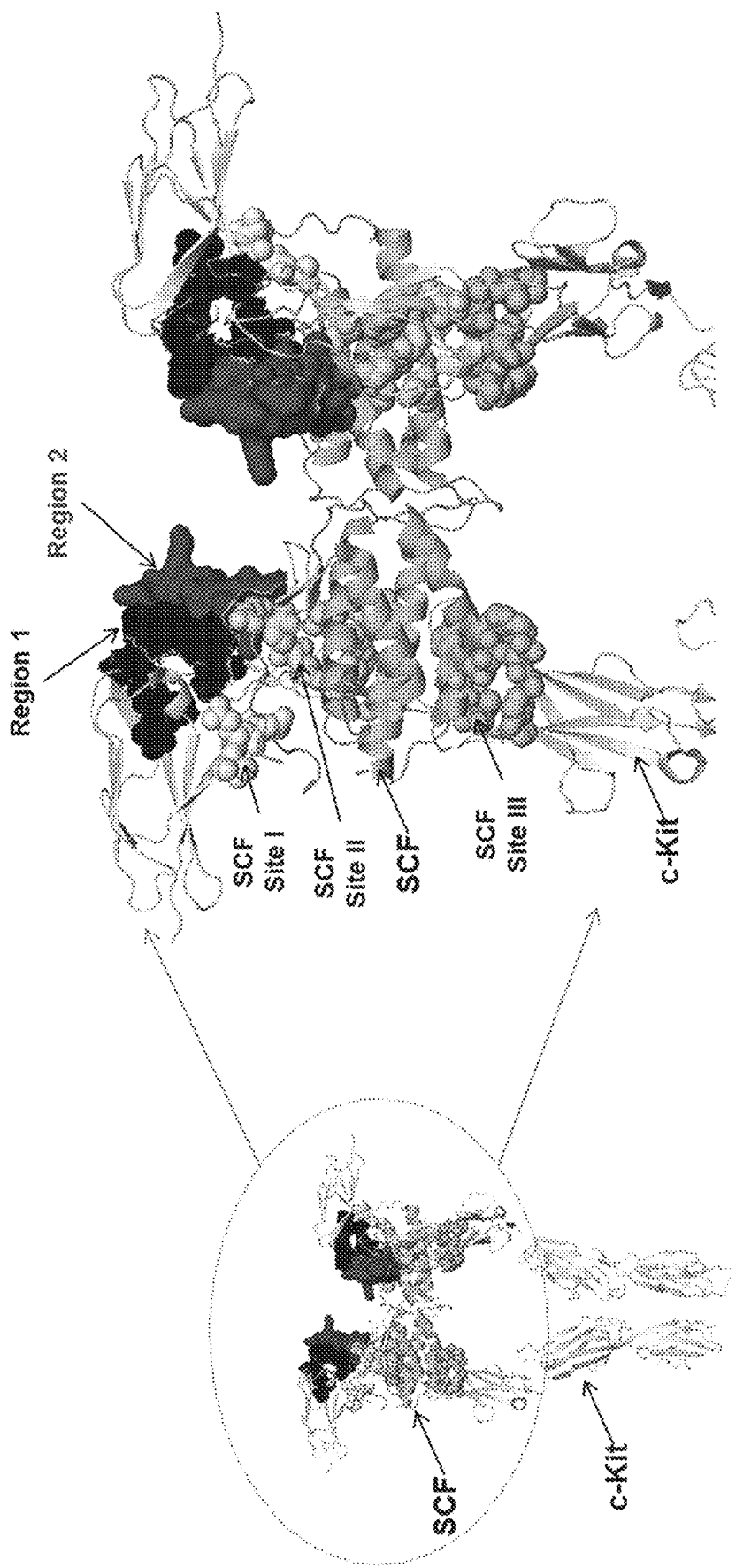
FIG. 2 shows regions of HDx-MS protection are mapped using surface fill: region 1 (black) and region 2 (dark grey). SCF binding sites are denoted as Site I (light grey spheres), Site II (medium grey spheres), and Site III (darker grey spheres).

The results of these measurements are summarized in FIG. 1 and FIG. 2. FIG. 1 shows the baseline corrected differences between the control and 9P3 antibody bound sample divided by the standard error in the measurement. In this plot the more negative value indicates a greater amount of protection in a given region upon binding of 9P3 antibody to cKIT antigen. Upon binding of 9P3 to cKIT we observe the most significant amounts of protection in the following two regions of cKIT: VFVRDPAKLFL ((Region 1, 109-119 (SEQ ID NO: 179)) and HCSVDQEGKSVLSE ((Region 2, 185-198 (SEQ ID NO:180)). Region 1 comprises residues 109-119 and is part of the D1 and D2 domains. Region 2 comprises residues 185-198 and is part of the D2 domain. In FIG. 2, we have mapped the two most protected regions (see FIG. 1) onto the crystal structure of cKIT extra-cellular domain (PDB ID 2e9w). In addition, we have also labeled the SCF binding sites on cKIT as site I, II, and III using literature values (Yuzawa et al., Cell 2007; 130: 323-334). There are two key findings from FIG. 2. First, regions 1 and 2 are very close together in the crystal structure even though they are far apart in primary sequence space. This observation suggests that both could potentially be part of the epitope and if so, the epitope for 9P3 is discontinuous. Second, regions 1 and 2 are remote from the SCF ligand binding sites reported in literature. This is an important observation because it suggests that 9P3 antibody does not directly interfere with ligand binding. Instead the antibody might sterically interfere with ligand binding and/or with the dimerization of the receptor upon ligand binding. In separate competition assays, using ELISA and FACS we observed partial blocking of SCF binding to cKIT by 9P3 so there appears to be partial steric interference. In conclusion, the HDx-MS data indicate that the epitope for 9P3 antibody consists of a discontinuous epitope that is remote from the SCF binding sites. NEG024, NEG085, NEG086, NEG027 and NEG087 are expected to have the same mechanism of action.

Example 9. Epitope Mapping of NEG085

In Situ Limited Proteolysis

Human cKIT (accession code NM_000222 domain 1 (D1)-domain 3 (D3) extracellular domain (ECD) protein was made with residues Q26-G311 (N130S, N145S- these changes results in glycosylation deficiency, in order to express the protein in a glycan free form). Equal molar ratios of human cKIT D1-D3 ECD and NEG085 Fab were mixed and subjected to a final gel filtration step equilibrated with 20 mM Tris-HCl pH 7.5 and 100 mM NaCl, and concentrated to 20 mg/ml. Trypsin was added to the protein complex crystallization sample to create a 1:100 w/w dilution. The protease/sample mixture was incubated at room temperature for 30 minutes before setting up the crystallization experiment.

Crystallization

Diffracting crystals of the cKIT ECD/NEG085 Fab complex were obtained directly from Protein Complex Suite F5 (0.1M NaCl, 0.1M Tris pH 8.0, 8% PEG 20 k; Qiagen) at 4° C. and, after minor optimization, led to crystals diffracting to 5 Å in-house. Crystals used for data collection grew at 4° C. by equilibrating equal volumes of protein (20 mg/mL) and reservoir solution (0.1M NaCl, 0.1M Tris pH 8.0, 10% PEG 20 k) by the sitting-drop vapor diffusion method. Before data collection, crystals were cryoprotected in reservoir solution containing 30% glycerol and flash cooled in liquid nitrogen.

Data Collection

Data were collected on a single crystal cooled to 100K using an ADSC QUANTUM 315 detector (ADSC, Poway CA) and synchrotron radiation ($\lambda$=1.0000 Å) at the beam line 5.0.2 of the Advanced Light Source. Crystals of cKIT ECD/NEG085 Fab diffracted to 3.1 Å resolution and belonged to the space group C2 with unit cell parameters a=213.76 Å, b=117.48 Å, c=171.92 Å, $\alpha$=90°, $\beta$=118.47°, $\gamma$=90°. The crystal contains four copies of the cKIT ECD/NEG085 Fab complex in the asymmetric unit with a calculated solvent content of 66%. Data were processed using autoPROC® (Global Phasing Ltd, Cambridge UK).

Structure Determination and Refinement

The structure of the cKIT ECD/NEG085 Fab complex was solved at 3.1 Å resolution by molecular replacement with PHASER (McCoy et al., J. Appl. Crystallogr. 2007; 40(4): 658-74) using the published crystal structure of the cKIT ECD (PDB ID code: 2EC8) (Yuzawa et al., Cell 2007;

130 (2):323-34) and anti-α1β1 integrin I Fab (PDB ID code: 1MHP) (Karpusas et al., J. Mol. Biol. 2003; 327 (5):1031-41) as starting models. CDR loops of the NEG085 Fab fragment were manually rebuilt in COOT (Emsley and Cowtan, Acta Crystallogr. D. Biol. Crystallogr. 2004; 60 (12): 2126-32) using simulated annealing composite omit map implemented in Phenix (Adams et al., Acta Crystallogr. D. Biol. Crystallogr. 2010; 66(2): 213-21). Subsequent rounds of model building and refinement with Phenix refine program were carried out until convergence.

Results: Structure of the Human cKIT D1-D2 in Complex with Fab Fragment of NEG085

The cKIT D1-D3/NEG085 Fab co-structure demonstrates that NEG085 recognizes and binds to the extracellular membrane-distal domain of cKIT by specifically interacting with a large number of residues contained within the domains 1, 2 and the linker residues between them. The cKIT epitope recognized by NEG085 can therefore be defined as:

cKIT domain 1 residues: R49, V50
cKIT domain 2 residues: Q152, G153, H185 and loop Q190-E198
Linker between domain 1 and 2: D113-L117

Figure 3:
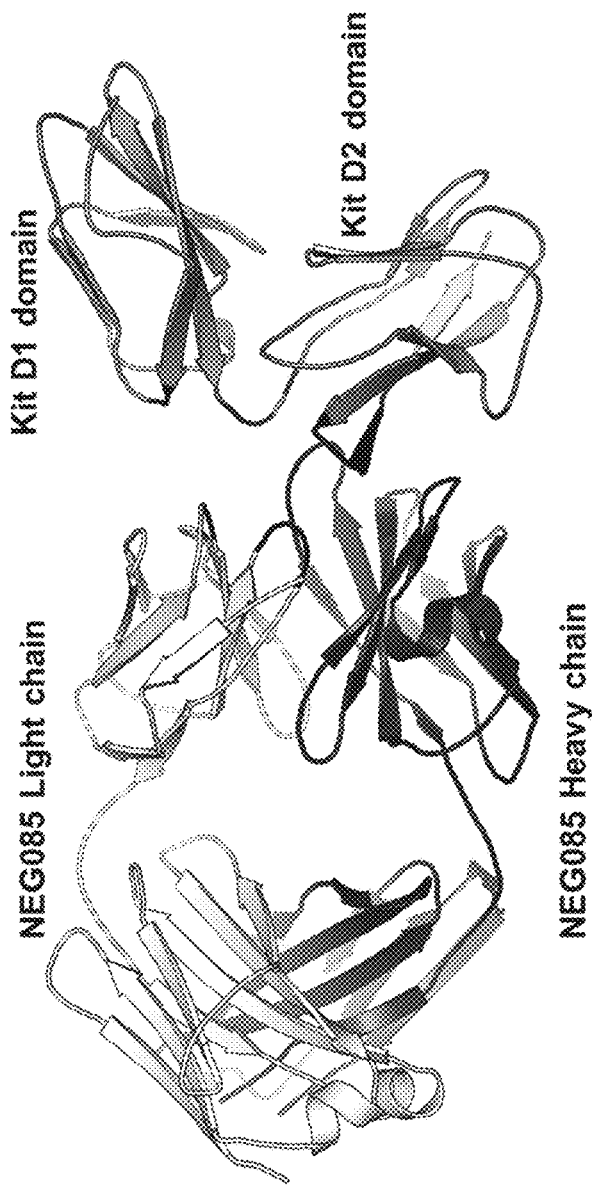
FIG. 3 is a representation of the crystal structure of the NEG085 Fab in complex with cKIT domains 1 and 2. Fab heavy chains are in dark grey, Fab light chains are in white and cKIT domains are in light grey. Epitopes and paratopes are in black.

NEG085 binds cKIT D1-D2 using all CDRs (H1-H3 and L1-L3) (FIG. 3). FIG. 3 is a representation of the 3.1-Å crystal structure of the Kit D1-D2/NEG085 Fab complex showing the Fab heavy chains (dark grey), Fab light chains (white), and Kit D1-D2 (light grey) domains Epitopes and paratopes are colored black. The NEG085/cKIT interface buries a total of ~1890 Å2 solvent-accessible surface area (1211 Å2 and 679 Å2 from H chain and L chain, respectively). The epitope is centered on the cKIT D1-D2 linker region D113-L117 ((DPAKL) (SEQ ID NO: 181)) and loop Q190-E198 ((QEGKSVLSE) (SEQ ID NO: 182)) these residues are bolded and underlined in Table 4, SEQ ID NO: 173 (above). It is noted that these epitiopes are discontinuous in primary sequence, but are very close together in the crystal structure. These epitope interactions are supplemented by peripheral interactions with R49, V50, Q152, G153, and H185. The intermolecular interactions between cKIT D1-D2 and NEG085 Fab were examined using the PISA (Protein Interfaces, Surfaces and Assemblies) (Krissinel and Henrick, J. Mol. Biol. 2007, 372(3):774-97). This data is shown in Table 9.

Superposition of cKIT in the dimeric cKIT/SCF signaling complex (Yuzawa et al. Cell 2007; 130 (2); 323-34) and cKIT/NEG085 complex shows that NEG085 and SCF appear to not compete with each other for binding to cKIT. NEG085 binds to an epitope that is distinct from the binding epitopes responsible for SCF binding. Therefore, the binding of NEG085 to cKIT would not compete directly for association for SCF.

TABLE 9

| NEG085 L chain | | Kit D1-D2 | | Distance (Å) |
|---|---|---|---|---|
| Hydrogen bonds and salt bridges | | | | |
| Ser31 | OG | Arg49 | NH2 | 3.6 |
| Tyr32 | OH | Gln190 | NE2 | 2.5 |
| Arg53 | NH2 | Asp113 | OD1 | 3.2 |
| Gly91 | O | Lys193 | NZ | 2.9 |
| Arg92 | NH1 | Glu191 | OE2 | 3.0 |
| Arg92 | NH1 | Glu191 | OE1 | 3.1 |
| Arg92 | O | Lys193 | NZ | 3.1 |
| Leu94 | N | Lys193 | NZ | 3.5 |
| Trp95 | | Lys193 | | Cation-pi |

TABLE 9-continued

| van der Waals contacts | |
|---|---|
| Tyr50 | Pro114 |
| Tyr53 | Val50, Pro114 |
| Arg93 | Lys193 |

| NEG085 H chain | | Kit D1-D2 | | Distance (Å) |
|---|---|---|---|---|
| Hydrogen bonds and salt bridges | | | | |
| Tyr33 | OH | Ser194 | N | 3.1 |
| Tyr33 | OH | Ser194 | O | 2.4 |
| Asn52 | ND2 | Ser194 | OG | 3.2 |
| Tyr59 | OH | Gly192 | O | 3.2 |
| Tyr59 | OH | Ser194 | N | 3.1 |
| Tyr101 | OH | Glu198 | OE2 | 2.6 |
| Gly103 | O | Leu117 | N | 3.4 |
| Gly103 | N | Leu196 | O | 3.0 |
| Thr105 | N | Pro114 | O | 2.9 |
| Trp107 | NE1 | Gln190 | OE1 | 3.1 |
| Trp107 | NE1 | Lys193 | | Cation-pi |

| van der Waals contacts | |
|---|---|
| Tyr53 | Leu196 |
| Pro54 | Gln152, Gly153 |
| Ser57 | Ser194 |
| Tyr59 | Lys193 |
| Tyr102 | His185, Leu196, Ser197, Lys199 |
| Thr104 | Pro114 |
| Thr105 | Pro114, Gln190 |
| Tyr106 | Pro114, Ala115 |
| Trp107 | Ser194, Val195 |

NEG085 Fab VH and VL residues are numbered based upon its linear amino acid sequence. cKIT residues are numbered base upon accession code NM_000222. The intermolecular interactions were examined using the PISA (Protein Interfaces, Surfaces and Assemblies) (Krissinel and Henrick, J. Mol. Biol. 2007, 372(3):774-97).

Figures 4A, 4B:
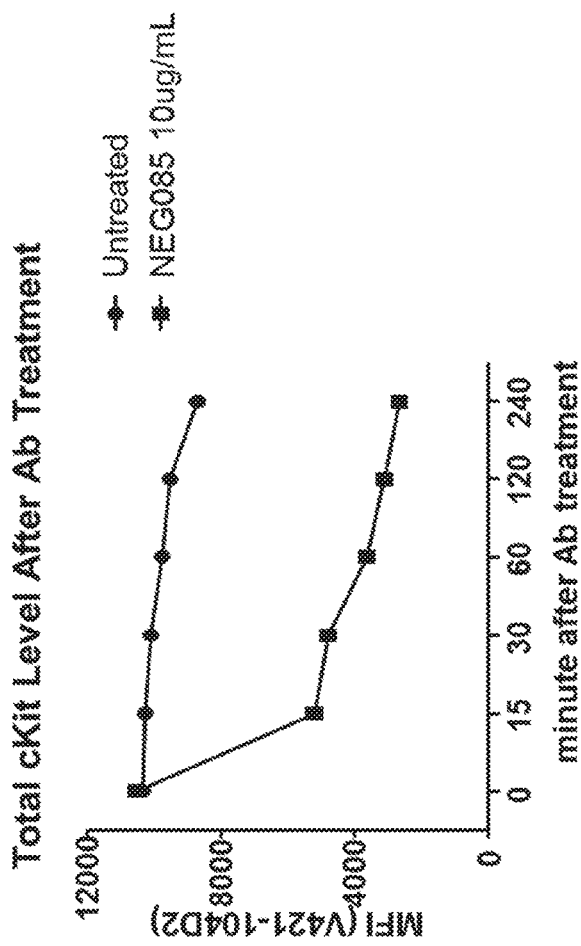
FIGS. 4A and 4B shows that NEG085 and 20376 Abs mediate rapid internalization of surface cKIT on GIST-T1 cells (A) and on human bone marrow cells (B).

Example 10: cKIT Ab-Mediated Internalization of Surface cKIT on GIST-T1 Cells as Determined by Flow Cytometry The kinetics of cKIT antibody mediated internalization was evaluated by treating with antibody in a cell monolayer using a temperature shift method and flow cytometry readout. GIST-T1 (kindly provided by Dr. Takahiro Taguchi, Kochi U., Japan) cells were seeded at 2.5×10E5 cells/well in five 12-well tissue culture treated plates (BD Falcon 353043). The cells were incubated in a tissue culture incubator at 37° C. with 5% $CO_2$ overnight. The following day medium was removed and replaced with 450 µl fresh medium. The cKIT antibodies NEG085, 20376 and an isotype control were prepared at 10×10 µg/ml concentration in appropriate cell culture medium and 50 µl of test cKIT antibody or isotype was added per well with final concentration of 10 µg/ml. All cells were incubated for 1 hr on ice, followed by two washes with 1 mL 1× Phosphate buffered saline (PBS) and resuspended in 500 µl cell culture medium. Plates #2-5 were transferred to 37° C. and harvested at time points; 30 min, 2 hr, 4 hr and 24 hr at 37° C. with 5% $CO_2$. 100 µl of cell dissociation buffer (Gibco Cat #13150-016, Life Technologies, Carlsbad, CA) was added to plate #1 (4° C. binding control) and incubated at 37° C. until cells were detached. Cells were neutralized with 100 µl of medium and transferred to a 96 well V-bottom tissue culture treated plate (Costar 3894). Cells were centrifuged and washed twice with FACS Buffer (1× Phosphate Buffered Saline, 2% Fetal Bovine Serum, 0.1% Sodium Azide). The Phycocrythrin conjugated goat anti-human IgG secondary Ab (Invitrogen H10104, Life Technologies, Carlsbad, CA) was prepared at a 1 to 100 ratio in FACS buffer. Secondary antibody was added to cells at 100 µl/well and incubated with cells on ice for 45 min. At the end of the incubation period, cells were centrifuged and washed with FACS Buffer three times. Cells were fixed with 100 µl/well of 1% paraformaldehyde and stored at 4° C. in the dark. Repeat cell disassociation, secondary antibody incubation and fixation steps for the cells incubated at 37° C. for the various time points. The following day, all samples were analyzed using the BD FACSCanto II 0 equipment using a HTS system (BD Biosciences, San Jose, CA). Samples were analyzed with FlowJo software to obtain the Geometric Mean values of fluorescence for the Phycoerythrin channel, FIG. 4A is a plot of % of initial cell surface binding vs Geometric Mean-PE 4° C. binding/Geometric Mean-PE timepoint at 37° C.×100. As demonstrated in FIG. 4A, both antibodies NEG085 and 20376 bind cKIT on the cell surface and are rapidly internalized into the cell. This indicates that the cKIT ADCs disclosed would be rapidly internalized, thus delivering the toxin into the cell efficiently.

In another internalization experiment, the impact of NEG085 on cKIT receptor levels was evaluated on human bone marrow cells. Normal human CD34+ bone marrow cells (All Cells, Cat #ABM022F, Emeryville, CA) were thawed and washed with 10 mL of StemPro®-34 SFM medium (Gibco, Life Technologies, Carlsbad, CA). Cells were resuspended in 1.25 mL of StemPro-34 SFM medium at $4 \times 10^5$ cells/mL and split equally into two tubes. One tube was untreated, and the other was treated with 10 µg/ml of NEG085 and both were incubated at 37° C., 5% $CO_2$. 100 µL of cell suspension was collected at each timepoint (0, 15, 30, 60, 120, and 240 min) from each condition, and placed into an ice cold collection tube to cease internalization. Cells were washed with 3 mL of ice-cold FBS stain buffer and resuspended in 100 µL of FBS stain buffer. 5 mL of 104D2-BV421 (mouse anti-human IgG1 k, Biolegend, San Diego CA) was added to each tube and incubated on ice for 1 hour. Following another wash with FBS stain buffer, total cKIT receptors were measured by flow cytometry by assessing the mean fluorescence intensity of BV421 on a FACS Canto II® (BD Biosciences, San Jose, CA).

As shown in FIG. 4B, cKIT is rapidly internalized upon binding of NEG085, with the bulk of the internalization happening rapidly (15 minutes) and then continuing to steadily decline the amount of cKIT on the surface until the endpoint of 4 hours.

Example 11: Evaluation of ADCC Activity In Vitro

The ability of the unconjugated anti-cKIT antibodies (NEG085, 20376) to mediate antibody dependent cellular cytotoxicity was determined versus Uke-1 cells (target cells; generously provided by Professor Walter Fiedler, University Hospital Eppendorf, Hamburg, Germany) in co-incubation with NK3.3 cells (killer cells or effector cells; kindly provided by Jacky Kornbluth from Saint Louis University). In brief, Uke-1 cells were stained with Calcein acetoxy-methyl ester (Calcein-AM; Sigma-Aldrich catalog #17783-5MG, St. Louis, MO), washed twice, pipetted into a 96-well microtiterplate (96 well, U-bottomed, clear plastic; Corning Costar, catalog #650 160, Tewksbury, MA) at a concentration of 5000 cells per well and pre-incubated for 10 min with a serial dilution of the above mentioned antibodies (from 50,000 to 0.003 µg per ml) before adding the effector NK3.3 cells for 1 hour in an effector to target ratio of 20 to 1. In order to calculate the antibody specific lysis of the target cells, a parallel incubation of target cells only without antibody or effector cells served as a baseline and negative control, whereas the positive control or maximal lysis or hundred percent specific lysis was determined by lysis of target cells only with a 1% Triton-X 100 solution. As an additional positive control, MabCampath® (Sanofi, Paris, FR) was used, recognizing CD52 on the Uke-1 cells. Following a co-incubation of target and effector cells, the microtiterplate was centrifuged and an aliquot of the supernatant fluid was transferred to another microtiterplate (96 well, flat-bottomed, black with clear bottom; (Corning Costar, catalog #3904, Tewksbury, MA) and the concentration of free Calcein in solution was determined with a fluorescence counter (Victor 3 ® multilabel counter, Perkin Elmer, Waltham, MA).

Figure 5:
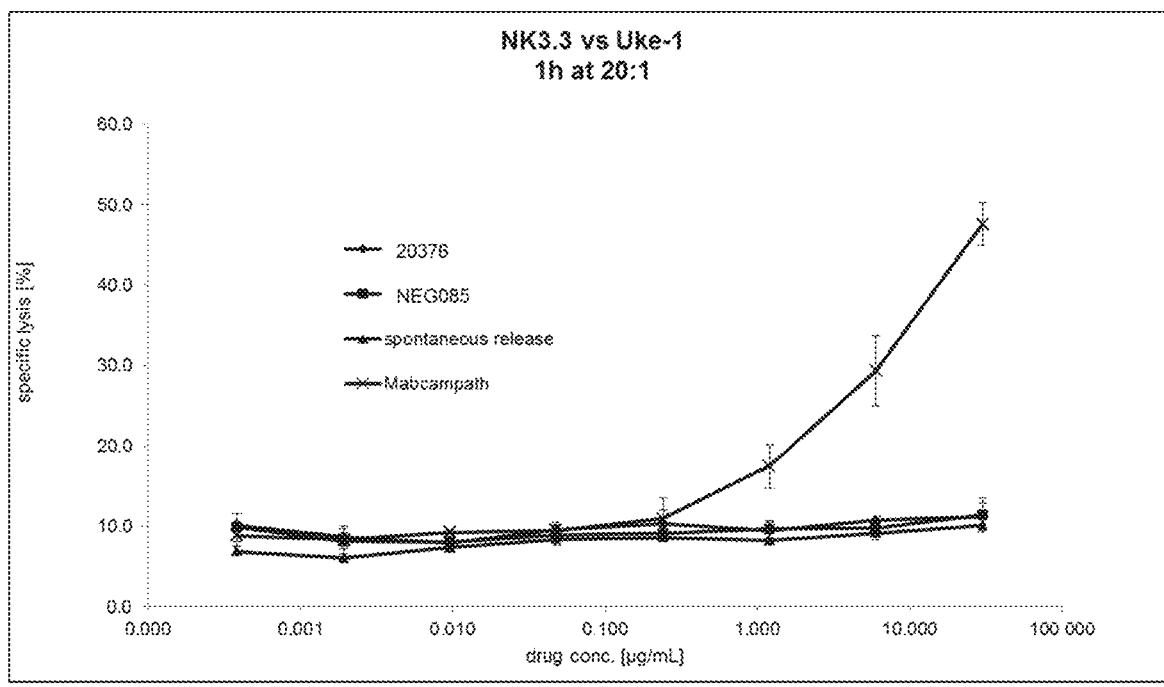
FIG. 5 shows that NEG085 or 20376 antibodies do not induce ADCC in vitro in Uke-1 cells.

Results are presented in FIG. 5. Antibody Dependent Cell Mediated Cytotoxicity (ADCC) is a mechanism of cell mediated immunity, whereby an effector cell lyses a target cell that has been bound by specific antibodies. In this experiment, MabCampath® as well as the anti-cKIT antibodies 20376 and NEG085 are unconjugated human IgG1 antibodies. As shown in FIG. 5, only the MabCampath® antibody mediated ADCC killing of the target cells. Both 20376 and NEG085 were not able to induce ADCC, even at higher concentrations. As such, any cell killing seen when one of the ADCs is used, for example, NEG085-5B, is not due to an ADCC mechanism of action.

Example 12: The Ability of NEG085 and 20376 to Cause Mast Cell Apoptosis was Investigated Using Primary Human Mast Cells Primary human mast cells were cultured from peripheral human blood according to the methods described by Saito et al., Nature Protocols 2006; 1(4):2178-2183. Mast cells, which had been in liquid culture for a minimum of one week, were incubated with increasing concentrations (0.05-100 nM) of the anti-human cKIT Abs, NEG085 and 20376, or an isotype control IgG, in the presence of 1.6 nM rhSCF (Genscript, Cat #Z00400, Piscataway, NJ), for 48 h at 37° C. before the addition of the Caspase-Glo® 3/7 reagent (Promega, Cat #G8093, Madison, WI) to measure apoptosis. Following 30 min incubation at room temperature, luminescence was recorded on the BioTek® Synergy plate reader (BioTek, Winooski, VT).

Figure 6:
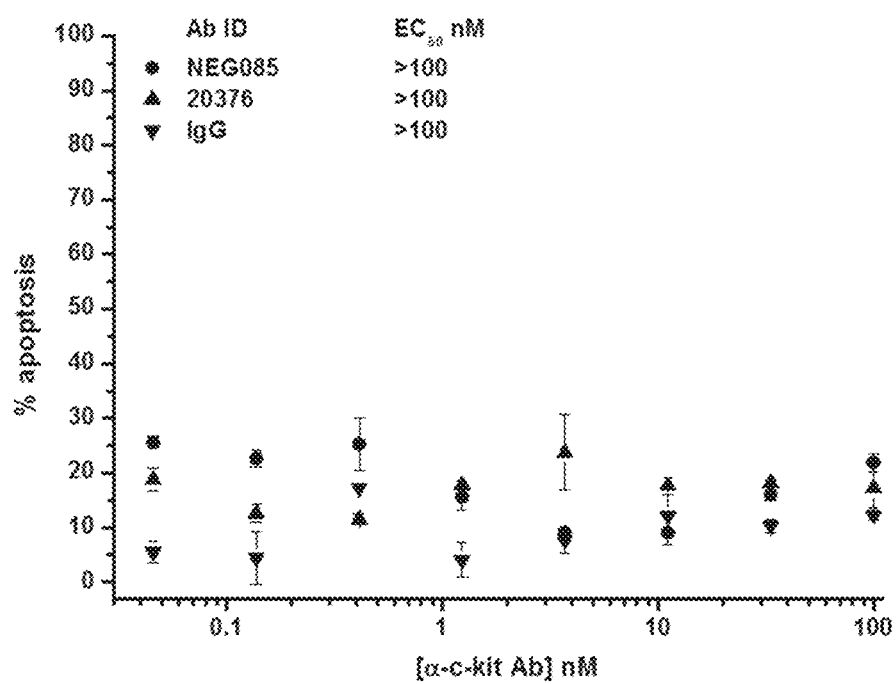
FIG. 6 shows NEG085 and 20376 do not mediate primary human mast cell apoptosis.

As cKIT is expressed on mast cells, any therapeutic anti cKIT antibodies should not cause depletion of mast cells. FIG. 6 shows an apoptosis assay with primary human mast cells following treatment with either anti-human cKIT Abs or an isotype control Ab, in the presence of 1.6 nM rhSCF. Primary human mast cells were incubated with increasing concentrations of the anti cKIT antibodies, NEG085 and 20376, or an isotype control IgG. As seen in FIG. 6, both the NEG085 and 20376 unconjugated antibodies do not lead to apoptosis of human primary mast cells ex vivo.

Example 13: The Ability of NEG085 and 20376 to Mediate Mast Cell Degranulation was Determined Using Primary Human Mast Cells Primary human mast cells were cultured from peripheral human blood according to the methods described by Saito et al., (supra). Mast cells, which had been in liquid culture for a minimum of one week, were pre-treated with 5% Ag-specific IgE JW8 (in-house batch ACE 27283), 95% non-specific monoclonal human IgE (Abbiotec, Cat #12030635, San Diego, CA) and 10 ng/mL rhIL-4 (R&D Systems Cat #204-IL, Minneapolis, MN) for 5 days at 37° C. The cells were then incubated with increasing concentrations (0.05-100 nM) of an isotype control IgG, the anti-human cKIT Abs, 20376 and NEG085, the anti-IgE Ab, LE27, or the NIP(5)BSA antigen, in the presence of a goat anti-human IgG (H+L) Fc-specific Ab (Jackson ImmunoResearch, Cat #109-005-008-JIR, West Grove, PA) for 90 min at 37° C. Cells were then centrifuged and the supernatants were transferred into 96-well black-walled plates prior to the addition of the β-hexosaminidase substrate. Following 90 min incubation at 37° C., the reaction was stopped by the specific isotype control (anti-glycoprotein H-5B at 16 mg/kg), 20507-5B (1.6, 3.2 or 6.5 mg/kg), or unconjugated 20507 (10 mg/kg). Tumor volumes and body weights were measured at least twice weekly (FIGS. 8A and 8B, Table 10). The non-specific isotype control was not active at 16 mg/kg. On Day 21, mice treated with 1.6 or 3.2 mg/kg 20507-5B or 10 mg/kg unconjugated 20507 had tumors that showed a percent mean change in tumor volume compared to the vehicle (tris buffer treated) control (%4T/ΔC) of 77, 62, and 96%, respectively. The mice treated with 20507-5B at 6.5 mg/kg had tumors that showed a −21% regression in volume. The treatments were well tolerated at all dose levels.

TABLE 10

20507-5B dose response in the cKIT positive NCI-H526 SCLC xenograft model on Day 21

| Drug | Dose | Schedule | Tumor Response | | | Host Response | |
|---|---|---|---|---|---|---|---|
| | | | Mean change of tumor volume vs control (ΔT/ΔC) (%) | Regression (%) | Mean change of tumor volume (mm3 ± SEM) | Mean change of body weight (% ± SEM) | Survival (survivors/total) |
| Vehicle | 0 mg/kg | Single Dose IV | 100 | — | 1390 ± 46 | 7.8 ± 1.2 | 5/5 |
| Anti-glycoprotein H-5B | 16 mg/kg | Single Dose IV | 97 | — | 1355 ± 244 | 3.6 ± 1.3 | 5/5 |
| 20507-5B | 1.6 mg/kg | Single Dose IV | 77 | — | 1065 ± 172 | 5.0 ± 1.3 | 5/5 |
| 20507-5B | 3.2 mg/kg | Single Dose IV | 62 | — | 868 ± 221 | 2.1 ± 1.0 | 5/5 |
| 20507-5B | 6.5 mg/kg | Single Dose IV | — | −21 | −40 ± 38 | − ± 1.2 | 5/5 |
| 20507 (unconjugated) | 10 mg/kg | Single Dose IV | 96 | — | 1330 ± 49 | 8.2 ± 1.2 | 5/5 | addition of tris-base (Sigma, Cat #T1503-500G, pH 12, St. Louis, MO) and the fluorescence intensity was recorded on the Envision® plate reader.

Figure 7:
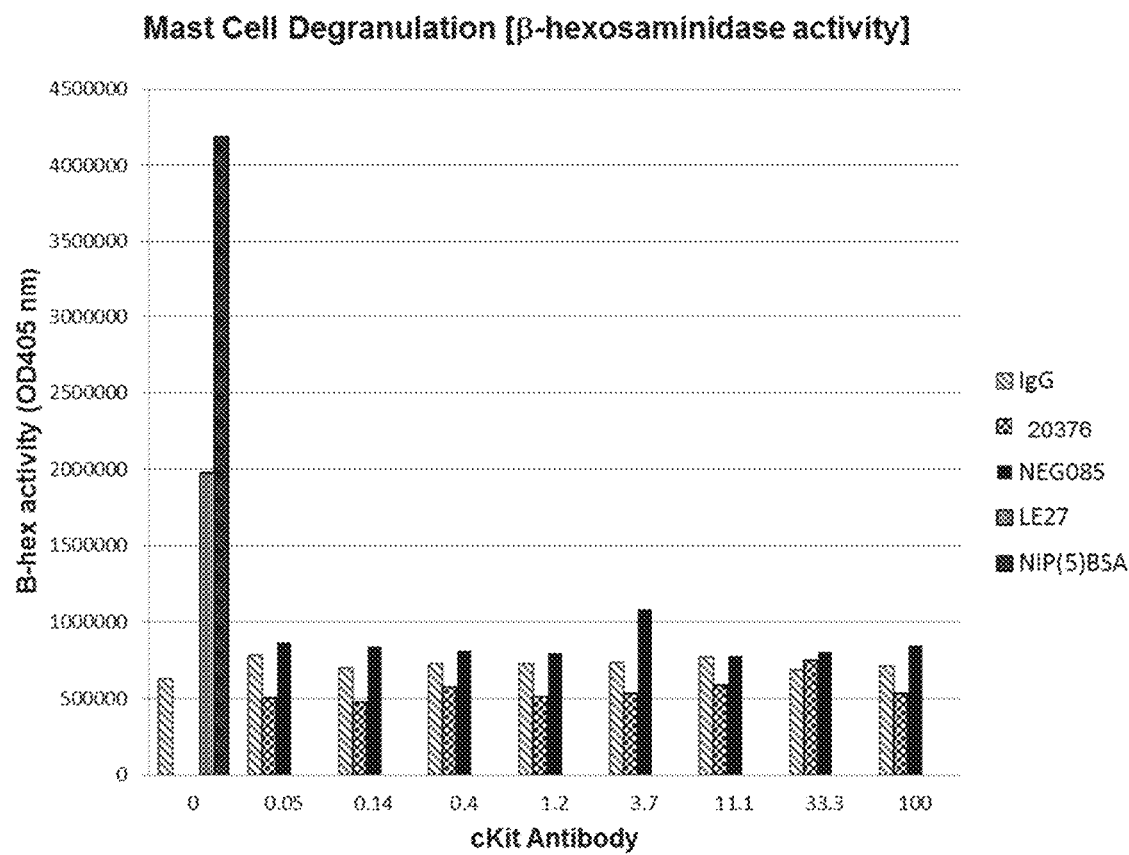
FIG. 7 shows NEG085 and 20376 do not mediate primary human mast cell degranulation.

As in the previous experiment in Example 12, it is important to assess any detrimental effect of anti-cKIT antibodies on mast cells. Where the previous experiment examined apoptosis of mast cells, here the experiments are directed to mast cell degranulation. As shown in FIG. 7, the positive controls NIP(5) and LE27 show high levels of mast cell degranulation. In contrast, anti-cKIT antibodies NEG085 and 20376 do not induce mast cell degranulation of human primary mast cells ex vivo.

Figure 9:
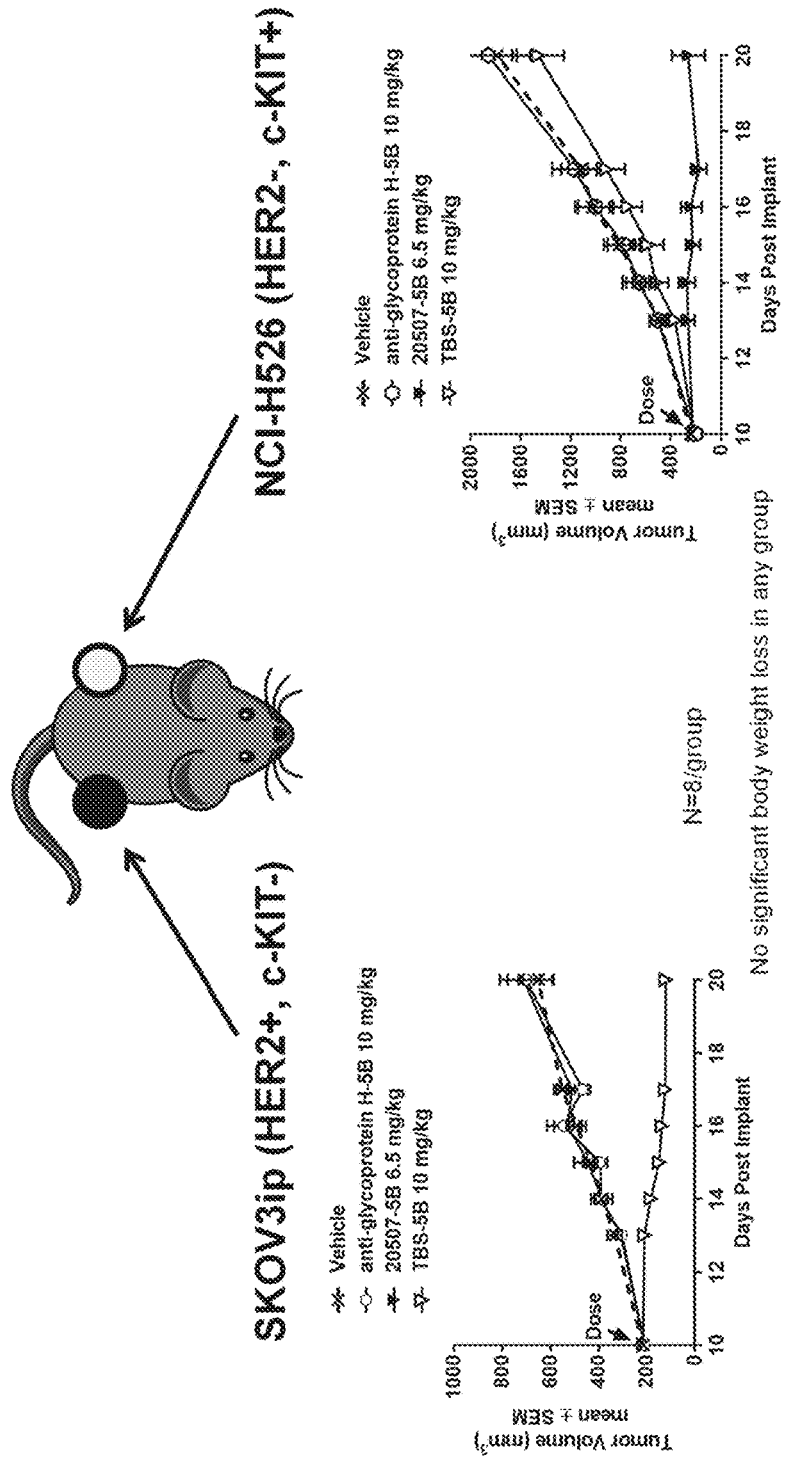
FIG. 9 is a depiction of a dual-flank xenograft mouse model that demonstrates the specificity of anti-cKIT-Eg5 inhibitor ADCs.

Example 14: Dose Dependent In Vivo Efficacy of an Anti-cKIT ADCs Conjugated with an Eg5 Inhibitor Against Small Cell Lung Cancer (SCLC) in Mice The dose dependent anti-tumor efficacy of the anti-cKIT antibody 20507 conjugated to Eg5 inhibitor 5B (20507-5B) was evaluated in the cKIT positive NCI-H526 SCLC tumor xenograft model in mice. For the structure of the Eg5 inhibitor 5B, see Table 1. Female SCID-beige mice were implanted subcutaneously with 10×10$^6$ cells containing 50% Matrigel™ (BD Biosciences) in Hank's balanced salt solution. The total injection volume containing cells in suspension was 200 μl. Mice were enrolled in the study 13 days post implantation with average tumor volume of ~182 mm$^3$-270 mm$^3$. After being randomly assigned to one of six groups (n=5/group), mice were administered a single i.v. dose of tris buffer (the antibody/ADC vehicle), a non- Example 15: Efficacy in Mice with c-KIT Positive H526 Small Cell Lung Cancer and SKOV3ip c-KIT Negative Ovarian Xenograft Models as a Dual Implant to Demonstrate Specificity Evaluation of the specificity of anti-cKIT antibody 20507 conjugated to Eg5 inhibitor 5B (20507-5B) was evaluated using a dual implant system with a HER2+, cKIT- ovarian xenograft model, SKOV3ip, and a HER2-, cKIT+SCLC xenograft model, NCI-H526. As a control, a second set of mice with this dual tumor implant were treated with an anti-Her2 antibody called TBS conjugated to 5B (TBS-5B). TBS is a Trastuzumab-like anti-Her2 antibody with the identical sequence as Trastuzumab, but was produced for experimental purposes and is not clinical material. Female SCID-beige mice were implanted subcutaneously on the right flank with 5×10$^6$ SKOV3ip cells and 10×10$^6$ NCI-H526 cells on the left flank, both containing 50% Matrigel™ (BD Biosciences) in Hank's balanced salt solution with a total injection volume of 200 μl containing cells in suspension for each cell line. Differences in growth kinetics were accounted for by staggering implant dates. Mice were enrolled in the with an average tumor volume of ~94¯277 mm$^3$. Mice were randomly assigned to one of 4 groups/xenograft model, with n=8/group. Mice were administered a single i.v. dose of ADC vehicle (tris buffer), a non-specific isotype control (anti-glycoprotein H-5B at 10 mg/kg), 20507-5B (6.5 mg/kg), or TBS-5B (10.0 mg/kg). Tumor volumes and body weights were measured at least twice weekly (FIG. 9). As expected, the treatments were well tolerated at all dose levels and no body weight loss was observed (body weight data not shown). TBS-5B induced anti-tumor efficacy in SKOV3ip (HER2+, cKIT−) tumors, but had no effect on NCI-H526 (HER−, cKIT+) tumors. Likewise, 20507-5B exhibited anti-tumor efficacy against NCI-H526 (HER−, cKIT+) tumors, but not against SKOV3ip (HER2+, cKIT−) tumors demonstrating specificity in activity for both TBS-5B and 20507-5B.

Example 16: ADC Efficacy in Mice with Site Directed Conjugation at 5 and 10 Mu/Ku in c-KIT Positive NCI-H526 Small Cell Lung Cancer Xenograft Model The anti-tumor activity of the anti-cKIT antibody 20507 with site directed conjugation to Eg5 inhibitor 5B was from mice treated with 5 and 10 mg/kg of 20507-HC-E152C-S375C-5B showed a %4T/AC of 10% and 5%, respectively. On Day 25, 5 mg/kg of 20507-HC-E152C-S375C-5B showed significantly increased efficacy compared with 20507-HC-K360C-LC-K107C-5B at the same dose, with a p-value of <0.05 using a Hold-Sidak post test. Furthermore, on Day 28, 10 mg/kg of 20507-HC-E152C-S375C-5B and 20507-HC-K360C-LC-K107C-5B induced significantly increased efficacy compared to 11.8 mg/kg of 20507-5B, which was conjugated through partially reduced native disulfides, with a p-value of <0.05 using the Holm-Sidak post test.

TABLE 11

ADC efficacy with site directed conjugation at 5 and 10 mg/kg in the cKIT positive NCI-H526 SCLC xenograft model on Day 22

Figure 10A:
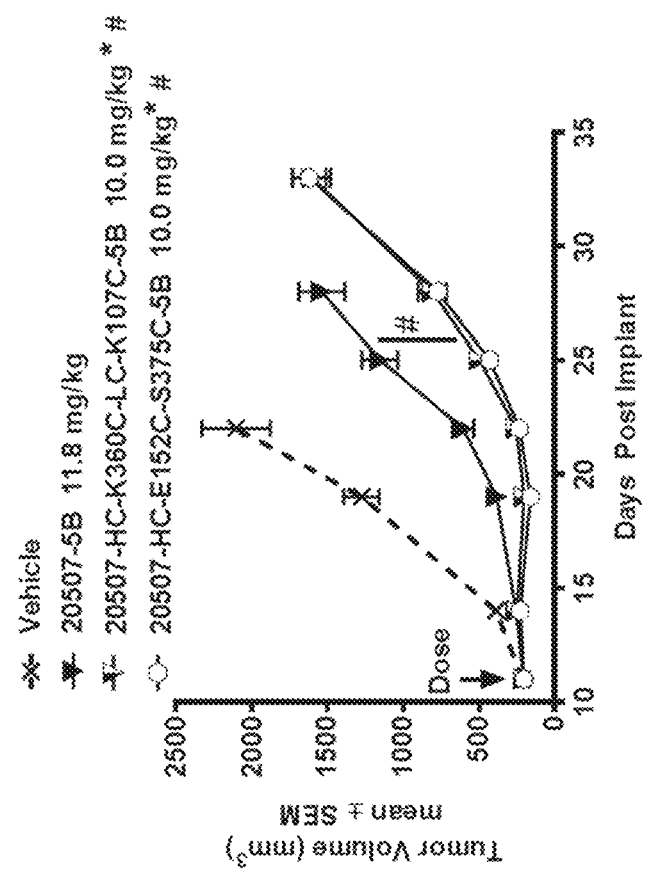
FIG. 10A/B shows the efficacy of anti-cKIT antibodies specifically conjugated to an Eg5 inhibitor payload in a small cell lung cancer mouse model.
Figure 10B:
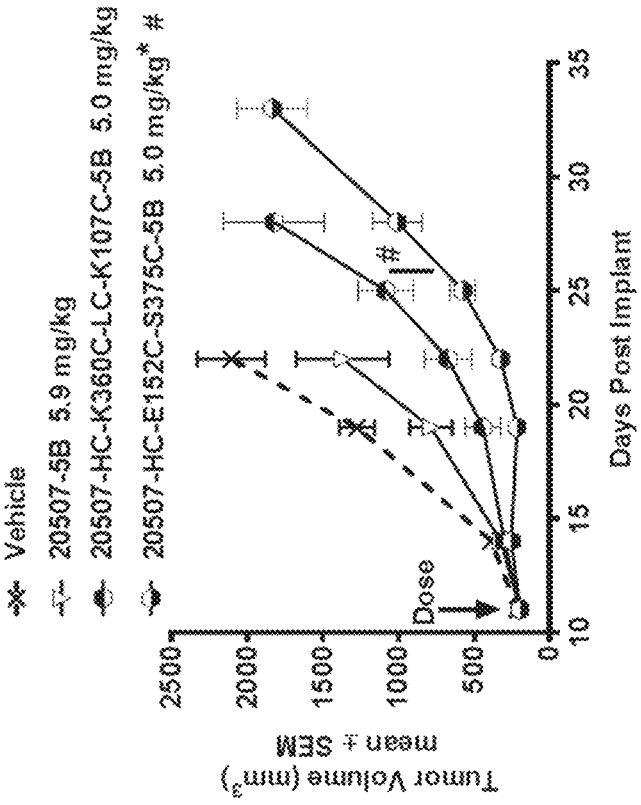
Figure 11A:
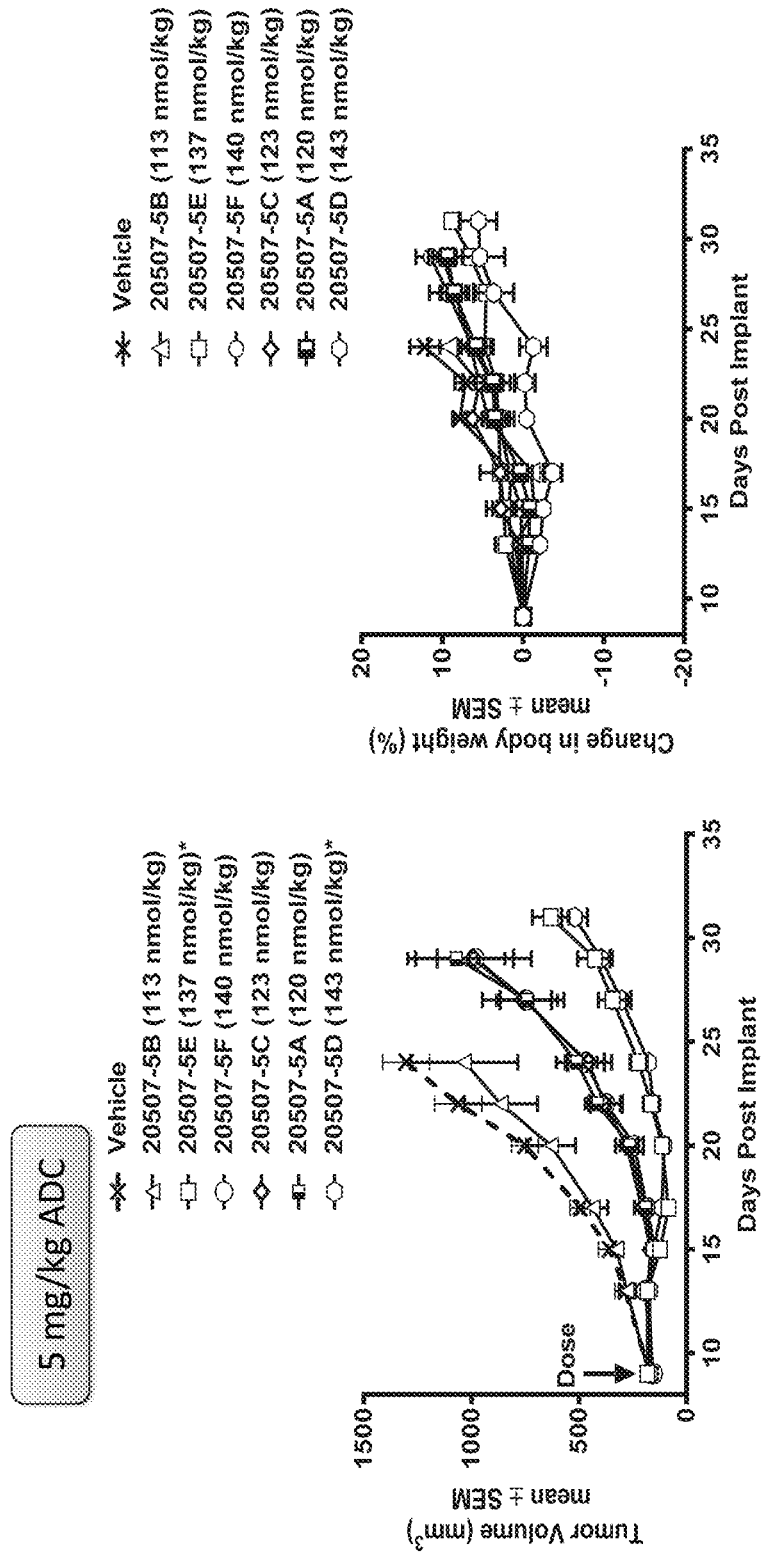
FIG. 11A graphically depicts the efficacy and body weight change of an anti-cKIT antibody conjugated to different Eg5 inhibitor payloads at a dose of 5 mg/kg in a small cell lung cancer xenograft mouse model.
Figure 12:
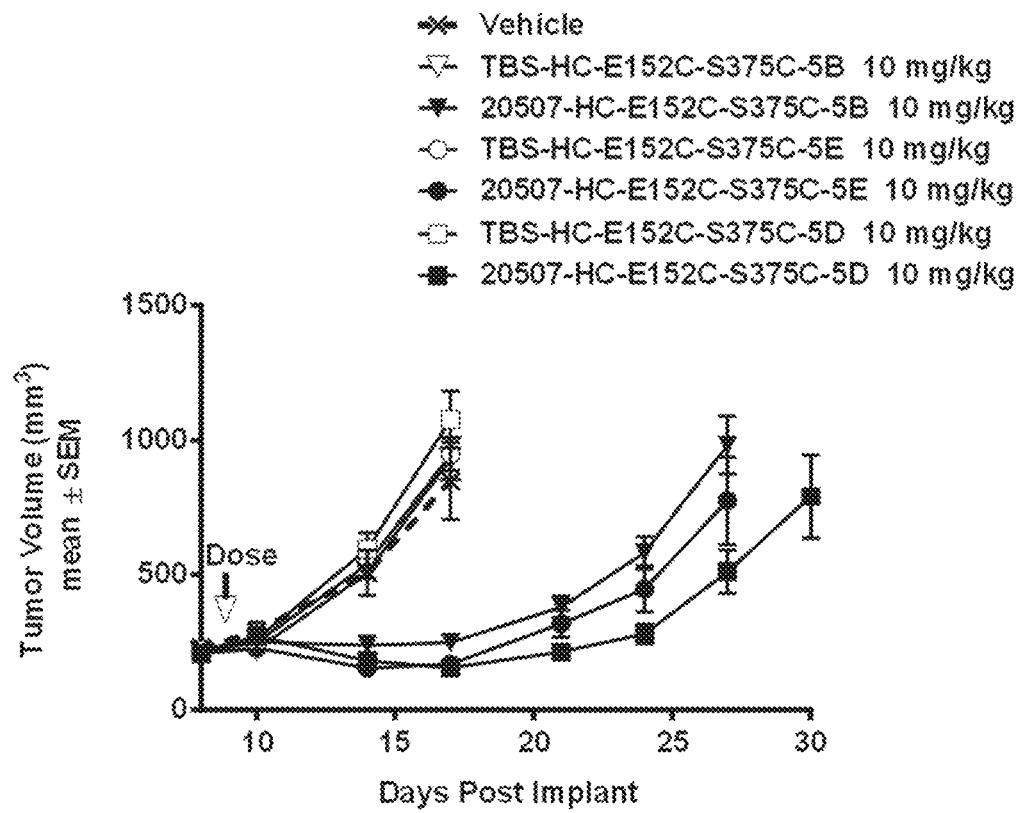
FIG. 12 is a graph of an anti-cKIT antibody and TBS antibody with site directed conjugations and Eg5 inhibitor payloads in a small cell lung cancer mouse model.

| | | | Tumor Response | | Host Response | |
|---|---|---|---|---|---|---|
| | | | Mean change | | | |
| Drug | Dose | Schedule | of tumor volume vs control (T/C) (%) | Mean change of tumor volume (mm3 ± SEM) | Mean change of body weight (% ± SEM) | Survival (Survivors/ total) |
| Vehicle | 0 mg/kg | Single Dose IV | 100 | 1961 ± 225 | 16.2 ± 2.0 | 6/6 |
| 20507-5B | 5.9 mg/kg | Single Dose IV | 63 | 1235 ± 325 | 14.9 ± 1.8 | 5/6 |
| 20507-5B | 11.8 mg/kg | Single Dose IV | 24 | 467 ± 65 | 5.2 ± 0.9 | 6/6 |
| 20507-HC-K360C-LC-K107K-5B | 5 mg/kg | Single Dose IV | 27 | 535 ± 157 | 10.9 ± 2.0 | 6/6 |
| 20507-HC-K360C-LC-K107K-5B | 10 mg/kg | Single Dose IV | 6 | 113 ± 46 | 6.9 ± 1.0 | 6/6 |
| 20507-HC-E152C-S375C-5B | 5 mg/kg | Single Dose IV | 10 | 195 ± 33 | 7.2 ± 1.4 | 6/6 |
| 20507-HC-E152C-S375C-5B | 10 mg/kg | Single Dose IV | 5 | 100 ± 24 | 7.8 ± 2.9 | 6/6 | evaluated in the NCI-H526 small cell lung cancer xenograft model. Female nu/nu mice were implanted subcutaneously with 5×10$^6$ cells containing 50% Matrigel™ (BD Biosciences) in Hank's balanced salt solution. The total injection volume containing cells in suspension was 200 Mice were enrolled in the study 11 days post implantation with an average tumor volume of ~148 mm$^3$–258 mm$^3$ After being randomly assigned to one of 7 groups (n=5 or 6/group), mice were administered a single i.v. dose of tris buffer (the ADC vehicle), 20507-5B (5.9 or 11.8 mg/kg), 20507-HC-K360C-LC-K107C-5B (5 or 10 mg/kg), 20507- HC-E152C-S375C-5B (5 or 10 mg/kg). Tumor volumes and body weights were measured at least twice weekly (FIG. 10A/B and Table 11). As expected, the treatments were well tolerated at all dose levels and no body weight loss was observed (body weight data not shown). On Day 22, tumors in mice treated with 5.9 and 11.8 mg/kg of 20507-5B showed a %4T/AC of 63% and 24%, respectively. Tumors from mice treated with the 5 and 10 mg/kg of 20507-HC-K360C-LC-K107K-5B showed %4T/AC of 27% and 6%, respectively. Moreover, tumors Example 17: ADC Efficacy in Mice Using Anti-c-KIT 20507 with Varying Eg5 Inhibitors in a c-KIT Positive NCI-H526 Small Cell Lung Cancer Xenograft Model at 5 and 10 mg/kg The anti-cKIT antibody 20507 conjugated to Eg5 inhibitor 5B (20507-5B), 5E (20507-5E), 5F (20507-5F), 5C (20507-5C), 5A (20507-5A), and 5D (20507-5D) was evaluated in the c-KIT positive NCI-H526 small cell lung cancer xenograft model. For the structures of these Eg5 inhibitors, see Table 1. Female SCID-bg mice were implanted subcutaneously with 5×10$^6$ NCI-H526 cells containing 50% Matrigel™ (BD Biosciences) in Hank's balanced salt solution. The total injection volume containing cells in suspension was 200 Mice were enrolled in the study 9 days post implantation with an average tumor volume of ~132 mm$^3$– 249 mm$^3$. After being randomly assigned to one of 13 groups (n=5 mice/group), mice were administered a single i.v. dose of tris buffer (the ADC vehicle), 20507-5B (5 or 10 mg/kg), 20507-5E (5 or 10 mg/kg), 20507-5F (5 or 10 mg/kg), 20507-5C (5 or 10 mg/kg), 20507-5A (5 or 10 mg/kg), or 20507-5D (5 or 10 mg/kg). Tumor volumes and body weights were measured at least twice weekly (FIGS. 11A and 11B). As expected, the treatments were well tolerated at all dose levels (FIG. 11A/B). On Day 24, tumors from mice treated with 5 or 10 mg/kg of 20507-5B showed a %ΔT/ΔC of 79% and 23%, respectively; The %ΔT/ΔC for 5 or 10 mg/kg of 20507-5E was 4%* and 5%*, respectively; for 5 and 10 mg/kg of 20507-5F the %ΔT/ΔC was 28 and 20%, respectively; for 5 and 10 mg/kg of 20507-5C the %ΔT/ΔC was 26% and 7%, respectively; for 5 and 10 mg/kg of 20507-5A the %4T/AC was 31% and 17%, respectively; mice treated with 20507-5D at 5 mg/kg had a 1% ΔT/ΔC*, while 10 mg/kg of 20507-5D regressed tumors by −31%*. Treatment groups labeled with * indicate significant activity (p-value <0.05) when compared with the vehicle control treated tumors using the ANOVA/Tukey's post test.

cKIT positive NCI-H526 small cell lung cancer xenograft model. Female SCID-bg mice were implanted subcutaneously with $5 \times 10^6$ cells containing 50% Matrigel™ (BD Biosciences) in Hank's balanced salt solution. The total injection volume containing cells in suspension was 200 μl. Mice were enrolled in the study 8 days post implantation with an average tumor volume of ~170 $mm^3$–330 $mm^3$. After being randomly assigned to one of 7 groups (n=6 mice/group), mice were administered a single i.v. dose of tris buffer alone (the ADC vehicle) or 10 mg/kg of ADC: TBS-HC-E152C-S375C-5B, 20507-HC-E152C-S375C-5B, TBS-HC-E152C-S375C-5E, 20507-HC-E152C-S375C-5E, TBS-HC-E152C-S375C-5D, or 20507-HC-E152C-S375C-5D. Tumor volumes and body weights were measured at least twice weekly (FIG. 12). As expected, the treatments were well tolerated at all dose levels and no body weight loss was observed (body weight data not shown). No efficacy

TABLE 12

Efficacy and body weight change of 20507 with varying linkers in NCI-H526 (SCLC) xenograft mouse model (*p < 0.05, ANOVA/Tukey's post test) at Day 24

| | | | Tumor Response | | | Host Response | |
|---|---|---|---|---|---|---|---|
| Drug | Dose | Schedule | Mean change of tumor volume vs control (T/C) (%) | Regression (%) | Mean change of tumor volume (mm3 ± SEM) | Mean change of body weight (% ± SEM) | Survival (Survivors/total) |
| Vehicle | 0 mg/kg | Single Dose IV | 100 | — | 1132 ± 114 | 12.2 ± 1.9 | 5/5 |
| 20507-5B | 5 mg/kg | Single Dose IV | 76 | — | 859 ± 248 | 9.2 ± 2.6 | 5/5 |
| 20507-5B | 10 mg/kg | Single Dose IV | 23 | — | 264 ± 54 | 7.4 ± 1.1 | 5/5 |
| 20507-5E | 5 mg/kg | Single Dose IV | 4* | — | 41 ± 30 | 4.7 ± 1.0 | 5/5 |
| 20507-5E | 10 mg/kg | Single Dose IV | 5* | — | 59 ± 56 | 0.7 ± 1.3 | 5/5 |
| 20507-5F | 5 mg/kg | Single Dose IV | 28 | — | 315 ± 81 | 6.2 ± 1.6 | 5/5 |
| 20507-5F | 10 mg/kg | Single Dose IV | 20 | — | 221 ± 46 | 4.4 ± 0.9 | 5/5 |
| 20507-5C | 5 mg/kg | Single Dose IV | 26 | — | 289 ± 115 | 6.5 ± 1.5 | 5/5 |
| 20507-5C | 10 mg/kg | Single Dose IV | 7 | — | 78 ± 47 | 3.3 ± 1.4 | 5/5 |
| 20507-5A | 5 mg/kg | Single Dose IV | 31 | — | 352 ± 102 | 5.8 ± 1.8 | 5/5 |
| 20507-5A | 10 mg/kg | Single Dose IV | 17 | — | 192 ± 52 | 8.7 ± 2.2 | 5/5 |
| 20507-5D | 5 mg/kg | Single Dose IV | 1* | — | 6 ± 18 | −1.3 ± 1.7 | 5/5 |
| 20507-5D | 10 mg/kg | Single Dose IV | — | −30.84* | −53 ± 11 | 6.3 ± 2.3 | 5/5 |

Example 18: ADC Efficacy in Mice Using Anti-c-KIT 20507 with Site Directed Conjugation to Varying Eg5 Inhibitors in a c-KIT Positive NCI-H526 Small Cell Lung Cancer Xenograft Model at 5 and 10 mg/kg The anti-cKIT antibody 20507 with different site directed conjugation to different Eg5 inhibitors was evaluated in the was observed with the TBS ADCs targeting Her2, as expected in this Her2 negative model. On Day 17, tumors from mice treated with 20507-HC-E152C-S375C-5B showed a 5% ΔT/ΔC, while 20507-HC-E152C-S375C-5E and 20507-HC-E152C-S375C-5D regressed tumors by −19% and −25%. No statistical difference was observed between the anti-cKIT 20507 ADC-treated groups.

TABLE 13

Efficacy and body weight change of 20507 and TBS ADC with different site directed conjugations in NCI-H526 (SCLC) xenograft mouse model at Day 17

| | | | Tumor Response | | Host Response | |
|---|---|---|---|---|---|---|
| | | | Mean change of tumor | Mean change | | |
| Drug | Dose | Schedule | volume vs control (T/C) (%) | Regression (%) | of tumor volume (mm3 ± SEM) | Mean change of body weight (% ± SEM) | Survival (Survivors / total) |
| Vehicle | 0 mg/kg | Single Dose IV | 100 | — | 619 ± 142 | 4.2 ± 0.7 | 6/6 |
| TBS-HC-E152C-S375C-5B | 10 mg/kg | Single Dose IV | 116 | — | 721 ± 77 | 3.2 ± 1.2 | 6/6 |
| 20507-HC-E152C-S375C-5B | 10 mg/kg | Single Dose IV | 5 | — | −34 ± 18 | 0.4 ± 1.0 | 6/6 |
| TBS-HC-E152C-S375C-5E | 10 mg/kg | Single Dose IV | 117 | — | 722 ± 71 | 2.0 ± 1.1 | 6/6 |
| 20507-HC-E152C-S375C-5E | 10 mg/kg | Single Dose IV | — | −19.29 | −41 ± 17 | −1.6 ± 1.3 | 6/6 |
| TBS-HC-E152C-S375C-5D | 10 mg/kg | Single Dose IV | 138 | — | 854 ± 101 | 4.07 ± 0.9 | 6/6 |
| 20507-HC-E152C-S375C-5D | 10 mg/kg | Single Dose IV | — | −24.95 | −52 ± 13 | 0.4 ± 1.8 | 6/6 |

Example 19: Antitumor Activity of Anti-c-Kit Antibody NEG085 Conjugated to Eg5 Inhibitor Payloads in NCI-H526 Cells 5000 NCI-H526 (SCLC) cells were seeded in 90 μl of RPMI per well in a black-walled 96-well plate. The cells were incubated at 3TC overnight. At the next day, a 10× stock of ADCs was prepared with the highest final concentration of 10 μg/ml. A 3 fold serial dilution was performed and 10 μl of ADC was added per well. The cells were incubated for 5 days at 3TC. On day 5, the cells were removed from the incubator and allowed to cool to room temperature. 50 μl of Cell TiterGlo reagent (Promega, cat #B7570) was added per well, shaken gently and briefly on an orbital shaker. The readout was measured on a Wallac MicroBeta® (Perkin Elmer, Waltham MA) for 3 sec/well. The luminescence data was saved in an Excel format or a format that is readable by Excel.

Figure 13:
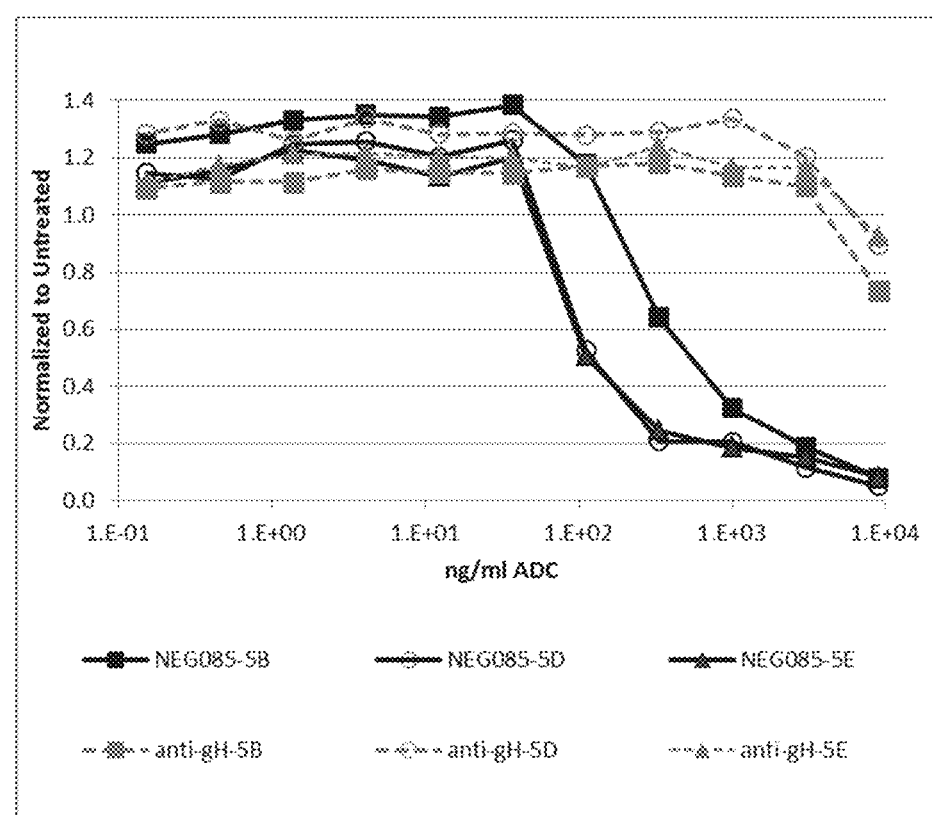
FIG. 13 is a graph of NEG085 antibody conjugated to different Eg5 inhibitor payloads showing efficacy in small cell lung cancer cells.

The NCI-H526 SCLC cell line was tested for its sensitivity to the various c-Kit Eg ADCs in a proliferation assay. As shown in FIG. 13, NEG-085 conjugated to 5B, 5E or 5D payloads is a potent inhibitor of tumor cell growth and thus are potent ADCs.

Example 20: Antitumor Activity of Anti-c-Kit Antibody NEG085 Conjugated to Eg5 Inhibitor Payload in NCI-H526 Xenograft Tumor Model Antitumor activity of the anti-cKit antibody NEG085 conjugated to 3 different Eg5 inhibitor (Eg5i) linker/payloads 5B, 5D, and 5E were evaluated in the NCI-H526 small cell lung cancer xenograft tumor model. Female SCID Beige mice were implanted subcutaneously with $5\times10^6$ NCI-H526 cells suspended in PBS. The total injection volume containing cells in suspension was 100 Mice were enrolled in the study nine days post implantation with average tumor volume of 198 mm³. After being randomly assigned to one of eight groups (n=5/group), mice were administered a single intravenous (i.v.) injection of PBS or NEG085 conjugated to one of three Eg5 inhibitor linker/payloads administered at 26 or 103 nM Eg5 inhibitor per kg of body weight. ADCs and amount administered are as follows: NEG085-5B at 26 nM/kg Eg5 inhibitor (1.25 mg/kg ADC) or 103 nM/kg Eg5 inhibitor (5.0 mg/kg ADC); NEG085-5E at 26 nM/kg Eg5 inhibitor (1.21 mg/kg ADC) or 103 nM/kg Eg5 inhibitor (4.84 mg/kg); NEG085-5D at 26 nM/kg Eg5 inhibitor (1.34 mg/kg ADC) or 103 nM/kg Eg5 inhibitor (5.34 mg/kg ADC). gH-5D, a non-targeted negative control ADC, was administered at 103 nM/kg Eg5 inhibitor (4.56 mg/kg ADC). Tumors were calipered twice per week.

Figure 14:
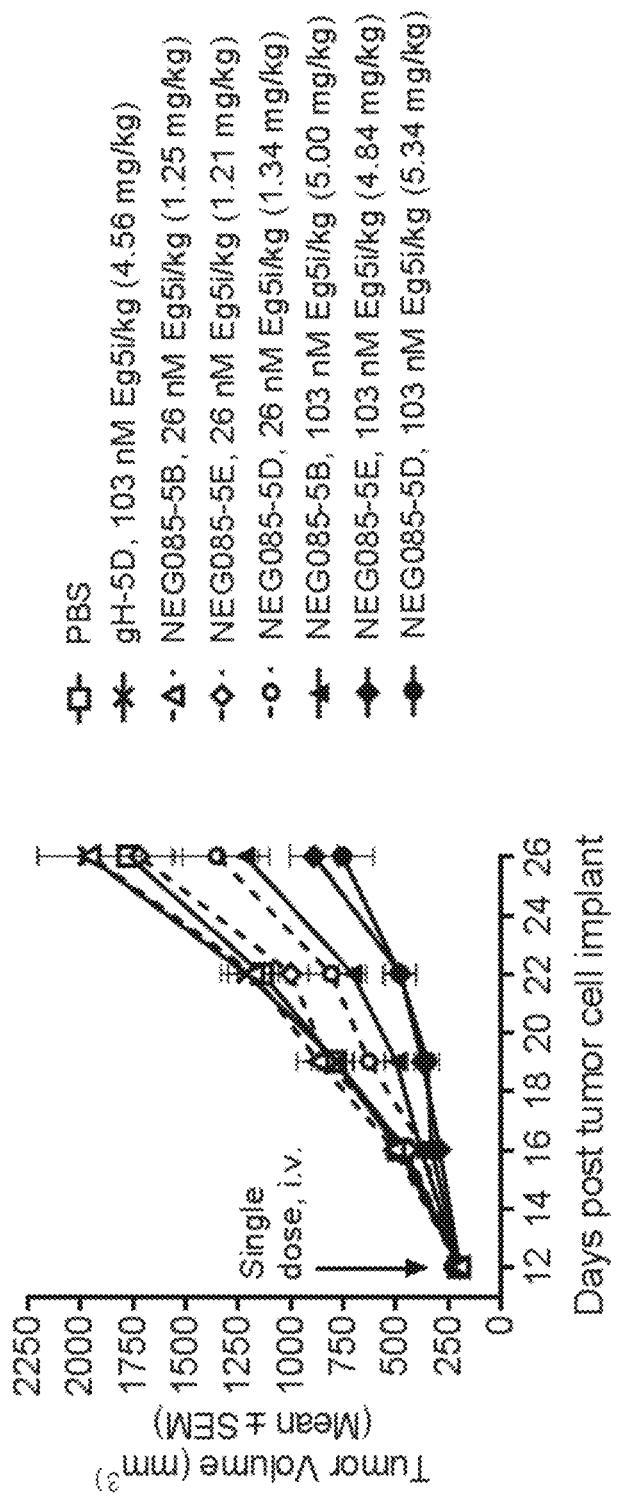
FIG. 14 is a graph depicting efficacy of different NEG085-Eg5 inhibitor payloads in a small cell lung cancer mouse xenograft model.

As anticipated, the non-targeted negative control ADC gH-5D was not active. Dose dependent anti-tumor activity was observed for all three anti-cKIT Eg5 inhibitor ADCs evaluated in this study. Anti-tumor activity at day 26 post cell implantation (14 days post dose) in the groups receiving 103 nM/kg Eg5 inhibitor was 35, 44, and 65% T/C for NEG085-5D,-5E, and -5B, respectively. The graph in FIG. 14 shows that NEG085-5B, 5E and 5D reduce tumor cell volume in a xenograft mouse model.

Example 21. NEG085-Eg5 Inhibitors in Combination Therapy

ADCs can be combined with small molecule inhibitors. Using either the Chalice software (Zalicus, Cambridge MA) or ComboExplorer application (Novartis, Basel CH), the response of the combination is compared to its single agents, against the widely used Loewe model for drug-with-itself dose-additivity (Lehar et al. Nat. Biotechnol. (2009) 27: 659-666; Zimmermann et al., Drug Discov. Today (2007) 12: 34-42). Excess inhibition compared to additivity can be plotted as a full dose-matrix chart to visualize the drug concentrations where synergies occur. Table 14 shows several NEG085-Eg5/combinations.

Cell viability can be determined by measuring cellular ATP content using the CellTiter Glo luminescence assay (Promega, Madison WI). One day before drug addition, 250-500 GIST cells from 2 different cell lines are plated into 384-well plates (Greiner, Monroe, NC) in 20 µl growth media. The GIST430 cells contain a double mutation in cKIT which makes them partially resistant to Glivec® (Imatinib). The GIST882 cells have a single mutation in cKIT and are sensitive to Glivec® (Imatinib) Cells are then incubated for 120 h with various concentrations of NEG085-Eg5 inhibitor (Table 1), as a single agent, single agent compounds or NEG085-Eg5/compound combinations before CellTiter Glo reagent is added to each well and luminescence recorded on an Envision® plate reader (Perkin Elmer, Waltham MA). Luminescence values are used to calculate the inhibition of cell viability relative to DMSO-treated cells (0% inhibition).

TABLE 14

| | NEG085-Eg5 inhibitor combinations | |
|---|---|---|
| Target of compound | NEG085-Eg5 inhibitor in combination with: | Structure |
| RTKi | Glivec® | Imatinib |
| RTKi | Sutent® | Sunitinib |
| IAPi | NVP-LCL161 | 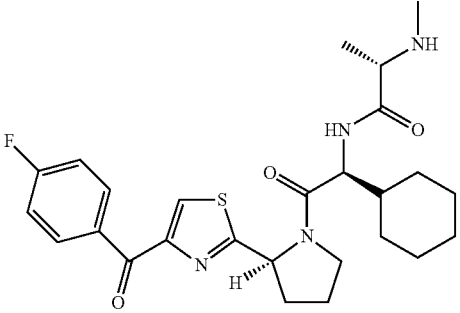 [SMILES: CN[C@@H](C)C(=O)N[C@H](C(=O)N1CCC[C@H]1c1nc(C(=O)c2ccc(F)cc2)cs1)C1CCCCC1] |
| PI3K fam. | NVP-BEZ235 | 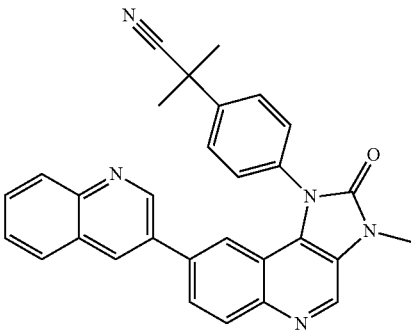 [SMILES: Cn1c(=O)n(-c2ccc(C(C)(C)C#N)cc2)c2c3cc(-c4cnc5ccccc5c4)ccc3ncc21] |
| pan PI3Ki | NVP-BKM120 | 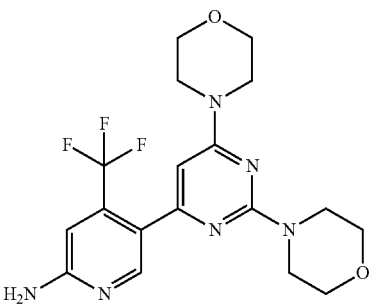 [SMILES: Nc1cc(C(F)(F)F)c(-c2cc(N3CCOCC3)nc(N3CCOCC3)n2)cn1] |

TABLE 14-continued
NEG085-Eg5 inhibitor combinations
| Target of compound | NEG085-Eg5 inhibitor in combination with: | Structure |
|---|---|---|
| PI3K | NVP-BYL719 | 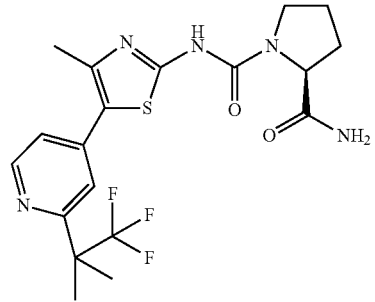 [SMILES: Cc1nc(NC(=O)N2CCC[C@H]2C(N)=O)sc1-c1ccnc(C(C)(C)C(F)(F)F)c1] |
| mTORi (cat.) | NVP-CCG168 | 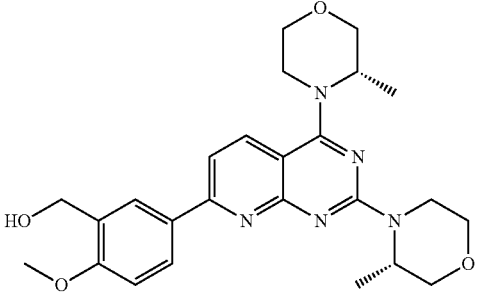 [SMILES: COc1ccc(-c2ccc3c(N4CCOC[C@@H]4C)nc(N4CCOC[C@@H]4C)nc3n2)cc1CO] |
| mTORi (allo.) | Afinitor ® | Everolimus |
| HSP90i | NVP-HSP990 | 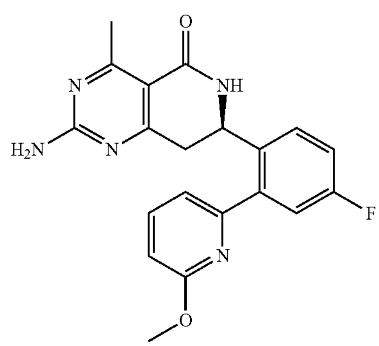 [SMILES: COc1cccc(-c2cc(F)ccc2[C@H]2Cc3nc(N)nc(C)c3C(=O)N2)n1] |
| JAK2 | NVP-BVB808 | 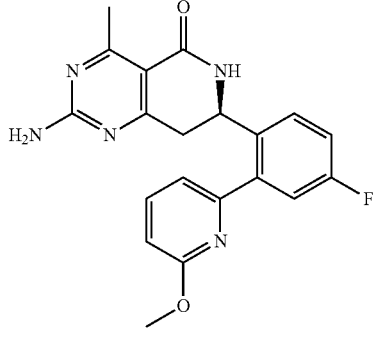 |

In summary, the anti-cKIT ADCs disclosed herein can synergistic effects when used in combination with other molecules to lead to more options for treatment.

Example 22 LC/MS Methods

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

DCM: dichloromethane
DIAD: Diisopropyl azodicarboxylate
DIPEA: diisopropyl ethylamine
DMF: N,N-dimethylformamide
ETOAC: ethyl acetate
TBSCl: tert-butyldimethylsilyl chloride
TFA: trifluoroacetic acid
THF: tetrahydrofuran All reactions were carried out under Ar using commercial grade solvents without any further distillation. Reagents were used as commercial grade without further purification. Thin layer chromatography was carried out using TLC-aluminum sheets with 0.2 mm of silica gel (Merck $F_{254}$). Column chromatography was carried out using an ISCO Combiflash Companion system, using flash grade prepacked Redisep® columns NMR spectra were recorded at 23° C. or 29° C. using the following spectrometers: Bruker 400 MHz and Bruker AVANCE 600 MHz proton frequency, equipped with a 1.7 mm $^1H\{^{13}C, ^{15}N\}$ CryoProbe™. Preparative HPLC was performed on Waters Autopurification system using the following conditions: Column Sunfire C18 30×100 mm, 5µ, gradient elution with $CH_3CN$ in water+0.1% TFA-$CH_3CN$ at 30 ml/min.

LC/MS data were produced with a Waters Acquity UPLC/SQD system, using a photodiode array detector and a single quadrupole mass detector. The following conditions were utilized:

Column: Waters Acquity HSS T3 1.8 µm 2.1×50 mm
Eluent A: Water+0.05% Formic acid+3.75 mM Ammonium acetate
Eluent B: Acetonitrile+0.04% Formic Acid
Column temperature: 60° C.
Injection-Vol. 1 µl, partial loop
PDA Full scan 210-450 nm and one user-selectable wavelength
Method A: LCMS_2_MINUTES
Flow 1.0 ml/min
Stop Time 2.00 min

| Gradient: | | |
|---|---|---|
| Time | % A (Eluent A) | % B (Eluent B) |
| 0.00 | 95 | 5 |
| 1.40 | 2 | 98 |
| 1.80 | 2 | 98 |
| 1.90 | 95 | 5 |
| 2.00 | 95 | 5 |

Mass range ESI +/−: 100-1200 m/z

Method B: LCMS_10_MINUTES
Flow 1.0 ml/min
Stop Time 10.00 min

| Gradient: | | |
|---|---|---|
| Time | % A (Eluent A) | % B (Eluent B) |
| 0.00 | 95 | 5 |
| 9.40 | 2 | 98 |
| 9.80 | 2 | 98 |
| 9.90 | 95 | 5 |
| 10.00 | 95 | 5 |

Mass range ESI +/−: 100-1600 m/z

Method C: LC-MS Column Acquity UPLC BEH C18 1.7 um, 2.1*50 mm
5 minutes (Flow 0.7 ml/min, solvent A: water+0.1% formic acid, solvent B: ACN+0.1% formic acid, Gradient: from 20 to 100% B in 4.3 min)

Where the LC method is not specified, Method A was used if retention time is under 1.5 minutes and Method B was used for retention times between 1.5 and 10 minutes.

UPLCMS—Method D (Polar Method, 2 mins Run):
System: Waters Acquity UPLC with Waters SQ detector.
Column: Acquity HSS T3 1.8 µm 2.1×50 mm.
Flow: 1 ml/min. Column temperature: 60° C.
Gradient: from 1 to 98% B in 1.4 min, A=water+0.05% formic acid+3.75 mM ammonium acetate, B=acetonitrile+0.0.4% formic acid.

UPLCMS Method E (4 minute runs)
System: Waters Acquity UPLC with Waters SQ detector.
Column: Sunfire C18 3.5 µm 2.1×20 mm.
Flow: 0.62 ml/min. Column temperature: 40° C.
Gradient: from 5 to 100% B in 4 min, A=water+0.1% trifluoroacetic acid, B=acetonitrile+0.1% trifluoroacetic acid.

Preparative LC Methods
Normal Phase Chromatography—PrepLC Method A
System: CombiFlash Rf200.
Column: RediSep Column Silica.
Gradiend: from 0 to 100% B, A=Heptane, B=Ethyl Acetate.
Normal Phase Chromatography—PrepLC Method B
System: CombiFlash Rf200.
Column: RediSep Column Silica.
Gradiend: from 0 to 100% B, A=Dichloromethane, B=MeOH.
Preparative Reverse Phase Chromatography—PrepLC Method C
System: Waters Acquity Prep LC/MS with Waters SQ detector.
Column: Sunfire Preparative C18, 5 µm, 30×100 mm.
Flow: 30 ml/min.
Gradient: from 5 to 100% B, A=acetonitrile+0.1% trifluoroacetic acid, B+water+0.1% trifluoroacetic acid.
Preparative Reverse Phase Chromatography—PrepLC Method D System: Waters Acquity Prep LC/MS with Waters SQ detector.
Column: Sunfire Preparative C18, 5 μm, 30×150 mm.
Flow: 60 ml/min.
Gradient: from 5 to 100% B, A=acetonitrile+0.1% trifluoroacetic acid, B+water+0.1% trifluoroacetic acid.

It is understood that the examples and aspects described herein are for illustrative purposes only and that various modifications or changes in light thereof will be suggested to persons skilled in the art and are to be included within the spirit and purview of this application and scope of the appended claims.

What is claimed is:

1. A method of treating a cKIT positive cancer in a patient in need thereof, comprising administering to said patient an antibody drug conjugate of the formula Ab-(L-(D)m)n or a pharmaceutically acceptable salt thereof; wherein
Ab is an antibody or antigen binding fragment thereof that specifically binds to an epitope of human cKIT, wherein said antibody or antigen binding fragment thereof comprises:
(i) a heavy chain variable region that comprises (a) a HCDR1 (CDR-Complementarity Determining Region) of SEQ ID NO: 76, (b) a HCDR2 of SEQ ID NO: 77, (c) a HCDR3 of SEQ ID NO: 78; and a light chain variable region that comprises: (d) a LCDR1 of SEQ ID NO: 85, (e) a LCDR2 of SEQ ID NO: 86, and (f) a LCDR3 of SEQ ID NO: 87; wherein the CDRs of (a)-(f) are defined in accordance with the Kabat definition; or
(ii) a heavy chain variable region that comprises (a) a HCDR1 of SEQ ID NO: 79, (b) a HCDR2 of SEQ ID NO: 80, (c) a HCDR3 of SEQ ID NO: 81; and a light chain variable region that comprises: (d) a LCDR1 of SEQ ID NO: 88, (e) a LCDR2 of SEQ ID NO: 89, and (f) a LCDR3 of SEQ ID NO: 90; wherein the CDRs of (a)-(f) are defined in accordance with the Chothia definition;
L is a linker;
D is a drug moiety;
m is an integer from 1 to 8; and
n is an integer from 1 to 10.

2. The method of claim 1, wherein said cancer is selected from the group consisting of gastrointestinal stromal tumors (GIST), small cell lung cancer (SCLC), acute myeloid leukemia (AML), melanoma, mast cell leukemia (MCL), mastocytosis, neurofibromatosis, breast cancer, non-small cell lung cancer (NSCLC), and pancreatic cancer.

3. The method of claim 1, wherein the antibody drug conjugate is administered in combination with another therapeutic agent.

4. The method of claim 1, wherein the antibody drug conjugate is administered in combination with imatinib, sunitinib, NVP-LCL16, NVP-BEZ235, NVP-BKM120, NVP-BYL719, NVP-CCG168, everolimus, NVP-HSP990 or NVP-BVB808.

5. The method of claim 1, wherein said n is 2 or 4.

6. The method of claim 1, wherein said antibody or antigen binding fragment thereof specifically binds the extracellular domain of human cKIT (SEQ ID NO:178).

7. The method of claim 6, wherein said antibody or antigen binding fragment thereof specifically binds to an epitope of human cKIT at domains 1-3 (SEQ ID NO:173) of the extracellular domain.

8. The method of claim 1, wherein one or two amino acids within a CDR have been modified, deleted or substituted.

9. The method of claim 1, wherein said antibody or antigen binding fragment thereof comprises:
(i) a heavy chain variable region (VH) that comprises (a) SEQ ID NO: 82, and a light chain variable region (VL) that comprises (b) SEQ ID NO: 91; or
(ii) a heavy chain that comprises (a) SEQ ID NO: 83, and a light chain that comprises (b) SEQ ID NO: 92.

10. The method of claim 1, wherein the antibody or antigen binding fragment thereof retains at least 90, 91, 92, 93, 94, 95, 96, 97, 98 or 99% identity over either the variable light chain or variable heavy chain region.

11. The method of claim 1, wherein the antibody is a monoclonal antibody, a chimeric antibody, a humanized antibody, a human engineered antibody, a human antibody, a single chain antibody (scFv) or an antibody fragment.

12. The method of claim 1, wherein said linker (L) is selected from the group consisting of a cleavable linker, a non-cleavable linker, a hydrophilic linker, a procharged linker and a dicarboxylic acid based linker.

13. The method of claim 1, wherein said linker (L) comprises a group of the formula —C(O)NR21- or —NR21-C(O)— wherein R21 is of the formula —(CH2)1-4-R22, where R22 is a polar group selected from —OH, —NH2, N(R23)2, COOR23, CON(R23)2, —(OCH2CH2O)k-OCH2CH2OR23, and —SO2R23, wherein k is 0 to 4 and each R23 is independently H or C1-4 alkyl.

14. The method of claim 1, wherein said drug moiety (D) is selected from a group consisting of: an Eg5 inhibitor, a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a MetAP (methionine aminopeptidase), an inhibitor of nuclear export of proteins CRM1, a DPPIV inhibitor, proteasome inhibitors, inhibitors of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder, a RNA polymerase inhibitor, a topoisomerase inhibitor and a DHFR inhibitor.

15. The method of claim 1, wherein the drug moiety (D) and linker (L) is selected from the group consisting of:

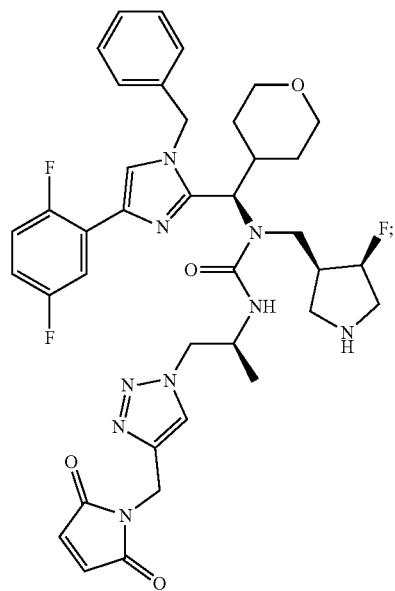

269
-continued

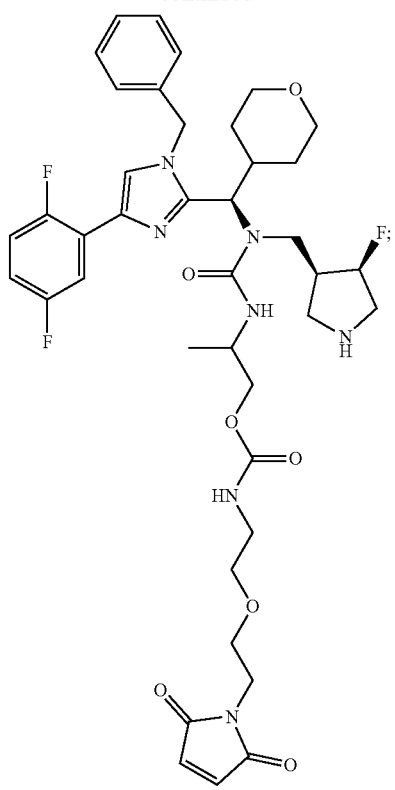

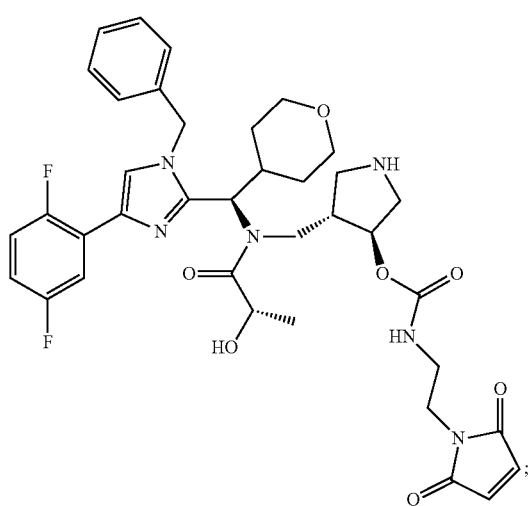

270
-continued

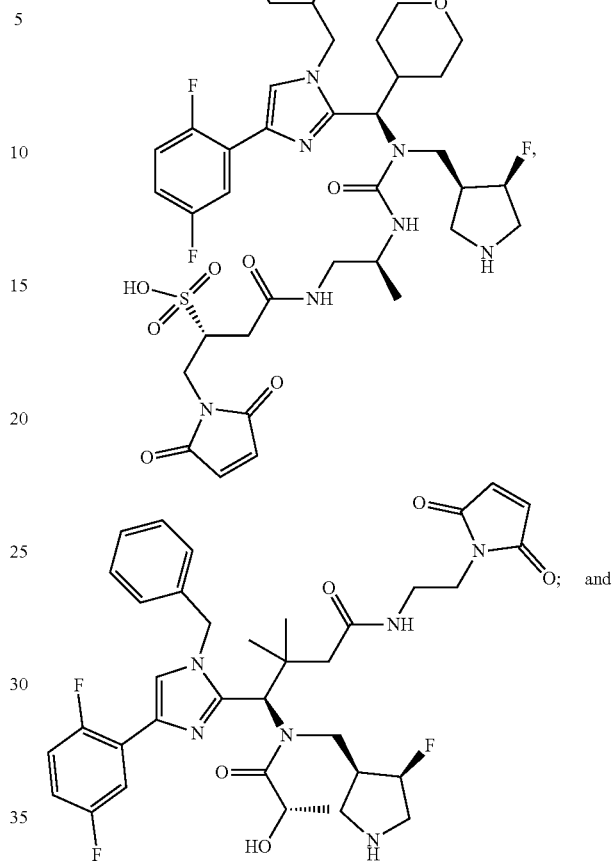

16. The method of claim 1, wherein the antibody or antigen binding fragment thereof contains at least one non-native cysteine introduced into a constant region, and the linker (L) is attached to the non-native cysteine.

17. The method of claim 16, wherein the at least one non-native cysteine introduced into the constant region is selected from the group consisting of SEQ ID NO: 185, SEQ ID NO:186, SEQ ID NO:187 and SEQ ID NO:188.

* * * * *

SEQUENCE LISTING

<160> NUMBER OF SEQ ID NOS: 188

<210> SEQ ID NO 1
<211> LENGTH: 5084
<212> TYPE: DNA
<213> ORGANISM: Homo sapiens

<400> SEQUENCE: 1

```
gatcccatcg cagctaccgc gatgagaggc gctcgcggcg cctgggattt tctctgcgtt      60
ctgctcctac tgcttcgcgt ccagacaggc tcttctcaac catctgtgag tccaggggaa     120
ccgtctccac catccatcca tccaggaaaa tcagacttaa tagtccgcgt gggcgacgag     180
attaggctgt tatgcactga tccgggcttt gtcaaatgga cttttgagat cctggatgaa     240
acgaatgaga ataagcagaa tgaatggatc acggaaaagg cagaagccac caacaccggc     300
aaatacacgt gcaccaacaa acacggctta agcaattcca tttatgtgtt tgttagagat     360
cctgccaagc ttttccttgt tgaccgctcc ttgtatggga aagaagacaa cgacacgctg     420
gtccgctgtc ctctcacaga cccagaagtg accaattatt ccctcaaggg gtgccagggg     480
aagcctcttc ccaaggactt gaggtttatt cctgaccccca aggcgggcat catgatcaaa     540
agtgtgaaac gcgcctacca tcggctctgt ctgcattgtt ctgtggacca ggagggcaag     600
tcagtgctgt cggaaaaatt catcctgaaa gtgaggccag ccttcaaagc tgtgcctgtt     660
gtgtctgtgt ccaaagcaag ctatcttctt agggaagggg aagaattcac agtgacgtgc     720
acaataaaag atgtgtctag ttctgtgtac tcaacgtgga aaagagaaaa cagtcagact     780
aaactacagg agaaatataa tagctggcat cacggtgact tcaattatga acgtcaggca     840
acgttgacta tcagttcagc gagagttaat gattctggag tgttcatgtg ttatgccaat     900
aatacttttg gatcagcaaa tgtcacaaca accttggaag tagtagataa aggattcatt     960
aatatcttcc ccatgataaa cactacagta tttgtaaacg atggagaaaa tgtagatttg    1020
attgttgaat atgaagcatt ccccaaacct gaacaccagc agtggatcta tatgaacaga    1080
accttcactg ataaatggga agattatccc aagtctgaga tgaaagtaa tatcagatac    1140 gtaagtgaac ttcatctaac gagattaaaa ggcaccgaag gaggcactta cacattccta    1200
gtgtccaatt ctgacgtcaa tgctgccata gcatttaatg tttatgtgaa tacaaaacca    1260
gaaatcctga cttacgacag gctcgtgaat ggcatgctcc aatgtgtggc agcaggattc    1320
ccagagccca caatagattg gtatttttgt ccaggaactg agcagagatg ctctgcttct    1380
gtactgccag tggatgtgca gacactaaac tcatctgggc caccgtttgg aaagctagtg    1440
gttcagagtt ctatagattc tagtgcattc aagcacaatg gcacggttga atgtaaggct    1500
tacaacgatg tgggcaagac ttctgcctat tttaactttg catttaaagg taacaacaaa    1560
gagcaaatcc atccccacac cctgttcact cctttgctga ttggtttcgt aatcgtagct    1620
ggcatgatgt gcattattgt gatgattctg acctacaaat atttacagaa acccatgtat    1680
gaagtacagt ggaaggttgt tgaggagata aatggaaaca attatgttta catagaccca    1740
acacaacttc cttatgatca caaatggagt ttcccagaa acaggctgag ttttgggaaa    1800
accctgggtg ctggagcttt cgggaaggtt gttgaggcaa ctgcttatgg cttaattaag    1860
```

```
tcagatgcgg ccatgactgt cgctgtaaag atgctcaagc cgagtgccca tttgacagaa    1920
cgggaagccc tcatgtctga actcaaagtc ctgagttacc ttggtaatca catgaatatt    1980
gtgaatctac ttggagcctg caccattgga gggcccaccc tggtcattac agaatattgt    2040
tgctatggtg atcttttgaa ttttttgaga agaaaacgtg attcatttat ttgttcaaag    2100
caggaagatc atgcagaagc tgcactttat aagaatcttc tgcattcaaa ggagtcttcc    2160
tgcagcgata gtactaatga gtacatggac atgaaacctg gagtttctta tgttgtccca    2220
accaaggccg acaaaaggag atctgtgaga ataggctcat acatagaaag agatgtgact    2280
cccgccatca tggaggatga cgagttggcc ctagacttag aagacttgct gagcttttct    2340
taccaggtgg caaagggcat ggctttcctc gcctccaaga attgtattca cagagacttg    2400
gcagccagaa atatcctcct tactcatggt cggatcacaa agatttgtga ttttggtcta    2460
gccagagaca tcaagaatga ttctaattat gtggttaaag gaaacgctcg actacctgtg    2520
aagtggatgg cacctgaaag catttttcaac tgtgtataca cgtttgaaag tgacgtctgg    2580
tcctatggga ttttttcttttg ggagctgttc tctttaggaa gcagcccctca tcctggaatg    2640
```

-continued

```
tagcttacca gaagcttcca tagtggtgca gaggaagtgg aaggcatcag tccctatgta    4260
tttgcagttc acctgcactt aaggcactct gttatttaga ctcatcttac tgtacctgtt    4320
ccttagacct tccataatgc tactgtctca ctgaaacatt taaattttac cctttagact    4380
gtagcctgga tattattctt gtagtttacc tctttaaaaa caaaacaaaa caaaacaaaa    4440
aactcccctt cctcactgcc caatataaaa ggcaaatgtg tacatggcag agtttgtgtg    4500
ttgtcttgaa agattcaggt atgttgcctt tatggtttcc cccttctaca tttcttagac    4560
tacatttaga gaactgtggc cgttatctgg aagtaaccat ttgcactgga gttctatgct    4620
ctcgcacctt tccaaagtta acagattttg gggttgtgtt gtcacccaag agattgttgt    4680
ttgccatact ttgtctgaaa aattcctttg tgtttctatt gacttcaatg atagtaagaa    4740
aagtggttgt tagttataga tgtctaggta cttcaggggc acttcattga gagttttgtc    4800
ttgccatact ttgtctgaaa aattcctttg tgtttctatt gacttcaatg atagtaagaa    4860
aagtggttgt tagttataga tgtctaggta cttcaggggc acttcattga gagttttgtc    4920
aatgtctttt gaatattccc aagcccatga gtccttgaaa atattttta tatatacagt    4980 aactttatgt gtaaatacat aagcggcgta agtttaaagg atgttggtgt tccacgtgtt    5040
ttattcctgt atgttgtcca attgttgaca gttctgaaga attc                    5084
```

<210> SEQ ID NO 2
<211> LENGTH: 976
<212> TYPE: PRT
<213> ORGANISM: Homo sapiens

<400> SEQUENCE: 2

```
Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220
```

-continued

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
            245                 250                 255

Glu Lys Tyr Asn Ser Trp His His Gly Asp Phe Asn Tyr Glu Arg Gln
                260                 265                 270

Ala Thr Leu Thr Ile Ser Ser Ala Arg Val Asn Asp Ser Gly Val Phe
            275                 280                 285

Met Cys Tyr Ala Asn Asn Thr Phe Gly Ser Ala Asn Val Thr Thr Thr
        290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
                405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
        435                 440                 445

Arg Cys Ser Ala Ser Val Leu Pro Val Asp Val Gln Thr Leu Asn Ser
450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
                485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
        515                 520                 525

Phe Val Ile Val Ala Gly Met Met Cys Ile Ile Val Met Ile Leu Thr
530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
        595                 600                 605

Tyr Gly Leu Ile Lys Ser Asp Ala Ala Met Thr Val Ala Val Lys Met
610                 615                 620

Leu Lys Pro Ser Ala His Leu Thr Glu Arg Glu Ala Leu Met Ser Glu
625                 630                 635                 640

```
Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
            660                 665                 670

Cys Cys Tyr Gly Asp Leu Leu Asn Phe Leu Arg Arg Lys Arg Asp Ser
        675                 680                 685

Phe Ile Cys Ser Lys Gln Glu Asp His Ala Glu Ala Leu Tyr Lys
690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Glu Leu Ala Leu Asp Leu Glu Asp
        755                 760                 765

Leu Leu Ser Phe Ser Tyr Gln Val Ala Lys Gly Met Ala Phe Leu Ala
770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
        835                 840                 845

Glu Ser Asp Val Trp Ser Tyr Gly Ile Phe Leu Trp Glu Leu Phe Ser
850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 3
<211> LENGTH: 5
<212> TYPE: PRT
<213> ORGANISM: Homo sapiens

<400> SEQUENCE: 3

Asp Tyr Tyr Met Ala
1               5

<210> SEQ ID NO 4
<211> LENGTH: 17
<212> TYPE: PRT
<213> ORGANISM: Homo sapiens
```

<400> SEQUENCE: 4

Asn Ile Asn Tyr Asp Gly Ser Ser Thr Tyr Tyr Leu Asp Ser Leu Lys
1               5                   10                  15

Ser

<210> SEQ ID NO 5
<211> LENGTH: 13
<212> TYPE: PRT
<213> ORGANISM: Homo sapiens

<400> SEQUENCE: 5

Gly Asp Tyr Tyr Gly Thr Thr Tyr Trp Tyr Phe Asp Val
1               5                   10

<210> SEQ ID NO 6
<211> LENGTH: 7
<212> TYPE: PRT
<213> ORGANISM: Homo sapiens

<400> SEQUENCE: 6

Gly Phe Thr Phe Ser Asp Tyr
1               5

<210> SEQ ID NO 7
<211> LENGTH: 6
<212> TYPE: PRT
<213> ORGANISM: Homo sapiens

<400> SEQUENCE: 7

Asn Tyr Asp Gly Ser Ser
1               5

<210> SEQ ID NO 8
<211> LENGTH: 13
<212> TYPE: PRT
<213> ORGANISM: Homo sapiens

<400> SEQUENCE: 8

Gly Asp Tyr Tyr Gly Thr Thr Tyr Trp Tyr Phe Asp Val
1               5                   10

<210> SEQ ID NO 9
<211> LENGTH: 122
<212> TYPE: PRT
<213> ORGANISM: Homo sapiens

<400> SEQUENCE: 9

Glu Val Arg Leu Val Glu Ser Glu Gly Leu Val Gln Pro Arg Ser
1               5                   10                  15

Ser Met Lys Leu Ser Cys Thr Ala Ser Gly Phe Thr Phe Ser Asp Tyr
                20                  25                  30

Tyr Met Ala Trp Val Arg Gln Val Pro Glu Lys Gly Leu Glu Trp Val
            35                  40                  45

Ala Asn Ile Asn Tyr Asp Gly Ser Ser Thr Tyr Tyr Leu Asp Ser Leu
        50                  55                  60

Lys Ser Arg Phe Ile Ile Ser Arg Asp Asn Lys Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Gly Asp Tyr Tyr Gly Thr Thr Tyr Trp Tyr Phe Asp Val Trp

```
                    100                 105                 110
Gly Thr Gly Thr Thr Val Thr Val Ser Ser
        115                 120

<210> SEQ ID NO 10
<211> LENGTH: 105
<212> TYPE: PRT
<213> ORGANISM: Homo sapiens

<400> SEQUENCE: 10

Val Ala Ala Pro Ser Val Phe Ile Phe Pro Ser Asp Glu Gln Leu
1               5                   10                  15

Lys Ser Gly Thr Ala Ser Val Val Cys Leu Leu Asn Asn Phe Tyr Pro
                20                  25                  30

Arg Glu Ala Lys Val Gln Trp Lys Val Asp Asn Ala Leu Gln Ser Gly
            35                  40                  45

Asn Ser Gln Glu Ser Val Thr Glu Gln Asp Ser Lys Asp Ser Thr Tyr
        50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105

<210> SEQ ID NO 11
<211> LENGTH: 452
<212> TYPE: PRT
<213> ORGANISM: Homo sapiens

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Tyr Met Ala Trp Val Arg Gln Ala Pro Gly Lys Gly Leu Glu Trp Val
            35                  40                  45

Ala Asn Ile Asn Tyr Asp Gly Ser Ser Thr Tyr Tyr Leu Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
```

195                 200                 205
        His Lys Pro Ser Asn Thr Lys Val Asp Lys Arg Val Glu Pro Lys Ser
            210                 215                 220

Cys Asp Lys Thr His Thr Cys Pro Pro Cys Pro Ala Pro Glu Leu Leu
        225                 230                 235                 240

Gly Gly Pro Ser Val Phe Leu Phe Pro Pro Lys Pro Lys Asp Thr Leu
                        245                 250                 255

Met Ile Ser Arg Thr Pro Glu Val Thr Cys Val Val Val Asp Val Ser
                    260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
        305                 310                 315                 320

Gly Lys Glu Tyr Lys Cys Lys Val Ser Asn Lys Ala Leu Pro Ala Pro
                        325                 330                 335

Ile Glu Lys Thr Ile Ser Lys Ala Lys Gly Gln Pro Arg Glu Pro Gln
                    340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
        385                 390                 395                 400

Pro Val Leu Asp Ser Asp Gly Ser Phe Phe Leu Tyr Ser Lys Leu Thr
                        405                 410                 415

Val Asp Lys Ser Arg Trp Gln Gln Gly Asn Val Phe Ser Cys Ser Val
                    420                 425                 430

Met His Glu Ala Leu His Asn His Tyr Thr Gln Lys Ser Leu Ser Leu
                435                 440                 445

Ser Pro Gly Lys
            450

<210> SEQ ID NO 12
<211> LENGTH: 11
<212> TYPE: PRT
<213> ORGANISM: Homo sapiens

<400> SEQUENCE: 12

Arg Ala Ser Gln Asp Ile Ser Asn Tyr Leu Asn
1               5                   10

<210> SEQ ID NO 13
<211> LENGTH: 7
<212> TYPE: PRT
<213> ORGANISM: Homo sapiens

<400> SEQUENCE: 13

Tyr Thr Ser Arg Leu Gln Ser
1               5

<210> SEQ ID NO 14
<211> LENGTH: 8
<212> TYPE: PRT
<213> ORGANISM: Homo sapiens

<400> SEQUENCE: 14

```
Gln Gln Gly Lys Lys Leu Trp Ser
1               5

<210> SEQ ID NO 15
<211> LENGTH: 7
<212> TYPE: PRT
<213> ORGANISM: Homo sapiens

<400> SEQUENCE: 15

Ser Gln Asp Ile Ser Asn Tyr
1               5

<210> SEQ ID NO 16
<211> LENGTH: 3
<212> TYPE: PRT
<213> ORGANISM: Homo sapiens

<400> SEQUENCE: 16

Tyr Thr Ser
1

<210> SEQ ID NO 17
<211> LENGTH: 5
<212> TYPE: PRT
<213> ORGANISM: Homo sapiens

<400> SEQUENCE: 17

Gly Lys Lys Leu Trp
1               5

<210> SEQ ID NO 18
<211> LENGTH: 107
<212> TYPE: PRT
<213> ORGANISM: Homo sapiens

<400> SEQUENCE: 18

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Lys Lys Leu Trp Ser
                85                  90                  95

Phe Gly Gly Gly Thr Lys Leu Glu Ile Lys Arg
            100                 105

<210> SEQ ID NO 19
<211> LENGTH: 330
<212> TYPE: PRT
<213> ORGANISM: Homo sapiens

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 213
<212> TYPE: PRT
<213> ORGANISM: Homo sapiens

<400> SEQUENCE: 20

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu Gln Ser Gly Val Pro Ser Arg Phe Ser Gly
     50                  55                  60

Ser Gly Ser Gly Thr Asp Tyr Thr Leu Thr Ile Ser Ser Leu Gln Pro
```

```
              65                  70                  75                  80
Glu Asp Phe Ala Thr Tyr Tyr Cys Gln Gln Gly Lys Lys Leu Trp Ser
                             85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 21
<211> LENGTH: 213
<212> TYPE: PRT
<213> ORGANISM: Homo sapiens

<400> SEQUENCE: 21

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Gly Lys Lys Leu Trp Ser
                             85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 22
<211> LENGTH: 5
<212> TYPE: PRT
<213> ORGANISM: Homo sapiens

<400> SEQUENCE: 22

Asp Tyr Tyr Met Ala
1               5

<210> SEQ ID NO 23
<211> LENGTH: 17
<212> TYPE: PRT
<213> ORGANISM: Homo sapiens

<400> SEQUENCE: 23

Asn Ile Asn Gln Ile Ala Gly Ser Thr Tyr Tyr Leu Asp Ser Val Arg
1               5                   10                  15

Gly

<210> SEQ ID NO 24
<211> LENGTH: 13
<212> TYPE: PRT
<213> ORGANISM: Homo sapiens

<400> SEQUENCE: 24

Gly Asp Tyr Tyr Gly Thr Thr Tyr Trp Tyr Phe Asp Val
1               5                   10

<210> SEQ ID NO 25
<211> LENGTH: 7
<212> TYPE: PRT
<213> ORGANISM: Homo sapiens

<400> SEQUENCE: 25

Gly Phe Thr Phe Ser Asp Tyr
1               5

<210> SEQ ID NO 26
<211> LENGTH: 6
<212> TYPE: PRT
<213> ORGANISM: Homo sapiens

<400> SEQUENCE: 26

Asn Gln Ile Ala Gly Ser
1               5

<210> SEQ ID NO 27
<211> LENGTH: 13
<212> TYPE: PRT
<213> ORGANISM: Homo sapiens

<400> SEQUENCE: 27

Gly Asp Tyr Tyr Gly Thr Thr Tyr Trp Tyr Phe Asp Val
1               5                   10

<210> SEQ ID NO 28
<211> LENGTH: 122
<212> TYPE: PRT
<213> ORGANISM: Homo sapiens

<400> SEQUENCE: 28

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
            35                  40                  45

Ala Asn Ile Asn Gln Ile Ala Gly Ser Thr Tyr Tyr Leu Asp Ser Val
 50                      55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
                100                 105                 110

Gly Gln Gly Thr Thr Val Thr Val Ser Ser
            115                 120

<210> SEQ ID NO 29
<211> LENGTH: 452
<212> TYPE: PRT
<213> ORGANISM: Homo sapiens

<400> SEQUENCE: 29

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
            35                  40                  45

Ala Asn Ile Asn Gln Ile Ala Gly Ser Thr Tyr Tyr Leu Asp Ser Val
 50                      55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
                100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

```
His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 30
<211> LENGTH: 1356
<212> TYPE: DNA
<213> ORGANISM: Homo sapiens

<400> SEQUENCE: 30
gaagtgcaat tggtggaaag cggcggaggc ctggtgcagc ctggcggctc tctgagactg      60
agctgtgccg ccagcggctt caccttcagc gactactaca tggcctgggt ccgacaggcc     120
cctggcaagg gcctggaatg ggtggccaat atcaaccaaa tcgccggcag cacctactac     180
ctggacagcg tgagaggccg gttcaccatc agccgggaca cgccaagaa cagcctgtac     240 ctgcagatga acagcctgcg ggccgaggac accgccgtgt actactgcgc cagaggcgat     300
tactacggca ccacctactg gtacttcgac gtgtggggcc agggcaccac cgtgaccgtc     360
agctcagcta gcaccaaggg ccccagcgtg ttccccctgg cccccagcag caagagcacc     420
agcggcggca cagccgccct gggctgcctg gtgaaggact acttccccga gcccgtgacc     480
gtgtcctgga caccggagc cctgacctcc ggcgtgcaca ccttcccgc cgtgctgcag     540 agcagcggcc tgtacagcct gtccagcgtg gtgacagtgc ccagcagcag cctgggcacc     600
cagacctaca tctgcaacgt gaaccacaag cccagcaaca ccaaggtgga caagagagtg     660
gagcccaaga gctgcgacaa gacccacacc tgccccccct gcccagcccc agagctgctg     720
ggcggaccct ccgtgttcct gttcccccc aagcccaagg acaccctgat gatcagcagg     780 accccccgagg tgacctgcgt ggtggtggac gtgagccacg aggacccaga ggtgaagttc     840
aactggtacg tggacggcgt ggaggtgcac aacgccaaga ccaagcccag agaggagcag     900
tacaacagca cctacagggt ggtgtccgtg ctgaccgtgc tgcaccagga ctggctgaac     960
ggcaaggaat acaagtgcaa ggtctccaac aaggccctgc cagcccccat cgaaaagacc    1020
```

```
atcagcaagg ccaagggcca gccacgggag ccccaggtgt acaccctgcc cccctcccgg    1080
gaggagatga ccaagaacca ggtgtccctg acctgtctgg tgaagggctt ctacccagc     1140 gacatcgccg tggagtggga gagcaacggc cagcccgaga caactacaa gaccaccccc     1200 ccagtgctgg acagcgacgg cagcttcttc ctgtacagca agctgaccgt ggacaagtcc    1260
aggtggcagc agggcaacgt gttcagctgc agcgtgatgc acgaggccct gcacaaccac    1320
tacacccaga gagcctgag cctgtccccc ggcaag                               1356
```

<210> SEQ ID NO 31
<211> LENGTH: 11
<212> TYPE: PRT
<213> ORGANISM: Homo sapiens

<400> SEQUENCE: 31

Arg Ala Ser Gln Asp Ile Ser Asn Tyr Leu Asn
1               5                   10

<210> SEQ ID NO 32
<211> LENGTH: 7
<212> TYPE: PRT
<213> ORGANISM: Homo sapiens

<400> SEQUENCE: 32

Tyr Thr Ser Arg Leu Gln Ser
1               5

<210> SEQ ID NO 33
<211> LENGTH: 8
<212> TYPE: PRT
<213> ORGANISM: Homo sapiens

<400> SEQUENCE: 33

Gln Gln Gly Lys Lys Leu Trp Ser
1               5

<210> SEQ ID NO 34
<211> LENGTH: 7
<212> TYPE: PRT
<213> ORGANISM: Homo sapiens

<400> SEQUENCE: 34

Ser Gln Asp Ile Ser Asn Tyr
1               5

<210> SEQ ID NO 35
<211> LENGTH: 3
<212> TYPE: PRT
<213> ORGANISM: Homo sapiens

<400> SEQUENCE: 35

Tyr Thr Ser
1

<210> SEQ ID NO 36
<211> LENGTH: 5
<212> TYPE: PRT
<213> ORGANISM: Homo sapiens

<400> SEQUENCE: 36

Gly Lys Lys Leu Trp
1               5

```
<210> SEQ ID NO 37
<211> LENGTH: 106
<212> TYPE: PRT
<213> ORGANISM: Homo sapiens

<400> SEQUENCE: 37

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Gly Lys Lys Leu Trp Ser
                85                  90                  95

Phe Gly Gly Gly Thr Lys Val Glu Ile Lys
            100                 105

<210> SEQ ID NO 38
<211> LENGTH: 213
<212> TYPE: PRT
<213> ORGANISM: Homo sapiens

<400> SEQUENCE: 38

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Gly Lys Lys Leu Trp Ser
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 39
<211> LENGTH: 639
<212> TYPE: DNA
<213> ORGANISM: Homo sapiens

<400> SEQUENCE: 39

```
gagatcgtga tgacccagag ccccgccacc ctgagcctga gccctggcga aagagccacc      60
ctgtcctgca gagccagcca ggacatcagc aactacctga actggtatca gcagaagccc     120
ggccaggccc ccagactgct gatctactac accagcggc tgcagagcgg catcccgcc       180
agatttctg gcagcggcag cggcaccgac tacaccctga ccatcagcag cctggaaccc      240
gaggacttcg ccgtgtacta ctgccagcag ggcaagaagc tgtggtcctt cggcggaggc     300
accaaggtgg aaatcaagcg tacggtggcc gctcccagcg tgttcatctt ccccccagc      360
gacgagcagc tgaagagcgg caccgccagc gtggtgtgcc tgctgaacaa cttctaccc     420
cgggaggcca aggtgcagtg aaggtggac aacgccctgc agagcggcaa cagccaggag      480
agcgtcaccg agcaggacag caaggactcc acctacagcc tgagcagcac cctgaccctg     540
agcaaggccg actacgagaa gcataaggtg tacgcctgcg aggtgaccca ccagggcctg     600
tccagccccg tgaccaagag cttcaacagg ggcgagtgc                            639
```

<210> SEQ ID NO 40
<211> LENGTH: 5
<212> TYPE: PRT
<213> ORGANISM: Homo sapiens

<400> SEQUENCE: 40

Asp Tyr Tyr Met Ala
1               5

<210> SEQ ID NO 41
<211> LENGTH: 17
<212> TYPE: PRT
<213> ORGANISM: Homo sapiens

<400> SEQUENCE: 41

Asn Ile Asn Gln Asn Thr Gly Ser Thr Tyr Tyr Val Asp Ser Val Gln
1               5                   10                  15

Gly

<210> SEQ ID NO 42
<211> LENGTH: 13
<212> TYPE: PRT
<213> ORGANISM: Homo sapiens

<400> SEQUENCE: 42

Gly Asp Tyr Tyr Gly Thr Thr Tyr Trp Tyr Phe Asp Val
1               5                   10

<210> SEQ ID NO 43
<211> LENGTH: 7
<212> TYPE: PRT
<213> ORGANISM: Homo sapiens

<400> SEQUENCE: 43

Gly Phe Thr Phe Ser Asp Tyr
1               5

<210> SEQ ID NO 44
<211> LENGTH: 6
<212> TYPE: PRT

```
<213> ORGANISM: Homo sapiens

<400> SEQUENCE: 44

Asn Gln Asn Thr Gly Ser
1               5

<210> SEQ ID NO 45
<211> LENGTH: 13
<212> TYPE: PRT
<213> ORGANISM: Homo sapiens

<400> SEQUENCE: 45

Gly Asp Tyr Tyr Gly Thr Thr Tyr Trp Tyr Phe Asp Val
1               5                   10

<210> SEQ ID NO 46
<211> LENGTH: 122
<212> TYPE: PRT
<213> ORGANISM: Homo sapiens

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Gln Asn Thr Gly Ser Thr Tyr Tyr Val Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser
        115                 120

<210> SEQ ID NO 47
<211> LENGTH: 452
<212> TYPE: PRT
<213> ORGANISM: Homo sapiens

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Gln Asn Thr Gly Ser Thr Tyr Tyr Val Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110
```

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 48
<211> LENGTH: 1356
<212> TYPE: DNA
<213> ORGANISM: Homo sapiens

<400> SEQUENCE: 48
gaagtgcaat tggtggaaag cggcggaggc ctggtgcagc ctggcggctc tctgagactg      60
agctgtgccg ccagcggctt caccttcagc gactactaca tggcctgggt ccgacaggcc     120
cctggcaagg gcctggaatg ggtggccaat atcaaccaaa acaccggcag cacctactac     180

```
gtggacagcg tgcaaggccg gttcaccatc agccgggaca cgccaagaa cagcctgtac    240 ctgcagatga acagcctgcg ggccgaggac accgccgtgt actactgcgc cagaggcgat    300
tactacggca ccacctactg gtacttcgac gtgtggggcc agggcaccac cgtgaccgtc    360
agctcagcta gcaccaaggg ccccagcgtg ttccccctgg cccccagcag caagagcacc    420
agcggcggca cagccgccct gggctgcctg gtgaaggact acttccccga gcccgtgacc    480
gtgtcctgga acagcggagc cctgacctcc ggcgtgcaca ccttccccgc cgtgctgcag    540
agcagcggcc tgtacagcct gtccagcgtg gtgacagtgc ccagcagcag cctgggcacc    600
cagacctaca tctgcaacgt gaaccacaag cccagcaaca ccaaggtgga caagagagtg    660
gagcccaaga gctgcgacaa gacccacacc tgcccccccc tgcccagccc cagagctgctg    720 ggcggacccct ccgtgttcct gttccccccc aagcccaagg acaccctgat gatcagcagg    780
acccccgagg tgacctgcgt ggtggtggac gtgagccacg aggacccaga ggtgaagttc    840
aactggtacg tggacggcgt ggaggtgcac aacgccaaga ccaagcccag agaggagcag    900
tacaacagca cctacagggt ggtgtccgtg ctgaccgtgc tgcaccagga ctggctgaac    960
ggcaaggaat acaagtgcaa ggtctccaac aaggccctgc cagcccccat cgaaaagacc    1020
atcagcaagg ccaagggcca gccacgggag ccccaggtgt acaccctgcc ccctcccgg    1080 gaggagatga ccaagaacca ggtgtccctg acctgtctgg tgaagggctt ctaccccagc    1140
gacatcgccg tggagtggga gagcaacggc cagcccgaga caactacaa gaccaccccc    1200 ccagtgctgg acagcgacgg cagcttcttc ctgtacagca agctgaccgt ggacaagtcc    1260
aggtggcagc agggcaacgt gttcagctgc agcgtgatgc acgaggccct gcacaaccac    1320
tacacccaga agagcctgag cctgtccccc ggcaag                              1356
```

<210> SEQ ID NO 49
<211> LENGTH: 11
<212> TYPE: PRT
<213> ORGANISM: Homo sapiens

<400> SEQUENCE: 49

Arg Ala Ser Gln Asp Ile Ser Asn Tyr Leu Asn
1               5                   10

<210> SEQ ID NO 50
<211> LENGTH: 7
<212> TYPE: PRT
<213> ORGANISM: Homo sapiens

<400> SEQUENCE: 50

Tyr Thr Ser Arg Leu Gln Ser
1               5

<210> SEQ ID NO 51
<211> LENGTH: 8
<212> TYPE: PRT
<213> ORGANISM: Homo sapiens

<400> SEQUENCE: 51

Gln Gln Gly Lys Lys Leu Trp Ser
1               5

<210> SEQ ID NO 52
<211> LENGTH: 7
<212> TYPE: PRT
<213> ORGANISM: Homo sapiens

<400> SEQUENCE: 52

Ser Gln Asp Ile Ser Asn Tyr
1               5

<210> SEQ ID NO 53
<211> LENGTH: 3
<212> TYPE: PRT
<213> ORGANISM: Homo sapiens

<400> SEQUENCE: 53

Tyr Thr Ser
1

<210> SEQ ID NO 54
<211> LENGTH: 5
<212> TYPE: PRT
<213> ORGANISM: Homo sapiens

<400> SEQUENCE: 54

Gly Lys Lys Leu Trp
1               5

<210> SEQ ID NO 55
<211> LENGTH: 106
<212> TYPE: PRT
<213> ORGANISM: Homo sapiens

<400> SEQUENCE: 55

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Gly Lys Lys Leu Trp Ser
                85                  90                  95

Phe Gly Gly Gly Thr Lys Val Glu Ile Lys
            100                 105

<210> SEQ ID NO 56
<211> LENGTH: 213
<212> TYPE: PRT
<213> ORGANISM: Homo sapiens

<400> SEQUENCE: 56

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Gly Lys Lys Leu Trp Ser
                85                  90                  95
Phe Gly Gly Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 57
<211> LENGTH: 639
<212> TYPE: DNA
<213> ORGANISM: Homo sapiens

<400> SEQUENCE: 57
gagatcgtga tgacccagag ccccgccacc ctgagcctga gccctggcga aagagccacc      60
ctgtcctgca gagccagcca ggacatcagc aactacctga actggtatca gcagaagccc     120
ggccaggccc ccagactgct gatctactac accagccggc tgcagagcgg catccccgcc     180
agattttctg gcagcggcag cggcaccgac tacaccctga ccatcagcag cctggaaccc     240
gaggacttcg ccgtgtacta ctgccagcag ggcaagaagc tgtggtcctt cggcggaggc     300
accaaggtgg aaatcaagcg tacggtggcc gctcccagcg tgttcatctt cccccccagc     360
gacgagcagc tgaagagcgg caccgccagc gtggtgtgcc tgctgaacaa cttctacccc     420
cgggaggcca aggtgcagtg gaaggtggac aacgccctgc agagcggcaa cagccaggag     480
agcgtcaccg agcaggacag caaggactcc acctacagcc tgagcagcac cctgaccctg     540
agcaaggccg actacgagaa gcataaggtg tacgcctgcg aggtgaccca ccagggcctg     600
tccagccccg tgaccaagag cttcaacagg ggcgagtgc                           639

<210> SEQ ID NO 58
<211> LENGTH: 5
<212> TYPE: PRT
<213> ORGANISM: Homo sapiens

<400> SEQUENCE: 58

Asp Tyr Tyr Met Ala
1               5

<210> SEQ ID NO 59
<211> LENGTH: 17
<212> TYPE: PRT
<213> ORGANISM: Homo sapiens

<400> SEQUENCE: 59

Ser Ile Asn Gln Asn Thr Gly Ser Thr Tyr Tyr Leu Asp Ser Val Arg
1               5                   10                  15

Gly

<210> SEQ ID NO 60
<211> LENGTH: 13
<212> TYPE: PRT
<213> ORGANISM: Homo sapiens

<400> SEQUENCE: 60

Gly Asp Tyr Tyr Gly Thr Thr Tyr Trp Tyr Phe Asp Val
1               5                   10

<210> SEQ ID NO 61
<211> LENGTH: 7
<212> TYPE: PRT
<213> ORGANISM: Homo sapiens

<400> SEQUENCE: 61

Gly Phe Thr Phe Ser Asp Tyr
1               5

<210> SEQ ID NO 62
<211> LENGTH: 6
<212> TYPE: PRT
<213> ORGANISM: Homo sapiens

<400> SEQUENCE: 62

Asn Gln Asn Thr Gly Ser
1               5

<210> SEQ ID NO 63
<211> LENGTH: 13
<212> TYPE: PRT
<213> ORGANISM: Homo sapiens

<400> SEQUENCE: 63

Gly Asp Tyr Tyr Gly Thr Thr Tyr Trp Tyr Phe Asp Val
1               5                   10

<210> SEQ ID NO 64
<211> LENGTH: 122
<212> TYPE: PRT
<213> ORGANISM: Homo sapiens

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Gln Asn Thr Gly Ser Thr Tyr Tyr Leu Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser
        115                 120

<210> SEQ ID NO 65
<211> LENGTH: 452
<212> TYPE: PRT
<213> ORGANISM: Homo sapiens

<400> SEQUENCE: 65

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Gln Asn Thr Gly Ser Thr Tyr Tyr Leu Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380
```

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 66
<211> LENGTH: 1356
<212> TYPE: DNA
<213> ORGANISM: Homo sapiens

<400> SEQUENCE: 66
gaagtgcaat tggtggaaag cggcggaggc ctggtgcagc ctggcggctc tctgagactg      60
agctgtgccg ccagcggctt caccttcagc gactactaca tggcctgggt ccgacaggcc     120
cctggcaagg gcctggaatg ggtggccagt atcaaccaaa acaccggcag cacctactac     180
ctggacagcg tgcgaggccg gttcaccatc agccgggaca cgccaagaa cagcctgtac     240 ctgcagatga acagcctgcg ggccgaggac accgccgtgt actactgcgc cagaggcgat     300
tactacggca ccacctactg gtacttcgac gtgtgggggcc agggcaccac cgtgaccgtc     360
agctcagcta gcaccaaggg ccccagcgtg ttccccctgg ccccagcag caagagcacc     420 agcggcggca cagccgccct gggctgcctg gtgaaggact acttccccga gcccgtgacc     480
gtgtcctgga cagcggagc cctgacctcc ggcgtgcaca ccttccccgc cgtgctgcag     540
agcagcggcc tgtacagcct gtccagcgtg gtgacagtgc ccagcagcag cctgggcacc     600
cagacctaca tctgcaacgt gaaccacaag cccagcaaca ccaaggtgga caagagagtg     660
gagcccaaga gctgcgacaa gacccacacc tgcccccct gcccagcccc agagctgctg     720
ggcggaccct ccgtgttcct gttcccccc aagcccaagg acaccctgat gatcagcagg     780 accccgagg tgacctgcgt ggtggtggac gtgagccacg aggacccaga ggtgaagttc     840
aactggtacg tggacggcgt ggaggtgcac aacgccaaga ccaagcccag agaggagcag     900
tacaacagca cctacagggt ggtgtccgtg ctgaccgtgc tgcaccagga ctggctgaac     960
ggcaaggaat acaagtgcaa ggtctccaac aaggccctgc cagcccccat cgaaaagacc    1020
atcagcaagg ccaagggcca gccacgggag ccccaggtgt acaccctgcc ccctcccgg    1080 gaggagatga ccaagaacca ggtgtccctg acctgtctgg tgaagggctt ctacccagc    1140 gacatcgccg tggagtggga gagcaacggc cagcccgaga caactacaa gaccaccccc    1200 ccagtgctgg acagcgacgg cagcttcttc ctgtacagca agctgaccgt ggacaagtcc    1260
aggtggcagc agggcaacgt gttcagctgc agcgtgatgc acgaggccct gcacaaccac    1320
tacacccaga gagcctgag cctgtccccc ggcaag                              1356

<210> SEQ ID NO 67
<211> LENGTH: 11
<212> TYPE: PRT
<213> ORGANISM: Homo sapiens

<400> SEQUENCE: 67

Arg Ala Ser Gln Asp Ile Ser Asn Tyr Leu Asn

```
                1               5                  10

<210> SEQ ID NO 68
<211> LENGTH: 7
<212> TYPE: PRT
<213> ORGANISM: Homo sapiens

<400> SEQUENCE: 68

Tyr Thr Ser Arg Leu Gln Ser
1               5

<210> SEQ ID NO 69
<211> LENGTH: 8
<212> TYPE: PRT
<213> ORGANISM: Homo sapiens

<400> SEQUENCE: 69

Gln Gln Gly Lys Lys Leu Trp Ser
1               5

<210> SEQ ID NO 70
<211> LENGTH: 7
<212> TYPE: PRT
<213> ORGANISM: Homo sapiens

<400> SEQUENCE: 70

Ser Gln Asp Ile Ser Asn Tyr
1               5

<210> SEQ ID NO 71
<211> LENGTH: 3
<212> TYPE: PRT
<213> ORGANISM: Homo sapiens

<400> SEQUENCE: 71

Tyr Thr Ser
1

<210> SEQ ID NO 72
<211> LENGTH: 5
<212> TYPE: PRT
<213> ORGANISM: Homo sapiens

<400> SEQUENCE: 72

Gly Lys Lys Leu Trp
1               5

<210> SEQ ID NO 73
<211> LENGTH: 106
<212> TYPE: PRT
<213> ORGANISM: Homo sapiens

<400> SEQUENCE: 73

Glu Ile Val Met Thr Gln Ser Pro Ala Thr Leu Ser Leu Ser Pro Gly
1               5                  10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
    50                  55                  60

Ser Gly Ser Gly Thr Asp Tyr Thr Leu Thr Ile Ser Ser Leu Glu Pro
65                  70                  75                  80
```

Glu Asp Phe Ala Val Tyr Tyr Cys Gln Gln Gly Lys Lys Leu Trp Ser
                85                  90                  95

Phe Gly Gly Gly Thr Lys Val Glu Ile Lys
            100                 105

<210> SEQ ID NO 74
<211> LENGTH: 213
<212> TYPE: PRT
<213> ORGANISM: Homo sapiens

<400> SEQUENCE: 74

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Asn Tyr
            20                  25                  30

Leu Asn Trp Tyr Gln Gln Lys Pro Gly Gln Ala Pro Arg Leu Leu Ile
        35                  40                  45

Tyr Tyr Thr Ser Arg Leu Gln Ser Gly Ile Pro Ala Arg Phe Ser Gly
    50                  55                  60

Ser Gly Ser Gly Thr Asp Tyr Thr Leu Thr Ile Ser Ser Leu Glu Pro
65                  70                  75                  80

Glu Asp Phe Ala Val Tyr Tyr Cys Gln Gln Gly Lys Lys Leu Trp Ser
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 75
<211> LENGTH: 639
<212> TYPE: DNA
<213> ORGANISM: Homo sapiens

<400> SEQUENCE: 75
gagatcgtga tgacccagag ccccgccacc ctgagcctga gccctggcga aagagccacc     60
ctgtcctgca gagccagcca ggacatcagc aactacctga actggtatca gcagaagccc    120
ggccaggccc ccagactgct gatctactac accagccggc tgcagagcgg catccccgcc    180
agattttctg gcagcggcag cggcaccgac tacaccctga ccatcagcag cctggaaccc    240
gaggacttcg ccgtgtacta ctgccagcag ggcaagaagc tgtggtcctt cggcggaggc    300
accaaggtgg aaatcaagcg tacggtggcc gctcccagcg tgttcatctt ccccccagc     360 gacgagcagc tgaagagcgg caccgccagc gtggtgtgcc tgctgaacaa cttctacccc    420

```
cgggaggcca aggtgcagtg gaaggtggac aacgccctgc agagcggcaa cagccaggag    480
agcgtcaccg agcaggacag caaggactcc acctacagcc tgagcagcac cctgaccctg    540
agcaaggccg actacgagaa gcataaggtg tacgcctgcg aggtgaccca ccagggcctg    600
tccagccccg tgaccaagag cttcaacagg ggcgagtgc                           639
```

```
<210> SEQ ID NO 76
<211> LENGTH: 5
<212> TYPE: PRT
<213> ORGANISM: Homo sapiens

<400> SEQUENCE: 76

Gly Tyr Tyr Met Ala
1               5

<210> SEQ ID NO 77
<211> LENGTH: 17
<212> TYPE: PRT
<213> ORGANISM: Homo sapiens

<400> SEQUENCE: 77

Asn Ile Asn Tyr Pro Gly Ser Ser Thr Tyr Tyr Leu Asp Ser Val Lys
1               5                   10                  15

Gly

<210> SEQ ID NO 78
<211> LENGTH: 13
<212> TYPE: PRT
<213> ORGANISM: Homo sapiens

<400> SEQUENCE: 78

Gly Asp Tyr Tyr Gly Thr Thr Tyr Trp Tyr Phe Asp Val
1               5                   10

<210> SEQ ID NO 79
<211> LENGTH: 7
<212> TYPE: PRT
<213> ORGANISM: Homo sapiens

<400> SEQUENCE: 79

Gly Phe Ala Phe Ser Gly Tyr
1               5

<210> SEQ ID NO 80
<211> LENGTH: 6
<212> TYPE: PRT
<213> ORGANISM: Homo sapiens

<400> SEQUENCE: 80

Asn Tyr Pro Gly Ser Ser
1               5

<210> SEQ ID NO 81
<211> LENGTH: 13
<212> TYPE: PRT
<213> ORGANISM: Homo sapiens

<400> SEQUENCE: 81

Gly Asp Tyr Tyr Gly Thr Thr Tyr Trp Tyr Phe Asp Val
1               5                   10

<210> SEQ ID NO 82
<211> LENGTH: 122
```

<212> TYPE: PRT
<213> ORGANISM: Homo sapiens

<400> SEQUENCE: 82

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Gly Tyr
            20                  25                  30

Tyr Met Ala Trp Val Arg Gln Ala Pro Gly Lys Gly Leu Glu Trp Val
        35                  40                  45

Ala Asn Ile Asn Tyr Pro Gly Ser Ser Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Asp Tyr Tyr Gly Thr Thr Tyr Trp Tyr Phe Asp Val Trp
        100                 105                 110

Gly Gln Gly Thr Thr Val Thr Val Ser Ser
            115                 120
```

<210> SEQ ID NO 83
<211> LENGTH: 452
<212> TYPE: PRT
<213> ORGANISM: Homo sapiens

<400> SEQUENCE: 83

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Gly Tyr
            20                  25                  30

Tyr Met Ala Trp Val Arg Gln Ala Pro Gly Lys Gly Leu Glu Trp Val
        35                  40                  45

Ala Asn Ile Asn Tyr Pro Gly Ser Ser Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Asp Tyr Tyr Gly Thr Thr Tyr Trp Tyr Phe Asp Val Trp
        100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Arg Val Glu Pro Lys Ser
    210                 215                 220
```

```
Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 84
<211> LENGTH: 1356
<212> TYPE: DNA
<213> ORGANISM: Homo sapiens

<400> SEQUENCE: 84
gaagtgcaat tggtggaaag cggcggaggc ctggtgcagc ctggcggctc tctgagactg     60
agctgtgccg ccagcggctt cgccttcagc ggctactaca tggcctgggt ccgacaggcc    120
cctggcaagg gcctggaatg ggtggccaac atcaactacc ccggcagcag cacctactac    180
ctggacagcg tgaagggccg gttcaccatc agccgggaca cgccaagaa cagcctgtac    240 ctgcagatga acagcctgcg ggccgaggac accgccgtgt actactgcgc cagaggcgat    300
tactacggca ccacctactg gtacttcgac gtgtggggcc agggcaccac cgtgaccgtc    360
agctcagcta gcaccaaggg cccagcgtg ttcccctgg cccccagcag caagagcacc    420
agcggcggca cagccgccct gggctgcctg gtgaaggact acttccccga gccgtgacc    480 gtgtcctgga cagcggagc cctgacctcc ggcgtgcaca ccttcccgc cgtgctgcag    540 agcagcggcc tgtacagcct gtccagcgtg gtgacagtgc ccagcagcag cctgggcacc    600
cagacctaca tctgcaacgt gaaccacaag cccagcaaca ccaaggtgga caagagagtg    660
gagcccaaga gctgcgacaa gacccacacc tgcccccct gcccagcccc agagctgctg    720
ggcggaccct ccgtgttcct gttccccccc aagcccaagg acaccctgat gatcagcagg    780
```

```
acccccgagg tgacctgcgt ggtggtggac gtgagccacg aggacccaga ggtgaagttc    840
aactggtacg tggacggcgt ggaggtgcac aacgccaaga ccaagcccag agaggagcag    900
tacaacagca cctacagggt ggtgtccgtg ctgaccgtgc tgcaccagga ctggctgaac    960
ggcaaggaat acaagtgcaa ggtctccaac aaggccctgc cagcccccat cgaaaagacc   1020
atcagcaagg ccaagggcca gccacgggag ccccaggtgt acaccctgcc ccctcccgg   1080 gaggagatga ccaagaacca ggtgtccctg acctgtctgg tgaagggctt ctaccccagc   1140
gacatcgccg tggagtggga gagcaacggc cagcccgaga caactacaa gaccaccccc    1200 ccagtgctgg acagcgacgg cagcttcttc ctgtacagca agctgaccgt ggacaagtcc   1260
aggtggcagc agggcaacgt gttcagctgc agcgtgatgc acgaggccct gcacaaccac   1320
tacacccaga gagcctgag cctgtccccc ggcaag                              1356
```

<210> SEQ ID NO 85
<211> LENGTH: 11
<212> TYPE: PRT
<213> ORGANISM: Homo sapiens

<400> SEQUENCE: 85

Arg Ala Ser Gln Ser Ile Ser Ser Tyr Leu Asn
1               5                   10

<210> SEQ ID NO 86
<211> LENGTH: 7
<212> TYPE: PRT
<213> ORGANISM: Homo sapiens

<400> SEQUENCE: 86

Tyr Thr Ser Arg Leu Gln Ser
1               5

<210> SEQ ID NO 87
<211> LENGTH: 8
<212> TYPE: PRT
<213> ORGANISM: Homo sapiens

<400> SEQUENCE: 87

Gln Gln Gly Arg Arg Leu Trp Ser
1               5

<210> SEQ ID NO 88
<211> LENGTH: 7
<212> TYPE: PRT
<213> ORGANISM: Homo sapiens

<400> SEQUENCE: 88

Ser Gln Ser Ile Ser Ser Tyr
1               5

<210> SEQ ID NO 89
<211> LENGTH: 3
<212> TYPE: PRT
<213> ORGANISM: Homo sapiens

<400> SEQUENCE: 89

Tyr Thr Ser
1

<210> SEQ ID NO 90
<211> LENGTH: 5
<212> TYPE: PRT

-continued

<213> ORGANISM: Homo sapiens

<400> SEQUENCE: 90

Gly Arg Arg Leu Trp
1               5

<210> SEQ ID NO 91
<211> LENGTH: 106
<212> TYPE: PRT
<213> ORGANISM: Homo sapiens

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Arg Leu Trp Ser
                85                  90                  95

Phe Gly Gly Gly Thr Lys Val Glu Ile Lys
            100                 105

<210> SEQ ID NO 92
<211> LENGTH: 213
<212> TYPE: PRT
<213> ORGANISM: Homo sapiens

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Arg Leu Trp Ser
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
Asn Arg Gly Glu Cys
    210

<210> SEQ ID NO 93
<211> LENGTH: 639
<212> TYPE: DNA
<213> ORGANISM: Homo sapiens

<400> SEQUENCE: 93
gatatccaga tgacccagag ccccagcagc ctgagcgcca gcgtgggcga cagagtgacc      60
atcacctgtc gggccagcca gagcatcagc agctacctga actggtatca gcagaagccc    120
ggcaaggccc ccaagctgct gatctactac accagccggc tgcagagcgg cgtgcccagc    180
agatttctg gcagcggcag cggcaccgac ttcaccctga ccatcagcag cctgcagccc     240
gaggacttcg ccacctacta ctgccagcag ggccgccgcc tgtggtcctt cggcggaggc    300
accaaggtgg aaatcaagcg tacggtggcc gctcccagcg tgttcatctt cccccccagc    360
gacgagcagc tgaagagcgg caccgccagc gtggtgtgcc tgctgaacaa cttctacccc    420
cgggaggcca aggtgcagtg gaaggtggac aacgccctgc agagcggcaa cagccaggag    480
agcgtcaccg agcaggacag caaggactcc acctacagcc tgagcagcac cctgaccctg    540
agcaaggccg actacgagaa gcataaggtg tacgcctgcg aggtgaccca ccagggcctg    600
tccagccccg tgaccaagag cttcaacagg ggcgagtgc                           639

<210> SEQ ID NO 94
<211> LENGTH: 5
<212> TYPE: PRT
<213> ORGANISM: Homo sapiens

<400> SEQUENCE: 94

Asp Tyr Tyr Met Ala
1               5

<210> SEQ ID NO 95
<211> LENGTH: 17
<212> TYPE: PRT
<213> ORGANISM: Homo sapiens

<400> SEQUENCE: 95

Asn Ile Asn Gln Ile Ala Gly Ser Thr Tyr Tyr Val Asp Ser Val Gln
1               5                   10                  15
Gly

<210> SEQ ID NO 96
<211> LENGTH: 13
<212> TYPE: PRT
<213> ORGANISM: Homo sapiens

<400> SEQUENCE: 96

Gly Asp Tyr Tyr Gly Thr Thr Tyr Trp Tyr Phe Asp Val
1               5                   10

<210> SEQ ID NO 97
<211> LENGTH: 7
<212> TYPE: PRT
<213> ORGANISM: Homo sapiens

<400> SEQUENCE: 97

```
Gly Phe Thr Phe Ser Asp Tyr
1               5

<210> SEQ ID NO 98
<211> LENGTH: 6
<212> TYPE: PRT
<213> ORGANISM: Homo sapiens

<400> SEQUENCE: 98

Asn Gln Ile Ala Gly Ser
1               5

<210> SEQ ID NO 99
<211> LENGTH: 13
<212> TYPE: PRT
<213> ORGANISM: Homo sapiens

<400> SEQUENCE: 99

Gly Asp Tyr Tyr Gly Thr Thr Tyr Trp Tyr Phe Asp Val
1               5                   10

<210> SEQ ID NO 100
<211> LENGTH: 122
<212> TYPE: PRT
<213> ORGANISM: Homo sapiens

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Gln Ile Ala Gly Ser Thr Tyr Tyr Val Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
            100                 105                 110

Gly Gln Gly Thr Thr Val Thr Val Ser Ser
        115                 120

<210> SEQ ID NO 101
<211> LENGTH: 452
<212> TYPE: PRT
<213> ORGANISM: Homo sapiens

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Asn Ile Asn Gln Ile Ala Gly Ser Thr Tyr Tyr Val Asp Ser Val
    50                  55                  60

Gln Gly Arg Phe Thr Ile Ser Arg Asp Asn Ala Lys Asn Ser Leu Tyr
```

```
                65                  70                  75                  80
        Leu Gln Met Asn Ser Leu Arg Ala Glu Asp Thr Ala Val Tyr Tyr Cys
                        85                  90                  95

Ala Arg Gly Asp Tyr Tyr Gly Thr Thr Tyr Trp Tyr Phe Asp Val Trp
                        100                 105                 110

Gly Gln Gly Thr Thr Val Thr Val Ser Ser Ala Ser Thr Lys Gly Pro
                        115                 120                 125

Ser Val Phe Pro Leu Ala Pro Ser Ser Lys Ser Thr Ser Gly Gly Thr
                130                 135                 140

Ala Ala Leu Gly Cys Leu Val Lys Asp Tyr Phe Pro Glu Pro Val Thr
        145                 150                 155                 160

Val Ser Trp Asn Ser Gly Ala Leu Thr Ser Gly Val His Thr Phe Pro
                        165                 170                 175

Ala Val Leu Gln Ser Ser Gly Leu Tyr Ser Leu Ser Ser Val Val Thr
                        180                 185                 190

Val Pro Ser Ser Ser Leu Gly Thr Gln Thr Tyr Ile Cys Asn Val Asn
                        195                 200                 205

His Lys Pro Ser Asn Thr Lys Val Asp Lys Arg Val Glu Pro Lys Ser
                210                 215                 220

Cys Asp Lys Thr His Thr Cys Pro Pro Cys Pro Ala Pro Glu Leu Leu
        225                 230                 235                 240

Gly Gly Pro Ser Val Phe Leu Phe Pro Pro Lys Pro Lys Asp Thr Leu
                        245                 250                 255

Met Ile Ser Arg Thr Pro Glu Val Thr Cys Val Val Val Asp Val Ser
                        260                 265                 270

His Glu Asp Pro Glu Val Lys Phe Asn Trp Tyr Val Asp Gly Val Glu
                        275                 280                 285

Val His Asn Ala Lys Thr Lys Pro Arg Glu Glu Gln Tyr Asn Ser Thr
                290                 295                 300

Tyr Arg Val Val Ser Val Leu Thr Val Leu His Gln Asp Trp Leu Asn
        305                 310                 315                 320

Gly Lys Glu Tyr Lys Cys Lys Val Ser Asn Lys Ala Leu Pro Ala Pro
                        325                 330                 335

Ile Glu Lys Thr Ile Ser Lys Ala Lys Gly Gln Pro Arg Glu Pro Gln
                        340                 345                 350

Val Tyr Thr Leu Pro Pro Ser Arg Glu Glu Met Thr Lys Asn Gln Val
                        355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
        385                 390                 395                 400

Pro Val Leu Asp Ser Asp Gly Ser Phe Phe Leu Tyr Ser Lys Leu Thr
                        405                 410                 415

Val Asp Lys Ser Arg Trp Gln Gln Gly Asn Val Phe Ser Cys Ser Val
                        420                 425                 430

Met His Glu Ala Leu His Asn His Tyr Thr Gln Lys Ser Leu Ser Leu
                        435                 440                 445

Ser Pro Gly Lys
                450

<210> SEQ ID NO 102
<211> LENGTH: 1356
<212> TYPE: DNA
<213> ORGANISM: Homo sapiens
```

<400> SEQUENCE: 102

```
gaagtgcaat tggtggaaag cggcggaggc ctggtgcagc ctggcggctc tctgagactg     60
agctgtgccg ccagcggctt caccttcagc gactactaca tggcctgggt ccgacaggcc    120
cctggcaagg gcctggaatg ggtggccaat atcaaccaaa tcgccggcag cacctactac    180
gtggacagcg tgcaaggccg gttcaccatc agccgggaca cgccaagaa cagcctgtac     240
ctgcagatga acagcctgcg ggccgaggac accgccgtgt actactgcgc cagaggcgat    300
tactacggca ccacctactg gtacttcgac gtgtggggcc agggcaccac cgtgaccgtc    360
agctcagcta gcaccaaggg ccccagcgtg ttccccctgg cccccagcag caagagcacc    420
agcggcggca cagccgccct gggctgcctg gtgaaggact acttccccga gcccgtgacc    480
gtgtcctgga acagcggagc cctgacctcc ggcgtgcaca ccttcccgc cgtgctgcag    540
agcagcggcc tgtacagcct gtccagcgtg gtgacagtgc ccagcagcag cctgggcacc    600
cagacctaca tctgcaacgt gaaccacaag cccagcaaca ccaaggtgga caagagagtg    660
gagcccaaga gctgcgacaa gacccacacc tgcccccccct gcccagcccc agagctgctg    720
ggcggaccct ccgtgttcct gttccccccc aagcccaagg acaccctgat gatcagcagg    780
accccccgagg tgacctgcgt ggtggtggac gtgagccacg aggacccaga ggtgaagttc    840
aactggtacg tggacggcgt ggaggtgcac aacgccaaga ccaagcccag agaggagcag    900
tacaacagca cctacagggt ggtgtccgtg ctgaccgtgc tgcaccagga ctggctgaac    960
ggcaaggaat acaagtgcaa ggtctccaac aaggccctgc cagcccccat cgaaaagacc   1020
atcagcaagg ccaagggcca gccacgggag ccccaggtgt acaccctgcc ccctcccgg   1080
gaggagatga ccaagaacca ggtgtccctg acctgtctgg tgaagggctt ctacccagc   1140
gacatcgccg tggagtggga gagcaacggc cagcccgaga caactacaa gaccacccc   1200
ccagtgctgg acagcgacgg cagcttcttc ctgtacagca agctgaccgt ggacaagtcc   1260
aggtggcagc agggcaacgt gttcagctgc agcgtgatgc acgaggccct gcacaaccac   1320
tacacccaga gagcctgag cctgtccccc ggcaag                              1356
```

<210> SEQ ID NO 103
<211> LENGTH: 11
<212> TYPE: PRT
<213> ORGANISM: Homo sapiens

<400> SEQUENCE: 103

Arg Ala Ser Gln Ser Ile Ser Ser Tyr Leu Asn
1               5                   10

<210> SEQ ID NO 104
<211> LENGTH: 7
<212> TYPE: PRT
<213> ORGANISM: Homo sapiens

<400> SEQUENCE: 104

Tyr Thr Ser Arg Leu Gln Ser
1               5

<210> SEQ ID NO 105
<211> LENGTH: 8
<212> TYPE: PRT
<213> ORGANISM: Homo sapiens

<400> SEQUENCE: 105

-continued

Gln Gln Gly Arg Arg Leu Trp Ser
1               5

<210> SEQ ID NO 106
<211> LENGTH: 7
<212> TYPE: PRT
<213> ORGANISM: Homo sapiens

<400> SEQUENCE: 106

Ser Gln Ser Ile Ser Ser Tyr
1               5

<210> SEQ ID NO 107
<211> LENGTH: 3
<212> TYPE: PRT
<213> ORGANISM: Homo sapiens

<400> SEQUENCE: 107

Tyr Thr Ser
1

<210> SEQ ID NO 108
<211> LENGTH: 5
<212> TYPE: PRT
<213> ORGANISM: Homo sapiens

<400> SEQUENCE: 108

Gly Arg Arg Leu Trp
1               5

<210> SEQ ID NO 109
<211> LENGTH: 106
<212> TYPE: PRT
<213> ORGANISM: Homo sapiens

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Arg Leu Trp Ser
                85                  90                  95

Phe Gly Gly Gly Thr Lys Val Glu Ile Lys
            100                 105

<210> SEQ ID NO 110
<211> LENGTH: 213
<212> TYPE: PRT
<213> ORGANISM: Homo sapiens

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

-continued

```
Leu Asn Trp Tyr Gln Gln Lys Pro Gly Lys Ala Pro Lys Leu Leu Ile
         35                  40                  45
Tyr Tyr Thr Ser Arg Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Gly Arg Arg Leu Trp Ser
                 85                  90                  95
Phe Gly Gly Gly Thr Lys Val Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 111
<211> LENGTH: 639
<212> TYPE: DNA
<213> ORGANISM: Homo sapiens

<400> SEQUENCE: 111

```
gatatccaga tgacccagag ccccagcagc ctgagcgcca gcgtgggcga cagagtgacc    60
atcacctgtc gggccagcca gagcatcagc agctacctga actggtatca gcagaagccc   120
ggcaaggccc ccaagctgct gatctactac accagcggc tgcagagcgg cgtgcccagc   180
agatttctg gcagcggcag cggcaccgac ttcaccctga ccatcagcag cctgcagccc   240
gaggacttcg ccacctacta ctgccagcag ggccgccgcc tgtggtcctt cggcggaggc   300
accaaggtgg aaatcaagcg tacggtggcc gctcccagcg tgttcatctt cccccccagc   360
gacgagcagc tgaagagcgg caccgccagc gtggtgtgcc tgctgaacaa cttctacccc   420
cgggaggcca aggtgcagtg gaaggtggac aacgccctgc agagcggcaa cagccaggag   480
agcgtcaccg agcaggacag caaggactcc acctacagcc tgagcagcac cctgaccctg   540
agcaaggccg actacgagaa gcataaggtg tacgcctgcg aggtgaccca ccagggcctg   600
tccagccccg tgaccaagag cttcaacagg ggcgagtgc                          639
```

<210> SEQ ID NO 112
<211> LENGTH: 5
<212> TYPE: PRT
<213> ORGANISM: Homo sapiens

<400> SEQUENCE: 112

```
Asp Tyr Tyr Met Ala
1               5
```

<210> SEQ ID NO 113

```
<211> LENGTH: 17
<212> TYPE: PRT
<213> ORGANISM: Homo sapiens

<400> SEQUENCE: 113

Ser Ile Asn Gln Asn Thr Gly Ser Thr Tyr Tyr Leu Asp Ser Val Arg
1               5                   10                  15

Gly

<210> SEQ ID NO 114
<211> LENGTH: 13
<212> TYPE: PRT
<213> ORGANISM: Homo sapiens

<400> SEQUENCE: 114

Gly Asp Tyr Tyr Gly Thr Thr Tyr Trp Tyr Phe Asp Val
1               5                   10

<210> SEQ ID NO 115
<211> LENGTH: 7
<212> TYPE: PRT
<213> ORGANISM: Homo sapiens

<400> SEQUENCE: 115

Gly Phe Thr Phe Ser Asp Tyr
1               5

<210> SEQ ID NO 116
<211> LENGTH: 6
<212> TYPE: PRT
<213> ORGANISM: Homo sapiens

<400> SEQUENCE: 116

Asn Gln Asn Thr Gly Ser
1               5

<210> SEQ ID NO 117
<211> LENGTH: 13
<212> TYPE: PRT
<213> ORGANISM: Homo sapiens

<400> SEQUENCE: 117

Gly Asp Tyr Tyr Gly Thr Thr Tyr Trp Tyr Phe Asp Val
1               5                   10

<210> SEQ ID NO 118
<211> LENGTH: 122
<212> TYPE: PRT
<213> ORGANISM: Homo sapiens

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Gln Asn Thr Gly Ser Thr Tyr Tyr Leu Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

```
                        85                  90                  95

Ala Arg Gly Asp Tyr Tyr Gly Thr Thr Tyr Trp Tyr Phe Asp Val Trp
                   100                 105                 110

Gly Gln Gly Thr Thr Val Thr Val Ser Ser
            115                 120

<210> SEQ ID NO 119
<211> LENGTH: 452
<212> TYPE: PRT
<213> ORGANISM: Homo sapiens

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Gln Asn Thr Gly Ser Thr Tyr Tyr Leu Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Tyr Gly Thr Thr Tyr Trp Tyr Phe Asp Val Trp
                   100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Arg Val Glu Pro Lys Ser
        210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335
```

```
Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450
```

```
<210> SEQ ID NO 120
<211> LENGTH: 1356
<212> TYPE: DNA
<213> ORGANISM: Homo sapiens

<400> SEQUENCE: 120
gaagtgcaat tggtggaaag cggcggaggc ctggtgcagc ctggcggctc tctgagactg      60
agctgtgccg ccagcggctt caccttcagc gactactaca tggcctgggt ccgacaggcc     120
cctggcaagg gcctggaatg ggtggccagt atcaaccaaa acaccggcag cacctactac     180
ctggacagcg tgcgaggccg gttcaccatc agccgggaca cgccaagaa cagcctgtac      240 ctgcagatga acagcctgcg ggccgaggac accgccgtgt actactgcgc cagaggcgat     300
tactacggca ccacctactg gtacttcgac gtgtggggcc agggcaccac cgtgaccgtc     360
agctcagcta gcaccaaggg ccccagcgtg ttccccctgg cccccagcag caagagcacc     420
agcggcggca cagccgccct gggctgcctg gtgaaggact acttccccga gcccgtgacc     480
gtgtcctgga cagcggagc cctgaccctcc ggcgtgcaca ccttccccgc cgtgctgcag     540
agcagcggcc tgtacagcct gtccagcgtg gtgacagtgc ccagcagcag cctgggcacc     600
cagacctaca tctgcaacgt gaaccacaag cccagcaaca ccaaggtgga caagagagtg     660
gagcccaaga gctgcgacaa gacccacacc tgccccccct gcccagcccc agagctgctg     720
ggcggaccct ccgtgttcct gttcccccc aagcccaagg acaccctgat gatcagcagg     780 accccgagg tgacctgcgt ggtggtggac gtgagccacg aggacccaga ggtgaagttc     840
aactggtacg tggacggcgt ggaggtgcac aacgccaaga ccaagccag agaggagcag     900 tacaacagca cctacagggt ggtgtccgtg ctgaccgtgc tgcaccagga ctggctgaac     960
ggcaaggaat acaagtgcaa ggtctccaac aaggccctgc cagcccccat cgaaaagacc    1020
atcagcaagg ccaagggcca gccacgggag ccccaggtgt acaccctgcc ccctcccgg    1080 gaggagatga ccaagaacca ggtgtccctg acctgtctgg tgaagggctt ctaccccagc    1140
gacatcgccg tggagtggga gagcaacggc cagcccgaga caactacaa gaccaccccc    1200 ccagtgctgg acagcgacgg cagcttcttc ctgtacagca agctgaccgt ggacaagtcc    1260
aggtggcagc agggcaacgt gttcagctgc agcgtgatgc acgaggccct gcacaaccac    1320
tacacccaga agagcctgag cctgtccccc ggcaag                              1356
```

<210> SEQ ID NO 121
<211> LENGTH: 11
<212> TYPE: PRT
<213> ORGANISM: Homo sapiens

<400> SEQUENCE: 121

Arg Ala Ser Gln Ser Ile Ser Ser Tyr Leu Asn
1               5                   10

<210> SEQ ID NO 122
<211> LENGTH: 7
<212> TYPE: PRT
<213> ORGANISM: Homo sapiens

<400> SEQUENCE: 122

Tyr Thr Ser Arg Leu Gln Ser
1               5

<210> SEQ ID NO 123
<211> LENGTH: 8
<212> TYPE: PRT
<213> ORGANISM: Homo sapiens

<400> SEQUENCE: 123

Gln Gln Gly Arg Arg Leu Trp Ser
1               5

<210> SEQ ID NO 124
<211> LENGTH: 7
<212> TYPE: PRT
<213> ORGANISM: Homo sapiens

<400> SEQUENCE: 124

Ser Gln Ser Ile Ser Ser Tyr
1               5

<210> SEQ ID NO 125
<211> LENGTH: 3
<212> TYPE: PRT
<213> ORGANISM: Homo sapiens

<400> SEQUENCE: 125

Tyr Thr Ser
1

<210> SEQ ID NO 126
<211> LENGTH: 5
<212> TYPE: PRT
<213> ORGANISM: Homo sapiens

<400> SEQUENCE: 126

Gly Arg Arg Leu Trp
1               5

<210> SEQ ID NO 127
<211> LENGTH: 106
<212> TYPE: PRT
<213> ORGANISM: Homo sapiens

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

```
Leu Asn Trp Tyr Gln Gln Lys Pro Gly Lys Ala Pro Lys Leu Leu Ile
            35                  40                  45

Tyr Tyr Thr Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Arg Arg Leu Trp Ser
                 85                  90                  95

Phe Gly Gly Gly Thr Lys Val Glu Ile Lys
                100                 105

<210> SEQ ID NO 128
<211> LENGTH: 213
<212> TYPE: PRT
<213> ORGANISM: Homo sapiens

<400> SEQUENCE: 128

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Arg Arg Leu Trp Ser
                 85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 129
<211> LENGTH: 639
<212> TYPE: DNA
<213> ORGANISM: Homo sapiens

<400> SEQUENCE: 129
gatatccaga tgacccagag ccccagcagc ctgagcgcca gcgtgggcga cagagtgacc      60
atcacctgtc gggccagcca gagcatcagc agctacctga actggtatca gcagaagccc     120
ggcaaggccc ccaagctgct gatctactac accagccggc tgcagagcgg cgtgcccagc     180
```

```
agattttctg gcagcggcag cggcaccgac ttcaccctga ccatcagcag cctgcagccc    240
gaggacttcg ccacctacta ctgccagcag ggccgccgcc tgtggtcctt cggcggaggc    300
accaaggtgg aaatcaagcg tacggtggcc gctcccagcg tgttcatctt ccccccccagc   360 gacgagcagc tgaagagcgg caccgccagc gtggtgtgcc tgctgaacaa cttctacccc    420
cgggaggcca aggtgcagtg gaaggtggac aacgccctgc agagcggcaa cagccaggag    480
agcgtcaccg agcaggacag caaggactcc acctacagcc tgagcagcac cctgaccctg    540
agcaaggccg actacgagaa gcataaggtg tacgcctgcg aggtgaccca ccagggcctg    600
tccagccccg tgaccaagag cttcaacagg ggcgagtgc                          639
```

<210> SEQ ID NO 130
<211> LENGTH: 5
<212> TYPE: PRT
<213> ORGANISM: Homo sapiens

<400> SEQUENCE: 130

Ser Tyr Ala Ile Ser
1               5

<210> SEQ ID NO 131
<211> LENGTH: 17
<212> TYPE: PRT
<213> ORGANISM: Homo sapiens

<400> SEQUENCE: 131

Gly Ile Ile Pro Met Ser Gly Arg Thr Thr Tyr Ala Gln Lys Phe Gln
1               5                   10                  15

Gly

<210> SEQ ID NO 132
<211> LENGTH: 23
<212> TYPE: PRT
<213> ORGANISM: Homo sapiens

<400> SEQUENCE: 132

Asp Tyr Gly Pro Glu Ala Pro Asp Tyr Gly Gln Ser Thr Ser Tyr Phe
1               5                   10                  15

Trp Tyr Tyr Ala Phe Asp Pro
            20

<210> SEQ ID NO 133
<211> LENGTH: 7
<212> TYPE: PRT
<213> ORGANISM: Homo sapiens

<400> SEQUENCE: 133

Gly Gly Thr Phe Ser Ser Tyr
1               5

<210> SEQ ID NO 134
<211> LENGTH: 6
<212> TYPE: PRT
<213> ORGANISM: Homo sapiens

<400> SEQUENCE: 134

Ile Pro Met Ser Gly Arg
1               5

<210> SEQ ID NO 135
<211> LENGTH: 23

<212> TYPE: PRT
<213> ORGANISM: Homo sapiens

<400> SEQUENCE: 135

Asp Tyr Gly Pro Glu Ala Pro Asp Tyr Gly Gln Ser Thr Ser Tyr Phe
1               5                   10                  15

Trp Tyr Tyr Ala Phe Asp Pro
            20

<210> SEQ ID NO 136
<211> LENGTH: 132
<212> TYPE: PRT
<213> ORGANISM: Homo sapiens

<400> SEQUENCE: 136

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Met Ser Gly Arg Thr Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Gly Pro Glu Ala Pro Asp Tyr Gly Gln Ser Thr Ser
            100                 105                 110

Tyr Phe Trp Tyr Tyr Ala Phe Asp Pro Trp Gly Gln Gly Thr Leu Val
        115                 120                 125

Thr Val Ser Ser
    130

<210> SEQ ID NO 137
<211> LENGTH: 462
<212> TYPE: PRT
<213> ORGANISM: Homo sapiens

<400> SEQUENCE: 137

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Met Ser Gly Arg Thr Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Gly Pro Glu Ala Pro Asp Tyr Gly Gln Ser Thr Ser
            100                 105                 110

Tyr Phe Trp Tyr Tyr Ala Phe Asp Pro Trp Gly Gln Gly Thr Leu Val
        115                 120                 125

Thr Val Ser Ser Ala Ser Thr Lys Gly Pro Ser Val Phe Pro Leu Ala

```
                    130                 135                 140
Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Ile Cys Asn Val Asn His Lys Pro Ser Asn Thr
    210                 215                 220

Lys Val Asp Lys Arg Val Glu Pro Lys Ser Cys Asp Lys Thr His Thr
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
                340                 345                 350

Lys Ala Lys Gly Gln Pro Arg Glu Pro Gln Val Tyr Thr Leu Pro Pro
            355                 360                 365

Ser Arg Glu Glu Met Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
        450                 455                 460

<210> SEQ ID NO 138
<211> LENGTH: 1386
<212> TYPE: DNA
<213> ORGANISM: Homo sapiens

<400> SEQUENCE: 138
caggtgcagc tggtgcagtc aggcgccgaa gtgaagaaac ccggctctag cgtgaaagtc     60
agctgtaaag ctagtggggg caccttctct agctacgcta ttagctgggt cagacaggcc    120
ccaggtcaag gcttggagtg gatgggcgga attatcccta tgagcggtag aactacctac    180
gctcagaaat ttcagggtag agtgactatc accgccgacg agtctactag caccgcctat    240
atggaactga gttctctgag gtcagaggac accgccgtct actactgcgc tagagactac    300
```

-continued

```
ggccccgagg cccccgacta cggtcaatca actagctact tctggtacta cgccttcgac    360
ccttggggtc aaggcaccct ggtcaccgtg tcttcagcta gcactaaggg cccaagtgtg    420
tttcccctgg cccccagcag caagtctact tccggcggaa ctgctgccct gggttgcctg    480
gtgaaggact acttccccga gcccgtgaca gtgtcctgga actctggggc tctgacttcc    540
ggcgtgcaca ccttccccgc cgtgctgcag agcagcggcc tgtacagcct gagcagcgtg    600
gtgacagtgc cctccagctc tctgggaacc cagacctata tctgcaacgt gaaccacaag    660
cccagcaaca ccaaggtgga caagagagtg gagcccaaga gctgcgacaa gacccacacc    720
tgccccccct gcccagctcc agaactgctg ggagggcctt ccgtgttcct gttccccccc    780
aagcccaagg acaccctgat gatcagcagg accccgagg tgacctgcgt ggtggtggac    840
gtgtcccacg aggacccaga ggtgaagttc aactggtacg tggacggcgt ggaggtgcac    900
aacgccaaga ccaagcccag agaggagcag tacaacagca cctacagggt ggtgtccgtg    960
ctgaccgtgc tgcaccagga ctggctgaac ggcaaagaat acaagtgcaa agtctccaac   1020
aaggccctgc cagccccaat cgaaaagaca atcagcaagg ccaagggcca gccacgggag   1080
ccccaggtgt acaccctgcc ccccagccgg gaggagatga ccaagaacca ggtgtccctg   1140
acctgtctgg tgaagggctt ctaccccagc gatatcgccg tggagtggga gagcaacggc   1200
cagcccgaga caactacaa gaccacccc ccagtgctgg acagcgacgg cagcttcttc   1260
ctgtacagca agctgaccgt ggacaagtcc aggtggcagc agggcaacgt gttcagctgc   1320
agcgtgatgc acgaggccct gcacaaccac tacacccaga gtccctgag cctgagcccc   1380 ggcaag                                                              1386
```

<210> SEQ ID NO 139
<211> LENGTH: 11
<212> TYPE: PRT
<213> ORGANISM: Homo sapiens

<400> SEQUENCE: 139

Ser Gly Asp Asn Ile Pro Ser Tyr Phe Val His
1               5                   10

<210> SEQ ID NO 140
<211> LENGTH: 7
<212> TYPE: PRT
<213> ORGANISM: Homo sapiens

<400> SEQUENCE: 140

Asp Asp Asn Asp Arg Pro Ser
1               5

<210> SEQ ID NO 141
<211> LENGTH: 9
<212> TYPE: PRT
<213> ORGANISM: Homo sapiens

<400> SEQUENCE: 141

Ser Ser Trp Asp Gln Asp Thr Val Val
1               5

<210> SEQ ID NO 142
<211> LENGTH: 7
<212> TYPE: PRT
<213> ORGANISM: Homo sapiens

<400> SEQUENCE: 142

Asp Asn Ile Pro Ser Tyr Phe
1               5

<210> SEQ ID NO 143
<211> LENGTH: 3
<212> TYPE: PRT
<213> ORGANISM: Homo sapiens

<400> SEQUENCE: 143

Asp Asp Asn
1

<210> SEQ ID NO 144
<211> LENGTH: 6
<212> TYPE: PRT
<213> ORGANISM: Homo sapiens

<400> SEQUENCE: 144

Trp Asp Gln Asp Thr Val
1               5

<210> SEQ ID NO 145
<211> LENGTH: 106
<212> TYPE: PRT
<213> ORGANISM: Homo sapiens

<400> SEQUENCE: 145

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Pro Ser Tyr Phe Val
            20                  25                  30

His Trp Tyr Gln Gln Lys Pro Gly Gln Ala Pro Val Leu Val Ile Tyr
        35                  40                  45

Asp Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Trp Asp Gln Asp Thr Val Val
                85                  90                  95

Phe Gly Gly Gly Thr Lys Leu Thr Val Leu
            100                 105

<210> SEQ ID NO 146
<211> LENGTH: 212
<212> TYPE: PRT
<213> ORGANISM: Homo sapiens

<400> SEQUENCE: 146

Asp Ile Glu Leu Thr Gln Pro Pro Ser Val Ser Val Ser Pro Gly Gln
1               5                   10                  15

Thr Ala Ser Ile Thr Cys Ser Gly Asp Asn Ile Pro Ser Tyr Phe Val
            20                  25                  30

His Trp Tyr Gln Gln Lys Pro Gly Gln Ala Pro Val Leu Val Ile Tyr
        35                  40                  45

Asp Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Trp Asp Gln Asp Thr Val Val

```
                     85                  90                  95
Phe Gly Gly Gly Thr Lys Leu Thr Val Leu Gly Gln Pro Lys Ala Ala
                100                 105                 110

Pro Ser Val Thr Leu Phe Pro Pro Ser Ser Glu Glu Leu Gln Ala Asn
            115                 120                 125

Lys Ala Thr Leu Val Cys Leu Ile Ser Asp Phe Tyr Pro Gly Ala Val
        130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
                180                 185                 190

Cys Gln Val Thr His Glu Gly Ser Thr Val Glu Lys Thr Val Ala Pro
            195                 200                 205

Thr Glu Cys Ser
        210

<210> SEQ ID NO 147
<211> LENGTH: 636
<212> TYPE: DNA
<213> ORGANISM: Homo sapiens

<400> SEQUENCE: 147
gatatcgagc tgactcagcc ccctagcgtc agcgtcagcc ctggtcaaac cgcctctatc        60
acctgtagcg gcgataatat ccctagctac ttcgtgcact ggtatcagca gaagcccggt       120
caagcccccg tgctggtgat ctacgacgat aacgatagac tagcggaat ccccgagcgg        180 tttagcggct ctaatagcgg taacaccgct accctgacta ttagcggcac tcaggccgag       240
gacgaggccg actactactg ctctagctgg gatcaggaca ccgtggtgtt cggcggaggc       300
actaagctga ccgtgctggg tcaacctaag gctgccccca gcgtgaccct gttccccccc       360
agcagcgagg agctgcaggc caacaaggcc accctggtgt gcctgatcag cgacttctac       420
ccaggcgccg tgaccgtggc ctggaaggcc gacagcagcc ccgtgaaggc cggcgtggag       480
accaccaccc ccagcaagca gagcaacaac aagtacgccg ccagcagcta cctgagcctg       540
accccggagc agtggaagag ccacaggtcc tacagctgcc aggtgaccca cgagggcagc       600
accgtggaaa agaccgtggc cccaaccgag tgcagc                                 636

<210> SEQ ID NO 148
<211> LENGTH: 5
<212> TYPE: PRT
<213> ORGANISM: Homo sapiens

<400> SEQUENCE: 148

Ser Tyr Ala Ile Ser
1               5

<210> SEQ ID NO 149
<211> LENGTH: 17
<212> TYPE: PRT
<213> ORGANISM: Homo sapiens

<400> SEQUENCE: 149

Thr Ile Gly Pro Phe Glu Gly Gln Pro Arg Tyr Ala Gln Lys Phe Gln
1               5                   10                  15

Gly
```

<210> SEQ ID NO 150
<211> LENGTH: 9
<212> TYPE: PRT
<213> ORGANISM: Homo sapiens

<400> SEQUENCE: 150

Gly Gly Tyr Ile Ser Asp Phe Asp Val
1               5

<210> SEQ ID NO 151
<211> LENGTH: 7
<212> TYPE: PRT
<213> ORGANISM: Homo sapiens

<400> SEQUENCE: 151

Gly Gly Thr Phe Ser Ser Tyr
1               5

<210> SEQ ID NO 152
<211> LENGTH: 6
<212> TYPE: PRT
<213> ORGANISM: Homo sapiens

<400> SEQUENCE: 152

Gly Pro Phe Glu Gly Gln
1               5

<210> SEQ ID NO 153
<211> LENGTH: 8
<212> TYPE: PRT
<213> ORGANISM: Homo sapiens

<400> SEQUENCE: 153

Gly Tyr Ile Ser Asp Phe Asp Val
1               5

<210> SEQ ID NO 154
<211> LENGTH: 118
<212> TYPE: PRT
<213> ORGANISM: Homo sapiens

<400> SEQUENCE: 154

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Thr Ile Gly Pro Phe Glu Gly Gln Pro Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ile Ser Asp Phe Asp Val Trp Gly Gln Gly Thr
            100                 105                 110

Leu Val Thr Val Ser Ser
        115

<210> SEQ ID NO 155

```
<211> LENGTH: 448
<212> TYPE: PRT
<213> ORGANISM: Homo sapiens

<400> SEQUENCE: 155

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Thr Ile Gly Pro Phe Glu Gly Gln Pro Arg Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ile Ser Asp Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
```

```
                385               390               395               400
Ser Asp Gly Ser Phe Phe Leu Tyr Ser Lys Leu Thr Val Asp Lys Ser
                    405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```

<210> SEQ ID NO 156
<211> LENGTH: 1344
<212> TYPE: DNA
<213> ORGANISM: Homo sapiens

<400> SEQUENCE: 156

```
caggtgcaat tggtgcagag cggtgccgaa gtgaaaaaac cgggcagcag cgtgaaagtt      60
agctgcaaag catccggagg gacgtttagc agctatgcga ttagctgggt gcgccaggcc     120
ccgggccagg gcctcgagtg gatgggcact atcggtccgt tcgaaggcca gccgcgttac     180
gcccagaaat tcagggccgg ggtgaccatt accgccgatg aaagcaccag caccgcctat     240
atggaactga gcagcctgcg cagcgaagat acggccgtgt attattgcgc gcgtggtggt     300
tacatctctg acttcgatgt ttggggccaa ggcaccctgg tgactgttag ctcagcctcc     360
accaagggtc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcacccca gacctacatc     600
tgcaacgtga atcacaagcc cagcaacacc aaggtggaca gagagttga gcccaaatct      660
tgtgacaaaa ctcacacatg cccaccgtgc ccagcacctg aactcctggg gggaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
taccgggtgg tcagcgtcct caccgtcctg caccaggact ggctgaatgg caaggagtac     960
aagtgcaagg tctccaacaa agccctccca gcccccatcg agaaaaccat ctccaaagcc    1020
aaagggcagc cccgagaacc acaggtgtac accctgcccc catcccggga ggagatgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaa                                           1344
```

<210> SEQ ID NO 157
<211> LENGTH: 11
<212> TYPE: PRT
<213> ORGANISM: Homo sapiens

<400> SEQUENCE: 157

```
Arg Ala Ser Gln Ser Ile Ser Asn Tyr Leu Ala
1               5                   10
```

<210> SEQ ID NO 158
<211> LENGTH: 7

```
<212> TYPE: PRT
<213> ORGANISM: Homo sapiens

<400> SEQUENCE: 158

Asp Ala Ser Ser Leu Gln Ser
1               5

<210> SEQ ID NO 159
<211> LENGTH: 8
<212> TYPE: PRT
<213> ORGANISM: Homo sapiens

<400> SEQUENCE: 159

Gln Gln Tyr Tyr Glu Ser Ile Thr
1               5

<210> SEQ ID NO 160
<211> LENGTH: 11
<212> TYPE: PRT
<213> ORGANISM: Homo sapiens

<400> SEQUENCE: 160

Arg Ala Ser Gln Ser Ile Ser Asn Tyr Leu Ala
1               5                   10

<210> SEQ ID NO 161
<211> LENGTH: 7
<212> TYPE: PRT
<213> ORGANISM: Homo sapiens

<400> SEQUENCE: 161

Asp Ala Ser Ser Leu Gln Ser
1               5

<210> SEQ ID NO 162
<211> LENGTH: 8
<212> TYPE: PRT
<213> ORGANISM: Homo sapiens

<400> SEQUENCE: 162

Gln Gln Tyr Tyr Glu Ser Ile Thr
1               5

<210> SEQ ID NO 163
<211> LENGTH: 108
<212> TYPE: PRT
<213> ORGANISM: Homo sapiens

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Glu Ser Ile
                85                  90                  95

Thr Phe Gly Gln Gly Thr Lys Val Glu Ile Lys Arg
```

100        105

<210> SEQ ID NO 164
<211> LENGTH: 214
<212> TYPE: PRT
<213> ORGANISM: Homo sapiens

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Glu Ser Ile
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 165
<211> LENGTH: 642
<212> TYPE: DNA
<213> ORGANISM: Homo sapiens

<400> SEQUENCE: 165
gatatccaga tgacccagag cccgagcagc ctgagcgcca gcgtgggcga tcgcgtgacc        60
attacctgca gagccagcca gtctatttct aactacctgg cttggtacca gcagaaaccg       120
ggcaaagcgc cgaaactatt aatctacgac gcttcttctc tgcaaagcgg cgtgccgagc       180
cgctttagcg gcagcggatc cggcaccgat ttcaccctga ccattagctc tctgcaaccg       240
gaagactttg cgacctatta ttgccagcag tactactacg aatctatcac ctttggccag       300
ggcacgaaag ttgaaattaa acgtacggtg gccgctccca gcgtgttcat cttcccccc       360 agcgacgagc agctgaagag cggcaccgcc agcgtggtgt gcctgctgaa caacttctac       420
ccccgggagg ccaaggtgca gtggaaggtg gacaacgccc tgcagagcgg caacagccag       480
gaaagcgtca ccgagcagga cagcaaggac tccacctaca gcctgagcag caccctgacc       540
ctgagcaagg ccgactacga aaagcacaag gtgtacgcct gcgaggtgac ccaccagggc       600
ctgtccagcc ccgtgaccaa gagcttcaac cggggcgagt gt    642

<210> SEQ ID NO 166
<211> LENGTH: 10
<212> TYPE: PRT
<213> ORGANISM: Homo sapiens

<400> SEQUENCE: 166

Gly Phe Thr Phe Ser Asp Tyr Tyr Met Ala
1               5                   10

<210> SEQ ID NO 167
<211> LENGTH: 14
<212> TYPE: PRT
<213> ORGANISM: Homo sapiens

<400> SEQUENCE: 167

Asn Ile Asn Tyr Asp Gly Ser Ser Thr Tyr Tyr Leu Asp Ser
1               5                   10

<210> SEQ ID NO 168
<211> LENGTH: 13
<212> TYPE: PRT
<213> ORGANISM: Homo sapiens

<400> SEQUENCE: 168

Gly Asp Tyr Tyr Gly Thr Thr Tyr Trp Tyr Phe Asp Val
1               5                   10

<210> SEQ ID NO 169
<211> LENGTH: 11
<212> TYPE: PRT
<213> ORGANISM: Homo sapiens

<400> SEQUENCE: 169

Arg Ala Ser Gln Asp Ile Ser Asn Tyr Leu Asn
1               5                   10

<210> SEQ ID NO 170
<211> LENGTH: 7
<212> TYPE: PRT
<213> ORGANISM: Homo sapiens

<400> SEQUENCE: 170

Tyr Thr Ser Arg Leu Gln Ser
1               5

<210> SEQ ID NO 171
<211> LENGTH: 8
<212> TYPE: PRT
<213> ORGANISM: Homo sapiens

<400> SEQUENCE: 171

Gln Gln Gly Lys Lys Leu Trp Ser
1               5

<210> SEQ ID NO 172
<211> LENGTH: 503
<212> TYPE: PRT
<213> ORGANISM: Homo sapiens

<400> SEQUENCE: 172

Gln Pro Ser Val Ser Pro Gly Glu Pro Ser Pro Ser Ile His Pro
1               5                   10                  15

```
Gly Lys Ser Asp Leu Ile Val Arg Val Gly Asp Glu Ile Arg Leu Leu
             20                  25                  30

Cys Thr Asp Pro Gly Phe Val Lys Trp Thr Phe Glu Ile Leu Asp Glu
             35                  40                  45

Thr Asn Glu Asn Lys Gln Asn Glu Trp Ile Thr Glu Lys Ala Glu Ala
             50                  55                  60

Thr Asn Thr Gly Lys Tyr Thr Cys Thr Asn Lys His Gly Leu Ser Asn
 65                  70                  75                  80

Ser Ile Tyr Val Phe Val Arg Asp Pro Ala Lys Leu Phe Leu Val Asp
             85                  90                  95

Arg Ser Leu Tyr Gly Lys Glu Asp Asn Asp Thr Leu Val Arg Cys Pro
             100                 105                 110

Leu Thr Asp Pro Glu Val Thr Asn Tyr Ser Leu Lys Gly Cys Gln Gly
             115                 120                 125

Lys Pro Leu Pro Lys Asp Leu Arg Phe Ile Pro Asp Pro Lys Ala Gly
 130                 135                 140

Ile Met Ile Lys Ser Val Lys Arg Ala Tyr His Arg Leu Cys Leu His
145                  150                 155                 160

Cys Ser Val Asp Gln Glu Gly Lys Ser Val Leu Ser Glu Lys Phe Ile
             165                 170                 175

Leu Lys Val Arg Pro Ala Phe Lys Ala Val Pro Val Val Ser Val Ser
             180                 185                 190

Lys Ala Ser Tyr Leu Leu Arg Glu Gly Glu Glu Phe Thr Val Thr Cys
             195                 200                 205

Thr Ile Lys Asp Val Ser Ser Ser Val Tyr Ser Thr Trp Lys Arg Glu
             210                 215                 220

Asn Ser Gln Thr Lys Leu Gln Glu Lys Tyr Asn Ser Trp His His Gly
225                  230                 235                 240

Asp Phe Asn Tyr Glu Arg Gln Ala Thr Leu Thr Ile Ser Ser Ala Arg
             245                 250                 255

Val Asn Asp Ser Gly Val Phe Met Cys Tyr Ala Asn Asn Thr Phe Gly
             260                 265                 270

Ser Ala Asn Val Thr Thr Thr Leu Glu Val Val Asp Lys Gly Phe Ile
             275                 280                 285

Asn Ile Phe Pro Met Ile Asn Thr Thr Val Phe Val Asn Asp Gly Glu
             290                 295                 300

Asn Val Asp Leu Ile Val Glu Tyr Glu Ala Phe Pro Lys Pro Glu His
305                  310                 315                 320

Gln Gln Trp Ile Tyr Met Asn Arg Thr Phe Thr Asp Lys Trp Glu Asp
             325                 330                 335

Tyr Pro Lys Ser Glu Asn Glu Ser Asn Ile Arg Tyr Val Ser Glu Leu
             340                 345                 350

His Leu Thr Arg Leu Lys Gly Thr Glu Gly Gly Thr Tyr Thr Phe Leu
             355                 360                 365

Val Ser Asn Ser Asp Val Asn Ala Ala Ile Ala Phe Asn Val Tyr Val
             370                 375                 380

Asn Thr Lys Pro Glu Ile Leu Thr Tyr Asp Arg Leu Val Asn Gly Met
385                  390                 395                 400

Leu Gln Cys Val Ala Ala Gly Phe Pro Glu Pro Thr Ile Asp Trp Tyr
             405                 410                 415

Phe Cys Pro Gly Thr Glu Gln Arg Cys Ser Ala Ser Val Leu Pro Val
             420                 425                 430
```

-continued

```
Asp Val Gln Thr Leu Asn Ser Gly Pro Pro Phe Lys Leu Val
        435                 440                 445

Val Gln Ser Ser Ile Asp Ser Ser Ala Phe Lys His Asn Gly Thr Val
450                 455                 460

Glu Cys Lys Ala Tyr Asn Asp Val Gly Lys Thr Ser Ala Tyr Phe Asn
465                 470                 475                 480

Phe Ala Phe Lys Glu Gln Ile His Pro His Thr Leu Phe Thr Pro Arg
                485                 490                 495

Ser His His His His His His
            500

<210> SEQ ID NO 173
<211> LENGTH: 294
<212> TYPE: PRT
<213> ORGANISM: Homo sapiens

<400> SEQUENCE: 173

Gln Pro Ser Val Ser Pro Gly Glu Pro Ser Pro Ser Ile His Pro
1               5                   10                  15

Gly Lys Ser Asp Leu Ile Val Arg Val Gly Asp Glu Ile Arg Leu Leu
            20                  25                  30

Cys Thr Asp Pro Gly Phe Val Lys Trp Thr Phe Glu Ile Leu Asp Glu
        35                  40                  45

Thr Asn Glu Asn Lys Gln Asn Glu Trp Ile Thr Glu Lys Ala Glu Ala
50                  55                  60

Thr Asn Thr Gly Lys Tyr Thr Cys Thr Asn Lys His Gly Leu Ser Asn
65                  70                  75                  80

Ser Ile Tyr Val Phe Val Arg Asp Pro Ala Lys Leu Phe Leu Val Asp
                85                  90                  95

Arg Ser Leu Tyr Gly Lys Glu Asp Asn Asp Thr Leu Val Arg Cys Pro
            100                 105                 110

Leu Thr Asp Pro Glu Val Thr Asn Tyr Ser Leu Lys Gly Cys Gln Gly
        115                 120                 125

Lys Pro Leu Pro Lys Asp Leu Arg Phe Ile Pro Asp Pro Lys Ala Gly
130                 135                 140

Ile Met Ile Lys Ser Val Lys Arg Ala Tyr His Arg Leu Cys Leu His
145                 150                 155                 160

Cys Ser Val Asp Gln Glu Gly Lys Ser Val Leu Ser Glu Lys Phe Ile
                165                 170                 175

Leu Lys Val Arg Pro Ala Phe Lys Ala Val Pro Val Val Ser Val Ser
            180                 185                 190

Lys Ala Ser Tyr Leu Leu Arg Glu Gly Glu Glu Phe Thr Val Thr Cys
        195                 200                 205

Thr Ile Lys Asp Val Ser Ser Ser Val Tyr Ser Thr Trp Lys Arg Glu
210                 215                 220

Asn Ser Gln Thr Lys Leu Gln Glu Lys Tyr Asn Ser Trp His His Gly
225                 230                 235                 240

Asp Phe Asn Tyr Glu Arg Gln Ala Thr Leu Thr Ile Ser Ser Ala Arg
                245                 250                 255

Val Asn Asp Ser Gly Val Phe Met Cys Tyr Ala Asn Asn Thr Phe Gly
            260                 265                 270

Ser Ala Asn Val Thr Thr Thr Leu Glu Val Val Asp Lys Gly Arg Ser
        275                 280                 285

His His His His His His
    290
```

<210> SEQ ID NO 174
<211> LENGTH: 222
<212> TYPE: PRT
<213> ORGANISM: Homo sapiens

<400> SEQUENCE: 174

Gly Phe Ile Asn Ile Phe Pro Met Ile Asn Thr Thr Val Phe Val Asn
1               5                   10                  15

Asp Gly Glu Asn Val Asp Leu Ile Val Glu Tyr Glu Ala Phe Pro Lys
            20                  25                  30

Pro Glu His Gln Gln Trp Ile Tyr Met Asn Arg Thr Phe Thr Asp Lys
        35                  40                  45

Trp Glu Asp Tyr Pro Lys Ser Glu Asn Glu Ser Asn Ile Arg Tyr Val
50                  55                  60

Ser Glu Leu His Leu Thr Arg Leu Lys Gly Thr Glu Gly Gly Thr Tyr
65                  70                  75                  80

Thr Phe Leu Val Ser Asn Ser Asp Val Asn Ala Ala Ile Ala Phe Asn
                85                  90                  95

Val Tyr Val Asn Thr Lys Pro Glu Ile Leu Thr Tyr Asp Arg Leu Val
            100                 105                 110

Asn Gly Met Leu Gln Cys Val Ala Ala Gly Phe Pro Glu Pro Thr Ile
        115                 120                 125

Asp Trp Tyr Phe Cys Pro Gly Thr Glu Gln Arg Cys Ser Ala Ser Val
130                 135                 140

Leu Pro Val Asp Val Gln Thr Leu Asn Ser Ser Gly Pro Pro Phe Gly
145                 150                 155                 160

Lys Leu Val Val Gln Ser Ser Ile Asp Ser Ser Ala Phe Lys His Asn
                165                 170                 175

Gly Thr Val Glu Cys Lys Ala Tyr Asn Asp Val Gly Lys Thr Ser Ala
            180                 185                 190

Tyr Phe Asn Phe Ala Phe Lys Gly Asn Asn Lys Glu Gln Ile His Pro
        195                 200                 205

His Thr Leu Phe Thr Pro Arg Ser His His His His His
    210                 215                 220

<210> SEQ ID NO 175
<211> LENGTH: 741
<212> TYPE: PRT
<213> ORGANISM: Homo sapiens

<400> SEQUENCE: 175

Ser Gln Pro Ser Ala Ser Pro Gly Glu Pro Ser Pro Ser Ile His
1               5                   10                  15

Pro Ala Gln Ser Glu Leu Ile Val Glu Ala Gly Asp Thr Leu Ser Leu
            20                  25                  30

Thr Cys Ile Asp Pro Asp Phe Val Arg Trp Thr Phe Lys Thr Tyr Phe
        35                  40                  45

Asn Glu Met Val Glu Asn Lys Lys Asn Glu Trp Ile Gln Glu Lys Ala
50                  55                  60

Glu Ala Thr Arg Thr Gly Thr Tyr Thr Cys Ser Asn Ser Asn Gly Leu
65                  70                  75                  80

Thr Ser Ser Ile Tyr Val Phe Val Arg Asp Pro Ala Lys Leu Phe Leu
                85                  90                  95

Val Gly Leu Pro Leu Phe Gly Lys Glu Asp Ser Asp Ala Leu Val Arg
            100                 105                 110

```
Cys Pro Leu Thr Asp Pro Gln Val Ser Asn Tyr Ser Leu Ile Glu Cys
            115                 120                 125

Asp Gly Lys Ser Leu Pro Thr Asp Leu Thr Phe Val Pro Asn Pro Lys
130                 135                 140

Ala Gly Ile Thr Ile Lys Asn Val Lys Arg Ala Tyr His Arg Leu Cys
145                 150                 155                 160

Val Arg Cys Ala Ala Gln Arg Asp Gly Thr Trp Leu His Ser Asp Lys
                165                 170                 175

Phe Thr Leu Lys Val Arg Ala Ala Ile Lys Ala Ile Pro Val Val Ser
            180                 185                 190

Val Pro Glu Thr Ser His Leu Leu Lys Lys Gly Asp Thr Phe Thr Val
            195                 200                 205

Val Cys Thr Ile Lys Asp Val Ser Thr Ser Val Asn Ser Met Trp Leu
            210                 215                 220

Lys Met Asn Pro Gln Pro Gln His Ile Ala Gln Val Lys His Asn Ser
225                 230                 235                 240

Trp His Arg Gly Asp Phe Asn Tyr Glu Arg Gln Glu Thr Leu Thr Ile
                245                 250                 255

Ser Ser Ala Arg Val Asp Asp Ser Gly Val Phe Met Cys Tyr Ala Asn
            260                 265                 270

Asn Thr Phe Gly Ser Ala Asn Val Thr Thr Thr Leu Lys Val Val Glu
            275                 280                 285

Lys Gly Phe Ile Asn Ile Ser Pro Val Lys Asn Thr Thr Val Phe Val
290                 295                 300

Thr Asp Gly Glu Asn Val Asp Leu Val Val Glu Tyr Glu Ala Tyr Pro
305                 310                 315                 320

Lys Pro Glu His Gln Gln Trp Ile Tyr Met Asn Arg Thr Ser Ala Asn
                325                 330                 335

Lys Gly Lys Asp Tyr Val Lys Ser Asp Asn Lys Ser Asn Ile Arg Tyr
            340                 345                 350

Val Asn Gln Leu Arg Leu Thr Arg Leu Lys Gly Thr Glu Gly Gly Thr
            355                 360                 365

Tyr Thr Phe Leu Val Ser Asn Ser Asp Ala Ser Ala Ser Val Thr Phe
            370                 375                 380

Asn Val Tyr Val Asn Thr Lys Pro Glu Ile Leu Thr Tyr Asp Arg Leu
385                 390                 395                 400

Ile Asn Gly Met Leu Gln Cys Val Ala Glu Gly Phe Pro Glu Pro Thr
                405                 410                 415

Ile Asp Trp Tyr Phe Cys Thr Gly Ala Glu Gln Arg Cys Thr Thr Pro
            420                 425                 430

Val Ser Pro Val Asp Val Gln Val Gln Asn Val Ser Val Ser Pro Phe
            435                 440                 445

Gly Lys Leu Val Val Gln Ser Ser Ile Asp Ser Ser Val Phe Arg His
450                 455                 460

Asn Gly Thr Val Glu Cys Lys Ala Ser Asn Asp Val Gly Lys Ser Ser
465                 470                 475                 480

Ala Phe Phe Asn Phe Ala Phe Lys Glu Gln Ile Gln Ala His Thr Leu
                485                 490                 495

Phe Thr Pro Leu Glu Val Leu Phe Gln Gly Pro Arg Ser Pro Arg Gly
            500                 505                 510

Pro Thr Ile Lys Pro Cys Pro Pro Cys Lys Cys Pro Ala Pro Asn Leu
            515                 520                 525
```

```
Leu Gly Gly Pro Ser Val Phe Ile Pro Pro Lys Ile Lys Asp Val
            530                 535                 540
Leu Met Ile Ser Leu Ser Pro Ile Val Thr Cys Val Val Asp Val
545                 550                 555                 560
Ser Glu Asp Asp Pro Asp Val Gln Ile Ser Trp Phe Val Asn Asn Val
                565                 570                 575
Glu Val His Thr Ala Gln Thr Gln Thr His Arg Glu Asp Tyr Asn Ser
            580                 585                 590
Thr Leu Arg Val Val Ser Ala Leu Pro Ile Gln His Gln Asp Trp Met
            595                 600                 605
Ser Gly Lys Glu Phe Lys Cys Lys Val Asn Asn Lys Asp Leu Pro Ala
            610                 615                 620
Pro Ile Glu Arg Thr Ile Ser Lys Pro Lys Gly Ser Val Arg Ala Pro
625                 630                 635                 640
Gln Val Tyr Val Leu Pro Pro Glu Glu Glu Met Thr Lys Lys Gln
                645                 650                 655
Val Thr Leu Thr Cys Met Val Thr Asp Phe Met Pro Glu Asp Ile Tyr
                660                 665                 670
Val Glu Trp Thr Asn Asn Gly Lys Thr Glu Leu Asn Tyr Lys Asn Thr
            675                 680                 685
Glu Pro Val Leu Asp Ser Asp Gly Ser Tyr Phe Met Tyr Ser Lys Leu
            690                 695                 700
Arg Val Glu Lys Lys Asn Trp Val Glu Arg Asn Ser Tyr Ser Cys Ser
705                 710                 715                 720
Val Val His Glu Gly Leu His Asn His His Thr Thr Lys Ser Phe Ser
                725                 730                 735
Arg Thr Pro Gly Lys
                740

<210> SEQ ID NO 176
<211> LENGTH: 741
<212> TYPE: PRT
<213> ORGANISM: Homo sapiens

<400> SEQUENCE: 176

Ser Gln Pro Ser Ala Ser Pro Gly Glu Pro Ser Pro Ser Ile Gln
1               5                   10                  15
Pro Ala Gln Ser Glu Leu Ile Val Glu Ala Gly Asp Thr Ile Arg Leu
                20                  25                  30
Thr Cys Thr Asp Pro Ala Phe Val Lys Trp Thr Phe Glu Ile Leu Asp
            35                  40                  45
Val Arg Ile Glu Asn Lys Gln Ser Glu Trp Ile Arg Glu Lys Ala Glu
50                  55                  60
Ala Thr His Thr Gly Lys Tyr Thr Cys Val Gly Ser Gly Leu Arg
65                  70                  75                  80
Ser Ser Ile Tyr Val Phe Val Arg Asp Pro Ala Val Leu Phe Leu Val
                85                  90                  95
Gly Leu Pro Leu Phe Gly Lys Glu Asp Asn Asp Ala Leu Val Arg Cys
                100                 105                 110
Pro Leu Thr Asp Pro Gln Val Ser Asn Tyr Ser Leu Ile Glu Cys Asp
            115                 120                 125
Gly Lys Ser Leu Pro Thr Asp Leu Lys Phe Val Pro Asn Pro Lys Ala
            130                 135                 140
Gly Ile Thr Ile Lys Asn Val Lys Arg Ala Tyr His Arg Leu Cys Ile
145                 150                 155                 160
```

```
Arg Cys Ala Ala Gln Arg Glu Gly Lys Trp Met Arg Ser Asp Lys Phe
                165                 170                 175
Thr Leu Lys Val Arg Ala Ala Ile Lys Ala Ile Pro Val Val Ser Val
                180                 185                 190
Pro Glu Thr Ser His Leu Leu Lys Glu Gly Asp Thr Phe Thr Val Ile
                195                 200                 205
Cys Thr Ile Lys Asp Val Ser Thr Ser Val Asp Ser Met Trp Ile Lys
            210                 215                 220
Leu Asn Pro Gln Pro Gln Ser Lys Ala Gln Val Lys Arg Asn Ser Trp
225                 230                 235                 240
His Gln Gly Asp Phe Asn Tyr Glu Arg Gln Glu Thr Leu Thr Ile Ser
                245                 250                 255
Ser Ala Arg Val Asn Asp Ser Gly Val Phe Met Cys Tyr Ala Asn Asn
                260                 265                 270
Thr Phe Gly Ser Ala Asn Val Thr Thr Thr Leu Lys Val Val Glu Lys
            275                 280                 285
Gly Phe Ile Asn Ile Phe Pro Val Lys Asn Thr Thr Val Phe Val Thr
            290                 295                 300
Asp Gly Glu Asn Val Asp Leu Val Val Glu Phe Glu Ala Tyr Pro Lys
305                 310                 315                 320
Pro Glu His Gln Gln Trp Ile Tyr Met Asn Arg Thr Pro Thr Asn Arg
                325                 330                 335
Gly Glu Asp Tyr Val Lys Ser Asp Asn Gln Ser Asn Ile Arg Tyr Val
                340                 345                 350
Asn Glu Leu Arg Leu Thr Arg Leu Lys Gly Thr Glu Gly Gly Thr Tyr
                355                 360                 365
Thr Phe Leu Val Ser Asn Ser Asp Val Ser Ala Ser Val Thr Phe Asp
            370                 375                 380
Val Tyr Val Asn Thr Lys Pro Glu Ile Leu Thr Tyr Asp Arg Leu Met
385                 390                 395                 400
Asn Gly Arg Leu Gln Cys Val Ala Ala Gly Phe Pro Glu Pro Thr Ile
                405                 410                 415
Asp Trp Tyr Phe Cys Thr Gly Ala Glu Gln Arg Cys Thr Val Pro Val
                420                 425                 430
Pro Pro Val Asp Val Gln Ile Gln Asn Ala Ser Val Ser Pro Phe Gly
            435                 440                 445
Lys Leu Val Val Gln Ser Ser Ile Asp Ser Ser Val Phe Arg His Asn
            450                 455                 460
Gly Thr Val Glu Cys Lys Ala Ser Asn Ala Val Gly Lys Ser Ser Ala
465                 470                 475                 480
Phe Phe Asn Phe Ala Phe Lys Gly Asn Ser Lys Glu Gln Ile Gln Pro
                485                 490                 495
His Thr Leu Phe Thr Pro Arg Ser Leu Glu Val Leu Phe Gln Gly Pro
                500                 505                 510
Gly Ser Pro Pro Leu Lys Glu Cys Pro Pro Cys Ala Ala Pro Asp Leu
            515                 520                 525
Leu Gly Gly Pro Ser Val Phe Ile Phe Pro Pro Lys Ile Lys Asp Val
            530                 535                 540
Leu Met Ile Ser Leu Ser Pro Met Val Thr Cys Val Val Val Asp Val
545                 550                 555                 560
Ser Glu Asp Asp Pro Asp Val Gln Ile Ser Trp Phe Val Asn Asn Val
                565                 570                 575
```

-continued

```
Glu Val His Thr Ala Gln Thr Gln Thr His Arg Glu Asp Tyr Asn Ser
            580                 585                 590

Thr Leu Arg Val Val Ser Ala Leu Pro Ile Gln His Gln Asp Trp Met
        595                 600                 605

Ser Gly Lys Glu Phe Lys Cys Lys Val Asn Asn Arg Ala Leu Pro Ser
    610                 615                 620

Pro Ile Glu Lys Thr Ile Ser Lys Pro Arg Gly Pro Val Arg Ala Pro
625                 630                 635                 640

Gln Val Tyr Val Leu Pro Pro Ala Glu Glu Met Thr Lys Lys Glu
                645                 650                 655

Phe Ser Leu Thr Cys Met Ile Thr Gly Phe Leu Pro Ala Glu Ile Ala
            660                 665                 670

Val Asp Trp Thr Ser Asn Gly Arg Thr Glu Gln Asn Tyr Lys Asn Thr
        675                 680                 685

Ala Thr Val Leu Asp Ser Asp Gly Ser Tyr Phe Met Tyr Ser Lys Leu
    690                 695                 700

Arg Val Gln Lys Ser Thr Trp Glu Arg Gly Ser Leu Phe Ala Cys Ser
705                 710                 715                 720

Val Val His Glu Gly Leu His Asn His Leu Thr Thr Lys Thr Ile Ser
                725                 730                 735

Arg Ser Leu Gly Lys
            740

<210> SEQ ID NO 177
<211> LENGTH: 527
<212> TYPE: PRT
<213> ORGANISM: Homo sapiens

<400> SEQUENCE: 177

Met Tyr Arg Met Gln Leu Leu Ser Cys Ile Ala Leu Ser Leu Ala Leu
1               5                   10                  15

Val Thr Asn Ser Gln Pro Ser Val Ser Pro Gly Glu Pro Ser Pro Pro
            20                  25                  30

Ser Ile His Pro Ala Lys Ser Glu Leu Ile Val Arg Val Gly Asn Glu
        35                  40                  45

Ile Arg Leu Leu Cys Ile Asp Pro Gly Phe Val Lys Trp Thr Phe Glu
    50                  55                  60

Ile Leu Asp Glu Thr Asn Glu Asn Lys Gln Asn Glu Trp Ile Thr Glu
65                  70                  75                  80

Lys Ala Glu Ala Thr Asn Thr Gly Lys Tyr Thr Cys Thr Asn Lys His
                85                  90                  95

Gly Leu Ser Ser Ser Ile Tyr Val Phe Val Arg Asp Pro Ala Lys Leu
            100                 105                 110

Phe Leu Val Asp Arg Ser Leu Tyr Gly Lys Glu Asp Asn Asp Thr Leu
        115                 120                 125

Val Arg Cys Pro Leu Thr Asp Pro Glu Val Thr Ser Tyr Ser Leu Lys
    130                 135                 140

Gly Cys Gln Gly Lys Pro Leu Pro Lys Asp Leu Arg Phe Val Pro Asp
145                 150                 155                 160

Pro Lys Ala Gly Ile Thr Ile Lys Ser Val Lys Arg Ala Tyr His Arg
                165                 170                 175

Leu Cys Leu His Cys Ser Ala Asp Gln Glu Gly Lys Ser Val Leu Ser
            180                 185                 190

Asp Lys Phe Ile Leu Lys Val Arg Pro Ala Phe Lys Ala Val Pro Val
        195                 200                 205
```

Val Ser Val Ser Lys Ala Ser Tyr Leu Leu Arg Glu Gly Glu Glu Phe
    210                 215                 220

Thr Val Thr Cys Thr Ile Lys Asp Val Ser Ser Val Tyr Ser Thr
225                 230                 235                 240

Trp Lys Arg Glu Asn Ser Gln Thr Lys Leu Gln Glu Lys Tyr Asn Ser
                245                 250                 255

Trp His His Gly Asp Phe Asn Tyr Glu Arg Gln Ala Thr Leu Thr Ile
                260                 265                 270

Ser Ser Ala Arg Val Asn Asp Ser Gly Val Phe Met Cys Tyr Ala Asn
                275                 280                 285

Asn Thr Phe Gly Ser Ala Asn Val Thr Thr Thr Leu Glu Val Val Asp
    290                 295                 300

Lys Gly Phe Ile Asn Ile Phe Pro Met Ile Asn Thr Thr Val Phe Val
305                 310                 315                 320

Asn Asp Gly Glu Asn Val Asp Leu Ile Val Glu Tyr Glu Ala Phe Pro
                325                 330                 335

Lys Pro Glu His Gln Gln Trp Ile Tyr Met Asn Arg Thr Phe Thr Asp
                340                 345                 350

Lys Trp Glu Asp Tyr Pro Lys Ser Glu Asn Glu Ser Asn Ile Arg Tyr
                355                 360                 365

Val Ser Glu Leu His Leu Thr Arg Leu Lys Gly Thr Glu Gly Gly Thr
    370                 375                 380

Tyr Thr Phe Leu Val Ser Asn Ser Asp Val Asn Ala Ser Ile Ala Phe
385                 390                 395                 400

Asn Val Tyr Val Asn Thr Lys Pro Glu Ile Leu Thr Tyr Asp Arg Leu
                405                 410                 415

Val Asn Gly Met Leu Gln Cys Val Ala Ala Gly Phe Pro Glu Pro Thr
                420                 425                 430

Ile Asp Trp Tyr Phe Cys Pro Gly Thr Glu Gln Arg Cys Ser Ala Ser
                435                 440                 445

Val Leu Pro Val Asp Val Gln Thr Leu Asn Ala Ser Gly Pro Pro Phe
    450                 455                 460

Gly Lys Leu Val Val Gln Ser Ser Ile Asp Ser Ser Ala Phe Lys His
465                 470                 475                 480

Asn Gly Thr Val Glu Cys Lys Ala Tyr Asn Asp Val Gly Lys Thr Ser
                485                 490                 495

Ala Tyr Phe Asn Phe Ala Phe Lys Gly Asn Asn Lys Glu Gln Ile His
                500                 505                 510

Pro His Thr Leu Phe Thr Pro Arg Ser His His His His His
    515                 520                 525

```
<210> SEQ ID NO 178
<211> LENGTH: 503
<212> TYPE: PRT
<213> ORGANISM: Homo sapiens

<400> SEQUENCE: 178
```

Gln Pro Ser Val Ser Pro Gly Glu Pro Ser Pro Ser Ile His Pro
1               5                   10                  15

Gly Lys Ser Asp Leu Ile Val Arg Val Gly Asp Glu Ile Arg Leu Leu
                20                  25                  30

Cys Thr Asp Pro Gly Phe Val Lys Trp Thr Phe Glu Ile Leu Asp Glu
                35                  40                  45

Thr Asn Glu Asn Lys Gln Asn Glu Trp Ile Thr Glu Lys Ala Glu Ala

```
            50                  55                  60
Thr Asn Thr Gly Lys Tyr Thr Cys Thr Asn Lys His Gly Leu Ser Asn
 65                  70                  75                  80

Ser Ile Tyr Val Phe Val Arg Asp Pro Ala Lys Leu Phe Leu Val Asp
                     85                  90                  95

Arg Ser Leu Tyr Gly Lys Glu Asp Asn Asp Thr Leu Val Arg Cys Pro
                    100                 105                 110

Leu Thr Asp Pro Glu Val Thr Asn Tyr Ser Leu Lys Gly Cys Gln Gly
                    115                 120                 125

Lys Pro Leu Pro Lys Asp Leu Arg Phe Ile Pro Asp Pro Lys Ala Gly
                130                 135                 140

Ile Met Ile Lys Ser Val Lys Arg Ala Tyr His Arg Leu Cys Leu His
145                 150                 155                 160

Cys Ser Val Asp Gln Glu Gly Lys Ser Val Leu Ser Glu Lys Phe Ile
                    165                 170                 175

Leu Lys Val Arg Pro Ala Phe Lys Ala Val Pro Val Val Ser Val Ser
                180                 185                 190

Lys Ala Ser Tyr Leu Leu Arg Glu Gly Glu Glu Phe Thr Val Thr Cys
                195                 200                 205

Thr Ile Lys Asp Val Ser Ser Ser Val Tyr Ser Thr Trp Lys Arg Glu
210                 215                 220

Asn Ser Gln Thr Lys Leu Gln Glu Lys Tyr Asn Ser Trp His His Gly
225                 230                 235                 240

Asp Phe Asn Tyr Glu Arg Gln Ala Thr Leu Thr Ile Ser Ser Ala Arg
                    245                 250                 255

Val Asn Asp Ser Gly Val Phe Met Cys Tyr Ala Asn Asn Thr Phe Gly
                260                 265                 270

Ser Ala Asn Val Thr Thr Thr Leu Glu Val Val Asp Lys Gly Phe Ile
                275                 280                 285

Asn Ile Phe Pro Met Ile Asn Thr Thr Val Phe Val Asn Asp Gly Glu
                290                 295                 300

Asn Val Asp Leu Ile Val Glu Tyr Glu Ala Phe Pro Lys Pro Glu His
305                 310                 315                 320

Gln Gln Trp Ile Tyr Met Asn Arg Thr Phe Thr Asp Lys Trp Glu Asp
                    325                 330                 335

Tyr Pro Lys Ser Glu Asn Glu Ser Asn Ile Arg Tyr Val Ser Glu Leu
                340                 345                 350

His Leu Thr Arg Leu Lys Gly Thr Glu Gly Gly Thr Tyr Thr Phe Leu
                355                 360                 365

Val Ser Asn Ser Asp Val Asn Ala Ala Ile Ala Phe Asn Val Tyr Val
370                 375                 380

Asn Thr Lys Pro Glu Ile Leu Thr Tyr Asp Arg Leu Val Asn Gly Met
385                 390                 395                 400

Leu Gln Cys Val Ala Ala Gly Phe Pro Glu Pro Thr Ile Asp Trp Tyr
                    405                 410                 415

Phe Cys Pro Gly Thr Glu Gln Arg Cys Ser Ala Ser Val Leu Pro Val
                    420                 425                 430

Asp Val Gln Thr Leu Asn Ser Ser Gly Pro Pro Phe Gly Lys Leu Val
                435                 440                 445

Val Gln Ser Ser Ile Asp Ser Ser Ala Phe Lys His Asn Gly Thr Val
                450                 455                 460

Glu Cys Lys Ala Tyr Asn Asp Val Gly Lys Thr Ser Ala Tyr Phe Asn
465                 470                 475                 480
```

```
Phe Ala Phe Lys Glu Gln Ile His Pro His Thr Leu Phe Thr Pro Arg
                485                 490                 495

Ser His His His His His His
            500
```

```
<210> SEQ ID NO 179
<211> LENGTH: 11
<212> TYPE: PRT
<213> ORGANISM: Homo sapiens

<400> SEQUENCE: 179

Val Phe Val Arg Asp Pro Ala Lys Leu Phe Leu
1               5                   10
```

```
<210> SEQ ID NO 180
<211> LENGTH: 14
<212> TYPE: PRT
<213> ORGANISM: Homo sapiens

<400> SEQUENCE: 180

His Cys Ser Val Asp Gln Glu Gly Lys Ser Val Leu Ser Glu
1               5                   10
```

```
<210> SEQ ID NO 181
<211> LENGTH: 5
<212> TYPE: PRT
<213> ORGANISM: Homo sapiens

<400> SEQUENCE: 181

Asp Pro Ala Lys Leu
1               5
```

```
<210> SEQ ID NO 182
<211> LENGTH: 9
<212> TYPE: PRT
<213> ORGANISM: Homo sapiens

<400> SEQUENCE: 182

Gln Glu Gly Lys Ser Val Leu Ser Glu
1               5
```

```
<210> SEQ ID NO 183
<211> LENGTH: 331
<212> TYPE: PRT
<213> ORGANISM: Homo sapiens

<400> SEQUENCE: 183

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
                20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110
```

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
        130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 184
<211> LENGTH: 108
<212> TYPE: PRT
<213> ORGANISM: Homo sapiens

<400> SEQUENCE: 184

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 185
<211> LENGTH: 331
<212> TYPE: PRT
<213> ORGANISM: Homo sapiens

<400> SEQUENCE: 185

```
Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
                100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
        130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
                180                 185                 190

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Cys Asp Ile Ala Val Glu Trp Glu Ser Asn Gly Gln Pro Glu
                260                 265                 270

Asn Asn Tyr Lys Thr Thr Pro Pro Val Leu Asp Ser Asp Gly Ser Phe
                275                 280                 285

Phe Leu Tyr Ser Lys Leu Thr Val Asp Lys Ser Arg Trp Gln Gln Gly
            290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 186
<211> LENGTH: 108
<212> TYPE: PRT
<213> ORGANISM: Homo sapiens

<400> SEQUENCE: 186

Cys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
```

```
            35                  40                  45
Gln Ser Gly Asn Ser Gln Glu Ser Val Thr Glu Gln Asp Ser Lys Asp
         50                  55                  60

Ser Thr Tyr Ser Leu Ser Ser Thr Leu Thr Leu Ser Lys Ala Asp Tyr
 65                  70                  75                  80

Glu Lys His Lys Val Tyr Ala Cys Glu Val Thr His Gln Gly Leu Ser
                 85                  90                  95

Ser Pro Val Thr Lys Ser Phe Asn Arg Gly Glu Cys
             100                 105

<210> SEQ ID NO 187
<211> LENGTH: 331
<212> TYPE: PRT
<213> ORGANISM: Homo sapiens

<400> SEQUENCE: 187

Ser Ala Ser Thr Lys Gly Pro Ser Val Phe Pro Leu Ala Pro Ser Ser
 1               5                  10                  15

Lys Ser Thr Ser Gly Gly Thr Ala Ala Leu Gly Cys Leu Val Lys Asp
                 20                  25                  30

Tyr Phe Pro Cys Pro Val Thr Val Ser Trp Asn Ser Gly Ala Leu Thr
             35                  40                  45

Ser Gly Val His Thr Phe Pro Ala Val Leu Gln Ser Ser Gly Leu Tyr
         50                  55                  60

Ser Leu Ser Ser Val Val Thr Val Pro Ser Ser Ser Leu Gly Thr Gln
 65                  70                  75                  80

Thr Tyr Ile Cys Asn Val Asn His Lys Pro Ser Asn Thr Lys Val Asp
                 85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Cys Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300
```

```
Asn Val Phe Ser Cys Ser Val Met His Glu Ala Leu His Asn His Tyr
305                 310                 315                 320

Thr Gln Lys Ser Leu Ser Leu Ser Pro Gly Lys
            325                 330

<210> SEQ ID NO 188
<211> LENGTH: 331
<212> TYPE: PRT
<213> ORGANISM: Homo sapiens

<400> SEQUENCE: 188

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
210                 215                 220

Gly Gln Pro Arg Glu Pro Gln Val Tyr Thr Leu Pro Pro Ser Arg Glu
225                 230                 235                 240

Glu Met Thr Cys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
            325                 330
```